(12) United States Patent
Moritani et al.

(10) Patent No.: US 8,188,097 B2
(45) Date of Patent: May 29, 2012

(54) PYRAZOLO[1,5-A]PYRIMIDINE COMPOUNDS

(75) Inventors: Yasunori Moritani, Osaka (JP); Kimihiro Shirai, Osaka (JP); Mariko Oi, Osaka (JP)

(73) Assignee: Mitsubishi Tanabe Pharma Corporation, Osaka (JP)

( * ) Notice: Subject to any disclaimer, the term of this patent is extended or adjusted under 35 U.S.C. 154(b) by 734 days.

(21) Appl. No.: 12/083,268

(22) PCT Filed: Oct. 20, 2006

(86) PCT No.: PCT/JP2006/321441
§ 371 (c)(1),
(2), (4) Date: Apr. 7, 2008

(87) PCT Pub. No.: WO2007/046548
PCT Pub. Date: Apr. 26, 2007

(65) Prior Publication Data
US 2009/0069298 A1    Mar. 12, 2009

(30) Foreign Application Priority Data

Oct. 21, 2005 (JP) ................. 2005-306816
May 31, 2006 (JP) ................. 2006-151470

(51) Int. Cl.
*A01N 43/90* (2006.01)
*A61K 31/519* (2006.01)
*C07D 487/00* (2006.01)

(52) U.S. Cl. ................... 514/259.3; 544/281
(58) Field of Classification Search .......... None
See application file for complete search history.

(56) References Cited

U.S. PATENT DOCUMENTS

| 2005/0187224 A1 | 8/2005 | Gebauer et al. |
| 2009/0069298 A1 | 3/2009 | Moritani et al. |

FOREIGN PATENT DOCUMENTS

| WO | WO-03/101993 A1 | 12/2003 |
| WO | WO03101993 | * 12/2003 |
| WO | WO-2004/069838 A1 | 8/2004 |
| WO | WO-2004/094417 A1 | 11/2004 |
| WO | WO-2004/106341 A1 | 12/2004 |
| WO | WO-2005/018645 A1 | 3/2005 |
| WO | WO 2005/061507 A1 | 7/2005 |
| WO | WO 2005/082907 A2 | 9/2005 |
| WO | WO 2005/103052 A1 | 11/2005 |
| WO | WO-2006/016715 A1 | 2/2006 |
| WO | WO-2006/072828 A1 | 7/2006 |
| WO | WO 2007/046548 A1 | 4/2007 |

OTHER PUBLICATIONS

Matsuda et al., "Structure of a Cannabinoid receptor and functional expression of the cloned cDNA," Nature, vol. 346, pp. 561-564, 1990.
Munro et al., "Molecular characterization of a peripheral receptor for cannabinoids," Nature, vol. 365, pp. 61-65, 1993.
Colombo et al., "Appetite Suppression and Weight Loss after the Cannabinoid Antagonist SR 141716," Life Sciences, vol. 63, No. 8, pp. 113-117, 1998.
Lange et al., "Synthesis, Biological Properties, and Molecular Modeling Investigations of Novel 3, 4-Diarylpyrazolines as Potent and Selective $CB_1$ Cannabinoid Receptor Antagonists," Journal of Medicinal Chemistry, vol. 47, No. 3, pp. 627-643, 2003.
Office Action dated Jul. 25, 2011 in Japanese Application No. 2008-108647.
Office Action dated Jul. 26, 2011 in Japanese Application No. 2006-285609.
Office Action for corresponding U.S. Appl. No. 12/303,177 dated Jan. 27, 2011.
Office Action for corresponding U.S. Appl. No. 12/303,177 dated Mar. 21, 2011.

* cited by examiner

*Primary Examiner* — Jeffrey Murray
(74) *Attorney, Agent, or Firm* — Birch, Stewart, Kolasch & Birch, LLP

(57) ABSTRACT

The present invention relates to a novel pyrazolo[1,5-a]pyrimidine compound of the formula [I]:

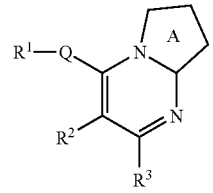

[I]

wherein $R^1$ and $R^2$ are the same or different and an optionally substituted aryl group etc.

Q is single bond, a methylene group or a group of the formula: —N($R^Q$)—, $R^Q$ is an alkyl group, Ring A is a substituted pyrazole ring fused to the adjacent pyrimidine ring having the following formula (A), (B) or (C),

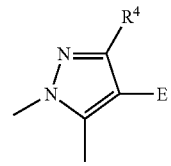

(A)

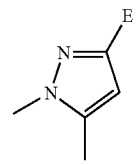

(B)

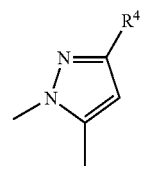

(C)

$R^3$ and $R^4$ are the same or different and a hydrogen atom, a cyano group etc.

E is one of the following groups (i) to (v):

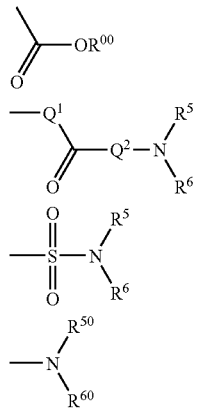

$R^{00}$ is an alkyl group, $Q^1$ is a single bond etc., $Q^2$ is a single bond or an alkylene group, one of $R^5$ and $R^6$ is a hydrogen atom or an alkyl group and the other is an alkyl group etc., one of $R^{50}$ and $R^{60}$ is a hydrogen atom or an alkyl group and the other is a hydrogen atom, an alkyl group etc., $R^{51}$ is an alkyl group or an optionally substituted arylsulfonyl group, $R^{61}$ is an alkylamino group or an azido group, or a pharmaceutically acceptable salt thereof.

17 Claims, No Drawings

PYRAZOLO[1,5-A]PYRIMIDINE COMPOUNDS

TECHNICAL FIELD

The present invention relates to a novel pyrazolo[1,5-a] pyrimidine compound or a pharmaceutically acceptable salt thereof which has potent central cannabinoid receptor (CB1) antagonizing activity and hence is useful as a medicine.

BACKGROUND ART

It is well known that, by intake of marijuana, various psychiatric or neurological reactions such as confusion of temporal or space sense, euphoria, alteration of memories, analgesia, hallucination and the like would be produced. The compounds generally referred to as "cannabinoid" including Δ9-tetrahydrocannabinol (Δ9-THC) are responsible for many of such reactions. The effect of cannabinoid is considered to be produced by an interaction between the compound and its endogenous specific/high-affinity receptors. Two subtypes of cannabinoid receptors (CB1 and CB2) have been identified and cloned. The CB1 receptor is distributed in central nervous system (CNS) regions including brain (Nature, Vol. 346, 1990, pp 561-564) while the CB2 receptor is distributed in immune system including spleen (Nature, Vol. 365, 1993, pp 61-65).

Substances having affinity to such cannabinoid receptors (agonists, antagonists or inverse agonists) may produce various pharmacological effects like marijuana. In particular, substances having affinity to central CB1 receptor may be useful for treatment of a CNS disease such as a psychotic disorder, a neurological disorder and the like.

There have been known various compounds, including pyrazol-3-carboxamide compounds such as SR141716 (Life Science, Vol. 63, 1998, PL113-PL117), 4,5-dihydropyrazole compounds such as SLV-319 (Journal of Medicinal Chemistry, Vol. 47(3), 2004, pp. 627-643), dihydropyrazolo[3,4-c]pyridin-7-one compounds, 2H-pyrazolo[4,3-d]pyrimidin-7(6H)-one (WO2004/094417) and the like as the substances having affinity to such cannabinoid receptors. Among them, at least SR141716 and SLV-319 are under clinical studies on the efficacy thereof as anorexigenics (anti-obesity agent).

DISCLOSURE OF INVENTION

The object of the present invention is to provide a novel pyrazolo[1,5-a]-pyrimidine compound which has potent CB1 receptor-antagonizing activity and hence is useful as a medicine.

The present invention relates to a pyrazolo[1,5-a]pyrimidine compound of the formula [I]:

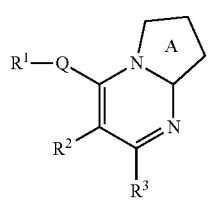

wherein
$R^1$ and $R^2$ are the same or different and an optionally substituted aryl group or an optionally substituted saturated or unsaturated heterocyclic group, Q is single bond, a methylene group or a group of the formula: $-N(R^Q)-$, $R^Q$ is an alkyl group, Ring A is a substituted pyrazole ring fused to the adjacent pyrimidine ring having the following formula (A), (B) or (C),

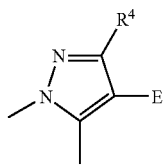

(A)

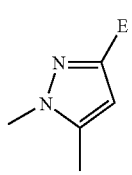

(B)

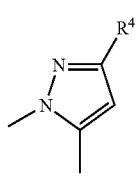

(C)

$R^3$ and $R^4$ are the same or different and (a) a hydrogen atom, (b) a cyano group, (c) an alkyl group optionally substituted by one to three halogen atom(s), (d) an alkyloxy group (the alkyl moiety of said group being optionally substituted by one to three group(s) selected from a halogen atom, a hydroxyl group, an amino group optionally substituted by one or two alkyl group(s), an alkyloxy group and an alkylsulfonyl group), (e) an alkylthio group, (f) an alkylsulfinyl group, (g) an alkylsulfonyl group or (h) a group of the formula: $-N(R')(R'')$, $R'$ and $R''$ are the same or different and (a) a hydrogen atom, (b) an alkyl group optionally substituted by one to three group(s) selected from a halogen atom, an amino group optionally substituted by one or two alkyl group(s) and an alkyloxy group, (c) an acyl group, (d) an alkylsulfonyl group or (e) an amino sulfonyl group optionally substituted by one to two alkyl group(s), or both $R'$ and $R''$ combine each other at their termini to form together with an adjacent nitrogen atom an optionally substituted, saturated or unsaturated nitrogen-containing heterocyclic group, E is one of the following groups (i) to (v):

(i)

(ii)

(iii)

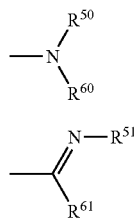
(iv)

(v)

$R^{00}$ is an alkyl group, $Q^1$ is a single bond, an alkylene group or a group of the formula: —N($R^7$)—, $R^7$ is a hydrogen atom or an alkyl group, $Q^2$ is a single bond or an alkylene group, one of $R^5$ and $R^6$ is a hydrogen atom or an alkyl group and the other is (a) an alkyl group optionally substituted by one to three group(s) selected from a halogen atom, a cyano group, an alkyloxy group, an optionally substituted cycloalkyl group, an amino group optionally substituted by one or two alkyl group(s), an alkylthio group, an alkylsulfinyl group, an alkylsulfonyl group, an acyl group, an optionally substituted aryl group and optionally substituted saturated or unsaturated heterocyclic group, (b) an optionally substituted cycloalkyl group, (c) a group of the formula: —N($R^8$)($R^9$), (d) an optionally substituted aryl group or (e) an optionally substituted, saturated or unsaturated heterocyclic group, or both of $R^5$ and $R^6$ combine each other to form together with an adjacent nitrogen atom an optionally substituted, saturated or unsaturated nitrogen-containing heterocyclic group, one of $R^8$ and $R^9$ is a hydrogen atom or an alkyl group and the other is (a) an alkyl group optionally substituted by one to three group(s) selected from a halogen atom, a cyano group and an aryl group, (b) a cycloalkyl group, (c) an optionally substituted aryl group or (d) an acyl group or (e) an optionally substituted saturated or unsaturated heterocyclic group, one of $R^{50}$ and $R^{60}$ is a hydrogen atom or an alkyl group and the other is a hydrogen atom, an alkyl group or an acyl group, or both of them combine together with the adjacent nitrogen atom to form a cyclic group of the following formula:

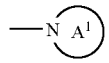

in which Ring $A^1$ is a 5- to 7-membered aliphatic nitrogen-containing heterocyclic group optionally substituted by an oxo group, $R^{51}$ is an alkyl group or an optionally substituted arylsulfonyl group, $R^{61}$ is an alkylamino group or an azido group, or a pharmaceutically acceptable salt thereof.

BEST MODE TO CARRY OUT INVENTION

With regard to the compound [I] of the present invention, in case that each of $R^1$ and $R^2$ is an aryl group, examples of such aryl group include a 6- to 10-membered monocyclic or bicyclic aryl group such as a phenyl group or a naphthyl group. Among them, preferred example of such aryl group is a phenyl group.

With regard to the compound [I] of the present invention, in case that $R^1$, $R^2$, $R^3$ or $R^4$ is a saturated or unsaturated heterocyclic group, examples of such heterocyclic group include a 5- to 7-membered heteromonocyclic group including one to three heteroatom(s) selected from a sulfur atom, an oxygen atom and a nitrogen atom. More concretely, such heterocyclic group may be a saturated or unsaturated 5- to 6-membered oxygen-containing heterocyclic group such as a furyl group, a tetrahydrofuranyl group, a pyranyl group or a tetrahydropyranyl group, a saturated or unsaturated 5- to 6-membered sulfur-containing heterocyclic group such as thienyl group, a tetrahydrothienyl group, a thiopyranyl group or a tetrahydrothiopyranyl group or a saturated or unsaturated 5- to 7-membered nitrogen-containing heterocyclic group such as a pyrrolidinyl group, an imidazolyl group, a pyrazolyl group, an oxazolyl group, an isoxazolyl group, a thiazolyl group, an isothiazolyl group, a pyridyl group, a piperidyl group, a pyrimidinyl group, a pyrazinyl group, a pyridazinyl group, a morpholinyl group, a thiomorpholinyl group or an azacycloheptyl group. Among them, preferred example of $R^1$ or $R^2$ is a saturated or unsaturated 5- or 6-membered sulfur- or nitrogen-containing heterocyclic group such as a thienyl group, a pyrrolidinyl group, a piperidyl group or a pyridyl group, and preferred example of $R^3$ or $R^4$ is a unsaturated 5- or 6-membered sulfur-, oxygen- or nitrogen-containing heterocyclic group such as a pyrrolidinyl group, a piperidyl group, a morpholino group or a thiomorpholino group.

The aryl group and/or the saturated or unsaturated heterocyclic group in $R^1$, $R^2$, $R^3$ or $R^4$ mentioned above may be substituted by one to three groups selected from a halogen atom, a cyano group, an alkyl group optionally substituted by one to three halogen atom(s), an alkyloxy group optionally substituted by one to three halogen atom(s), an amino group optionally substituted by one to two alkyl group(s), an alkylthio group, an alkylsulfinyl group and an alkylsulfonyl group.

In case that $R^5$, $R^6$, $R^8$ or $R^9$ is a cycloalkyl group, such cycloalkyl group may be substituted by one to two group(s) selected from a cyano group and an alkyl group.

The aryl group in $R^5$, $R^6$, $R^8$ or $R^9$ mentioned above may be a 6- to 10-membered monocyclic or bicyclic aryl group such as a phenyl group, a naphthyl group and the like, preferably a phenyl group. The aryl group may be substituted by one to two halogen atom(s).

In case that $R^5$, $R^6$, $R^8$ or $R^9$ is a saturated or unsaturated heterocyclic group, examples of such heterocyclic group include (a) a saturated or unsaturated, 4- to 7-membered heteromonocyclic group, said heteromonocyclic group containing one to four heteroatoms selected from oxygen atom, sulfur atom and nitrogen atom; (b) a saturated or unsaturated, 8- to 15-membered nitrogen-containing bicyclic or tricyclic heterocyclic group formed by fusing the aforementioned heteromonocyclic group with one or two other cyclic group(s) selected from a $C_{3-8}$ cycloalkyl group, a 5- to 6-membered monocyclic aryl group and a saturated or unsaturated, 4- to 7-membered heteromonocyclic group, said heteromonocyclic group containing one to four heteroatom(s) selected from an oxygen atom, a sulfur atom and a nitrogen atom; or (c) a saturated or unsaturated, 8- to 11-membered nitrogen-containing spiro-heterocyclic group.

Examples of the saturated or unsaturated heterocyclic group in $R^5$, $R^6$, $R^8$ or $R^9$ is (A) an oxygen- or sulfur-containing heterocyclic group selected from a furyl group, a tetrahydrofuranyl group, a pyranyl group, a tetrahydropyranyl group, a thiacyclobutyl group, a thienyl group, a tetrahydrothienyl group, a thiopyranyl group, a tetrahydrothiopyranyl group, a benzofuranyl group, a dihydrobenzofuranyl group, an isobenzofuranyl group, a chromanyl group, an isochromanyl group, a chromenyl group, an isochromenyl group, a benzothienyl group and a dihydrobenzothienyl group; or (B) a nitrogen-containing heterocyclic group selected from an azetidyl group, a pyrrolidinyl group, a pyrrolinyl group, an imidazolidinyl group, an imidazolinyl group, a pyrazolidinyl group, a pyrazolinyl group, a pyrrolyl group, a 2H-pyrrolyl group, an imidazolyl group, a pyrazolyl group, a dihydropyrazolyl group, a thiazolidinyl group, a thiazolyl group, an isothiazolyl group, an isoxazolyl group, an oxazolidinyl group, a pyridyl group, a dihydropyridyl group, a tetrahydropyridyl group, a piperidyl group, a pyrazinyl group, a piperazinyl group, a pyrimidinyl group, a tetrahydropyrimidinyl group, a pyridazinyl group, a morpholinyl group, an azocinyl group, an azacycloheptyl group, an indolizinyl group, a benzimidazolyl group, a benzotriazolyl group, an indolyl group, an isoindolyl group, a 3H-indolyl group, an indolinyl group, an isoindolinyl group, a 1H-indazolyl group, a pyrrolopyridyl group, a pyrrolopyrimidinyl group, a purinyl group, a pteridinyl group, a 4H-quinolizinyl group, a quinolyl group, a dihydroquinolyl group, a tetrahydroquinolyl group, an isoquinolyl group, a dihydroisoquinolyl group, a tetrahydroisoquinolyl group, a phthalazinyl group, a dihydrophthalazinyl group, a naphthyridinyl group, a dihydronaphthyridinyl group, a tetrahydronaphthyridinyl group, a quinoxalinyl group, a quinazolinyl group, a dihydroquinazolinyl group, a dihydrobenzothiazinyl group, a dihydrobenzoxazinyl group, a cinnolinyl group, a xanthenyl group, a carbazolyl group, a beta-carbolinyl group, a phenanthridinyl group, an acridinyl group, a 5H-dihydro-dibenzazepinyl group and a spiro-heterocyclic group of the formula:

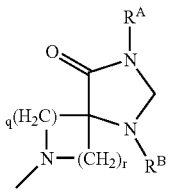

wherein $R^A$ and $R^B$ are the same or different and a hydrogen atom or an alkyl group, and q and r are an integer of 1 or 2.

Among them, preferred examples of the saturated or unsaturated heterocyclic group include a tetrahydrofuranyl group, a pyrrolyl group, a pyrrolidinyl group, a piperidyl group, an azacycloheptyl group, a tetrahydropyranyl group, piperazinyl group, a morpholinyl group, a thiomorpholinyl group, a thiacyclobutyl group, a tetrahydrothienyl group, a tetrahydrothiopyranyl group, a thiazolyl group, a pyridyl group, a pyrimidinyl group, an indolyl group, a pyrrolopyridyl group or a tetrahydronaphthyridinyl group.

In case that $R^5$ and $R^6$ combine each other to form a saturated or unsaturated nitrogen-containing heterocyclic group, examples of such nitrogen-containing heterocyclic group include (a) a saturated or unsaturated, 4- to 7-membered nitrogen-containing heteromonocyclic group, said heteromonocyclic group optionally containing two or more nitrogen atoms and optionally containing one to two heteroatoms other than such nitrogen atoms selected from oxygen atom and sulfur atom; (b) a saturated or unsaturated, 8- to 15-membered nitrogen-containing bicyclic or tricyclic heterocyclic group formed by fusing the aforementioned heteromonocyclic group with one or two other cyclic group(s) selected from a $C_{3-8}$ cycloalkyl group, a 5- to 6-membered monocyclic aryl group and a saturated or unsaturated, 4- to 7-membered heteromonocyclic group, said heteromonocyclic group containing one to four heteroatoms selected from oxygen atom, sulfur atom and nitrogen atom; or (c) a saturated or unsaturated, 8- to 11-membered nitrogen-containing spiro-heterocyclic group.

Examples of the saturated or unsaturated nitrogen-containing heterocyclic group mentioned above include a nitrogen-containing heterocyclic group selected from an azetidyl group, a pyrrolidinyl group, a pyrrolinyl group, an imidazolidinyl group, an imidazolinyl group, a pyrazolidinyl group, a pyrazolinyl group, a pyrrolyl group, an imidazolyl group, a pyrazolyl group, a dihydropyrazolyl group, a thiazolidinyl group, an oxazolidinyl group, a dihydropyridyl group, a tetrahydropyridyl group, a piperidyl group, a piperazinyl group, a tetrahydropyrimidinyl group, a morpholinyl group, an azacycloheptyl group, a benzimidazolyl group, a benzotriazolyl group, an indolyl group, an isoindolyl group, an indolinyl group, an isoindolinyl group, a 1H-indazolyl group, a purinyl group, a dihydroquinolyl group, a tetrahydroquinolyl group, a dihydro-isoquinolyl group, a tetrahydroisoquinolyl group, a dihydrophthalazinyl group, a dihydroquinazolinyl group, a dihydrobenzothiazinyl group, a dihydrobenzoxazinyl group, a carbazolyl group, a beta-carbolinyl group, a 5H-dihydro-dibenzazepinyl group and a spiro-heterocyclic group of the formula:

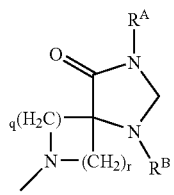

wherein $R^A$ and $R^B$ are the same or different and a hydrogen atom or an alkyl group, and q and r are an integer of 1 or 2.

Among them, preferred examples of the saturated or unsaturated heterocyclic group include a saturated 5- to 7-membered, nitrogen-containing heteromonocyclic group such as a morpholino group, a thiomorpholino group, a piperidino group, a piperazino group or an azacycloheptyl group.

Moreover, the saturated or unsaturated heterocyclic group in $R^5$, $R^6$, $R^8$ or $R^9$ (and the saturated or unsaturated nitrogen-containing heterocyclic group formed by combining $R^5$ with $R^6$) may be substituted by one to four group(s) selected from a halogen atom, a hydroxyl group, a cyano group, an oxo group, an alkyl group, an alkyl group substituted by one to three halogen atom(s), an alkyloxyalkyl group, an aminoalkyl group, a cycloalkyl group, an arylalkyl group, an alkyloxy group, an alkyloxy group substituted by one to three halogen atom(s), an acyl group, an amino group optionally substituted by one to two alkyl group(s), an acylamino group, an alkylsulfonyl group, an aminosulfonyl group optionally substituted by one to two alkyl group(s), an aryl group optionally substituted by one to two halogen atom(s) and a saturated or unsaturated 5- to 6-membered, nitrogen-containing heterocyclic group.

Examples of the acyl group in $R^4$, $R^5$, $R^6$, $R^8$ or $R^9$ include a group formed by removing a hydroxyl group from a carboxylic acid having the following formula [Ac-I]: $R^x$—COOH [Ac-I], namely a group of the formula: $R^x$—CO—, in which $R^x$ is (a) a hydrogen atom, (b) an alkyl group optionally substituted by one to three group(s) selected from a halogen atom, a cyano group, an alkylsulfonyl group and a pyridyl group, (c) an alkyloxy group optionally substituted by an aryl group, (d) a cycloalkyl group, (e) an aryl group optionally substituted by a halogen atom, a cyano group, an alkyl group, a trihalogenoalkyl group and an alkyloxy group, (f) an amino group optionally substituted by one to two alkyl group(s) or (g) a saturated or unsaturated heterocyclic group. Concrete examples of such acyl group include (a1) a formyl group, (b1) a $C_{1-6}$ alkyl-carbonyl group such as an acetyl group, a propionyl group and the like, a trihalogeno-$C_{1-6}$ alkyl-carbonyl group such as a trifluoroacetyl group and the like, a cyano-$C_{1-6}$ alkyl-carbonyl group such as cyanoacetyl group and the like, a pyridyl-$C_{1-6}$ alkyl-carbonyl group such as a pyridylacetyl group and the like, (c1) a $C_{1-6}$ alkyloxy-carbonyl group such as a methoxycarbonyl group, an ethoxycarbonyl group, a tert-butoxycarbonyl group and the like, an aryl-$C_{1-6}$ alkyloxy-carbonyl group such as a benzyloxycarbonyl group, (d1) a $C_{3-8}$ cycloalkyl-carbonyl group such as a cyclopropylcarbonyl group, a cyclopentylcarbonyl group and the like, (e1) an aryl-carbonyl group such as a benzoyl group and the like, a mono- or di-halogeno-aryl-carbonyl group such as a chlorobenzoyl group, a fluorobenzoyl group, a difluorobenzoyl group and the like, a cyano-aryl-carbonyl group such as a cyanobenzoyl group, a trihalogeno-$C_{1-6}$ alkyl-aryl-carbonyl group such as a trifluoromethylbenzoyl group and the like, a $C_{1-6}$ alkyloxy-aryl-carbonyl group such as a methoxybenzoyl group and the like, (f) a carbamoyl group, a N—($C_{1-6}$ alkyl)carbamoyl group, or (g1) a furoyl group, a thenoyl group, a bromothenoyl group, a cyanothenoyl group, a pyridylcarbonyl group, a chloropyridylcarbonyl group, a cyanopyridylcarbonyl group, a trifluoromethylpyridylcarbonyl group or a pyrazinylcarbonyl group.

In case that E is a group of the formula (II) in the compound [I] of the present invention, examples of the group (ii) include a group of the following formula:

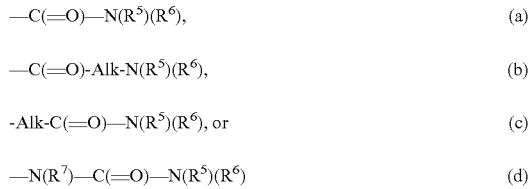

wherein Alk is a straight or branched chain $C_{1-6}$ alkylene group and other symbols are the same as defined above.

Among the compounds [I] of the present invention, examples of preferred compound include a compound of the following Group A to E.

Group A: Compound [I] in which
$R^1$ and $R^2$ are the same or different and (a) a phenyl group optionally substituted by one to two group(s) selected from a halogen atom and a trihalogenoalkyl group,
Q is a single bond,
Ring A is a substituted pyrazole ring of the formula (A),
E is a group of the following formula: —C(=O)O—$R^{00}$ (i)
$R^4$ is (a) an amino group optionally substituted by one to two group(s) selected from an alkyl group and an alkylsulfonyl group or (b) an aminosulfonyl group optionally substituted by one to two alkyl group(s) or a pharmaceutically acceptable salt thereof.

Among the compounds of Group A, preferred examples include a compound wherein $R^1$ is a chlorophenyl group or a trifluoro-$C_{1-4}$ alkyl-phenyl group, $R^2$ is a chlorophenyl group, $R^3$ is a $C_{1-4}$ alkyl group and $R^4$ is an amino group substituted by one to two group(s) selected from a $C_{1-4}$ alkyl group and a $C_{1-4}$ alkylsulfonyl group or a pharmaceutically acceptable salt thereof.

Group B: Compound [I] in which
$R^1$ and $R^2$ are the same or different and (a) a phenyl group optionally substituted by one to three group(s) selected from a halogen atom, a cyano group, an alkyl group optionally substituted by one to three halogen atom(s), an alkyloxy group optionally substituted by one to three halogen atom(s), an amino group optionally substituted by one to two alkyl group(s) and an alkylsulfonyl group or (b) a saturated or unsaturated 5- to 7-membered heterocyclic group optionally substituted by one to three group(s) selected from a halogen atom, an oxo group, an alkyl group optionally substituted by one to three halogen atom(s), an alkyloxy group, an alkyloxyalkyl group and an alkyloxyalkyloxy group, Ring A is a substituted pyrazole ring of the formula (A) or (B), E is one of the groups of the following formula (a) to (e):

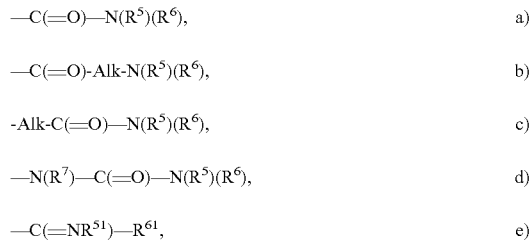

$R^3$ is a hydrogen atom, a cyano group or an alkyloxy group, $R^4$ is (a) a hydrogen atom, (b) a cyano group, (c) an alkyl group optionally substituted by one to three group(s) selected from a halogen atom and a hydroxyl group, (d) an alkyloxy group optionally substituted by one to three group(s) selected from a halogen atom, a hydroxyl group, an amino group optionally substituted by one to two alkyl group(s), an alkyloxy group and an alkylsulfonyl group, (e) an alkylthio group, (f) an alkylsulfinyl group, (g) an alkylsulfonyl group or (h) a group of the formula: —N(R')(R"), R' and R" are the same or different and (a) a hydrogen atom, (b) an alkyl group optionally substituted by one to three group(s) selected from a halogen atom, an amino group optionally substituted by one to two alkyl group(s) and an alkyloxy group, (c) an acyl group, (d) an alkylsulfonyl group or (e) an aminosulfonyl group optionally substituted by one to two alkyl group(s), or (f) both of them combine together with the adjacent nitrogen atom to form a saturated or unsaturated 5- to 6-membered nitrogen-containing heteromonocyclic group optionally substituted by a hydroxyl group or an alkyloxy group, one of $R^5$ and $R^6$ is a hydrogen atom or an alkyl group and the other is (1) an alkyl group optionally substituted by one to three group(s) selected from a halogen atom, an alkyloxy group, a cycloalkyl group, an alkylthio group, an alkylsulfonyl group, an amino group optionally substituted by one or two alkyl group(s), a morpholinocarbonyl group, a phenyl group optionally substituted by a cyano group and a saturated or unsaturated 5- to 6-membered nitrogen-containing heteromonocyclic group, said heteromonocyclic group being optionally substituted by a group selected from a halogen atom, an alkyl group and a trihalogenoalkyl group;

(2) a cycloalkyl group optionally substituted by a cyano group or an alkyl group;

(3) a group of the formula: —N($R^8$)($R^9$); or (4) a phenyl group; or (5) a saturated or unsaturated 4- to 10-membered monocyclic- or bicyclic heterocyclic group optionally substituted by one to four group(s) selected from a halogen atom, a cyano group, a hydroxyl group, an oxo group, an alkyl group optionally substituted by one to three halogen atom(s), a cycloalkyl group, an alkylcarbonyl group, an alkyloxycarbonyl group, an alkylsulfonyl group, an aminosulfonyl group optionally substituted by one or two alkyl group(s), a carbamoyl group optionally substituted by one to two alkyl group(s), an alkyloxycarbonyl group, an alkyloxycarbonylamino group a phenyl group optionally substituted by one to two halogen atom(s) and saturated or unsaturated 5- to 6-membered heteromonocyclic group; or (6) both of $R^5$ and $R^6$ combine each other together with the adjacent nitrogen atom to form a saturated or unsaturated 4- to 7-membered nitrogen-containing heterocyclic group optionally substituted by one to two group(s) selected from a halogen atom and an oxo group, $R^8$ is hydrogen atom or an alkyl group, $R^9$ is (a) an alkyl group optionally substituted by one to three group(s) selected from a halogen atom, a cyano group and a phenyl group; (b) a phenyl group optionally substituted by a group selected from a halogen atom, a cyano group, an alkyl group, a trihalogenoalkyl group, a cycloalkyl group, a trihalogenoalkyloxy group, an alkyloxy group, an alkylthio group and an alkylsulfonyl group; (c) an alkyloxycarbonyl group; or (d) a saturated or unsaturated 5- to 6-membered heteromonocyclic group optionally substituted by a group selected from a halogen atom, a cyano group, an alkyl group, an alkyloxy group and a trihalogenoalkyl group, $R^7$ is a hydrogen atom, $R^{51}$ is an alkyl group or a phenylsulfonyl group optionally substituted by one to two halogen atom(s) and $R^{61}$ is an alkylamino group or an azido group or a pharmaceutically acceptable salt thereof.

Among the compounds of the Group B, examples of more preferred compound include a compound wherein $R^1$ is (a) a phenyl group optionally substituted by one or two group(s) selected from a halogen atom, a cyano group, a dihalogenoalkyl group, a trihalogenoalkyl group, an alkyloxy group, an alkyloxyalkyl group and di(alkyl)amino group or (b) a saturated or unsaturated 5- to 7-membered heterocyclic group optionally substituted by one to two group(s) selected from an oxo group, an alkyl group, a trihalogenoalkyl group, an alkyloxy group, an alkyloxyalkyl, an alkyloxyalkyloxy group and a di(alkyl)amino group, $R^2$ is (a) a phenyl group optionally substituted by one or two group(s) selected from a halogen atom and a cyano group or (b) a saturated or unsaturated 5- to 6-membered heterocyclic group optionally substituted by a halogen atom, $R^3$ is a hydrogen atom, $R^4$ is a hydrogen atom, an alkyl group, a dihalogenoalkyl group, a hydroxyalkyl group, a trihalogenoalkyl group, an alkyloxyalkyl group, a hydroxyalkyloxy group, an alkyloxyalkyloxy group, an alkylsulfonylalkyl group or a group of the formula: —N(R')(R''), one of R' and R'' is a hydrogen atom or an alkyl group and the other is an acyl group or an alkylsulfonyl group, E is one of the groups of the following formula (a), (b) and (e):

—C(=O)—N(R$^5$)(R$^6$), (a)

—C(=O)-Alk-N(R$^5$)(R$^6$), (b)

—C(=NR$^{51}$)—R$^{61}$, (e)

one of $R^5$ and $R^6$ is a hydrogen atom or an alkyl group, the other is (a) an alkyl group, (b) a cycloalkyl group, (c) a phenyl group, (d) a saturated or unsaturated 4- to 10-membered mono- or bi-cyclic heterocyclic group optionally substituted by one to four groups) selected from a halogen atom, an oxo group, a cyano group, a hydroxyl group, an alkyl group, a trihalogenoalkyl group, an alkyloxy group, an alkyloxyalkyl group, an alkylcarbonyl group, a di(alkyl)carbamoyl group, an alkylsulfonyl group, a di(alkyl)aminosulfonyl group, a phenyl group, a halogenophenyl group and a pyridyl group or (e) a group of the formula: —N(R$^8$)(R$^9$), or (f) both of them combine together with the adjacent nitrogen atom to form a saturated or unsaturated 5- to 6-membered heteromonocyclic group optionally substituted by one to two group(s) selected from a halogen atom and an oxo group, $R^8$ is an alkyl group, $R^9$ is (a) an alkyl group, (b) a phenyl group optionally substituted by a halogen atom, (c) an alkyl group optionally substituted by a pyridyl group or (d) a saturated or unsaturated 4- to 6-membered heteromonocyclic group optionally substituted by a group selected from a halogen atom, an alkyl group, a trihalogenoalkyl group and an alkyloxy group, $R^{51}$ is an alkyl group or a halogenophenyl-sulfonyl group, and $R^{61}$ is an alkylamino group or an azido group.

Among the compounds of the Group B, examples of further preferred compound include a compound wherein $R^1$ is (a) a phenyl group optionally substituted by a group selected from a chlorine atom, a fluorine atom, a cyano group, a difluoro-$C_{1-4}$ alkyl group and a trifluoro-$C_{1-4}$ alkyl group or (b) a pyridyl group optionally substituted by a trifluoro-$C_{1-4}$ alkyl group, $R^2$ is a phenyl group optionally substituted by one to two groups selected from a chlorine atom, a fluorine atom, a bromine atom and a cyano group, $R^3$ is a hydrogen atom, $R^4$ is a hydrogen atom, a $C_{1-4}$ alkyl group, a difluoro-$C_{1-4}$ alkyl group, a trifluoro-$C_{1-4}$ alkyl group, a $C_{1-4}$ alkyloxy-$C_{1-4}$ alkyl group or a $C_{1-4}$ alkyl-carbonyl-amino group, E is one of the groups of the following formula (a) and (b):

—C(=O)—N(R$^5$)(R$^6$), (a)

—C(=O)-Alk-N(R$^5$)(R$^6$), (b)

one of $R^5$ and $R^6$ is a hydrogen atom and the other is a $C_{1-4}$ alkyl group, a pyridyl-$C_{1-4}$ alkyl group, a $C_{5-7}$ cycloalkyl group, a chlorophenyl group, a saturated or unsaturated 4- to 6-membered heteromonocyclic group optionally substituted by one to two group(s) selected from a halogen atom, an oxo group and $C_{1-4}$ alkyloxy-$C_{1-4}$ alkyl group or a group of the formula: —N(R$^8$)(R$^9$), or both of them combine together with the adjacent nitrogen atom to form a saturated or unsaturated 5- to 6-membered heteromonocyclic group optionally substituted by one to two oxo group(s), $R^8$ is a $C_{1-4}$ alkyl group and $R^9$ is a $C_{1-4}$ alkyl group, a chlorophenyl group, a pyridyl group or a $C_{1-4}$ alkyloxy-pyridyl group.

Group C: A compound [I] wherein $R^1$ and $R^2$ are the same or different and a phenyl group optionally substituted by one to two group(s) selected from a halogen atom and a trihalogenoalkyl group, Q is a single bond, Ring A is a substituted pyrazole ring of the formula (A), $R^3$ is a hydrogen atom, $R^4$ is a hydrogen atom or an alkyl group, E is a group of the formula (iii):

(iii)

one of $R^5$ and $R^6$ is a hydrogen atom or an alkyl group and the other is (a) an alkyl group, (b) a cycloalkyl group or (c) a saturated or unsaturated 5- to 6-membered sulfur- or nitrogen-containing heteromonocyclic group, or (d) both of them combine together with the adjacent nitrogen atom to form a saturated or unsaturated 5- to 6-membered nitrogen-containing heterocyclic group optionally substituted by one to two oxo group(s) or a pharmaceutically acceptable salt thereof.

Among the compounds of the Group C, examples of more preferred compound include a compound wherein $R^1$ is a trihalogenoalkyl-phenyl group, $R^2$ is a halogenophenyl group,
$R^4$ is an alkyl group,
one of $R^5$ and $R^6$ is a hydrogen atom or an alkyl group, the other is (a) an alkyl group, (b) a cycloalkyl group, (c) a saturated or unsaturated 5- to 6-membered sulfur- or nitrogen-containing heteromonocyclic group optionally substituted by one to two oxo group(s), or (d) both of them combine together with the adjacent nitrogen atom to form a saturated or unsaturated 5- to 6-membered heteromonocyclic group optionally substituted by one to two oxo group(s).

Group D: A compound [I] wherein $R^1$ and $R^2$ are the same or different and a phenyl group optionally substituted by one to two group(s) selected from a halogen atom and a trihalogenoalkyl group, Q is a single bond, Ring A is a substituted pyrazole ring of the formula (A), $R^3$ is a hydrogen atom, $R^4$ is a hydrogen atom or an alkyl group, E is a group of the formula (Iv):

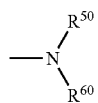

(iv)

one of $R^{50}$ and $R^{60}$ is a hydrogen atom or an alkyl group and the other is an alkyl group or an acyl group, or both of them combine together with the adjacent nitrogen atom to form a saturated or unsaturated 5- to 6-membered nitrogen-containing heterocyclic group optionally substituted by one to two oxo group(s) or a pharmaceutically acceptable salt thereof.

Group E: A compound [I] wherein $R^1$ and $R^2$ are the same or different and a phenyl group optionally substituted by one to two group(s) selected from a halogen atom and a trihalogenoalkyl group, Q is a single bond, Ring A is a substituted pyrazole ring of the formula (C), $R^3$ is a hydrogen atom, $R^4$ is a group of the formula —N(R')(R"), R' and R" are the same or different and a hydrogen atom or an alkyl group, or both of them combine together with the adjacent nitrogen atom to form a saturated or unsaturated 5- to 6-membered nitrogen-containing heterocyclic group or a pharmaceutically acceptable salt thereof.

Among the compounds [I] of the present invention, examples of particularly preferred compound include a compound selected from the group consisting of:
6-(2-chlorophenyl)-7-(4-chlorophenyl)-3-(N-piperidinocarbamoyl)pyrazolo[1,5-a]-pyrimidine;
6-(2-chlorophenyl)-7-(4-chlorophenyl)-3-[(N'-methyl-N'-phenylhydrazino)-carbonyl]pyrazolo[1,5-a]pyrimidine;
6-(2-chlorophenyl)-7-(4-chlorophenyl)-3-(N-cyclohexylcarbamoyl)pyrazolo[1,5-a]-pyrimidine;
6-(2-chlorophenyl)-7-(4-chlorophenyl)-3-[(N',N'-dimethylhydrazino)carbonyl]-pyrazolo[1,5-a]pyrimidine;
6-(2-chlorophenyl)-7-(4-chlorophenyl)-3-(N-pyrrolidinocarbamoyl)pyrazolo[1,5-a]-pyrimidine;
6-(2-chlorophenyl)-7-(4-chlorophenyl)-3-(N-cyclopentylcarbamoyl)-pyrazolo[1,5-a]-pyrimidine;
6-(2-chlorophenyl)-7-(4-chlorophenyl)-3-[N-(4-tetrahydropyranyl)carbamoyl]-pyrazolo[1,5-a]pyrimidine;
6-(2-chlorophenyl)-7-(4-chlorophenyl)-3-[N-(1,1-dioxo-tetrahydrothiophen-3-yl)-carbamoyl]pyrazolo[1,5-a]pyrimidine;
(R)-6-(2-chlorophenyl)-7-(4-difluoromethylphenyl)-3-[N-(1,1-dioxo-tetrahydro-thiophen-3-yl)carbamoyl]pyrazolo[1,5-a]pyrimidine;
(R)-6-(2-chlorophenyl)-7-(4-trifluoromethylphenyl)-2-methyl-3-[N-(1,1-dioxo-tetrahydrothiophen-3-yl)carbamoyl]pyrazolo[1,5-a]pyrimidine;
(S)-6-(2-chlorophenyl)-7-(4-trifluoromethylphenyl)-2-methyl-3-[N-(1,1-dioxo-tetrahydrothiophen-3-yl)carbamoyl]pyrazolo[1,5-a]pyrimidine;
6-(2-chlorophenyl)-7-(4-chlorophenyl)-3-[N-[2-(2-pyridyl)ethyl]carbamoyl]-pyrazolo[1,5-a]pyrimidine;
6-(2-chlorophenyl)-7-(4-chlorophenyl)-3-(N-cyclopentylcarbamoyl)-2-methoxy-pyrazolo[1,5-a]pyrimidine;
(R)-6-(2-chlorophenyl)-7-(4-chlorophenyl)-2-methyl-3-[N-(1,1-dioxo-tetrahydro-thiophen-3-yl)carbamoyl]pyrazolo[1,5-a]pyrimidine;
(S)-6-(2-chlorophenyl)-7-(4-chlorophenyl)-2-methyl-3-[N-(1,1-dioxo-tetrahydro-thiophen-3-yl)carbamoyl]pyrazolo[1,5-a]pyrimidine;
6-(2-bromophenyl)-7-(4-chlorophenyl)-3-(N-cyclopentylcarbamoyl)pyrazolo[1,5-a]-pyrimidine;
(R,S)-6-(2-bromophenyl)-7-(4-chlorophenyl)-3-[N-(1,1-dioxo-tetrahydrothiophen-3-yl)carbamoyl]pyrazolo[1,5-a]pyrimidine;
(S)-6-(2-chlorophenyl)-7-(4-trifluoromethylphenyl)-3-[N-(1,1-dioxo-tetrahydro-thiophen-3-yl)carbamoyl]pyrazolo[1,5-a]pyrimidine;
(R)-6-(2-chlorophenyl)-7-(4-trifluoromethylphenyl)-3-[N-(1,1-dioxo-tetrahydro-thiophen-3-yl)carbamoyl]pyrazolo[1,5-a]pyrimidine;
6-(2-chlorophenyl)-7-(4-chlorophenyl)-3-[N—[N-(3-chlorophenyl)-N-methylamino]-carbamoyl]pyrazolo[1,5-a]pyrimidine;
6-(2-cyanophenyl)-7-(4-chlorophenyl)-3-[N—[N-methyl-N-(2-pyridyl)amino]-carbamoyl]pyrazolo[1,5-a]pyrimidine;
6-(2-chlorophenyl)-7-(4-chlorophenyl)-3-(N-isobutylcarbamoyl)pyrazolo[1,5-a]-pyrimidine;
6-(2-chlorophenyl)-7-(4-trifluoromethylphenyl)-3-[N-(1,1-dioxo-tetrahydro-thiophen-3-yl)carbamoyl]pyrazolo[1,5-a]pyrimidine;
6-(2-chlorophenyl)-7-(4-trifluoromethylphenyl)-3-(N-cyclopentylcarbamoyl)-pyrazolo[1,5-a]pyrimidine;
6-(2-chlorophenyl)-7-(4-trifluoromethylphenyl)-3-[N—[N-methyl-N-(2-pyridyl)-amino]carbamoyl]pyrazolo[1,5-a]pyrimidine;
(R)-6-(2-chlorophenyl)-7-(4-chlorophenyl)-3-[N-(1,1-dioxo-tetrahydrothiophen-3-yl)carbamoyl]pyrazolo[1,5-a]pyrimidine;
6-(2-chlorophenyl)-7-(4-cyanophenyl)-3-(N-cyclopentylcarbamoyl)pyrazolo[1,5-a]-pyrimidine;
(R,S)-6-(2-chlorophenyl)-7-(4-chlorophenyl)-2-methyl-3-[N-(1,1-dioxo-tetrahydro-thiophen-3-yl]carbamoyl]pyrazolo[1,5-a]pyrimidine;
6-(2-chlorophenyl)-7-(4-fluorophenyl)-3-(N-cyclopentylcarbamoyl)pyrazolo[1,5-a]-pyrimidine;
6-(2-chlorophenyl)-7-(4-chlorophenyl)-3-[N—[N-methyl-N-(2-pyridyl)amino]-carbamoyl]pyrazolo[1,5-a]pyrimidine;
(S)-6-(2-chlorophenyl)-7-(4-chlorophenyl)-3-[N-(1,1-dioxo-tetrahydrothiophen-3-yl]carbamoyl]pyrazolo[1,5-a]pyrimidine;
6-(2-chlorophenyl)-7-(4-chlorophenyl)-3-(N-ethylcarbamoyl)pyrazolo[1,5-a]-pyrimidine;
6-(2-chlorophenyl)-7-(4-chlorophenyl)-3-(N-cyclopropylcarbamoyl)-pyrazolo[1,5-a]pyrimidine;

(S)-6-(2-chlorophenyl)-7-(4-chloro-2-fluorophenyl)-3-[N-(1,1-dioxotetrahydro-thiophen-3-yl)carbamoyl]pyrazolo[1,5-a]pyrimidine;

(S)-6-(2-chlorophenyl)-7-(4-difluoromethylphenyl)-3-[N-(1,1-dioxotetrahydro-thiophen-3-yl)carbamoyl]pyrazolo[1,5-a]pyrimidine;

(R)-6-(2-cyanophenyl)-7-(4-trifluoromethylphenyl)-3-[N-(1,1-dioxotetrahydro-thiophen-3-yl)carbamoyl]-2-methylpyrazolo[1,5-a]pyrimidine;

(S)-6-(2-cyanophenyl)-7-(4-trifluoromethylphenyl)-3-[N-(1,1-dioxotetrahydro-thiophen-3-yl)carbamoyl]-2-methylpyrazolo[1,5-a]pyrimidine;

6-(2-chlorophenyl)-7-(4-chlorophenyl)-3-[[N'-methyl-N'-(2-methoxypyridin-5-yl)-hydrazino]carbonyl]pyrazolo[1,5-a]pyrimidine;

6-(2-cyanophenyl)-7-(4-chlorophenyl)-3-[N-(1-pyrrolidinyl)carbamoyl]-pyrazolo[1,5-a]pyrimidine;

6-(2-chlorophenyl)-7-(2-trifluoromethylpyridin-5-yl)-3-(N-cyclopentylcarbamoyl)-pyrazolo[1,5-a]pyrimidine;

(R)-6-(2-cyanophenyl)-7-(4-chlorophenyl)-3-[N-(1,1-dioxotetrahydro-thiophen-3-yl)carbamoyl]-2-methylpyrazolo[1,5-a]pyrimidine;

6-(2-cyanophenyl)-7-(4-chlorophenyl)-3-[[N'-methyl-N'-(2-pyridyl)hydrazino]-carbonyl]-2-methylpyrazolo[1,5-a]pyrimidine;

(R)-6-(2-chlorophenyl)-7-(4-chlorophenyl)-3-[N-(1,1-dioxotetrahydro-thiophen-3-yl)carbamoyl]-2-trifluoromethylpyrazolo[1,5-a]pyrimidine;

6-(2-chlorophenyl)-7-(4-trifluoromethylphenyl)-3-[(N',N'-dimethylhydrazino)-carbonyl]-2-acetylaminopyrazolo[1,5-a]pyrimidine;

6-(2-chlorophenyl)-7-(4-chlorophenyl)-3-[[N'-methyl-N'-(2-pyridyl)hydrazino]-carbonyl]-2-acetylaminopyrazolo[1,5-a]pyrimidine;

6-(2-chlorophenyl)-7-(4-chlorophenyl)-3-[[N'-methyl-N'-(2-pyridyl)hydrazino]-carbonyl]-2-(trifluoromethyl)pyrazolo[1,5-a]pyrimidine;

6-(2-chlorophenyl)-7-(4-chlorophenyl)-3-[N-(1-pyrrolidinyl)carbamoyl]-2-difluoromethylpyrazolo[1,5-a]pyrimidine;

(R)-6-(2-chlorophenyl)-7-(4-trifluoromethylphenyl)-3-[N-(1,1-dioxotetrahydro-thiophen-3-yl)carbamoyl]-2-difluoromethylpyrazolo[1,5-a]pyrimidine;

(S)-6-(2-chlorophenyl)-7-(4-trifluoromethylphenyl)-3-[N-(1,1-dioxotetrahydro-thiophen-3-yl)carbamoyl]-2-difluoromethylpyrazolo[1,5-a]pyrimidine;

6-(2-cyanophenyl)-7-(4-chlorophenyl)-3-(N-piperidinocarbamoyl)-2-difluoromethylpyrazolo[1,5-a]pyrimidine;

6-(2-chlorophenyl)-7-(4-chlorophenyl)-3-[N-(1,1-dioxothiacyclobutan-3-yl)-carbamoyl]pyrazolo[1,5-a]pyrimidine;

7-(4-chlorophenyl)-6-(2-cyano-4-fluorophenyl)-3-[N-(1-pyrrolidinyl)carbamoyl]-pyrazolo[1,5-a]pyrimidine;

7-(4-chlorophenyl)-6-(2-cyanophenyl)-3-(N-piperidinocarbamoyl)-2-methyl-pyrazolo[1,5-a]pyrimidine;

7-(4-chlorophenyl)-6-(2-cyanophenyl)-3-[N-(1-pyrrolidinyl)carbamoyl]-2-methyl-pyrazolo[1,5-a]pyrimidine;

(S)-6-(2-chlorophenyl)-7-(4-chlorophenyl)-3-[N-(2-methoxymethyl-1-pyrrolidinyl)-carbamoyl]pyrazolo[1,5-a]pyrimidine;

6-(2-chlorophenyl)-7-(4-chlorophenyl)-3-[N-(4-fluoropiperidino)carbamoyl]pyrazolo[1,5-a]pyrimidine;

(R)-7-(4-chloro-2-fluorophenyl)-6-(2-cyanophenyl)-3-[N-(1,1-dioxotetrahydro-thiophen-3-yl)carbamoyl]-2-methylpyrazolo[1,5-a]pyrimidine;

6-(2-chlorophenyl)-7-(4-chlorophenyl)-3-[[N'-methyl-N'-(2-ethoxypyridin-5-yl)-hydrazino]carbonyl]pyrazolo[1,5-a]pyrimidine;

(R)-6-(2-chlorophenyl)-7-(4-chlorophenyl)-3-[N-(1,1-dioxotetrahydro-thiophen-3-yl)carbamoyl]-2-methoxymethylpyrazolo[1,5-a]pyrimidine;

(S)-6-(2-chlorophenyl)-7-(4-chlorophenyl)-3-[N-(1,1-dioxotetrahydro-thiophen-3-yl)carbamoyl]-2-methoxymethylpyrazolo[1,5-a]pyrimidine;

6-(2-chlorophenyl)-7-(4-chlorophenyl)-3-[[N'-methyl-N'-(2-pyridyl)hydrazino]-carbonyl]-2-methoxymethylpyrazolo[1,5-a]pyrimidine;

6-(2-chlorophenyl)-7-(4-chlorophenyl)-3-[N-(1-pyrrolidinyl)carbamoyl]-2-methoxymethylpyrazolo[1,5-a]pyrimidine;

7-(4-chloro-2-fluorophenyl)-6-(2-cyanophenyl)-3-[N-(1-pyrrolidinyl)carbamoyl]-2-methylpyrazolo[1,5-a]pyrimidine;

6-(2-chlorophenyl)-7-(4-chlorophenyl)-3-[2-(1,1-dioxothiomorpholino)acetyl]-2-methylpyrazolo[1,5-a]pyrimidine;

6-(2-cyanophenyl)-7-(4-chlorophenyl)-3-[N-(4-fluoropiperidino)carbamoyl]-2-methylpyrazolo[1,5-a]pyrimidine; and 6-(2-chlorophenyl)-7-(4-trifluoromethylphenyl)-3-[N-(tetrahydrothiophen-3-yl)-carbamoyl]pyrazolo[1,5-a]pyrimidine or a pharmaceutically acceptable salt thereof.

When the compound [I] of the present invention has an asymmetric carbon atom(s) in its molecule, it may exist in the form of a stereoisomer thereof (diastereoisomers, optical isomers) owing to said asymmetric carbon atom(s) thereof, and the present invention also includes one of the stereoisomers and a mixture thereof.

A compound [I] of the present invention shows a potent antagonistic activity against CB1 receptor and may be useful as an agent for prevention and/or treatment of a CB1 receptor-mediated diseases such as psychosis including schizophrenia, anxiety disorders, stress, depression, epilepsy, neurodegenerative disorders, spinocerebellar disorders, cognitive disorders, craniocerebral trauma, panic attack, peripheral neuropathy, glaucoma, migraine, Parkinson's disease, Alzheimer's disease, Huntington's disease, Raynaud's syndrome, tremor, obsessive-compulsive disorders, amnesia, geriatric dementia, thymic disorders, Tourette's syndrome, tardive dyskinesia, bipolar disorders, cancer, drug-induced dyskinesia, dystonia, septic shock, hemorrhagic shock, hypotension, insomnia, immunological diseases including inflammations, multiple sclerosis, emesis, diarrhea, asthma, appetite disorders such as bulimarexia, anorexia and the like, obesity, non insulin-dependent diabetes mellitus (NIDDM), memory disorders, urinary disorders, cardiovascular disorders, infertility disorders, infections, demyelination-related diseases, neuroinflammation, viral encephalitis, cerebral vascular incidents, cirrhosis of the liver or gastrointestinal disorders including intestinal transit disorders.

In addition, a compound [I] of the present invention may be useful as an agent for withdrawal from a chronic treatment, alcohol dependence or drug abuse (e.g., an opioid, barbiturate, marijuana, cocaine, amphethamine, phencyclidine, a hallucinogenic agent, a benzodiazepine compound and the like).

Furthermore, a compound [I] of the present invention may be useful as an agent for enhancing analgesic activity of analgesic or narcotic drugs and the like; or an agent for smoking cessation (withdrawal from smoking or nicotine dependence).

Moreover, a compound [I] of the present invention can be useful for treatment of a condition relating to metabolic diseases including obesity, diabetes, impaired glucose tolerance, hyperinsulinemia, hyperlipidemia, hypercholesterolemia, hypertriglyceridemia, lipid metabolism disorder, atherosclerosis, hypertension, cardiovascular disease, coronary heart disease, depression, anxiety, drug addiction, and substance addiction.

Besides, the compound [I] of the present invention can be advantageous as a medicine due to its low toxicity.

The compound [I] of the present invention can be clinically used either in the free form or in the form of a pharmaceutically acceptable salt thereof. The pharmaceutically acceptable salt of the compound [I] includes a salt with an inorganic acid such as hydrochloride, sulfate, phosphate or hydrobromide, or a salt with an organic acid such as acetate, fumarate, oxalate, citrate, methanesulfonate, benzenesulfonate, tosylate or maleate. Besides, when the compound [I] of the present invention has a carboxyl group(s) and the like in its molecule, examples of the pharmaceutically acceptable salt include, salts with a base such as alkaline metal (e.g., sodium salt, potassium salt) or alkaline earth metal (e.g., calcium salt).

The compound [I] or a pharmaceutically acceptable salt thereof includes either intramolecular salt or an additive thereof, and solvates or hydrates thereof.

The present compound [I] or a pharmaceutically acceptable salt thereof can be either orally or parenterally, and can be formulated into a conventional pharmaceutical preparation such as tablets, granules, capsules, powders, injections or inhalants.

The dose of the compound [I] of the present invention or a pharmaceutically acceptable salt thereof may vary in accordance with the administration routes, and the ages, weights and conditions of the patients. For example, when administered in an injection preparation, it is usually in the range of about 0.0001 to 1.0 mg/kg/day, preferably in the range of about 0.001 to 0.1 mg/kg/day. When administered in an oral preparation, it is usually in the range of about 0.001 to 100 mg/kg/day, preferably in the range of 0.01 to 10 mg/kg/day.

A compound [I] of the present invention may also be useful as adjunctive, add-on or supplementary therapy for the treatment of the above-mentioned diseases/disorders. Said adjunctive, add-on or supplementary therapy means the concomitant or sequential administration of a compound of the present invention to a patient who has already received administration of, who is receiving administration of, or who will receive administration of one or more additional therapeutic agents for the treatment of the indicated conditions, for example, one or more known anti-depressant, anti-psychotics or anxiolytic agents.

The compound [I] of the present invention can be prepared by the following methods but should not be construed to be limited thereto.

(1) Among the compound of the present invention, a compound [I] in which Ring A is a substituted pyrazole ring of the formula (A) and E is a group of the following formula (II):

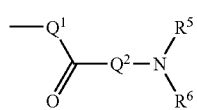 (ii)

can be prepared in accordance with, for example, the following methods A to D.

(Method A)

A compound [I] in which $Q^2$ is a single bond, namely having the following formula [I-A]:

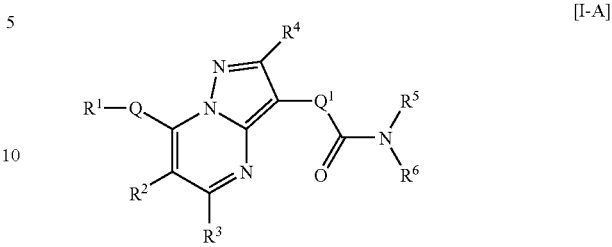 [I-A]

wherein the symbols are the same as defined above can be prepared by reacting a compound of the formula [II-A]:

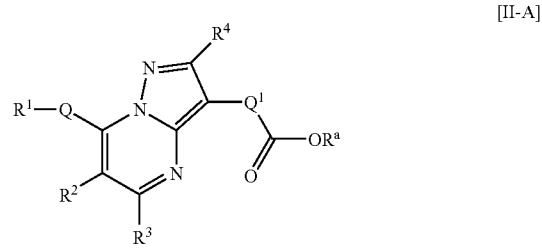 [II-A]

wherein $R^a$ is a hydrogen atom, an alkyl group or a benzyl group and the other symbols are the same as defined above with an amine compound of the following formula [III]:

$HN(R^5)(R^6)$ [III]

wherein the symbols are the same as defined above or a salt thereof.

When $R^a$ is a hydrogen atom, the above-mentioned reaction can be carried out in a solvent in the presence of a condensing agent, and in the presence or absence of an activating agent and a base. Examples of the solvent include any solvent which does not disturb the reaction, such as methylene chloride, chloroform, dimethylformaide, dimethylacetamide, tetrahydrofuran, dioxane, toluene, benzene, 1,2-dichloroethane, 1-methylpyrrolidinone, 1,2-dimethoxyethane and the like. The condensing agent may be dicyclohexylcarbodiimide (DCC), 1-ethyl-3-(3-dimethylamino-propyl)carbodiimide hydrochloride (WSC HCl), diphenylphosphoryl azide (DPPA), carbonyldiimidazole (CDI), diethylcyanophosphonate (DEPC), diisopropylcarbodiimide (DIPCI), benzotriazol-1-yloxytrispyrrolidinophosphonium hexafluorophosphate (PyBOP), carbonylditriazole, N-cyclohexylcarbodiimide-N'-propyloxymethylpolystyrene (PS-carbodiimide), N-ethoxycarbonyl-2-ethoxy-1,2-dihydroquinoline (EEDQ), 2-(7-azabenzotriazol-1-yl)-1,1,3,3-tetramethyluronium hexafluorophosphate (HATU), 2-(1H-benzotriazol-1-yl-1,1,3,3-tetramethyluronium hexafluorophosphate (HBTU), bromotrispyrrolidinophosphonium hexafluorophosphate (PyBroP), 2-(1H-benzotriazol-1-yl)-1,1,3,3-tetramethyluronium tetrafluoroborate (TBTU), chloro-1,1,3,3-tetramethyl-uronium hexachloroantimonate (ACTU) and the like. Examples of the activating agent include 1-hydroxybenzotriazole (HOBt), 1-hydroxysuccinimide (HOSu), dimethylaminopyridine (DMAP), 1-hydroxy-7-azabenzotriazole (HOAt), hydroxyphthalimide (HOPht), pentafluorophenol (Pfp-OH), 1-hydroxybenzotriazole-6-sulfonamidomethylpolystyrene (PS-HOBt) and the like. The base includes, for example, pyridine, triethylamine, diisopropylethylamine, 4-methylmorpholine, 1,8-diazabicyclo[5,4,0]-7-undecene (DBU) and the like.

In the above-mentioned process, the compound [II-A] can be used in an amount of 0.33 to 1.5 moles, preferably 0.5 to 1.2 moles per one mole of the compound [III]. The condensing agent can be used in an amount of 1.0 to 3.0 moles, preferably 1.0 to 1.2 moles per one mole of the compound [II-A] or [III]. The base can be used in an amount of 1.0 to 3.0 moles, preferably 1.0 to 1.2 moles per one mole of the compound [II-A] or [III]. The activating agent can be used in an amount of 0.01 to 2.0 moles, preferably 0.1 to 1.0 moles per one mole of the compound [II-A] or [III]. The reaction can be carried out at 0 to 150° C., preferably 20 to 80° C.

When R$^a$ in the compound [II-A] is hydrogen atom, the compound [1-A] can be prepared by converting the compound [II-A] to a corresponding reactive derivative (e.g., an acid halide, a mixed acid anhydride) and reacting such reactive derivative with the compound [III] in the presence of the base in or without the solvent.

When R$^a$ in the compound [II-A] is an alkyl group or a benzyl group, the present process A can be also carried out by converting the ester compound to a corresponding carboxylic acid compound of the following formula [II-Aa]:

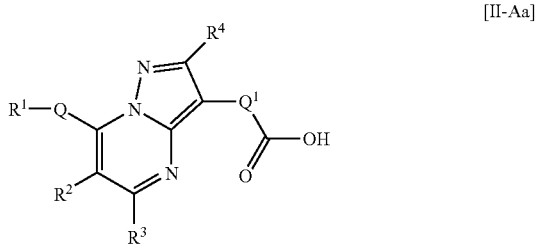

[II-Aa]

wherein the symbols are the same as defined above by a conventional manner such as hydrolysis, acidolysis with hydrochloric acid, formic acid, trifluoroacetic acid and the like or hydrogenation and then reacting the carboxylic acid compound [II-Aa] with the compound [III] in the same manner as described above.

Meanwhile, a compound [I] in which Ring A is a group of the following formula (C):

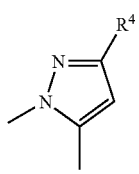

(C)

wherein the symbol is the same as defined above, can be obtained as a by-product in the reaction of the compound [II-Aa] and the compound [III].

(Method B)

A compound [I] in which Q$^2$ is an alkylene group, namely a compound of the following formula [I-B]:

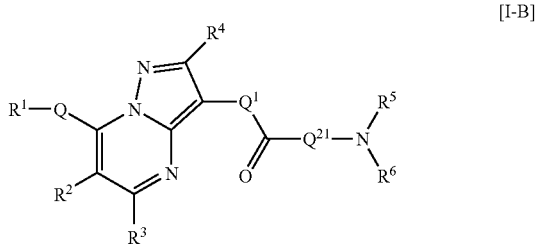

[I-B]

wherein Q$^{21}$ is an alkylene group and the other symbols are the same as defined above can be prepared by reacting a compound of the following formula [II-B]:

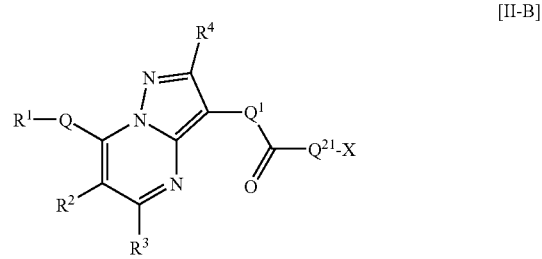

[II-B]

wherein X is a halogen atom and the other symbols are the same as defined above with the compound [III] or a salt thereof.

The reaction of the compound [II-B] with the compound [III] can be carried out in a solvent in the presence or absence of a base. Examples of the solvent include any solvent which does not disturb the reaction, such as methylene chloride, chloroform, dimethylformaide, dimethylacetamide, dimethylsulfoxide, tetrahydrofuran, dioxane, toluene, benzene, 1,2-dichloroethane, 1-methyl-pyrrolidinone, 1,2-dimethoxyethane and the like. The base includes, for example, sodium hydride, potassium carbonate, pyridine, triethylamine, diisopropylethylamine, 4-methylmorpholine, 1,8-diazabicyclo[5,4,0]-7-undecene (DBU) and the like.

In the above-mentioned process, the compound [III] can be used in an amount of 1.0 to 20 moles, preferably 1.0 to 3.0 moles per one mole of the compound [II-B]. The base can be used in an amount of 0 to 20 moles, preferably 1.0 to 3.0 moles per one mole of the compound [III] or [II-B]. The reaction can be carried out at −20 to 100° C., preferably 0 to 50° C.

(Method C)

Among the compounds [I] of the present invention, a compound in which Q$^1$ is a group of the formula: —N(R$^7$)— and Q$^2$ is a single bond, namely, a compound of the following formula [I-C]:

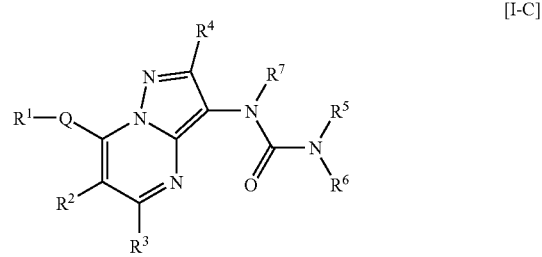

[I-C]

wherein the symbols are the same as defined above can be prepared by reacting a compound of the following formula [II-C]:

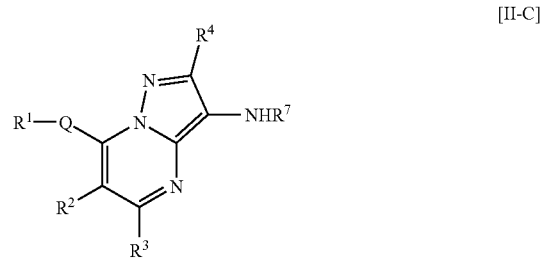

[II-C]

wherein the symbols are the same as defined above with the compound [III] in the presence of a compound of the formula [a]:

$$W^1-CO-W^2 \quad [a]$$

wherein $W^1$ and $W^2$ are the same or different and a removing group.

In the compound [α], examples of $W^1$ and $W^2$ include an imidazolyl group, a halogen atom, a phenoxy group and the like. Concrete examples of such compound include 1,1'-carbonyldiimidazole, phosgene, triphosgene and the like. Examples of the solvent include any solvent which does not disturb the reaction, such as acetonitrile, dichloromethane, chloroform, 1,2-dichloroethane, tetrahydrofuran, dioxane, benzene, toluene, dimethylformamide and the like. The compound [III] can be used in an amount of 1.0 to 5.0 moles, preferably 1.0 to 1.2 moles per one mole of the compound [II-C]. The compound [a] can be used in an amount of 0.33 to 5.0 moles, preferably 1.0 to 2.0 moles per one mole of the compound [II-C] or [III]. The reaction can be carried out at −20 to 100° C., preferably 0 to 50° C.

Moreover, the compound [1-C] can be also prepared by reacting the compound [II-C] with the compound [a] to obtain a compound of the formula [IV]:

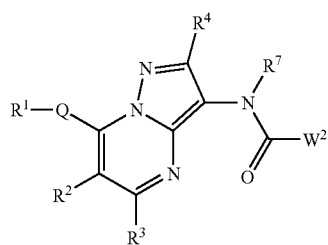

[IV]

wherein the symbols are the same as defined above and reacting the product or a reactive derivative thereof with the compound [III], or reacting the compound [III] with the compound [a] to obtain a compound of the formula [V]:

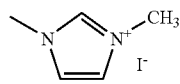

[V]

wherein the symbols are the same as defined above and reacting the product or a reactive derivative thereof with the compound [II-C].

Examples of the reactive derivative of the compound [IV] or [V] include those in which $W^2$ is converted to a group of the formula:

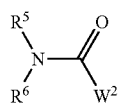

and such reactive derivative can be obtained by reacting a compound [IV] or [V] in which $W^2$ is an imidazolyl group with methyl iodide.

The reaction of the compound [II-C] or the compound [III] with the compound [a] can be carried in a solvent. Examples of the solvent include any solvent which does not disturb the reaction, such as acetonitrile, dichloromethane, 1,2-dichloroethane, benzene, toluene, tetrahydrofuran, dioxane, 1,2-dimethoxyethane, dimethylformamide and the like. The compound [a] can be used in an amount of 1.0 to 3.0 moles, preferably 1.0 to 2.0 moles per one mole of the compound [II-C] or compound [III]. The present reaction can be carried out at 0 to 150° C., preferably at 20 to 80° C.

The reactive derivative of the compound [IV] or [V] can be prepared by, for example, treating such compound [IV] or [V] with an alkyl halide such as methyl iodide in a solvent. The present reaction can be carried out at 0 to 150° C., preferably at 20 to 80° C.

The reaction of the compound [IV] (or its reactive derivative) with the compound [III] or the reaction of the compound [V] (or its reactive derivative) with the compound [II-C] can be conducted in a solvent in the presence of a base. Examples of the solvent include any solvent which does not disturb the reaction, such as methylene chloride, chloroform, dimethylformamide, dimethylacetamide, dimethylsulfoxide, tetrahydrofuran, dioxane, toluene, benzene, 1,2-dichloroethane, 1-methylpyrrolidinone, 1,2-dimethoxyethane and the like. Examples of the base include pyridine, triethylamine, diisopropylethylamine, 4-methylmorpholine, 1,8-diazabicyclo[5,4,0]undecene and the like. Such reactive derivative can be used in an amount of 0.33 to 3.0 moles, preferably 0.5 to 1.2 moles per one mole of the compound [III] or [II-C]. The present reaction can be conducted at −30 to 100° C., preferably at 0 to 50° C.

(Method D)

A compound of the following formula [I-D]:

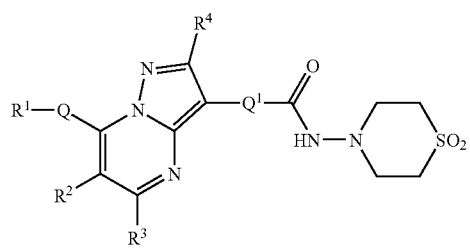

[I-D]

wherein the symbols are the same as defined above can be prepared by a compound of the following formula [II-D]:

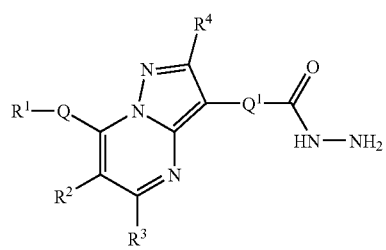

[II-D]

wherein the symbols are the same as defined above with divinylsulfone in an appropriate solvent in the presence of a base. Examples of the solvent include any solvent which does not disturb the reaction, such as ethanol, isopropyl alcohol, dioxane, toluene, N,N-dimethylformamide, dimethylsulfoxide and the like. Examples of the base include triethylamine, diisopropylethylamine, N-methylmorpholine, dimethylaminopyridine and the like. The divinylsulfone can be used in an amount of 1.0 to 3.0 moles, preferably 1.2 to 1.5 moles per one mole of the compound [II-D]. The present reaction can be conducted at 60 to 200° C., preferably at 80 to 150° C.

(2) Among the compound of the present invention, a compound [I] in which Ring A is a substituted pyrazole ring of the formula (B) and E is a group of the following formula (II):

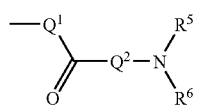
(ii)

can be prepared in accordance with, for example, a) treating a compound [II-A$^{01}$]:

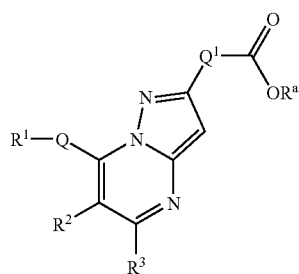
[II-A$^{01}$]

wherein the symbols are the same as define above in the same manner as described in Method A mentioned above, or b) treating a compound [II-B$^{01}$]:

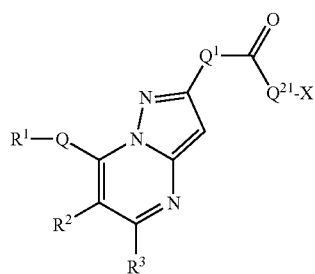
[II-B$^{01}$]

wherein the symbols are the same as define above in the same manner as described in Method B mentioned above, or c) treating a compound [II-C$^{01}$]:

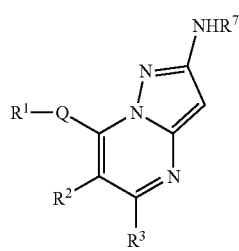
[II-C$^{01}$]

wherein the symbols are the same as define above in the same manner as described in Method C mentioned above, or d) treating a compound [II-D$^{01}$]:

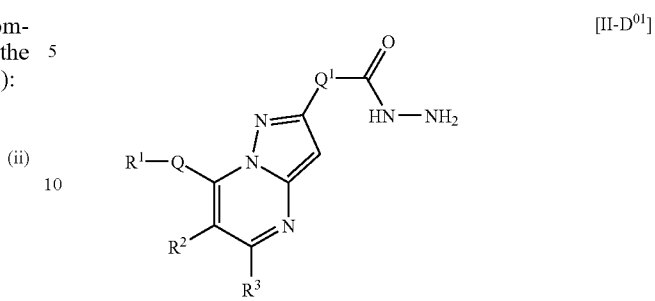
[II-D$^{01}$]

wherein the symbols are the same as define above in the same manner as described in Method D mentioned above.

Besides, a compound [I] in which $R^{50}$ and $R^{60}$ in the group of the formula (Iv) is an alkyl group can be prepared by, for example, reacting a compound [II-C] or a compound [II-C$^{01}$] in which $R^7$ is a hydrogen atom (compound [II-Ca] or compound [II-Ca$^{01}$]) with an aldehyde compound of the formula [a-1]:

$R^y$—CHO [a-1]

wherein $R^y$ is a hydrogen atom or an alkyl group in the presence of a reducing agent in the presence or absence of a base (Method E). Examples of the reducing agent include sodium triacetoxyborohydride, sodium borohydride, sodium cyanoborohydride and the like. Examples of the base include triethylamine, diisopropylethylamine, N-methylmorpholine, dimethylaminopyridine and the like. The compound [a-1] can be used in an amount of 1.0 to 3.0 moles, preferably 1.2 to 1.5 moles per one mole of the compound [II-Ca]. The base can be used in an amount of 1.2 to 5.0 moles, preferably 1.5 to 2.0 moles per one mole of the compound [II-Ca]. The present reaction can be conducted at −50 to 100° C., preferably at −10 to 40° C.

Moreover, a compound [I] in which $R^{50}$ and $R^{60}$ in the group of the formula (Iv) is a cyclic group of the following formula:

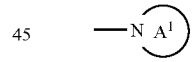

in which Ring A$^1$ is a 5- to 7-membered aliphatic nitrogen-containing heteromonocyclic group optionally substituted by an oxo group, can be prepared by, for example, a) reacting a compound [II-C] or a compound [II-C$^{01}$] in which $R^7$ is a hydrogen atom (a compound [II-Ca] or a compound [II-Ca$^{01}$]) with a compound of the following formula:

$X^{01}$-Alk$^1$-$X^{02}$ wherein $X^{01}$ and $X^{02}$ are a halogen atom and Alk$^1$ is a C$_{4-6}$ alkylene group in a solvent such as acetonitrile and the like in the presence of a base such as potassium carbonate and in the presence or absence of an additive such as sodium iodide and the like, or b) reacting a compound [II-Ca] or a compound [II-Ca$^{01}$] with divinylsulfone. The reaction of the compound [II-Ca] or the compound [II-Ca$^{01}$] with divinylsulfone can be conducted in the same manner as described in Method D mentioned above.

(3) Among the compounds [I] of the present invention, a compound in which Ring A is a substituted pyrazole ring of the formula (A) or (B) and E is group of the formula (v) can be prepared by, for example, reacting the compound [II-Aa] or the compound [II-Da] with an alkylamine such as methylamine and the like in a solvent such as methanol and the like in the presence of a condensing agent such as water-soluble carbodiimide and the like and an activating agent such as 1-hydroxybenzotriazole and the like, and then treating the resultant product with Lawesson's reagent, and further reacting the reaction product with a sulfoneazide compound of the following formula:

Ar—SO$_2$—N$_3$ wherein Ar is an optionally substituted aryl group in a solvent such as pyridine and the like. Meanwhile, examples of the substituent in Ar include a halogen atom.

The objective compound [I] of the present invention can be also prepared by, for example, intramolecularly converting the substituent(s) in R$^1$, R$^2$ and the like of such a compound [I] as obtained above to the other desired substituent(s). The intramolecular conversion processes can be selected according to the kinds of the objective substituents, and may be carried out, for example, in the following methods (a) to (h).

Method (a): A compound [I] having a cyano group (or a group containing a cyano group) as a substituent can be obtained by reacting a corresponding compound [I] having a halogen atom or an alkylsulfonyl group (or a halogen- or alkylsulfonyl group-containing group) as a substituent with cyanide compound (e.g., zinc cyanide, copper cyanide, trimethylsilyl cyanide, potassium cyanide and the like) in the presence or absence of a catalyst, a base and an additive. Examples of the base include triethylamine, N-methylpiperidine, diisopropylethylamine and the like. Examples of said catalyst include a palladium catalyst such as palladium acetate, tris(dibenzylideneacetone)dipalladium, trans-dichlorobis-(tricyclohexylphosphine)-palladium, tetrakis-(triphenylphosphine)palladium and the like or a nickel catalyst such as dibromobis(triphenylphosphine)nickel and the like. Examples of the additive include a phosphine compound such as triphenylphosiphine, 1,1'-bis(diphenylphosphino)-ferrocene, racemic 2,2'-bis(diphenylphosphino)-1,1'-binaphthyl, 2-(di-tert-butyl-phosphino)biphenyl, 2-(dicyclohexylphosphino)biphenyl, 2-dicyclohexylphosphino-2'-(N,N-dimethylamino)biphenyl or tri-tert-butylphosphine and the like.

Method (b): A compound [I] having an alkylamino group or a cycloalkylamino group as a substituent (or an alkylamino- or cycloalkylamino-containing group) can be obtained by reacting a corresponding compound [I] having a halogen atom with a mono- or di-alkylamine or a cycloalkylamine in an appropriate solvent in the presence of a catalyst, an additive and a base. Examples of the catalyst may be the palladium compounds or copper compounds used in Method (a). Examples of the additive may be the phosphine compounds used in Method (a). Examples of the base include potassium acetate, potassium carbonate, cesium carbonate, potassium tert-butoxide and the like.

Method (c): A compound [I] having an alkyloxy group as a substituent (or a an alkyloxy-containing group) can be obtained by, for example, (i) reacting a corresponding compound [I] having a hydroxyl group as a substituent (or a hydroxy-containing group) with an alkyl halide in a solvent, or (ii) reacting a corresponding compound [I] having a hydroxyl group as a substituent (or a hydroxy-containing group) with an alkanol in a solvent in the presence of a base (e.g., potassium carbonate, cesium carbonate, sodium hydride and the like) or an activating agent (e.g., diethyl azodicarboxylate and the like) and in the presence of a tri-substituted phosphine or (iii) reacting a corresponding compound [I] having an alkylsulfonyl group (or an alkylsulfonyl-containing group) with an alkali metal alkoxide in an appropriate solvent.

Method (d): A compound [I] having an alkylsulfinyl group or an alkylsulfonyl group as a substituent (or an alkylsulfinyl- or alkylsulfonyl-containing group) can be obtained by reacting a corresponding compound [I] having an alkylthio group as a substituent (or an alkylthio-containing group) with an oxidizing agent such as 3-chloroperbenzoic acid in an appropriate solvent.

Method (e): A compound [I] having an acylamino group such as an alkylcarbonylamino group as a substituent (or an acylamino-containing group) can be obtained by reacting a corresponding compound [I] having an amino group (or an amino-containing group) with a carboxylic acid compound of the following formula:

R$^x$—COOH        [Ac-1]

wherein R$^x$ is an alkyl group optionally substituted by an aryl group or an optionally substituted aryl group or a reactive derivative thereof (e.g., a corresponding acid anhydride or a corresponding acid halide). The present reaction can be carried out in a solvent in the presence of a base such as triethylamine and the like or a condensing agent such as water-soluble carbodiimide and in the presence or absence of an activating agent such as 1-hydroxybenzotriazole. Besides, such acyl group can be removed, in accordance with the kind of said acyl group, by a conventional manner such as acid treatment or catalytic hydrogenation.

Method (f): A compound [I] having a carbamoyl group as a substituent (or a carbamoyl-containing group) can be obtained by reacting a corresponding compound [I] having an alkyloxycarbonyl group as a substituent (or an alkyloxycarbonyl-containing group) with an aqueous ammonia in an appropriate solvent.

Method (g): A compound [I] having an alkylcarbamoylamino group as a substituent (or an alkylcarbamoylamino-containing group) can be obtained by reacting a corresponding compound [I] having an amino group as a substituent (or an amino-containing group) with an alkyl isocyanate in an appropriate solvent.

Method (h): A compound [I] having a group of the formula:

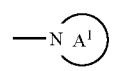

wherein Ring A$^1$ is a 5- to 7-membered nitrogen-containing aliphatic heterocyclic group can be obtained by reacting a corresponding compound [I] having an amino group with a compound of the formula:

X$^{01}$-Alk$^1$-X$^{02}$ wherein the symbols are the same as defined above in a solvent such as acetonitrile in the presence of a base such as potassium carbonate and in the presence or absence of an additive such as sodium iodide. Examples of such nitrogen-containing aliphatic heterocyclic group include 1-pyrrolidinyl group, 1-piperidyl group and the like.

If necessary, the compounds [I] of the present invention obtained in the aforementioned Processes can be converted to a pharmaceutically acceptable salt thereof by a conventional manner.

[Preparation of Intermediate Compound]

i) For example, a compound [II-A] in which $Q^1$ is a single bond or an alkylene group can be prepared in a manner as described in the following reaction scheme A1 to A4.

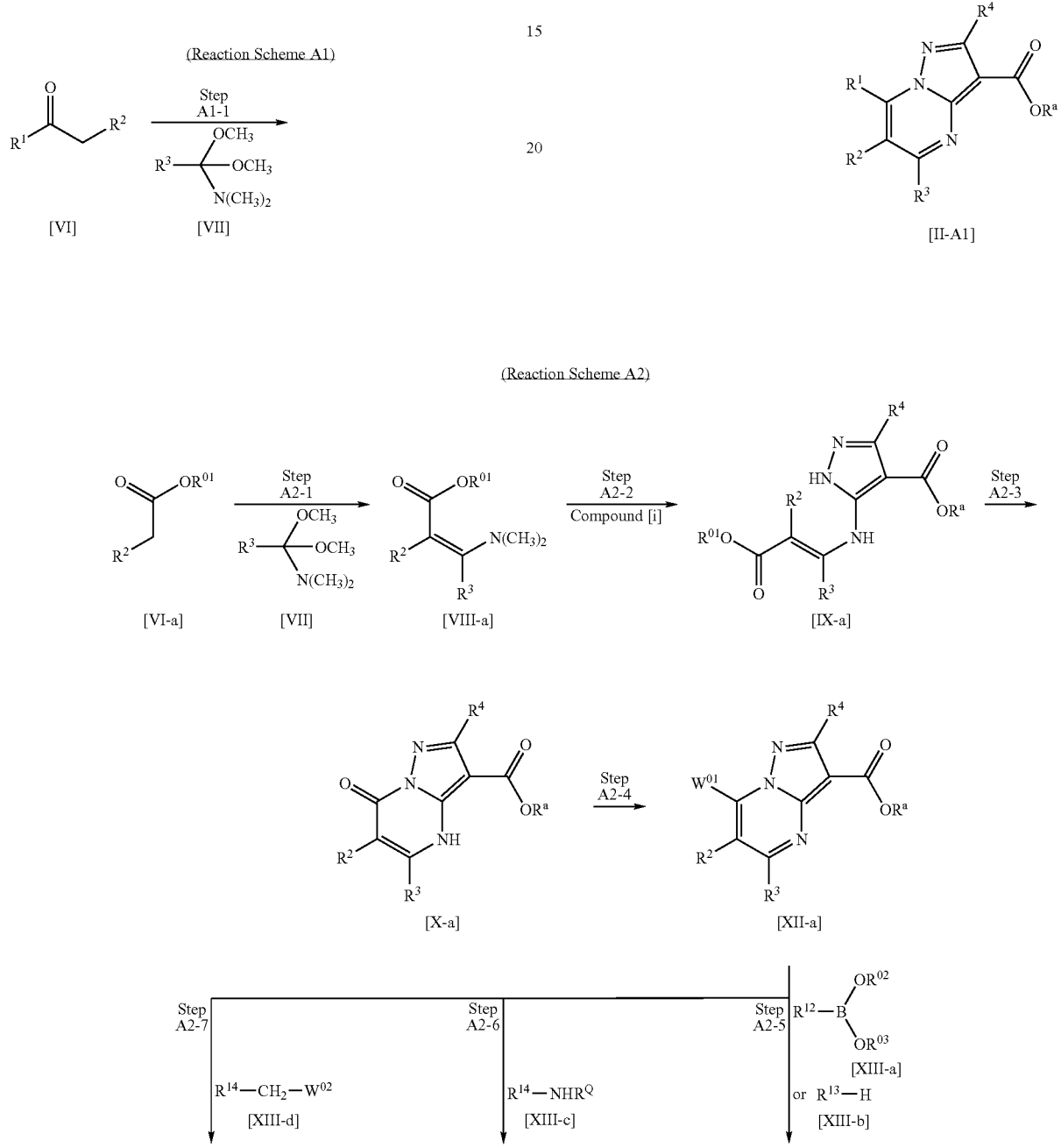

-continued
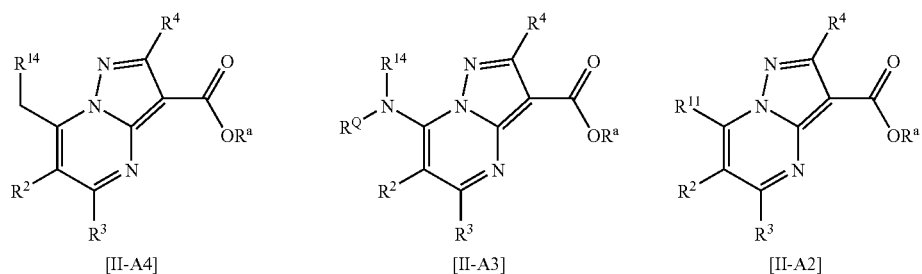
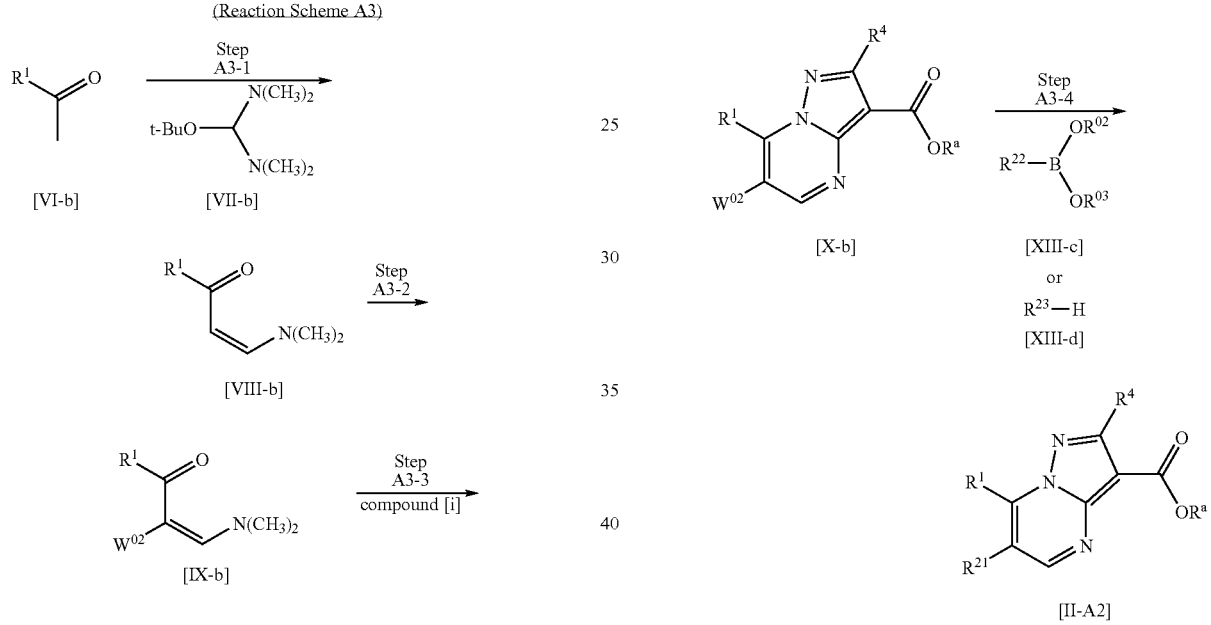
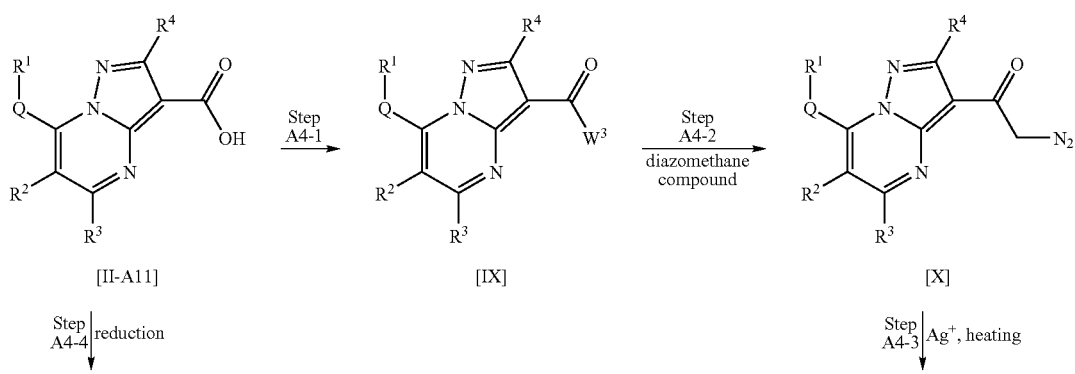

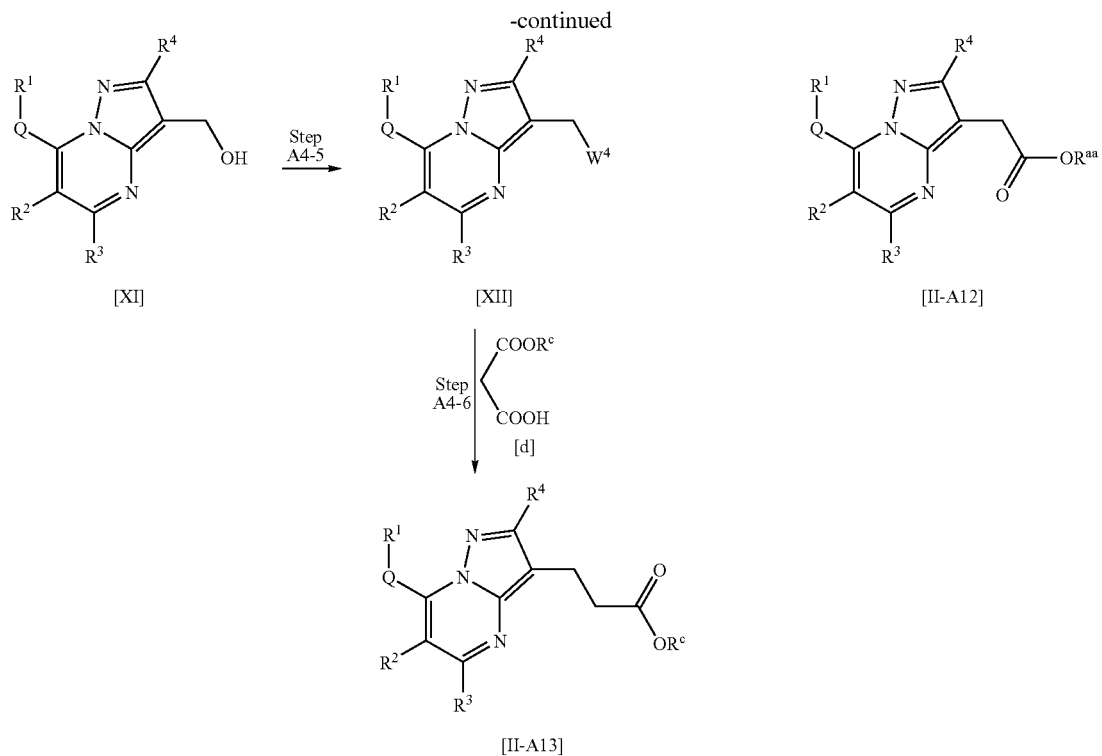

In the above-mentioned reaction scheme A1 to A4, $R^{aa}$ is hydrogen atom or an alkyl group, $R^c$ is an alkyl group, $W^3$ and $W^4$ are a reactive residue, $R^{01}$ is an alkyl group, $R^{11}$ and $R^{21}$ are an optionally substituted aryl group, an optionally substituted heteroaryl group or an optionally substituted nitrogen-containing aliphatic heterocyclic group, $R^{12}$ and $R^{22}$ are an optionally substituted aryl group or an optionally substituted heteroaryl group, $R^{13}$ and $R^{23}$ are an optionally substituted nitrogen-containing aliphatic heterocyclic group, $R^{14}$ is an optionally substituted aryl group or an optionally substituted heteroaryl group, $R^{02}$ and $R^{03}$ are the same or different and a hydrogen atom or an alkyl group or both of them combine each other to form an alkylene group, t-Bu is a tert-butyl group, $W^{01}$ and $W^{02}$ are a halogen atom and the other symbols are the same as defined above.

Examples of the aryl group in $R^{11}$, $R^{12}$, $R^{21}$ or $R^{22}$ include a 6- to 10-membered mono- or bicyclic aryl group such as a phenyl group or a naphthyl group. Among them, phenyl group is preferable.

Examples of the heteroaryl group in $R^{11}$, $R^{12}$, $R^{21}$ or $R^{22}$ include a 5- to 10-membered mono- or bicyclic heteroaryl group having one to three heteroatom(s) selected from oxygen atom, sulfur atom and nitrogen atom. Among them, a furyl group, a thienyl group or a pyridyl group is preferable.

Examples of the nitrogen-containing aliphatic heterocyclic group in $R^{11}$, $R^{12}R^{21}$ or $R^{22}$ include a 5- to 10-membered mono- or bicyclic aliphatic heterocyclic group further having one or two heteroatom(s) selected from oxygen atom, sulfur atom and nitrogen atom. Among them, a furyl group, a 1-pyrrolidinyl group, 1-piperidyl group, a morpholino group or a thiomorpholino group is preferable.

Each of the aryl group, heteroaryl group or nitrogen-containing aliphatic heterocyclic group in $R^{11}$, $R^{12}$, $R^{21}$ or $R^{22}$ may be substituted by one to three group(s) selected from a halogen atom, a cyano group, an alkyl group optionally substituted by one to three halogen atom(s), an alkyloxy group optionally substituted by one to three halogen atom(s) and an alkylsulfonyl group.

The alkylene group formed by combining $R^{02}$ with $R^{03}$ may be a straight or branched chain $C_{2-6}$ alkylene group such as ethylene group, trimethylene group or 1,1,2,2-tetramethylethylene group. Example of the substituent of said alkylene group include an alkyl group such as methyl group.

Each reaction described in the above-mentioned scheme A1 to A4 can be carried out, for example, in accordance with the manner as illustrated bellow.

Step A1-1:

The reaction of the compound [VI] with the compound [VII] can be carried out in an appropriate solvent under heating. Examples of the solvent include any solvent which does not disturb the reaction, such as dimethylformamide, dimethylacetamide, dioxane, 1,2-dichloroethane, toluene, xylene and the like. The compound [VII] can be used in an amount of 1.0 to 10 moles, preferably 1.0 to 3.0 moles per one mole of the compound [VI]. The reaction can be carried out at 50 to 200° C., preferably 80 to 150° C.

Step A1-2:

The reaction of the compound [VIII] with the compound [i] can be conducted in an appropriate solvent in the presence or absence of a base. Examples of the base include piperidine, morpholine, N-methylpiperazine, diethylamine and the like. Examples of the solvent include any solvent which does not disturb the reaction, such as acetic acid, methanol, ethanol, isopropanol, ethyleneglycol and the like. The compound [i] can be used in an amount of 0.5 to 2.0 moles, preferably 0.8 to 1.2 moles per one mole of the compound [VIII]. The base can be used in an amount of 0.01 to 2.0 moles, preferably 0.1 to 1.0 moles per one mole of the compound [VIII]. The reaction can be carried out at 50 to 150° C., preferably 70 to 100° C.

Besides, the present reaction can be carried out in a solvent in the presence or absence of an acid. Examples of the acid include hydrobromic acid, hydrochloric acid, acetic acid and the like. Examples of the solvent include any solvent which does not disturb the reaction, such as acetic acid, methanol, ethanol, isopropanol, ethyleneglycol and the like. The compound [i] can be used in an amount of 0.5 to 2.0 moles, preferably 0.8 to 1.2 moles per one mole of the compound [VIII]. The acid can be used in an amount of 0.1 to 3.0 moles, preferably 0.3 to 1.0 moles per one mole of the compound [VIII]. The reaction can be carried out at 0 to 150° C., preferably 60 to 100° C.

Step A2-1:

The reaction of the compound [VI-a] with the compound [VII] can be carried out in the same manner as described in Step A1-1.

Step A2-2:

The reaction of compound [VIII-a] with compound [i] can be carried out in the same manner as described in Step A1-2. Besides, the compound [X-a] can be obtained without conducting the next step A2-3, when the present reaction is conducted in the presence of acetic acid.

Step A2-3:

The intramolecular cyclization of the compound [IX-a] can be carried out in a solvent in the presence of a base. Examples of the solvent include any solvent which does not disturb the reaction, such as ethanol, acetonitrile, chloroform, tetrahydrofuran, dioxane, toluene, N,N-dimethylformamide and the like. Examples of the base include sodium carbonate, cesium carbonate, triethylamine, diisopropylethylamine, dimethylaminopyridine and the like. The base can be used in an amount of 0.1 to 10.0 moles, preferably 1.2 to 3.0 moles per one mole of the compound [IX-a]. The reaction can be carried out at 30 to 150° C., preferably 60 to 100° C.

Step A2-4:

The conversion of the compound [X-a] to the compound [XII-a] can be carried out in a solvent in the presence of a halogenating agent and in the presence or absence of a base. Examples of the solvent include any solvent which does not disturb the reaction, such as acetonitrile, chloroform, tetrahydrofuran, dioxane, toluene, N,N-dimethylformamide and the like. Examples of the halogenating agent include phosphorus oxychloride, thionyl chloride, phosphorus pentachloride, oxalyl chloride and the like. Examples of the base include N,N-dimethylaniline, diisopropylethylamine, N-methylmorpholine and the like. The halogenating agent can be used in an amount of 1.1 to 5.0 moles, preferably 1.2 to 1.5 moles per one mole of the compound [X-a]. The base can be used in an amount of 1.2 to 10.0 moles, preferably 1.5 to 2.0 moles per one mole of the compound [X-a]. The reaction can be carried out at 50 to 200° C., preferably 80 to 150° C.

Step A2-5:

(1) The reaction of the compound [XII-a] with the boronate compound [XIII-a] can be carried out in a solvent in the presence of a catalyst and a base. Examples of the boronate compound [XIII-a] include a compound in which $R^{02}$ and $R^{03}$ are a hydrogen atom or an alkyl group such as methyl group, ethyl group, isopropyl group and the like, or both $R^{02}$ and $R^{03}$ combine each other to form an alkylene group such as ethylene group, propylene group, 1,1,2,2-tetramethylethylene group and the like. Among them, a preferable example includes a compound [XIII-a] in which $R^{02}$ and $R^{03}$ are hydrogen atom or a corresponding boroxin compound of the formula: $[R^{12}—BO]_3$. Examples of the solvent include any solvent which does not disturb the reaction, such as dioxane, toluene, dimethoxyethane, ethanol, N,N-dimethylformamide, tetrahydrofuran, water and the like. Examples of the catalyst include a palladium catalyst such as tetrakis(triphenylphosphine)palladium (0), palladium acetate (II), bis (dibenzylidene-acetone)palladium (0), bis(triphenylphosphine)palladium (II) dichloride, bis(tri-o-tolyl-phosphine) palladium (II) dichloride, bis(tricyclohexylphosphine) palladium (II) dichloride or [1,1'-bis(diphenylphosphino) ferrocene]palladium (II) dichloride, a nickel catalyst such as 1,3-bis(diphenylphosphino)propane nickel (II) dichloride or bis(triphenylphosphine)nickel (II) dichloride and the like. Examples of the base include potassium phosphate, sodium carbonate, cesium carbonate, sodium hydrogencarbonate, potassium fluoride, triethylamine, lithium chloride and the like. The compound [XIII-a] can be used in an amount of 1.0 to 5.0 moles, preferably 1.1 to 2.0 moles per one mole of the compound [XII-a]. The catalyst can be used in an amount of 0.001 to 0.5 moles, preferably 0.01 to 0.05 moles per one mole of the compound [XII-a]. The base can be used in an amount of 1.0 to 10.0 moles, preferably 2.0 to 5.0 moles per one mole of the compound [XII-a]. The reaction can be carried out at 20 to 150° C., preferably 60 to 120° C.

(2) The reaction of the compound [XII-a] with the nitrogen-containing heterocyclic compound [XIII-b] can be carried out in a solvent in the presence of a base. Examples of the solvent include any solvent which does not disturb the reaction, such as N,N-dimethylformamide, toluene, dioxane, tetrahydrofuran and the like. Examples of the base include potassium carbonate, sodium carbonate, cesium carbonate, sodium hydrogencarbonate, potassium fluoride, triethylamine, diisopropylethylamine, dimethylaminopyridine and the like. The compound [XIII-b] can be used in an amount of 0.8 to 5.0 moles, preferably 1.0 to 1.5 moles per one mole of the compound [XII-a]. The base can be used in an amount of 1.0 to 10.0 moles, preferably 2.0 to 5.0 moles per one mole of the compound [XII-a]. The reaction can be carried out at 80 to 200° C., preferably 120 to 180° C.

Step A2-6:

The reaction of the compound [XII-a] and the compound [XIII-c] can be carried out in a solvent in the presence of a base. Examples of the solvent include any solvent which does not disturb the reaction, such as N,N-dimethylformamide, dimethylsulfoxide, dimethoxyethane, tetrahydrofuran and the like. Examples of the base include sodium hydride, potassium hydride, sodium ethoxide, potassium tert-butoxide and the like. The compound [XIII-c] can be used in an amount of 0.5 to 5.0 moles, preferably 1.0 to 3.0 moles per one mole of the compound [XII-a]. The base can be used in an amount of 0.5 to 10.0 moles, preferably 1.2 to 6.0 moles per one mole of the compound [XII-a]. The reaction can be carried out at 40 to 200° C., preferably 60 to 120° C.

Step A2-7:

The reaction of the compound [XII-a] and the compound [XIII-d] can be carried out in a solvent in the presence of a catalyst and zinc. Examples of the solvent include any solvent which does not disturb the reaction, such as dimethoxyethane, tetrahydrofuran, N,N-dimethylformamide and the like. Examples of the catalyst include a palladium catalyst such as bis(triphenylphosphine)palladium (II) dichloride, tetrakis(triphenylphosphine)palladium (0), palladium acetate (II), bis(dibenzylidene-acetone)palladium (0), bis(tri-o-tolylphosphine)palladium (II) dichloride, bis(tricyclohexylphosphine)palladium (II) dichloride or [1,1'-bis(diphenylphosphino)-ferrocene]palladium (II) dichloride and the like. The compound [XIII-d] can be used in an amount of 0.5 to 5.0 moles, preferably 1.0 to 3.0 moles per one mole of the compound [XII-a]. The catalyst can be used in an amount of 0.001 to 1.0 moles, preferably 0.01 to 0.3 moles per one mole of the compound [XII-a]. Zinc can be used in an amount of 1.0 to 5.0 moles, preferably 1.5 to 3.0 moles per one mole of the compound [XII-a]. The reaction can be carried out at 40 to 200° C., preferably 60 to 120° C.

Step A3-1:

The reaction of the compound [VI-b] with the compound [VII-b] can be carried out in a solvent or without any solvent. Examples of the solvent include any solvent which does not disturb the reaction, such as dimethylformamide, toluene, dioxane, tetrahydrofuran, dimethoxyethane and the like. The compound [VII-b] can be used in an amount of 0.5 to 5.0 moles, preferably 0.9 to 1.5 moles per one mole of the compound [VI-b]. The reaction can be carried out at 0 to 150° C., preferably 50 to 80° C.

Step A3-2:

The halogenation of the compound [VIII-b] can be carried out in a solvent in the presence of a halogenating agent and in the presence or absence of a base. Examples of the solvent include any solvent which does not disturb the reaction, such as methylene chloride, carbon tetrachloride, chloroform, acetic acid, tetrahydrofuran and the like. Examples of the halogenating agent include bromine, N-bromosuccinimide, N-chlorosuccinimide and the like. Examples of the base include triethylamine, diisopropylethylamine, potassium carbonate, sodium carbonate and the like. The halogenating agent can be used in an amount of 0.5 to 10.0 moles, preferably 1.0 to 3.0 moles per one mole of the compound [VIII-b]. The reaction can be carried out at −40 to 100° C., preferably −5 to 20° C.

Step A3-3:

The reaction of the compound [IX-b] with the compound [i] can be carried out in the same manner as described in Step A1-2.

Step A3-4:

The reaction of the compound [X-b] with the boronate compound [XIII-c] or the nitrogen-containing heterocyclic compound [XIII-d] can be carried out in the same manner as described in Step A2-5 (1) or (2), respectively.

Step A4-1:

The conversion of the compound [II-A11] to a corresponding reactive derivative (compound [IX]) can be carried out in a conventional manner. Examples of such reactive derivative include a corresponding acid halide (a compound [IX] in which $W^3$ is a halogen atom) or a corresponding mixed acid anhydride (a compound [IX] in which $W^3$ is an alkyloxycarbonyloxy group and the like). The corresponding acid halide can be prepared by, for example, reacting the compound [II-A11] with a halogenating agent (e.g., thionyl chloride, phosphorus oxychloride, phosphorus pentachloride, oxalyl chloride and the like) in or without a solvent in the presence or absence of a catalytic amount of dimethylformamide. Examples of the solvent include any solvent which does not disturb the reaction, such as methylene chloride, chloroform, tetrahydrofuran, benzene, toluene and the like. The present reaction can be conducted at −20 to 150° C., preferably 0 to 120° C. Besides, the corresponding mixed acid anhydride can be prepared by, for example, reacting the compound [II-A11] with an alky chloroformate (e.g., ethyl chloroformate and the like) in a solvent in the presence of a base (e.g., triethylamine, diisopropylethylamine and the like). Examples of the solvent include any solvent which does not disturb the reaction, such as methylene chloride, chloroform, tetrahydrofuran, benzene, toluene and the like. The present reaction can be conducted at −60 to 1001° C., preferably −40 to 80° C.

Step A4-2:

The conversion of the compound [IX] to the compound [α] can be carried out in a solvent in the presence of a diazomethane compound (e.g., diazomethane, trimethylsilyl diazomethane and the like). Examples of the solvent include any solvent which does not disturb the reaction, such as diethylether, dioxane, benzene, toluene and the like. The diazomethane compound can be used in an amount of 1.0 to 10 moles, preferably 1.0 to 3.0 moles per one mole of the compound [IX]. The reaction can be carried out at −50 to 80° C., preferably −10 to 50° C.

Step A4-3:

The conversion of the compound [α] to the compound [II-A12] can be carried out in a solvent in the presence or absence of a silver salt under heating. Examples of the solvent include any solvent which does not disturb the reaction, such as water, an alkanol (e.g., methanol, ethanol) and the like. Examples of the silver salt include silver oxide, silver benzoate and the like. The silver salt can be used in an amount of 1.0 to 20 moles, preferably 1.0 to 5.0 moles per one mole of the compound [X]. The reaction can be carried out at 50 to 200° C., preferably 80 to 150° C.

Step A4-4:

The reaction to obtain the compound [XI] by reducing the compound [II-A11] can be carried out in a solvent in the presence of a reducing agent (e.g., lithium aluminum hydride and the like). Examples of the solvent include any solvent which does not disturb the reaction, such as diethylether, tetrahydrofuran and the like. The reducing agent can be used in an amount of 0.25 to 20 moles, preferably 2.0 to 5.0 moles per one mole of the compound [II-A11]. The reaction can be carried out at −50 to 100° C., preferably −10 to 40° C.

Meanwhile, the compound [XI] can be also prepared by reducing a compound [II-A1] in which $R^a$ is an alkyl group. The present reaction can be conducted in a solvent in the presence of a reducing agent such as sodium borohydride and the like. Examples of the solvent include any solvent which does not disturb the reaction, such as a mixture of tetrahydrofuran and methanol and the like. The reducing agent can be used in an amount of 1.0 to 20 moles, preferably 2.0 to 5.0 moles per one mole of the compound [II-A1]. The reaction can be carried out at 30 to 100° C., preferably 50 to 80° C.

Step A4-5:

The conversion of the compound [XI] to a corresponding reactive derivative (compound [XII]) can be carried out in a conventional manner. For example, a compound [XII] in which $W^4$ is a halogen atom or an alkylsulfonyloxy group can be prepared by treating the compound [XI] with a thionyl halide such as thionyl chloride or an alkylsulfonylhalide such as methanesulfonylchloride, respectively.

Step A4-6:

The reaction of the compound [XII] with the compound [d] or a salt thereof can be carried out in a solvent in the presence of a base. Examples of the salt of the compound [d] include a metal salt such as potassium salt. Examples of the solvent include any solvent which does not disturb the reaction, such as diethylether, tetrahydrofuran, benzene, dimethylformamide, dimethylacetamide, methanol, ethanol and the like. Examples of the base include sodium hydride, potassium hydride, sodium methoxide, sodium ethoxide, lithium diisopropylamide, lithium hexamethyl-disilazane and the like. The compound [d] or a salt thereof can be used in an amount of 1.0 to 10.0 moles, preferably 1.5 to 3.0 moles per one mole of the compound [XII]. The base can be used in an amount of 1.0 to 10.0 moles, preferably 1.5 to 3.0 moles per one mole of the compound [XII]. The reaction can be carried out at −20 to 200° C., preferably 20 to 100° C.

A compound [II-A] in which $Q^1$ is an alkylene group having 3 or more carbon atoms can be obtained by, for example, converting an objective compound obtained in the above Step A4-3 (or Step A4-6) to a corresponding carboxylic acid compound by deesterification, if necessary, and then subjecting such carboxylic acid compound to a serial reaction process of Step A4-1, A4-2 and A4-3 (or Step A4-4, A4-5 and A4-6), repeatedly in desired times.

Besides, a compound [II-A] in which $Q^1$ is a group of the formula: —N($R^7$)— can be obtained by, for example, subjecting the compound [II-Ae] or the compound [II-Af] (cf., Reaction Step C1-4 described bellow) to a conventional deesterification reaction.

ii) The compound [II-B] can be prepared, for example, in the manner as described bellow (Reaction Scheme B1) by using a compound [II-Aa] or a corresponding amide compound (e.g., a corresponding dimethylamide, a corresponding N-alkyl-N-alkyloxyamide compound and the like).

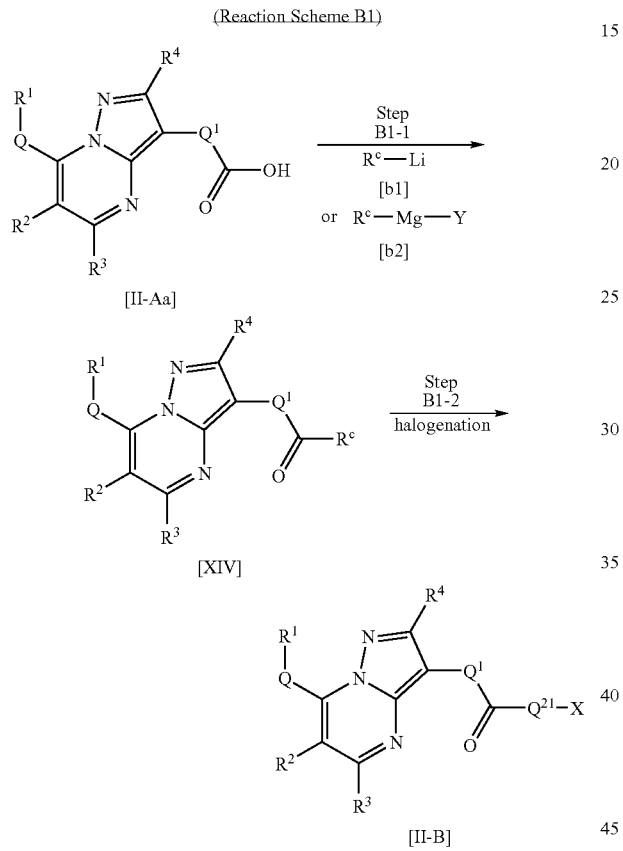

In the above scheme B1, $R^c$ is an alkyl group, Y is a halogen atom and the other symbols are the same as defined above.

Each reaction described in Scheme B1 can be carried out, for example, in accordance with a manner as illustrated bellow.

Step B1-1:
The reaction of the compound [II-Aa] or a corresponding amide compound with the compound [b1] or compound [b2] can be carried out in a solvent. Examples of the solvent include any solvent which does not disturb the reaction, such as diethylether, tetrahydrofuran, dioxane, dimethoxyethane, benzene, toluene and the like. The compound [b1] or compound [b2] can be used in an amount of 1.0 to 3.0 moles, preferably 1.0 to 2.2 moles per one mole of the compound [II-Aa] or a corresponding amide compound. The reaction can be carried out at −78 to 50° C., preferably −40 to 30° C.

Step B1-2:
The halogenation of the compound [XIV] can be carried out in a solvent. Examples of the halogenating agent include bromine, N-bromosuccinimide, bis(N,N-dimethylacetamide)hydrogen dibromobromate and the like. Examples of the solvent include any solvent which does not disturb the reaction, such as diethylether, dichloromethane, 1,2-dichloroethane, chloroform, carbon tetrachloride and the like. The halogenating agent can be used in an amount of 1.0 to 3.0 moles, preferably 1.0 to 2.0 moles per one mole of the compound [XIV]. The reaction can be carried out at −10 to 50° C., preferably 0 to 30° C.

iii) The compound [II-C] can be prepared, for example, by using a compound [II-Aa] in which Q' is a single bond (compound [IIa]) and in a manner as described in the following Reaction Scheme C1.

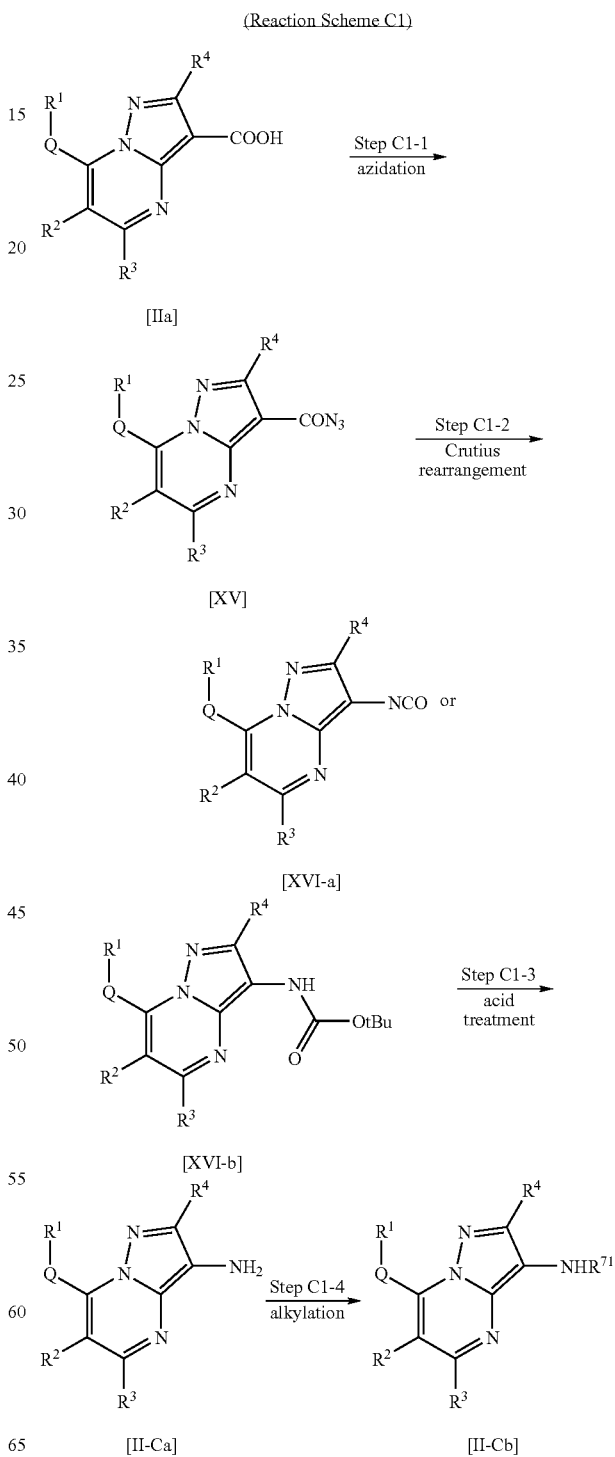

In the above Reaction Scheme, $R^{71}$ is an alkyl group, and tBu is a tert-butyl group and the other symbols are the same as defined above.

Each reaction described in Scheme C1 can be carried out, for example, in accordance with a manner as illustrated below.

Step C1-1:

The reaction of the compound [IIa] with an azidating agent can be carried out in a solvent in the presence or absence of a base. Examples of the solvent include any solvent which does not disturb the reaction, such as acetone, benzene, toluene, tetrahydrofuran, diethylether and the like. Examples of the azidating agent include diphenyl phosphorylazide, sodium azide and the like. Examples of the base include pyridine, triethylamine, diisopropylethylamine, 4-methylmorpholine, 1,8-diazabicyclo-5,4,0]undecene (DBU) and the like. The azidating agent can be used in an amount of 1.1 to 5.0 moles, preferably 1.2 to 1.5 moles per one mole of the compound [IIa]. The base can be used in an amount of 1.2 to 10.0 moles, preferably 1.5 to 3.0 moles per one mole of the compound [IIa]. The reaction can be carried out at −30 to 50° C., preferably −10 to 10° C.

Step C1-2:

The preparation of the compound [XVI-a] by Crutius rearrangement reaction can be carried out in a solvent under heating. Examples of the solvent include any solvent which does not disturb the reaction, such as benzene, toluene, dioxane, chloroform and the like. The reaction can be carried out at 40 to 200° C., preferably 60 to 120° C. Besides, the compound [XVI-b] can be obtained by carrying out the present reaction in tert-buthanol.

Step C1-3:

The treatment of the compound [XVI-a] or [XVI-b] with an acid can be carried out in or without a solvent. Examples of the solvent include water, ethyl acetate, tetrahydrofuran, dioxane, methylene chloride, chloroform, toluene and the like. Examples of the acid include a strong acid such as sulfuric acid, hydrochloric acid, nitric acid, trifluoroacetic acid, hydrobromic acid and the like. The acid can be used in an amount of 1.0 to 50.0 moles, preferably 5.0 to 10.0 moles per one mole of the compound [XVI-a] or [XVI-b]. The reaction can be carried out at −20 to 200° C., preferably 20 to 120° C.

Step C1-4:

The alkylation of the compound [1-Ca] can be carried out in a solvent by, for example, 1) in the presence of a base (e.g., sodium hydride, potassium carbonate, pyridine, triethylamine, diisopropylethylamine, 4-methylmorpholine, 1,8-diazabicyclo-[5,4,0]undecene and the like) and an alkylhalide of the formula [XVIII]:

  [XVIII]

wherein $R^{72}$ is an alkyl group and $X^4$ is a halogen atom; or 2) in the presence of a reducing agent (e.g., lithium aluminum hydride, sodium borohydride, sodium cyanoborohydride, sodium triacetoxyborohydride and the like), an acid (e.g., acetic acid, formic acid and the like) and an aldehyde compound [XIX]:

  [XIX]

wherein $R^{73}$ is an alkyl group; or 3) in the presence of an activating agent (e.g., diethyl azodicarboxylate and the like), a tri-substituted phosphine (e.g., triphenylphosphine, tributylphosphine and the like) and an alkanol compound of the formula [XX]:

  [XX]

wherein $R^{74}$ is an alkyl group. Examples of the solvent include methylene chloride, chloroform, dimethylformamide, dimethylacetamide, dimethylsulfoxide, tetrahydrofuran, dioxane, toluene, benzene, 1,2-dichloroethane, 1-methylpyrrolidinone, 1,2-dimethoxyethane and the like. The reaction can be carried out at −20 to 100° C., preferably 0 to 40° C.

Meanwhile, if required, an appropriate protecting group (e.g., an alkyloxycarbonyl group such tert-butoxycarbonyl group, an arylalkyloxycarbonyl group such as benzyloxycarbonyl group and the like) may be introduced to 3-amino group in the compound [II-Ca] prior to the alkylation thereof. Such protecting group can be introduced or removed by a conventional manner depending on the kind of said protecting group.

The compound [II-Cb] can be also prepared by conducting the above Crutius rearrangement reaction in an alkanol of the formula [e]:

  [e]

wherein $R^e$ is tert-butyl group or benzyl group to obtain a compound of the following formula [II-Ae]:

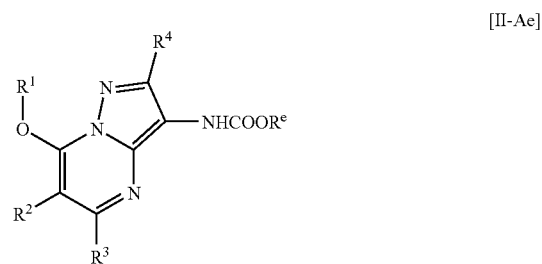

and reacting such compound [II-Ae] with the alkylhalide compound [XVIII] mentioned above or the alkanol compound [XX] to give a compound [II-Af]:

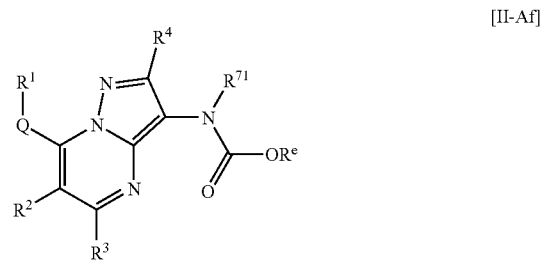

wherein the symbols are the same as defined above, and then removing the acyl group represented by the group of the formula: $R^eOCO$—. The removal of said acyl group can be conducted by (1) treating the product [II-Af] with an acid such as hydrochloric acid, trifluoroacetic acid, hydrobromic acid and the like; or (2) heating such product at about 150° C.; or (3) subjecting such product to catalytic hydrogenation.

iv) The compound [II-D] can be prepared by reacting the compound [II-Aa] with a hydrazine compound of the following formula [c]:

  [c]

wherein Z is an acyl group or a salt thereof in accordance with the same manner as described in Method A mentioned above, and then removing the acyl group (Z) from the reaction product in a conventional manner.

The intermediate compound [II-A$^{01}$], [II-B$^{01}$] or [II-C$^{01}$] can be prepared by, for example, treating the corresponding starting compound having a desired substituent at 2-position of the pyrazolo[1,5-a]pyrimidine moiety in the same manner as illustrated in Reaction scheme A1, B1 or C1.

Furthermore, the compound [II-D$^{01}$] can be prepared by, for example, reacting a compound of the following formula [II-Da]:

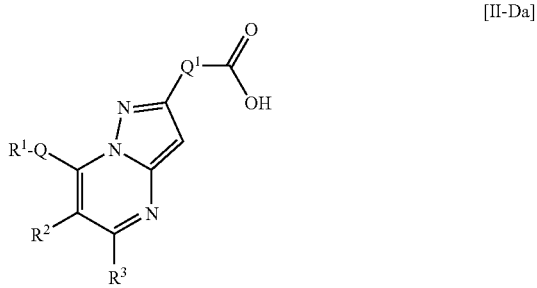

[II-Da]

wherein the symbols are the same as defined above with a hydrazine compound [c] in the same manner as described in Method A, and then removing the acyl group (Z) by a conventional method.

Among the above-mentioned intermediates, each of the compound [i], the compound [VI], the compound [VI-a], the compound [VI-b], the compound [VII], the compound [XIII-a], the compound [XIII-b], the compound [XIII-c] and the compound [XIII-d] is a known compound or a compound obtainable from a known compound by using a conventional process in synthetic chemistry.

Throughout the present description and claims, the "halogen atom" means fluorine, chlorine, iodine or bromine atom. The "alkyl group" means a straight or branched chain alkyl group having 1 to 6 carbon atoms, preferably 1 to 4 carbon atoms. The "cycloalkyl group" means a cycloalkyl group having 3 to 8 carbon atoms, preferably 5 to 7 carbon atoms. The "alkylene group" means a straight or branched chain alkylene group having 1 to 6 carbon atoms, preferably 1 to 4 carbon atoms.

EXAMPLES

The compounds of the present invention are illustrated in more detail by the following Examples but should not be construed to be limited thereto.

Example 1

To a suspension of 3-carboxyl-6-(2-chlorophenyl)-7-(4-chlorophenyl)-pyrazolo[1,5-a]pyrimidine (200 mg, compound obtained in Reference Example 1) in toluene (1.5 mL) was added thionyl chloride (114 µL), and the mixture was stirred at room temperature for 2 hours. The reaction mixture was concentrated in vacuo and the resultant crude product was dissolved in methylene chloride (1.5 mL). To a solution was added triethylamine (217 µL) and 1-aminopiperidine (56 µL) and the mixture was stirred at room temperature for 10 minutes. The reaction mixture was concentrated in vacuo and the resultant crude product was purified by column chromatography on silica gel (solvent: chloroform/methanol=100/0 to 19/5 and hexane/ethyl acetate=67/3 to 2/3) to obtain 6-(2-chlorophenyl)-7-(4-chlorophenyl)-3-(N-piperidinocarbamoyl)-pyrazolo[1,5-a]pyrimidine (162 mg; yield: 67%) as a powder.
MS (APCI)m/z; 466/468[M+H]$^+$

Example 2

To a suspension of the compound obtained in Reference Example 1 (200 mg,) in toluene (2 mL) was added oxalyl chloride (136 µL), and the mixture was stirred at 60° C. for 1 hours. The reaction mixture was concentrated in vacuo and the resultant crude product was dissolved in methylene chloride (2 mL). To a solution was added triethylamine (217 µL) and 1-methyl-1-phenylhydrazine (61 µL) and the mixture was stirred at room temperature for 2 hours. To the reaction mixture was added water and methylene chloride and the organic layer was washed with saturated brine, dried over magnesium sulfate and filtered. The filtrate was concentrated in vacuo and the resultant crude product was purified by column chromatography on silica gel (solvent: hexane/ethyl acetate=4/1 to 7/3) to obtain 6-(2-chlorophenyl)-7-(4-chlorophenyl)-3-[(N'-methyl-N'-phenylhydrazino)carbonyl] pyrazolo[1,5-a]pyrimidine (204 mg; yield: 80%) as a powder.
MS (APCI)m/z; 488/490[M+H]$^+$

Example 3

To a solution of the compound obtained in Reference Example 1 (57.6 mg) and 1-aminopyrrolidine HCl (24.5 mg) in chloroform (1.0 mL containing amylene) was added 1-hydroxybenzotriazole monohydrate (0.23 mL, 0.5M chloroform solution containing amylene), 1-(3-dimethylaminopropyl)-3-ethylcarbodiimide HCl (0.23 mL, 0.5M N,N-dimethylformamide solution) and triethylamine (63 µL) and the mixture was stirred at room temperature overnight. To the reaction mixture was added an aqueous saturated sodium hydrogencarbonate solution (2 mL), water (2 mL) and chloroform (5 mL) and the mixture was stirred vigorously for 15 minutes. After separating the organic layer, the aqueous layer was extracted with chloroform (3 mL). The combined organic layer was washed successively with an aqueous saturated sodium hydrogencarbonate solution (3 mL) and saturated brine (3 mL) and concentrated in vacuo. The resultant crude product was purified by liquid chromatograph-mass spectrometer (LCMS) (column; XTerra MS C18, solvent; 10 mM ammonium carbonate/methanol=40/60 to 10/90). The eluted fraction was concentrated and the residue was dissolved in tert-buthanol and lyophilized to give 6-(2-chlorophenyl)-7-(4-chlorophenyl)-3-(N-pyrrolidinocarbamoyl)pyrazolo[1,5-a]pyrimidine (47.2 mg; yield: 70%) as a powder.
MS (APCI)m/z; 452 [M+H]$^+$

Examples 4 to 27

The corresponding starting materials were treated in the same manner as described in either one of Examples 1 to 3 to obtain the compounds as shown in the following Table 1.

TABLE 1

(No. 1)

| Ex. Nos. | —N(R$^5$)(R$^6$) | Physicochemical properties etc. |
|---|---|---|
| 4 | HN—cyclopentyl | powder MS(ESI): 417[M + H]$^+$ |

TABLE 1-continued

| Ex. Nos. | —N(R⁵)(R⁶) | Physicochemical properties etc. |
|---|---|---|
| 5 | 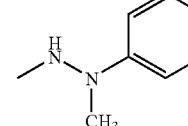 | powder MS(ESI): 504[M + H]⁺ |
| 6 | 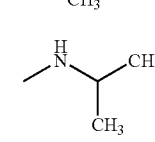 | powder MS(ESI): 454[M + H]⁺ |
| 7 | 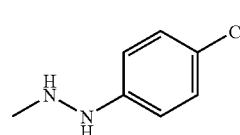 | powder MS(ESI): 391[M + H]⁺ |
| 8 | 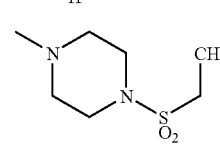 | powder MS(APCI): 465/467[M + H]⁺ |
| 9 | 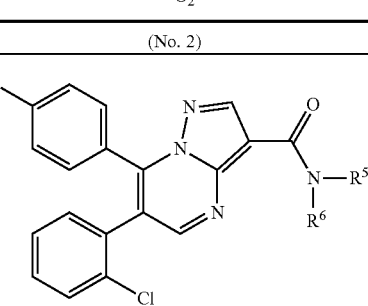 | powder MS(APCI): 510/512[M + H]⁺ |

(No. 2)

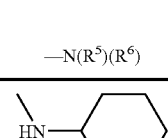

| Ex. Nos. | —N(R⁵)(R⁶) | Physicochemical properties etc. |
|---|---|---|
| 10 | 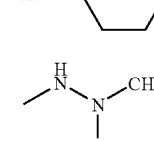 | powder MS(ESI): 465.07[M]⁺ |
| 11 | 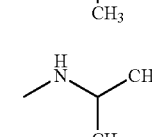 | powder MS(ESI): 426.07[M]⁺ |
| 12 | 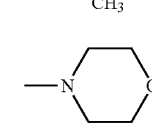 | powder MS(ESI): 425.06[M]⁺ |
| 13 | 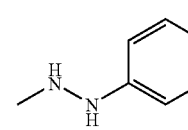 | powder MS(ESI): 453.09[M]⁺ |
| 14 | 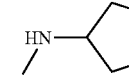 | powder MS(ESI): 474.01[M]⁺ |
| 15 | 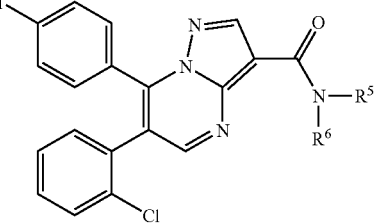 | powder MS(ESI): 451.07[M]⁺ |

(No. 3)

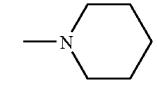

| Ex. Nos. | —N(R⁵)(R⁶) | Physicochemical properties etc. |
|---|---|---|
| 16 | 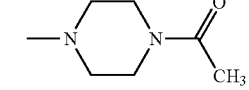 | powder MS(ESI): 451.08[M]⁺ |
| 17 | 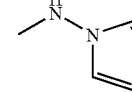 | powder MS(ESI): 494.11[M]⁺ |
| 18 | 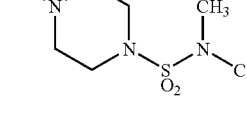 | powder MS(ESI): 477.99[M]⁺ |
| 19 | 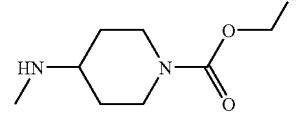 | powder MS(ESI): 559.07[M]⁺ |
| 20 | 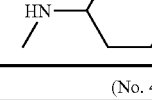 | powder MS(ESI): 538.09[M]⁺ |
| 21 | 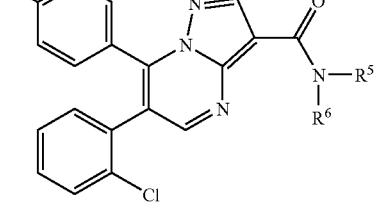 | powder MS(ESI): 457.08[M]⁺ |

(No. 4)

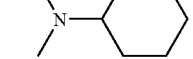

| Ex. Nos. | —N(R⁵)(R⁶) | Physicochemical properties etc. |
|---|---|---|
| 22 | H₃C–N(–)cyclohexyl | powder MS(ESI): 479.12[M]⁺ |

TABLE 1-continued

| | | |
|---|---|---|
| 23 | [structure: methylhydrazino-phenyl-CN] | powder MS(ESI): 499.02[M]+ |
| 24 | [structure: methylhydrazino-cyclohexyl] | powder MS(ESI): 480.06[M]+ |
| 25 | [structure: HN-N-piperazine-N-cyclopentyl] | powder MS(ESI): 535.17[M]+ |
| 26 | [structure: HN-N-morpholine] | powder MS(APCI): 468/470[M + H]+ |
| 27 | [structure: HN-tetrahydrothiophene-SO₂] | powder MS(APCI): 501/503[M + H]+ |

Example 28

To a solution of 3-carboxy-6-(2-chlorophenyl)-7-(4-chlorophenyl)-pyrazolo[1,5-a]pyrimidine (compound obtained in Reference Example 1(4), 165 mg) in chloroform (1.0 mL containing amylene) was added the compound obtained in Reference Example 13(2), water-soluble carbodiimide HCl (123 mg), 1-hydroxybenzotriazole monohydrate (97 mg), and triethylamine (178 µL) and the mixture was stirred at room temperature overnight. To the reaction mixture was added an aqueous saturated sodium hydrogencarbonate solution (2 mL) and the mixture was stirred and extracted with chloroform. The extract was concentrated in vacuo and the resultant crude product was purified by a column chromatography on silica gel (solvent; hexane/ethyl acetate=90/10 to 70/30) to give 6-(2-chlorophenyl)-7-(4-chlorophenyl)-3-[N-(4-tetrahydrothiopyranyl)carbamoyl]pyrazolo[1,5-a]pyrimidine (50 mg; yield: 24%) as a pale yellow powder.

MS (APCI)m/z; 483/485 [M+H]+

Example 29

To a solution of the compound obtained in Example 28 in methylene chloride (1.0 mL) was added methanesulfonic acid (20 µL) and 3-chloroperbenzoic acid (57 mg) and the mixture was stirred at room temperature for 1 hour. To the reaction mixture was added an aqueous saturated sodium hydrogencarbonate solution and the mixture was stirred. The organic layer was extracted and the extract was concentrated in vacuo. The resultant crude product was purified by a column chromatography on silica gel (solvent; chloroform/ethyl acetate=100/0 to 70/30) to give 6-(2-chlorophenyl)-7-(4-chlorophenyl)-3-[N-[4-(1,1-dioxo)tetrahydrothiopyranyl]carbamoyl]pyrazolo[1,5-a]pyrimidine (37.3 mg; yield: 73%) as a pale yellow powder.

MS (APCI)m/z; 515/517 [M+H]+

Example 30

To a solution of the compound obtained in Reference Example 9(2) (50 mL) in methanol (1 mL) was added 36% formaldehyde solution (118 µL), sodium triacetoxyborohydride (75 mg) and triethylamine (39 µL) and the mixture was stirred at room temperature for 3 hour. The reaction mixture was diluted with chloroform and thereto was added an aqueous sodium hydrogencarbonate solution. The mixture was extracted with chloroform and the extract was concentrated in vacuo. The resultant crude product was purified by a column chromatography on silica gel (solvent; chloroform/ethyl acetate=100/0 to 70/30), dissolved in tert-butanol and lyophilized to give 3-dimethylamino-6-(2-chlorophenyl)-7-(4-chlorophenyl)pyrazolo[1,5-a]pyrimidine 13.5 mg; yield: 26%) as a red powder.

MS (APCI)m/z; 383/385 [M+H]+

Example 31

(1) The corresponding material (200 mg) was treated in the same manner as described in Example 3 to give 6-(2-bromophenyl)-7-(4-chlorophenyl)-3-[[N'-methyl-N'-(2-pyridyl)hydrazino]carbonyl]pyrazolo[1,5-a]pyrimidine (249 mg) as a yellow powder.

MS (APCI)m/z; 533/535 [M+H]+

(2) To a solution of the compound obtained in the above step (1) (80 mg) in dimethylformamide (1 mL) was added zinc cyanide (20 mg) and tetrakis-(triphenylphosphine)palladium (0) (17 mg) and the mixture was stirred under nitrogen gas atmosphere at 110° C. for 19 hours. The reaction mixture was cooled to room temperature and thereto was added water and ethyl acetate and the mixture was stirred. The organic layer was extracted and the extract was concentrated in vacuo. The resultant crude product was purified by a column chromatography on silica gel (solvent; hexane/ethyl acetate=50/50 to 25/75), dissolved in tert-butanol and lyophilized to give 7-(4-chlorophenyl)-6-(2-cyanophenyl)-3-[N'-methyl-N'-(2-pyridyl)hydrazino]carbonyl-pyrazolo[1,5-a]pyrimidine (42 mg; yield: 58%) as a colorless solid.

MS (APCI)m/z; 480/482 [M+H]+

Example 32

To a solution of the compound obtained in Reference Example 6 (1.0 g) in chloroform (20 mL) was added cyclopentylamine (260 mg), water-soluble carbodiimide HCl salt (620 mg) and 1-hydroxybenzotriazole (540 mg) and the mixture was stirred at room temperature overnight. To the reaction mixture was added an aqueous saturated sodium hydrogencarbonate solution and chloroform and the mixture was stirred. The organic layer was extracted and the extract was concentrated in vacuo. The resultant crude product was purified by a column chromatography on silica gel (solvent; hexane/ethyl acetate=82/18 to 67/33) to give 6-(2-chlorophenyl)-7-(4-chloro-phenyl)-3-(N-cyclopentylcarbamoyl)-2-methylthiopyrazolo[1,5-a]pyrimidine (940 mg; yield: 81%) as a yellow solid.

MS (APCI)m/z; 497/499 [M+H]+

Example 33

To a solution of the compound obtained in Example 32 (940 mg) in methylene chloride (40 mL) was added 3-chloroperbenzoic acid (1.09 g) under ice-cooling and the mixture was stirred at room temperature for 3 hours. To the reaction mixture was added an aqueous sodium thiosulfate solution and the mixture was stirred and extracted with chloroform. The extract was concentrated in vacuo and the resultant crude product was purified by a column chromatography on NH-silica gel (Chromatorex NH silica gel/Fuji Silicia Chem., solvent; hexane/ethyl acetate=50/50 to 0/100) to give 6-(2-chlorophenyl)-7-(4-chlorophenyl)-3-(N-cyclopentylcarbamoyl)-2-methylsulfonyl-pyrazolo[1,5-a]pyrimidine (1.0 g; yield: 100%) as a colorless solid.

MS (APCI)m/z; 529/531 [M+H]$^+$

Example 34

To a solution of the compound obtained in Example 33 (100 mg) in tetrahydrofuran/methanol (3 mL/3 mL) was added sodium methoxide (102 mg) and the mixture was stirred at 50° C. overnight. After cooling to room temperature, to the reaction mixture was added water and ethyl acetate and the mixture was stirred. The organic layer was dried over magnesium sulfate and filtered. The filtrate was concentrated in vacuo and the resultant crude product was purified by a column chromatography on silica gel (solvent; hexane/ethyl acetate=80/20 to 60/40) to give 6-(2-chlorophenyl)-7-(4-chlorophenyl)-3-(N-cyclopentylcarbamoyl)-2-methoxy-pyrazolo[1,5-a]pyrimidine (57.2 mg; yield: 63%) as a pale yellow powder.

MS (APCI)m/z; 481/483 [M+H]$^+$

Example 35

To a solution of the compound obtained in Example 33 (300 mg) in dimethylformamide (7 mL) was added sodium cyanide (167 mg) and the mixture was stirred at 50° C. overnight. After cooling to room temperature, to the reaction mixture was added ethyl acetate and a sodium hydrogencarbonate solution and the mixture was stirred. After separating the organic layer, the aqueous layer was extracted with ethyl acetate. The combined organic layer was dried over magnesium sulfate and filtered. The filtrate was concentrated in vacuo and the resultant crude product was purified by a column chromatography on silica gel (solvent; hexane/ethyl acetate=90/10 to 70/30) to give 6-(2-chlorophenyl)-7-(4-chlorophenyl)-5-cyano-2-methylsulfonyl-3-(N-cyclopentylcarbamoyl)pyrazolo[1,5-a]pyrimidine (compound (a), 138 mg; yield: 44%) and 6-(2-chlorophenyl)-7-(4-chlorophenyl)-2,5-dicyano-3-(N-cyclopentylcarbamoyl)-pyrazolo[1,5-a]pyrimidine (compound (b), 18.3 mg; yield: 6%) as a pale yellow solid, respectively.

Compound (a): MS (APCI)m/z; 554/556 [M+H]$^+$
Compound (b): MS (APCI)m/z; 501/503 [M+H]$^+$ Example 36

To a solution of the compound (a) obtained in Example 35 (50 mg) in methanol/tetrahydrofuran (3 mL/3 mL) was added sodium methoxide (49 mg) and the mixture was stirred at room temperature overnight. To the reaction mixture was added ethyl acetate and a saturated brine and the organic layer was separated. The organic layer was dried over magnesium sulfate and filtered. The filtrate was concentrated in vacuo and the resultant crude product was purified by a column chromatography on silica gel (solvent; hexane/ethyl acetate=80/20 to 30/70) to give 6-(2-chlorophenyl)-7-(4-chlorophenyl)-3-(N-cyclopentylcarbamoyl)-5-methoxy-2-methylsulfonylpyrazolo[1,5-a]pyrimidine (50.5 mg; yield: 100%) as a colorless solid.

MS (APCI)m/z; 559/561 [M+H]$^+$

Example 37

To a solution of the compound obtained in Example 36 (24 mg) in methanol/tetrahydrofuran (2 mL/1 mL) was added sodium methoxide (23 mg) and the mixture was stirred at 100° C. for 2 hours in a microwave reactor. After cooling to room temperature, to the reaction mixture was added chloroform and water and the organic layer was separated and concentrated in vacuo and the resultant crude product was purified by a column chromatography on NH-silica gel (Chromatorex NH-silica gel/Fuji Silicia Chem., solvent; hexane/ethyl acetate=65/35 to 30/70) to give 6-(2-chlorophenyl)-7-(4-chlorophenyl)-3-(N-cyclopentylcarbamoyl)-2,5-dimethoxypyrazolo[1,5-a]pyrimidine (17.8 mg; yield: 81%) as a colorless solid.

MS (APCI)m/z; 511/513 [M+H]$^+$

Example 38

To a solution of the compound obtained in Example 33 (300 mg) in dimethylformamide (10 mL) was added sodium cyanide (42.1 mg) and the mixture was stirred at 10° C. for 1.5 hours in a microwave reactor. After cooling to room temperature, to the reaction mixture was added ethyl acetate and an aqueous sodium hydrogencarbonate solution and the mixture was stirred. The organic layer was washed with water and concentrated in vacuo. The resultant crude product was purified by a column chromatography on silica gel (solvent; hexane/ethyl acetate=80/20 to 65/35) to give 6-(2-chlorophenyl)-7-(4-chlorophenyl)-2-cyano-3-(N-cyclopentylcarbamoyl)pyrazolo[1,5-a]pyrimidine (17.8 mg; yield: 81%) as a pale yellow solid.

MS (APCI)m/z; 476/478 [M+H]$^+$

Example 39

To a solution of the compound obtained in Reference Example 10(2) (138 mg) in ethanol (7 mL) was added divinylsulfone (42 μL) and triethylamine (72 μL) and the mixture was refluxed under heating for 6 hours. After cooling to room temperature, the reaction mixture was concentrated in vacuo. To the residue was added water and methylene chloride and the mixture was stirred and the organic layer was extracted. The extract was washed with a brine, dried over sodium sulfate and filtered. The filtrate was concentrated in vacuo and the resultant crude product was purified by a column chromatography on silica gel (solvent; chloroform/methanol=100/0 to 95/5) and then on NH-silica gel (Chromatorex NH-silica gel/Fuji Silicia Chem., solvent; hexane/ethyl acetate=50/50 to 20/80), dissolved in tert-butanol and lyophilized to give 6-(2-chlorophenyl)-7-(4-chlorophenyl)-3-[N-[4-(1,1-dioxo)thiomorpholino]carbamoyl]-pyrazolo[1,5-a]pyrimidine (57 mg; yield: 31%) as a pale yellow powder.

MS(APCI)m/z; 516/518 [M+H]$^+$

Example 40

To a solution of the compound obtained in Reference Example 11 (1.1 g) in tetrahydrofuran/water (2.8 mL/4.2 mL) was added acetic acid (7 mL) and the mixture was stirred at 10° C. for 1 hours in a microwave reactor. After cooling to room temperature, to the reaction mixture was an aqueous 2N sodium hydroxide solution and the mixture was extracted with chloroform. The extract was dried over magnesium sulfate and filtered. The filtrate was concentrated in vacuo and the resultant crude product was purified by a column chromatography on silica gel (solvent; hexane/ethyl acetate=80/20 to 60/40) to give 2-amino-6-(2-chlorophenyl)-7-(4-chlorophenyl)-3-(N-cyclopentylcarbamoyl)pyrazolo[1,5-a]pyrimidine (529 mg; yield: 75%) as a yellow solid.

MS (APCI)m/z; 466/468 [M+H]$^+$

Example 42

A mixture of the compound obtained in Example 40 (60 mg), pyridine (600 μL) and acetic anhydride (200 μL) was stirred at 100° C. for 3 days. After cooling to room temperature, to the reaction mixture was added an aqueous 1N HCl and ethyl acetate and the mixture was stirred. The extract was dried over magnesium sulfate and filtered. The filtrate was concentrated in vacuo and the resultant crude product was purified by a column chromatography on NH-silica gel (Chromatorex NH-silica gel/Fuji Silicia Chem., solvent; hexane/ethyl acetate=90/10 to 50/50) to give 2-acetylamino-6-(2-chlorophenyl)-7-(4-chlorophenyl)-3-(N-cyclopentylcarbamoyl)pyrazolo[1,5-a]pyrimidine (38.2 mg; yield: 58%) as a pale yellow solid.

MS (APCI)m/z; 508/510 [M+H]$^+$

Example 43

To a solution of the compound obtained in Example 40 (60 mg) in water/acetonitrile (0.3 mL/2.4 mL) was added 1,4-dichlorobutane (81.6 mg), potassium carbonate (88.8 mg) and sodium iodide (6.8 mg) and the mixture was stirred at 150° C. for 3 hours in a microwave reactor. After cooling to room temperature, to the reaction mixture was added ethyl acetate and water and the mixture was stirred. The organic layer was extracted and dried over magnesium sulfate and filtered. The filtrate was concentrated in vacuo and the resultant crude product was purified by a column chromatography on silica gel (solvent; hexane/ethyl acetate=90/10 to 70/30) to give 6-(2-chlorophenyl)-7-(4-chlorophenyl)-3-(N-cyclopentylcarbamoyl)-2-(1-pyrrolidinyl)-pyrazolo[1,5-a]pyrimidine (25 mg; yield: 37%) as a yellow solid.

MS (APCI)m/z; 520/522 [M+H]$^+$

Example 44

To a solution of the compound obtained in Reference Example 1(4) (77 mg) in methylene chloride (1 mL) was added water-soluble carbodiimide HCl (58 mg), 1-hydroxybenzotriazole (46 mg) and triethylamine (84 μL) and the mixture was stirred at room temperature overnight. To the reaction mixture was added an aqueous sodium hydrogencarbonate solution and methylene chloride and the mixture was stirred. The organic layer was separated and concentrated in vacuo to give 6-(2-chlorophenyl)-7-(4-chlorophenyl)-3-[N-(4-cyano-tetrahydrothiopyran-4-yl)carbamoyl]pyrazolo[1,5-a]pyrimidine (50.8 mg; yield: 50%) as a pale yellow powder.

MS (APCI)m/z; 508/510 [M+H]$^+$

Examples 45 to 202

The corresponding materials were treated in the same manner as described in either one of Examples 1, 2 and 3 to obtain the compounds as shown in the following Tables 2 to 4.

TABLE 2

(No. 1)

| Ex. Nos. | —N(R$^5$)(R$^6$) | Physicochemical properties etc. |
|---|---|---|
| 45 | NH-CH$_2$-phenyl | powder<br>MS(APCI): 473/475 [M + H]$^+$ |
| 46 | NH-CH$_2$-(2-pyridyl) | powder<br>MS(APCI): 474/476 [M + H]$^+$ |
| 47 | NH-CH$_2$-(3-pyridyl) | powder<br>MS(APCI): 474/476 [M + H]$^+$ |
| 48 | NH-CH$_2$-(4-pyridyl) | powder<br>MS(APCI): 474/476 [M + H]$^+$ |
| 49 | NH-CH$_2$-cyclopropyl | powder<br>MS(APCI): 423/425 [M + H]$^+$ |

TABLE 2-continued

| Ex. No. | —N(R⁵)(R⁶) | Physicochemical properties etc. |
|---|---|---|
| 50 | CH₃NH-CH₂CH₂-N(CH₃)CH₃ | powder<br>MS(APCI): 454/456 [M + H]⁺ |
| 51 | CH₃NH-CF₃ | powder<br>MS(APCI): 465/467 [M + H]⁺ |
| 52 | HN-CH₂CH₂-morpholine | powder<br>MS(APCI): 496/498 [M + H]⁺ |

(No. 2)

| Ex. Nos. | R″ | —N(R⁵)(R⁶) | Physicochemical properties etc. |
|---|---|---|---|
| 53 | Cl | CH₃NH-CH₂-(tetrahydrofuran-2-yl) | powder<br>MS(APCI): 467/469 [M + H]⁺ |
| 54 | Cl | CH₃HN-CH₂CH₂-piperidin-1-yl | powder<br>MS(APCI): 494/496 [M + H]⁺ |
| 55 | Cl | CH₃HN-(2-oxo-tetrahydrofuran-3-yl) | powder<br>MS(APCI): 467/469 [M + H]⁺ |
| 56 | Cl | CH₃NH-CH₃ | powder<br>MS(ESI): 411 [M + H]⁺ |
| 57 | Cl | CH₃NH-CH₂CH₂-(1-methylpyrrolidin-2-yl) | powder<br>MS(APCI): 494/496 [M + H]⁺ |
| 58 | Cl | CH₃NH-(thiazol-2-yl) | powder<br>MS(APCI): 466/468 [M + H]⁺ |
| 59 | —OCH₃ | CH₃N(NH)-phenyl, N-methyl | powder<br>MS(APCI): 484/486 [M + H]⁺ |
| 60 | —OCH₃ | CH₃HN-cyclopentyl | powder<br>MS(APCI): 447/449 [M + H]⁺ |

TABLE 2-continued (No. 3)

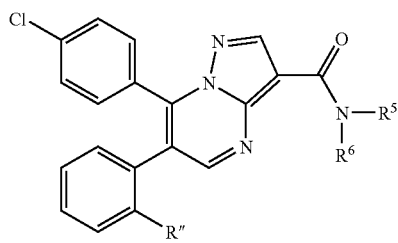

| Ex. Nos. | R" | —N(R$^5$)(R$^6$) | Physicochemical properties etc. |
| --- | --- | --- | --- |
| 61 | —CH$_3$ | HN—N(piperidine), N-methyl | powder MS(APCI): 446/448 [M + H]$^+$ |
| 62 | —CH$_3$ | N-methyl-N'-methyl-N'-phenylhydrazine | powder MS(APCI): 468/470 [M + H]$^+$ |
| 63 | —CH$_3$ | HN-cyclohexyl, N-methyl | powder MS(APCI): 445/447 [M + H]$^+$ |
| 64 | —CH$_3$ | HN-cyclopentyl, N-methyl | powder MS(APCI): 431/433 [M + H]$^+$ |
| 65 | —CH$_3$ | HN-tetrahydropyran-4-yl, N-methyl | powder MS(APCI): 447/449 [M + H]$^+$ |
| 66 | —CH$_3$ | HN-(tetrahydrothiophene-3-yl-1,1-dioxide), N-methyl | powder MS(APCI): 481/483 [M + H]$^+$ |
| 67 | F | HN—N(piperidine), N-methyl | powder MS(APCI): 450/452 [M + H]$^+$ |
| 68 | F | N-methyl-N'-methyl-N'-phenylhydrazine | powder MS(APCI): 472/474 [M + H]$^+$ |

(No. 4)

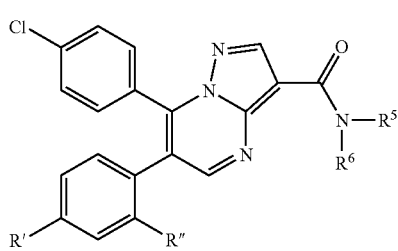

| Ex. Nos. | R' | R" | —N(R$^5$)(R$^6$) | Physicochemical properties etc. |
| --- | --- | --- | --- | --- |
| 69 | H | F | HN-cyclohexyl | powder MS(APCI): 449/451 [M + H]$^+$ |

TABLE 2-continued

| Ex. Nos. | R' | R" | —N(R⁵)(R⁶) | Physicochemical properties etc. |
|---|---|---|---|---|
| 70 | H | F | 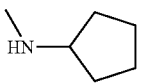 | powder<br>MS(APCI): 435/437 [M + H]⁺ |
| 71 | H | F | 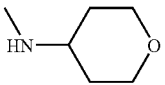 | powder<br>MS(APCI): 451/453 [M + H]⁺ |
| 72 | H | F | 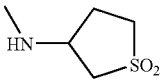 | powder<br>MS(APCI): 485/487 [M + H]⁺ |
| 73 | F | Cl | 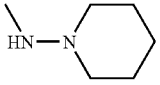 | powder<br>MS(APCI): 484/486 [M + H]⁺ |
| 74 | F | Cl | 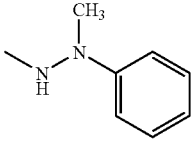 | powder<br>MS(APCI): 506/508 [M + H]⁺ |
| 75 | F | Cl | 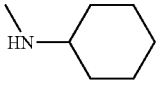 | powder<br>MS(APCI): 483/485 [M + H]⁺ |
| 76 | F | Cl | 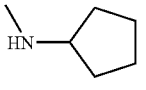 | powder<br>MS(APCI): 469/471 [M + H]⁺ |

(No. 5)

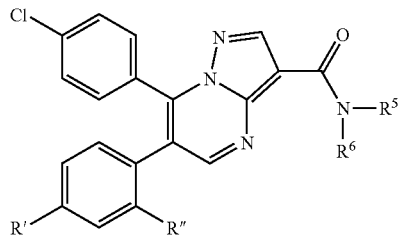

| Ex. Nos. | R' | R" | —N(R⁵)(R⁶) | Physicochemical properties etc. |
|---|---|---|---|---|
| 77 | F | Cl | 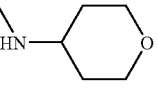 | powder<br>MS(APCI): 485/487 [M + H]⁺ |
| 78 | F | Cl | 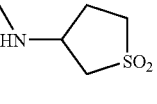 | powder<br>MS(APCI): 519/521 [M + H]⁺ |
| 79 | H | Cl | 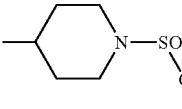 | powder<br>MS(APCI): 558/560 [M + H]⁺ |
| 80 | H | Cl | 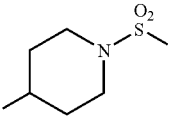 | powder<br>MS(APCI): 573/575 [M + H]⁺ |
| 81 | H | Cl |  | powder<br>MS(APCI): 501/503 [M + H]⁺ |

TABLE 2-continued

| Ex. Nos. | R' | R'' | —N(R⁵)(R⁶) | Physicochemical properties etc |
|---|---|---|---|---|
| 82 | H | Cl | HN-N(thiomorpholine, N-methyl) | powder MS(APCI): 484/486 [M + H]⁺ |
| 83 | H | Cl | N(CH₃)-NH-methyl-(2-pyridyl) | powder MS(APCI): 489/491 [M + H]⁺ |

(No. 6)

| Ex. Nos. | R' | R'' | —N(R⁵)(R⁶) | Physicochemical properties etc |
|---|---|---|---|---|
| 84 | F | Cl | HN-cyclopentyl | powder MS(APCI): 435/437 [M + H]⁺ |
| 85 | F | Cl | HN-tetrahydrothiophene-SO₂ | powder MS(APCI): 485/487 [M + H]⁺ |
| 86 | Cl | Br | HN-cyclohexyl | powder MS(APCI): 509/511 [M + H]⁺ |
| 87 | Cl | CN | HN-cyclohexyl | powder MS(APCI): 456/458 [M + H]⁺ |
| 88 | Cl | Cl | HN-cyclobutyl | powder MS(APCI): 437/439 [M + H]⁺ |
| 89 | CN | Cl | HN-cyclopentyl | powder MS(APCI): 442/444 [M + H]⁺ |
| 90 | CH₃— | Cl | HN-cyclopentyl | powder MS(APCI): 431/433 [M + H]⁺ |
| 91 | CH₃O— | Cl | HN-cyclopentyl | powder MS(APCI): 447/449 [M + H]⁺ |
| 92 | CH₃SO₂— | Cl | HN-cyclopentyl | powder MS(APCI): 495/497 [M + H]⁺ |

TABLE 2-continued (No. 7)

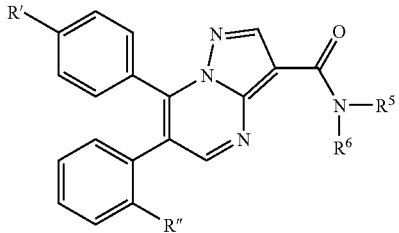

| Ex. Nos. | R' | R" | —N(R$^5$)(R$^6$) | Physicochemical properties etc |
|---|---|---|---|---|
| 93 | CN | Cl | 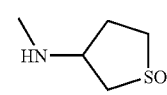 | powder<br>MS(APCI): 492/494 [M + H]$^+$ |
| 94 | CH$_3$— | Cl | 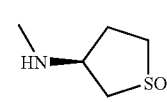 | powder<br>MS(APCI): 481/483 [M + H]$^+$ |
| 95 | Cl | Cl | 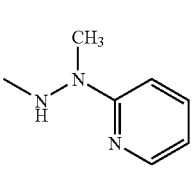 | powder<br>MS(APCI): 501/503 [M + H]$^+$ |
| 96 | CF$_3$— | Cl | 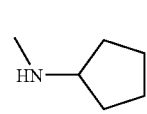 | powder<br>MS(APCI): 523/525 [M + H]$^+$ |
| 97 | CF$_3$— | Cl | 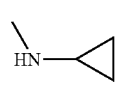 | powder<br>MS(APCI): 485/487 [M + H]$^+$ |
| 98 | CF$_3$— | Cl | 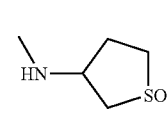 | powder<br>MS(APCI): 457/459 [M + H]$^+$ |
| 99 | CF$_3$— | Cl | 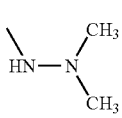 | powder<br>MS(APCI): 535/537 [M + H]$^+$ |
| 100 | CF$_3$— | Cl | 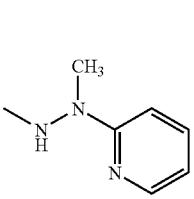 | powder<br>MS(APCI): 460/462 [M + H]$^+$ |
| 101 | Cl | F |  | powder<br>MS(APCI): 473/475 [M + H]$^+$ |

TABLE 2-continued (No. 8)

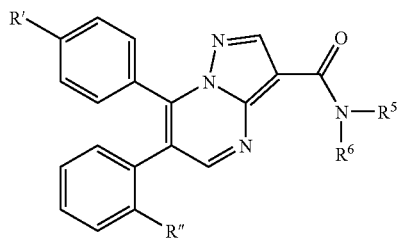

| Ex. Nos. | R' | R" | —N(R⁵)(R⁶) | Physicochemical properties etc |
|---|---|---|---|---|
| 102 | Cl | Cl | (methyl-(5-bromopyridin-2-yl)hydrazinyl with N-methyl) | powder<br>MS(APCI): 567/569 [M + H]⁺ |
| 103 | Cl | Cl | (N-methyl-hexahydroazepin-1-yl-amino) | powder<br>MS(ESI): 480 [M + H]⁺ |
| 104 | Cl | Cl | (N-methyl-4-cyanobenzyl-amino) | solid<br>MS(ESI): 498 [M + H]⁺ |
| 105 | Cl | Cl | (N-ethyl-methylamino) | solid<br>MS(ESI): 425 [M + H]⁺ |
| 106 | Cl | Cl | (N-methyl-cyclohexylmethyl-amino) | solid<br>MS(ESI): 479 [M + H]⁺ |
| 107 | Cl | Cl | (N-methyl-2-methoxyethyl-amino) | solid<br>MS(ESI): 441 [M + H]⁺ |

(No. 9)

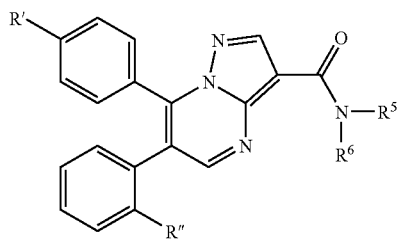

| Ex. Nos. | R' | R" | —N(R⁵)(R⁶) | Physicochemical properties etc |
|---|---|---|---|---|
| 108 | Cl | Cl | (N-methyl-isobutyl-amino) | solid<br>MS(ESI): 439 [M + H]⁺ |
| 109 | Cl | Cl | (N-cyclopropylmethyl-amino) | solid<br>MS(ESI): 437 [M + H]⁺ |

TABLE 2-continued

| Ex. Nos. | R' | R" | —N(R⁵)(R⁶) | Physicochemical properties etc |
|---|---|---|---|---|
| 110 | Cl | Cl | 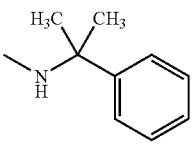 | powder<br>MS(ESI): 501 [M + H]⁺ |
| 111 | Cl | Cl | 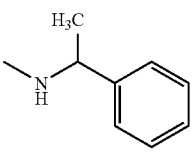 | powder<br>MS(ESI): 487 [M + H]⁺ |
| 112 | Cl | Cl | 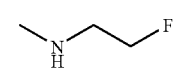 | solid<br>MS(ESI): 429 [M + H]⁺ |
| 113 | Cl | Cl | 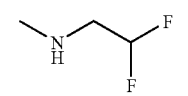 | solid<br>MS(ESI): 447 [M + H]⁺ |
| 114 | Cl | Cl | 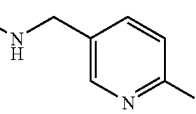 | solid<br>MS(ESI): 508 [M + H]⁺ |
| 115 | Cl | Cl | 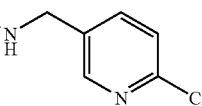 | solid<br>MS(ESI): 542 [M + H]⁺ |
| 116 | Cl | Cl | 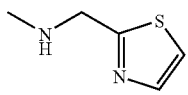 | solid<br>MS(ESI): 480 [M + H]⁺ |

(No. 10)

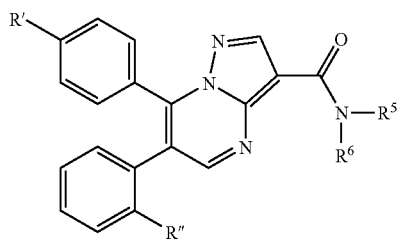

| Ex. Nos. | R' | R" | —N(R⁵)(R⁶) | Physicochemical properties etc |
|---|---|---|---|---|
| 117 | Cl | Cl | 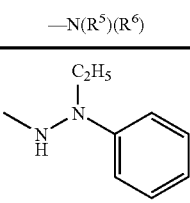 | powder<br>MS(APCI): 502/504 [M + H]⁺ |
| 118 | Cl | Cl | 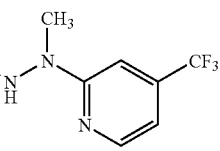 | powder<br>MS(APCI): 557/559 [M + H]⁺ |
| 119 | Cl | Cl | 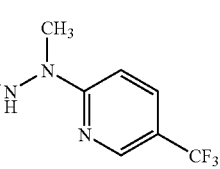 | powder<br>MS(APCI): 557/559 [M + H]⁺ |

TABLE 2-continued

| Ex. Nos. | R' | R" | —N(R⁵)(R⁶) | Physicochemical properties etc |
|---|---|---|---|---|
| 120 | Cl | Cl | (N-methyl-N'-methyl-N-benzyl hydrazine) | powder MS(APCI): 502/504 [M + H]⁺ |
| 121 | Cl | Cl | (N-methyl-N'-methyl-N-cyclohexyl hydrazine) | powder MS(APCI): 494/496 [M + H]⁺ |
| 122 | Cl | Cl | (N-methyl-N'-(2,2,2-trifluoroethyl) hydrazine) | powder MS(APCI): 480/482 [M + H]⁺ |

(No. 11)

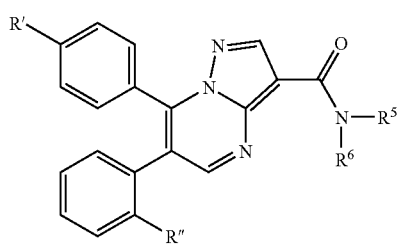

| Ex. Nos. | R' | R" | —N(R⁵)(R⁶) | Physicochemical properties etc |
|---|---|---|---|---|
| 123 | Cl | Cl | (1,2,2-trimethylhydrazine) | powder MS(APCI): 440/442 [M + H]⁺ |
| 124 | Cl | Cl | (1-aminoindoline, N-methyl) | powder MS(APCI): 500/502 [M + H]⁺ |
| 125 | Cl | Cl | (N-methylanilino) | powder MS(ESI): 459/461 [M + H]⁺ |
| 126 | Cl | Cl | (N-methyl-N-(4-chlorophenyl)-N'-methylhydrazine) | powder MS(APCI): 522/524 [M + H]⁺ |
| 127 | Cl | Cl | (N-methyl-N-(4-methoxyphenyl)-N'-methylhydrazine) | powder MS(APCI): 518/520 [M + H]⁺ |
| 128 | Cl | Cl | (N-methyl-N-(2-trifluoromethylphenyl)-N'-methylhydrazine) | powder MS(APCI): 556/558 [M + H]⁺ |

TABLE 2-continued

| Ex. Nos. | | | | Physicochemical properties etc |
|---|---|---|---|---|
| 129 | Cl | Cl | (N-methyl-N'-methyl hydrazino)-3-chlorophenyl group | powder MS(APCI): 522/524 [M + H]$^+$ |
| 130 | Cl | Cl | (N-methyl-N'-methyl hydrazino)-2-chlorophenyl group | powder MS(APCI): 522/524 [M + H]$^+$ |

(No. 12)

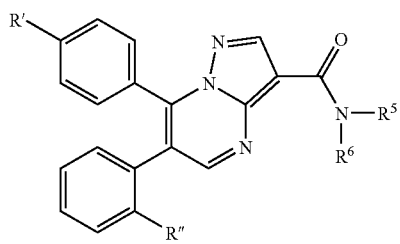

| Ex. Nos. | R' | R'' | —N(R$^5$)(R$^6$) | Physicochemical properties etc |
|---|---|---|---|---|
| 131 | CF$_3$— | Cl | (R)-3-(methylamino)tetrahydrothiophene-1,1-dioxide | powder MS(APCI): 535/537 [M + H]$^+$ |
| 132 | CF$_3$— | Cl | (S)-3-(methylamino)tetrahydrothiophene-1,1-dioxide | powder MS(APCI): 535/537 [M + H]$^+$ |
| 133 | Cl | Cl | N-methyl-3-aminopyridine | powder MS(APCI): 460/462 [M + H]$^+$ |
| 134 | Cl | Br | 3-(methylamino)tetrahydrothiophene-1,1-dioxide | powder MS(APCI): 545/547 [M + H]$^+$ |
| 135 | Cl | Br | N-methylcyclopentylamine | powder MS(APCI): 495/497 [M + H]$^+$ |
| 136 | Cl | CN | N-methylcyclopentylamine | powder MS(APCI): 442/444 [M + H]$^+$ |
| 137 | Cl | Cl | 1-(methylamino)-4,4-difluoropiperidine | powder MS(APCI): 502/504 [M + H]$^+$ |
| 138 | Cl | CN | 3-(methylamino)tetrahydrothiophene-1,1-dioxide | powder MS(APCI): 492/494 [M + H]$^+$ |
| 139 | Cl | CF$_3$— | 3-(methylamino)tetrahydrothiophene-1,1-dioxide | powder MS(APCI): 535/537 [M + H]$^+$ |
| 140 | Cl | CF$_3$— | N-methylcyclopentylamine | powder MS(APCI): 485/487 [M + H]$^+$ |

TABLE 2-continued

| 141 | Cl | CF₃— | HN-N(piperidine) with N-methyl | powder MS(APCI): 500/502 [M + H]⁺ |

(No. 13)

[Structure: pyrazolo[1,5-a]pyrimidine core with R' on 4-phenyl, R'' on 2-phenyl, and C(O)N(R⁵)(R⁶) amide]

| Ex. Nos. | R' | R'' | —N(R⁵)(R⁶) | Physicochemical properties etc |
|---|---|---|---|---|
| 142 | Cl | Cl | N-methyl-N'-(1,1-dioxo-tetrahydrothiophen-3-yl)hydrazine | powder MS(APCI): 516/518 [M + H]⁺ |
| 143 | Cl | Cl | N-methyl-1-(pyridin-2-yl)ethylamine | powder MS(APCI): 488/490 [M + H]⁺ |
| 144 | CF₃O— | Cl | N-methyl-(tetrahydrothiopyran-4-yl)amine | powder MS(APCI): 533/535 [M + H]⁺ |
| 145 | CF₃O— | Cl | N-methyl-(1,1-dioxo-tetrahydrothiophen-3-yl)amine | powder MS(APCI): 551/553 [M + H]⁺ |
| 146 | CF₃O— | Cl | N-methyl-(pyridin-2-ylmethyl)amine | powder MS(APCI): 524/526 [M + H]⁺ |
| 147 | CF₃O— | Cl | 1-methyl-2-methyl-1-(pyridin-2-yl)hydrazine | powder MS(APCI): 539/541 [M + H]⁺ |
| 148 | Cl | Cl | 1-methyl-2-methyl-1-(3-fluorophenyl)hydrazine | powder MS(APCI): 506/508 [M + H]⁺ |
| 149 | Cl | Cl | 1-methyl-2-methyl-1-(3-methylphenyl)hydrazine | powder MS(APCI): 502/504 [M + H]⁺ |

TABLE 2-continued (No. 14)

| Ex. Nos. | R' | R" | —N(R⁵)(R⁶) | Physicochemical properties etc |
|---|---|---|---|---|
| 150 | Cl | Cl | N-methyl-N'-methyl-N-(3-methoxyphenyl)hydrazine | powder<br>MS(APCI): 518/520 [M + H]⁺ |
| 151 | Cl | Cl | CH₃NH-CH₂CH₂-SCH₃ | powder<br>MS(APCI): 457/459 [M + H]⁺ |
| 152 | CF₃— | Cl | CH₃NH-CH₂CH₂-SCH₃ | powder<br>MS(APCI): 491/493 [M + H]⁺ |
| 153 | Cl | Cl | N-methyl-N'-methyl-N-(3-trifluoromethylphenyl)hydrazine | powder<br>MS(APCI): 556/558 [M + H]⁺ |
| 154 | Cl | Cl | N-methyl-N'-methyl-N-(3-trifluoromethoxyphenyl)hydrazine | powder<br>MS(APCI): 572/574 [M + H]⁺ |
| 155 | Cl | Cl | N-methyl-N'-methyl-N-(3-cyanophenyl)hydrazine | powder<br>MS(APCI): 513/515 [M + H]⁺ |
| 156 | Cl | Cl | N-methyl-N'-methyl-N-(3-methylthiophenyl)hydrazine | powder<br>MS(APCI): 534/536 [M + H]⁺ |
| 157 | Cl | Cl | 1-(methylamino)-4-chloro-2,3-dihydro-1H-indole | powder<br>MS(APCI): 534/536 [M + H]⁺ |

TABLE 2-continued (No. 15)

| Ex. Nos. | R' | R" | —N(R⁵)(R⁶) | Physicochemical properties etc |
|---|---|---|---|---|
| 158 | Cl | Cl | 5-chloro-indoline-N-NHMe | powder<br>MS(APCI): 534/536 [M + H]⁺ |
| 159 | Cl | Cl | 6-chloro-indoline-N-NHMe | powder<br>MS(APCI): 534/536 [M + H]⁺ |
| 160 | Cl | Cl | 7-chloro-indoline-N-NHMe | powder<br>MS(APCI): 534/536 [M + H]⁺ |
| 161 | CF₃— | Cl | 2-chlorophenyl-N(CH₃)-NH-CH₃ | powder<br>MS(APCI): 556/558 [M + H]⁺ |
| 162 | CF₃— | Cl | 3-chlorophenyl-N(CH₃)-NH-CH₃ | powder<br>MS(APCI): 556/558 [M + H]⁺ |
| 163 | CF₃— | Cl | (pyridin-2-yl)methyl-NH-CH₃ | powder<br>MS(APCI): 508/510 [M + H]⁺ |
| 164 | CF₃— | Cl | (pyridin-3-yl)methyl-NH-CH₃ | powder<br>MS(APCI): 508/510 [M + H]⁺ |
| 165 | CF₃— | Cl | 1-(pyridin-2-yl)ethyl-NH-CH₃ | powder<br>MS(APCI): 522/524 [M + H]⁺ |
| 166 | CF₃— | CN | 3-(1,1-dioxo-tetrahydrothiophene)-NH-CH₃ | powder<br>MS(APCI): 526 [M + H]⁺ |

TABLE 2-continued
(No. 16)
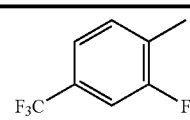
| Ex. Nos. | R¹ | —N(R⁵)(R⁶) | Physicochemical properties etc |
|---|---|---|---|
| 167 |  | 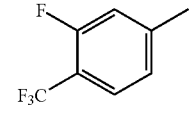 | powder<br>MS(APCI): 553/555 [M + H]⁺ |
| 168 | 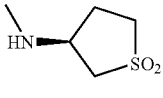 | 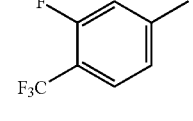 | powder<br>MS(APCI): 553/555 [M + H]⁺ |
| 169 | 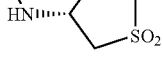 | 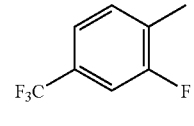 | powder<br>MS(APCI): 553/555 [M + H]⁺ |
| 170 | 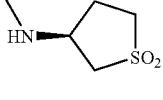 | 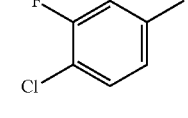 | powder<br>MS(APCI): 553/555 [M + H]⁺ |
| 171 | 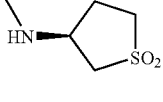 | 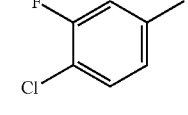 | powder<br>MS(APCI): 519/521 [M + H]⁺ |
| 172 | 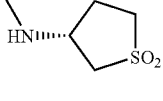 | 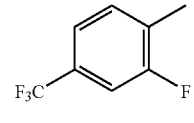 | powder<br>MS(APCI): 519/521 [M + H]⁺ |
| 173 | 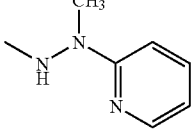 | 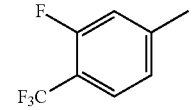 | powder<br>MS(APCI): 541/543 [M + H]⁺ |
| 174 | 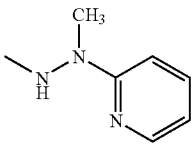 | 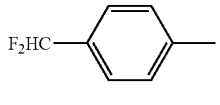 | powder<br>MS(APCI): 541/543 [M + H]⁺ |
| 175 | 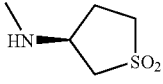 | 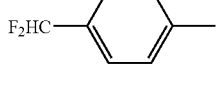 | powder<br>MS(APCI): 517/519 [M + H]⁺ |
| 176 | 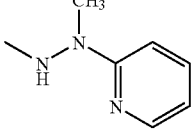 | | powder<br>MS(APCI): 505/507 [M + H]⁺ |

TABLE 3

(No. 1)

[Structure: pyrazolo pyrimidine core with 4-chlorophenyl, 2-chlorophenyl substituents and C(O)N(R5)(R6), R4 groups]

| Ex. Nos. | R⁴ | —N(R⁵)(R⁶) | Physicochemical properties etc |
|---|---|---|---|
| 177 | CH₃— | HN-cyclohexyl (N-methyl) | powder MS(APCI):479/481 [M + H]⁺ |
| 178 | CH₃— | HN-(tetrahydrothiophene-SO₂) (N-methyl) | powder MS(APCI):515/517 [M + H]⁺ |
| 179 | CH₃— | N(CH₃)-NH-(2-pyridyl), N-methyl | powder MS(APCI):503/505 [M + H]⁺ |
| 180 | CH₃S— | N(CH₃)-NH-(2-pyridyl), N-methyl | powder MS(APCI):535/537 [M + H]⁺ |
| 181 | CH₃S— | HN-(tetrahydrothiophene-SO₂) (N-methyl) | powder MS(APCI):547/549 [M + H]⁺ |
| 182 | C₂H₅— | N(CH₃)-NH-(2-pyridyl), N-methyl | powder MS(APCI):533/535 [M + H]⁺ |
| 183 | CH₃S— | HN-piperidinyl (N-methyl) | powder MS(APCI):512/514 [M + H]⁺ |
| 184 | CH₃— | HN-(tetrahydrothiophene-SO₂) (S) (N-methyl) | powder MS(APCI):515/517 [M + H]⁺ |
| 185 | CH₃— | HN-(tetrahydrothiophene-SO₂) (R) (N-methyl) | powder MS(APCI):515/517 [M + H]⁺ |
| 186 | C₂H₅— | HN-cyclopentyl (N-methyl) | powder MS(APCI):495/497 [M + H]⁺ |
| 187 | C₂H₅— | HN-(tetrahydrothiophene-SO₂) (N-methyl) | powder MS(APCI):545/547 [M + H]⁺ |

TABLE 3-continued (No. 2)

[Structure: pyrazolo pyrimidine core with R'-phenyl, 2-chlorophenyl substituents and C(O)N(R5)(R6), R4 groups]

| Ex. Nos. | R' | R⁴ | —N(R⁵)(R⁶) | Physicochemical properties etc |
|---|---|---|---|---|
| 188 | Cl | C₂H₅— | HN-piperidinyl (N-methyl) | powder MS(APCI):510/512 [M + H]⁺ |
| 189 | CF₃— | CH₃— | HN-(tetrahydrothiophene-SO₂) (S) (N-methyl) | powder MS(APCI):549/551 [M + H]⁺ |
| 190 | CF₃— | CH₃— | N(CH₃)-NH-(2-pyridyl), N-methyl | powder MS(APCI):537/539 [M + H]⁺ |
| 191 | CF₃— | CH₃— | N(CH₃)-NH-(2-chlorophenyl), N-methyl | powder MS(APCI):570/572 [M + H]⁺ |
| 192 | CF₃— | CH₃— | N(CH₃)-NH-(3-chlorophenyl), N-methyl | powder MS(APCI):570/572 [M + H]⁺ |
| 193 | CF₃— | CH₃— | N(CH₃)-NH-(4-CF₃-2-pyridyl), N-methyl | powder MS(APCI):605/607 [M + H]⁺ |
| 194 | CF₃— | CH₃— | HN-CH₂CH₂-SCH₃ (N-methyl) | powder MS(APCI):505/507 [M + H]⁺ |
| 195 | CF₃— | CH₃— | HN-(tetrahydrothiophene-SO₂) (S) (N-methyl) | powder MS(APCI):549/551 [M + H]⁺ |

TABLE 4

[Structure: pyrazolo[1,5-a]pyrimidine core with R¹ at 7-position, 2-chlorophenyl at 6-position, and C(O)N(R⁵)(R⁶) at 3-position]

| Ex. Nos. | R¹ | —N(R⁵)(R⁶) | Physiochemical properties etc |
|---|---|---|---|
| 196 | 3-chlorophenyl | HN-cyclopentyl | powder MS(APCI): 451/453 [M + H]⁺ |
| 197 | 6-methoxypyridin-3-yl | HN-cyclopentyl | powder MS(APCI): 448/450 [M + H]⁺ |
| 198 | 3-chlorophenyl | HN-(1,1-dioxo-tetrahydrothiophen-3-yl) | powder MS(APCI): 501/503 [M + H]⁺ |
| 199 | 6-methoxypyridin-3-yl | HN-(1,1-dioxo-tetrahydrothiophen-3-yl) | powder MS(APCI): 498/500 [M + H]⁺ |
| 200 | pyrrolidin-1-yl | N(CH₃)-NH-(pyridin-2-yl) | powder MS(APCI): 448/450 [M + H]⁺ |
| 201 | piperidin-1-yl | N(CH₃)-NH-(pyridin-2-yl) | powder MS(APCI): 462/464 [M + H]⁺ |
| 202 | 4,4-difluoropiperidin-1-yl | N(CH₃)-NH-(pyridin-2-yl) | powder MS(APCI): 498/500 [M + H]⁺ |

Example 203

The corresponding materials were treated in the same manner as described in Example 3 to obtain 6-(2-chloropyridin-3-yl)-7-(4-chlorophenyl)-3-(N-cyclopentyl-carbamoyl) pyrazolo[1,5-a]pyrimidine (39 mg, yield: 67%) as a pale yellow powder.

MS (APCI)m/z: 452/454 [M+H]⁺

Example 204

The compound obtained in Example 181 (36 mg) was treated in the same manner as described in Example 33 to obtain 6-(2-chlorophenyl)-7-(4-chlorophenyl)-2-methylsulfonyl-3-[N-(1,1-dioxo-tetrahydrothiophen-3-yl)carbamoyl]pyrazolo[1,5-a]-pyrimidine (33.1 mg, yield: 86%) as a colorless solid.

MS (APCI)m/z: 579/581 [M+H]⁺

Example 205

The compound obtained in Example 204 was treated in the same manner as described in Example 34 to obtain 6-(2-chlorophenyl)-7-(4-chlorophenyl)-2-methoxy-3-[N-(1,1-dioxo-tetrahydrothiophen-3-yl)carbamoyl]pyrazolo[1,5-a]pyrimidine (72 mg, yield: 79%) as a powder.

MS (APCI)m/z: 531/533 [M+H]⁺

Example 206

The compound obtained in Example 144 (80 mg) was treated in the same manner as described in Example 29 to obtain 6-(2-chlorophenyl)-7-(4-trifluoro-methoxyphenyl)-3-[N-(1,1-dioxo-tetrahydrothiopyran-4-yl)carbamoyl]pyrazolo[1,5-a]-pyrimidine (61.1 mg, yield: 72%) as a pale yellow powder.

MS (APCI)m/z: 565/567 [M+H]⁺

Example 207

(1) The compound obtained in Example 204 (300 mg) was treated in the same manner as described in Example 35 to obtain 5-cyano-6-(2-chlorophenyl)-7-(4-chlorophenyl)-2-methylsulfonyl-3-[N-(1,1-dioxo-tetrahydrothiophen-3-yl) carbamoyl]-pyrazolo[1,5-a]pyrimidine (60 mg, yield: 19%) as a pale yellow solid.

MS (APCI)m/z: 604/606 [M+H]⁺

(2) The compound obtained in the above step (1) (60 mg) was treated in the same manner as described in Example 36 to obtain 6-(2-chlorophenyl)-7-(4-chlorophenyl)-5-methoxy-2-methylsulfonyl-3-[N-(1,1-dioxo-tetrahydrothiophen-3-yl) carbamoyl]-pyrazolo[1,5-a]pyrimidine (29 mg, yield: 49%) as a pale yellow powder.

MS (APCI)m/z: 609/611 [M+H]+

Examples 208 to 209

The compound obtained in Reference Example 18 or 19 was treated in the same manner as described in Example 39 to obtain the compounds as shown in the following Table 5.

TABLE 5

| Ex. Nos. | R' | —N(R$^5$)(R$^6$) | Physicochemical properties etc |
|---|---|---|---|
| 208 | CF$_3$O— | HN—N(\_)SO$_2$ | powder MS(APCI):566/568 [M + H]+ |
| 209 | CF$_3$— | HN—N(\_)SO$_2$ | powder MS(APCI):550/552 [M + H]+ |

Examples 210 to 212

The compound obtained in Example 152, 194 or 156 was treated in the same manner as described in Example 29 to obtain the compounds as shown in the following Table 6.

TABLE 6

| Ex. Nos. | R' | R$^4$ | —N(R$^5$)(R$^6$) | Physicochemical properties etc |
|---|---|---|---|---|
| 210 | CF$_3$— | H | HN-CH$_2$CH$_2$-SO$_2$CH$_3$ | powder MS(APCI):523/525 [M + H]+ |
| 211 | CF$_3$— | CH$_3$ | HN-CH$_2$CH$_2$-SO$_2$CH$_3$ | powder MS(APCI):537/539 [M + H]+ |

TABLE 6-continued

| Ex. Nos. | R' | R$^4$ | —N(R$^5$)(R$^6$) | Physicochemical properties etc |
|---|---|---|---|---|
| 212 | Cl | H | CH$_3$-N(H)-N(CH$_3$)-(3-SO$_2$CH$_3$-phenyl) | powder MS(APCI):566/568 [M + H]+ |

Examples 213 to 214

The corresponding starting materials were treated in the same manner as described in Example 28 and then the product was treated in the same manner as described in Example 29 to obtain the compounds as shown in the following Table 7.

TABLE 7

| Ex. Nos. | R" | —N(R$^5$)(R$^6$) | Physicochemical properties etc |
|---|---|---|---|
| 213 | Cl | HN—(\_)SO$_2$ | powder MS(APCI):549/551 [M + H]+ |
| 214 | CN | HN—(\_)SO$_2$ | powder MS(APCI):540 [M + H]+ |

Examples 215

The compound obtained in Example 40 and 2-chloroethylether were treated in the same manner as described in Example 43 to obtain 6-(2-chlorophenyl)-7-(4-chlorophenyl)-2-morpholino-3-(N-cyclopentylcarbamoyl)pyrazolo[1,5-a]pyrimidine (23 mg, yield: 33%) as a powder.
MS (APCI)m/z: 536/538 [M+H]+

Examples 216 to 223

The corresponding starting materials were treated in the same manner as described in Example 11 and then the product was treated in the same manner as described in Example 40 to obtain the compounds as shown in the following Table 8.

TABLE 8

| Example Nos. | R' | —N(R⁵)(R⁶) | Physicochemical properties etc |
|---|---|---|---|
| 216 | Cl | HN-(tetrahydrothiophene-3-yl SO₂) | powder MS(APCI):516/518 [M + H]⁺ |
| 217 | Cl | HN—N(pyrrolidine) | powder MS(APCI):467/469 [M + H]⁺ |
| 218 | CF₃ | HN-(tetrahydrothiophene-3-yl SO₂) | powder MS(APCI):550/552 [M + H]⁺ |
| 219 | CF₃ | HN⋯(tetrahydrothiophene-3-yl SO₂) | powder MS(APCI):550/552 [M + H]⁺ |
| 220 | CF₃ | HN—N(pyrrolidine) | powder MS(APCI):501/503 [M + H]⁺ |
| 221 | CF₃ | HN—N(CH₃)₂ | powder MS(APCI):475/477 [M + H]⁺ |
| 222 | CF₃ | CH₃-N-N(CH₃)(pyridin-2-yl) | powder MS(APCI):538/540 [M + H]⁺ |
| 223 | Cl | CH₃-N-N(CH₃)(pyridin-2-yl) | powder MS(APCI):504/506 [M + H]⁺ |

Examples 224 to 231

The corresponding starting materials were treated in the same manner as described in Example 42 to obtain the compounds as shown in the following Table 9.

TABLE 9

| Example Nos. | R' | —N(R⁵)(R⁶) | Physicochemical properties etc. |
|---|---|---|---|
| 224 | Cl | HN-(tetrahydrothiophene-3-yl SO₂) | powder MS(APCI):558/560 [M + H]⁺ |
| 225 | Cl | HN—N(pyrrolidine) | powder MS(APCI):509/511 [M + H]⁺ |
| 226 | CF₃ | HN-(tetrahydrothiophene-3-yl SO₂) | powder MS(APCI):592/594 [M + H]⁺ |
| 227 | CF₃ | HN⋯(tetrahydrothiophene-3-yl SO₂) | powder MS(APCI):592/594 [M + H]⁺ |
| 228 | CF₃ | HN—N(pyrrolidine) | powder MS(APCI):543/545 [M + H]⁺ |
| 229 | CF₃ | HN—N(CH₃)₂ | powder MS(APCI):517/519 [M + H]⁺ |
| 230 | CF₃ | CH₃-N-N(CH₃)(pyridin-2-yl) | powder MS(APCI):580/582 [M + H]⁺ |
| 231 | Cl | CH₃-N-N(CH₃)(pyridin-2-yl) | powder MS(APCI):546/548 [M + H]⁺ |

Examples 232 to 237

The corresponding starting materials were treated in the same manner as described in Example 43 to obtain the compounds as shown in the following Table 10.

TABLE 10

[Structure: pyrazolo[1,5-a]pyrimidine core with R' on 4-phenyl, 2-chlorophenyl at 6-position, pyrrolidinyl at 2-position, and C(=O)N(R⁵)(R⁶) at 3-position]

| Example Nos. | R' | —N(R⁵)(R⁶) | Physicochemical properties etc. |
|---|---|---|---|
| 232 | Cl | HN—(3-sulfolanyl) SO₂ | powder MS(APCI):570/572 [M+H]⁺ |
| 233 | CF₃ | HN—(3-sulfolanyl, wedge) SO₂ | powder MS(APCI):604/606 [M+H]⁺ |
| 234 | CF₃ | HN—(3-sulfolanyl, dashed) SO₂ | powder MS(APCI):604/606 [M+H]⁺ |
| 235 | CF₃ | HN—N(pyrrolidinyl) | powder MS(APCI):555/557 [M+H]⁺ |
| 236 | CF₃ | CH₃-N(2-pyridyl)-NH-CH₃ | powder MS(APCI):592/594 [M+H]⁺ |
| 237 | Cl | CH₃-N(2-pyridyl)-NH-CH₃ | powder MS(APCI):558/560 [M+H]⁺ |

Example 238

To a solution of pyrrolidine (15.5 µL) and pyridine (20 µL) in chloroform (2 mL) was added dropwise a solution of the compound (60 mg) obtained in Reference Example 54 in chloroform (1 mL) under ice-cooling and the mixture was stirred at room temperature for 2.5 hours. To the reaction mixture was further added pyrrolidine (15.5 µL) and the mixture was stirred for 2.5 hours. To the reaction mixture was added water and the mixture was extracted with chloroform. The organic layer was concentrated in vacuo and the resultant crude product was purified by column chromatography on silica gel (solvent: hexane/ethyl acetate=82/18 to 67/33) to obtain 6-(2-chlorophenyl)-7-(4-trifluoromethylphenyl)-2-methyl-3-(1-pyrrolidinyl)sulfonylpyrazolo[1,5-a]pyrimidine (43.8 mg; yield: 68%) as a colorless solid.

MS (APCI)m/z; 521/523 [M+H]⁺

Example 239

To a solution of the compound obtained in Reference Example 53 (60 mg) in ethanol (0.5 mL) was added divinylsulfone (20 µL) and the mixture was stirred at 120° C. for 1 hour and at 130° C. for 4 hours in a microwave reactor. After cooling to room temperature, to the reaction mixture was added water and the mixture was extracted with ethyl acetate. The organic layer was concentrated in vacuo and the resultant crude product was purified by column chromatography on silica gel (solvent: hexane/ethyl acetate=70/30 to 55/45) to obtain 6-(2-chlorophenyl)-7-(4-trifluoromethylphenyl)-3-(1,1-dioxothiomorpholino)pyrazolo[1,5-a]pyrimidine (40 mg; yield: 51%) as a red solid.

MS (APCI)m/z; 507/509 [M+H]⁺

Example 240

To a solution of the compound obtained in Reference Example 55 (128 mg) in chloroform (2 mL) was added a solution of bromine (21 µL) in chloroform (1.3 mL) and the mixture was stirred at room temperature for 2 hours. The reaction mixture was concentrated in vacuo and to the residue was added dimethylformamide (2 mL) and N-methylaniline (181 µL) and the mixture was stirred at room temperature for 2 hours. To the reaction mixture was added water and an aqueous saturated sodium hydrogencarbonate solution and the mixture was extracted with ethyl acetate. The organic layer was concentrated in vacuo and the resultant crude product was purified by column chromatography on silica gel (solvent: hexane/ethyl acetate=88/12 to 75/25) to obtain 6-(2-chlorophenyl)-7-(4-chlorophenyl)-3-[2-(N-methyl-N-phenylamino)acetyl]-pyrazolo[1,5-a]pyrimidine (115 mg; yield: 70%) as a yellow solid.

MS (APCI)m/z; 487/489 [M+H]⁺

Example 241

To a solution of the compound obtained in Example 434 (125 mg) in dichloromethane (2 mL) was added m-chloroperbenzoic acid (146 mg) and the mixture was stirred at room temperature overnight. To the reaction mixture was added an aqueous saturated sodium hydrogencarbonate solution and the mixture was extracted with ethyl acetate. The organic layer was washed with a saturated brine, dried over magnesium sulfate and filtered. The filtrate was concentrated in vacuo and the resultant crude product was purified by column chromatography on NH-silica gel (Chromatorex NH-silica gel, solvent: hexane/ethyl acetate=50/50). The eluted fraction was concentrated and the precipitates were washed with hexane to obtain 6-(2-chlorophenyl)-7-(1,1-dioxothiomorpholino)-2-methyl-3-[[N'-methyl-N'-(2-pyridyl) hydrazino] carbonyl]pyrazolo[1,5-a]pyrimidine (70 mg; yield: 53%) as a solid.

MS (APCI)m/z; 526/528 [M+H]⁺

Example 242

(1) The corresponding starting materials were treated in the same manner as described in Reference Example 2 to obtain 6-(2-bromophenyl)-7-(4-chloro-2-fluorophenyl)-3-carboxy-2-methylpyrazolo[1,5-a]pyrimidine (1.51 g; yield: 20%) as a pale yellow powder.

MS (APCI)m/z; 460/462 [M+H]⁺

(2) To a solution of the compound obtained in the above step (1) (100 mg) in methylene chloride (3 mL) was added 1-methyl-1-(2-pyridyl)hydrazine (37 mg), water-soluble carbodiimide hydrochloride (58 mg) and 1-hydroxybenzoltriazole hydrate (46 mg) and the mixture was stirred at room temperature overnight. To the reaction mixture was added an aqueous saturated sodium hydrogencarbonate solution and the mixture was stirred and extracted with chloroform. The extract was concentrated in vacuo and the resultant crude product was purified by column chromatography on NH-silica gel (Chromatorex NH-silica gel, solvent: hexane/ethyl acetate=80/20 to 55/45) to obtain 6-(2-bromophenyl)-7-(4-chloro-2-fluorophenyl)-2-methyl-3-[[N'-methyl-N'-(2-pyridyl)hydrazino]carbonyl]pyrazolo[1,5-a]pyrimidine (119.5 mg; yield: 96%) as a pale yellow solid.

MS (APCI)m/z; 565/567 [M+H]$^+$ (3) To a solution of the compound obtained in the above step (2) (119 mg) in dimethylformamide (2 mL) was added zinc cyanide (15.5 mg), tris(dibenzylidene-acetone)dipalladium (4.2 mg) and 1,1'-bis(diphenylphosphino)ferrocene (5.1 mg) and the mixture was stirred at 180° C. for 20 minutes in a microwave reactor. To the reaction mixture was added an aqueous saturated sodium hydrogencarbonate solution and the mixture was stirred and extracted with chloroform. The extract was washed with water and concentrated in vacuo. The resultant crude product was purified by column chromatography on NH-silica gel (Chromatorex NH-silica gel, solvent: hexane/ethyl acetate=70/30 to 55/45) to obtain 6-(2-cyanophenyl)-7-(4-chloro-2-fluorophenyl)-2-methyl-3-[[N'-methyl-N'-(2-pyridyl)-hydrazino]carbonyl]pyrazolo[1,5-a]pyrimidine (22.1 mg; yield: 21%) as a yellow solid.

MS (APCI)m/z; 512/514 [M+H]$^+$

Example 243

(1) To a solution of the compound obtained in Reference Example 33 (2.08 g) in N,N-dimethylformamide (20 mL) was added 2M methylamine-methanol solution (5 mL), water-soluble carbodiimide (1.92 g) and 1-hydroxybenzoltriazole (1.53 g) and triethylamine (1.01 g) and the mixture was stirred at room temperature overnight. To the reaction mixture was added water and the mixture was extracted with ethyl acetate. The organic layer was dried over magnesium sulfate and filtered. The filtrate was concentrated in vacuo and the resultant crude product was purified by column chromatography on NH-silica gel (Chromatorex NH-silica gel, solvent: chloroform/methanol=100/0 to 95/5) to obtain 6-(2-chlorophenyl)-7-(4-trifluoromethylphenyl)-3-(N-methylcarbamoyl)pyrazolo[1,5-a]pyrimidine (1.83 g; yield: 85%) as a yellow powder.

MS (APCI)m/z; 431/433 [M+H]$^+$ (2) To a solution of the compound obtained in the above step (1) (832 mg) in toluene (10 mL) was added Lawesson reagent (809 mg) and the mixture was stirred at 110° C. for 2 hours. After cooling, to the reaction mixture was added NH-silica gel (2.0 g) and the mixture was filtered. The residue was washed with ethyl acetate and the organic layers were combined and concentrated in vacuo. The resultant crude product was purified by column chromatography on silica gel (solvent: hexane/ethyl acetate=80/20 to 60/40) to obtain 6-(2-chlorophenyl)-7-(4-trifluoromethylphenyl)-3-[N-(methyl)thiocarbamoyl]pyrazolo[1,5-a]pyrimidine (730 mg; yield: 82%) as a yellow powder.

MS (APCI)m/z; 447/449 [M+H]$^+$ (3) To a solution of 4-chlorobenzenesulfonyl chloride (5.28 g) in tetrahydrofuran (25 mL) was added a solution of sodium azide (1.79 g) in water (12.5 mL) and the mixture was stirred at room temperature overnight. To the reaction mixture was added water and the mixture was extracted with ethyl acetate. The organic layer was dried over magnesium sulfate and filtered. The filtrate was concentrated in vacuo to give 4-chlorobenzenesulfonyl azide (4.27 g, yield: 78%) as a colorless liquid.

(4) A solution of the compound obtained in the above step (2) (223 mg) and the compound obtained in the above step (3) (326 mg) in pyridine (5 mL) was stirred at 110° C. for 2 days. After cooling, to the reaction mixture was added water and the mixture was extracted with chloroform. The organic layer was concentrated in vacuo and the resultant crude product was purified by column chromatography on silica gel (solvent: hexane/ethyl acetate=30/70 to 50/50) to obtain the compound a (24 mg; yield: 8%) and the compound b (0.8 mg, yield: 0.4%) as shown in the following Table 11.

TABLE 11

| Example Nos. | E | Physicochemical properties etc. |
|---|---|---|
| 243 | HN—CH$_3$ structure with sulfonyl-4-chlorophenyl | Compound a yellow powder MS(APCI):604/606 [M + H]$^+$ |
| | N-CH$_3$ structure with N$_3$ | Compound b yellow powder MS(APCI):456/458 [M + H]$^+$ |

Example 244

The compound obtained in Example 332 was treated in the same manner as described in Example 31(2) to obtain 6-(2-chlorophenyl)-7-(4-chlorophenyl)-3-[[N'-methyl-N'-(6-cyanopyridin-3-yl)hydrazino]carbonyl]pyrazolo[1,5-a]pyrimidine.

MS (APCI)m/z; 514/516 [M+H]$^+$

Example 245

To a solution of the compound obtained in Example 292 (6-(2-chlorophenyl)-7-(4-chlorophenyl)-3-[[N'-methyl-N'-(6-fluoropyridin-2-yl)hydrazino]carbonyl]pyrazolo[1,5-a]pyrimidine) in N-methylpiperidine (1 mL) was added diisopropylethylamine (52 μL) and morpholine (26 μL) and the mixture was stirred at 90° C. overnight and 120° C. for 4 hours in a shield container. After cooling to room temperature, to the reaction mixture was added morpholine (60 μL) and the mixture was stirred at 120° C. overnight in a shield container and 100° C. for 15 minutes in a microwave reactor. After cooling to room temperature, the reaction mixture was concentrated in vacuo and the resultant crude product was purified by column chromatography on silica gel (solvent: hexane/ethyl acetate=70/30 to 40/60) and the eluted fraction was concentrated. The residue was purified by gel-permeation chromatography (mobile phase: chloroform) and the eluted fraction was concentrated. The resultant residue was dissolved in tert-butanol and the solution was lyophilized to obtain 6-(2- chlorophenyl)-7-(4-chlorophenyl)-3-[[N'-methyl-N'-(6-morpholinopyridin-2-yl)hydrazino]carbonyl]pyrazolo[1,5-a]pyrimidine (12.9 mg; yield: 23%) as a pale yellow powder.

MS (APCI)m/z; 574/576 [M+H]$^+$

Example 246

(1) The corresponding starting materials were treated in the same manner as described in Reference Example 2 to obtain 6-(2-bromophenyl)-7-(4-chloro-2-fluoro-phenyl)-3-carboxypyrazolo[1,5-a]pyrimidine (2.09 g; yield: 22%) as a pale yellow powder.

MS (APCI)m/z; 446/448 [M+H]$^+$ (2) The compound obtained in the above step (1) and the corresponding starting materials were treated in the same manner as described in Example 3 to obtain 6-(2-bromophenyl)-7-(4-chloro-2-fluorophenyl)-3-[[N'-methyl-N'-(2-pyridyl)hydrazino]carbonyl]pyrazolo[1,5-a]pyrimidine (148 mg, yield: 89%) as a pale yellow solid.

MS (APCI)m/z; 551/553 [M+H]$^+$ (3) The compound obtained in the above step (2) (119 mg) was treated in the same manner as described in Example 242(3) to give 6-(2-cyanophenyl)-7-(4-chloro-2-fluorophenyl)-3-[[N'-methyl-N'-(2-pyridyl)hydrazino]carbonyl]pyrazolo[1,5-a]pyrimidine (compound a: 51.6 mg, yield: 40%) as a yellow solid and 6-(2-cyanophenyl)-7-(4-cyano-2-fluorophenyl)-3-[[N'-methyl-N'-(2-pyridyl)hydrazino]carbonyl]pyrazolo[1, 5-a]pyrimidine (compound b: 34.1 mg, yield: 27%) as a yellow solid.

Compound a: MS (APCI)m/z; 498/500 [M+H]$^+$
Compound b: MS (APCI)m/z; 489 [M+H]$^+$

Example 247

(1) The corresponding starting material (3-carboxy-6-(2-chlorophenyl)-7-(4-chlorophenyl)pyrazolo[1,5-a]pyrimidine; 576 mg) was treated in the same manner as described in Example 3 to give 6-(2-chlorophenyl)-7-(4-chlorophenyl)-3-[N-[1-(tert-butoxycarbonyl)pyrrolidin-3-yl]carbamoyl]pyrazolo[1,5-a]pyrimidine (656 mg, yield: 79%) as a yellow solid.

MS (APCI)m/z; 552/554 [M+H]$^+$ (2) A solution of the compound obtained in the above step (1) (650 mg) in 4N-HCl-dioxane (5 mL) was stirred at room temperature overnight. The reaction mixture was neutralized (pH 7 to 8) with an aqueous saturated sodium hydrogencarbonate solution under ice cooling. The mixture was extracted with methylene chloride and the organic layer was dried over magnesium sulfate and concentrated in vacuo. The resultant crude product was purified by column chromatography on NH-silica gel (Chromatorex NH-silica gel, solvent: chloroform/methanol=100/0 to 95/5) and dried in vacuo to obtain 6-(2-chlorophenyl)-7-(4-chlorophenyl)-3-[N-(pyrrolidin-3-yl)carbamoyl]pyrazolo[1,5-a]pyrimidine (515.8 mg; yield: 97%) as a pale yellow solid.

MS (APCI)m/z; 452/454 [M+H]$^+$ (3) To a solution of the compound obtained in the above step (2) (46 mg) in dichloromethane (1 mL containing amylene) was added triethylamine (28 μL) and thereto was added dropwise acetyl chloride (9 μL) under nitrogen-gas atmosphere and the mixture was stirred at room temperature for 2 hours. To the reaction mixture was added an aqueous saturated sodium hydrogencarbonate solution and the mixture was extracted with methylene chloride. The extract was concentrated in vacuo and be resultant crude product was purified by column chromatography on silica gel (solvent: chloroform/methanol=100/0 to 95/5) and the eluted fraction was concentrated in vacuo. The resultant residue was dissolved in tert-butanol and lyophilized to obtain 6-(2-chlorophenyl)-7-(4-chlorophenyl)-3-[N-(1-acetylpyrrolidin-3-yl)carbamoyl]pyrazolo[1,5-a]pyrimidine (50.7 mg; yield: 100%) as a pale yellow powder.

MS (APCI)m/z; 494/496 [M+H]$^+$

Examples 248 to 250

The corresponding starting materials were treated in the same manner as described in Example 247 to obtain the compounds as shown in the following Table 12.

TABLE 12

| Example Nos. | R$^2$ | —N(R$^5$)(R$^6$) | Physicochemical properties etc. |
|---|---|---|---|
| 248 | 2-chlorophenyl | pyrrolidinyl with NHCH— and N-C(O)N(CH$_3$)$_2$ | powder MS(APCI):523/525 [M + H]$^+$ |
| 249 | 2-chlorophenyl | pyrrolidinyl with NHCH— and N-SO$_2$CH$_3$ | powder MS(APCI):530/532 [M + H]$^+$ |

TABLE 12-continued

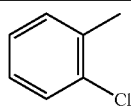

| Example Nos. | R² | —N(R⁵)(R⁶) | Physicochemical properties etc. |
|---|---|---|---|
| 250 | 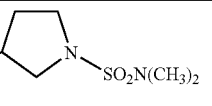 | 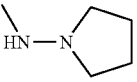 | powder MS(APCI):559/561 [M + H]⁺ |

Examples 251 to 278

The corresponding starting materials were treated in the same manner as described in Example 31 or 242 to obtain the compounds as shown in the following Table 13.

TABLE 13

(No. 1)

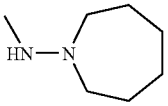

| Example Nos. | —N(R⁵)(R⁶) | Physicochemical properties etc. |
|---|---|---|
| 251 | 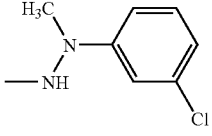 | powder MS(APCI):443/445 [M + H]⁺ |
| 252 | 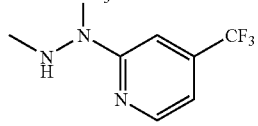 | powder MS(APCI):471/473 [M + H]⁺ |
| 253 | 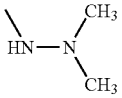 | powder MS(APCI):513/515 [M + H]⁺ |
| 254 | 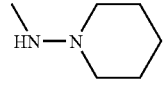 | powder MS(APCI):548/550 [M + H]⁺ |

TABLE 13-continued

| 255 | 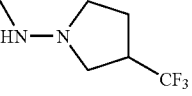 | powder MS(APCI):417/419 [M + H]⁺ |
| 256 | 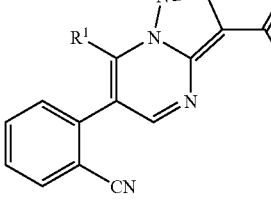 | powder MS(APCI):457/459 [M + H]⁺ |
| 257 | 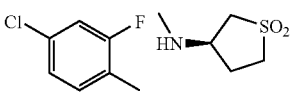 | solid MS(APCI):511/513 [M + H]⁺ |

(No.2)

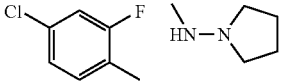

| Example Nos. | R¹ | —N(R⁵)(R⁶) | Physicochemical properties etc. |
|---|---|---|---|
| 258 | F₃C-pyridyl | N(CH₃)-N(CH₃)-pyridyl | powder MS(APCI):515 [M + H]⁺ |
| 259 | Cl-F-Me-phenyl | tetrahydrothiophene-SO₂ | solid MS(APCI):510/512 [M + H]⁺ |
| 260 | Cl-F-Me-phenyl | HN-N-pyrrolidine | solid MS(APCI):461/463 [M + H]⁺ |

TABLE 13-continued

| | | | | |
|---|---|---|---|---|
| 261 | 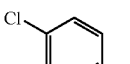 | 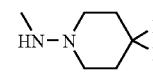 | solid MS(APCI):493/495 [M + H]+ | |
| 262 |  |  | powder MS(APCI):492 [M + H]+ | |
| 263 | 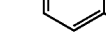 |  | powder MS(APCI):478 [M + H]+ | |

(No.3)

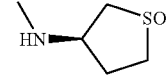

| Example Nos. | R' | —N(R⁵)(R⁶) | Physicochemical properties etc. |
|---|---|---|---|
| 264 | CF₃ | 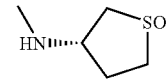 | powder MS(APCI):540 [M + H]+ |
| 265 | CF₃ | 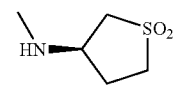 | powder MS(APCI):540 [M + H]+ |
| 266 | Cl | 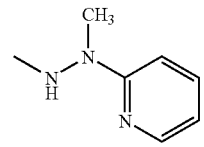 | powder MS(APCI):506/508 [M + H]+ |
| 267 | Cl | 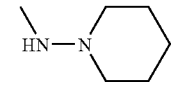 | powder MS(APCI):494/496 [M + H]+ |
| 268 | Cl | 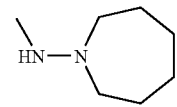 | powder MS(APCI):471/473 [M + H]+ |
| 269 | Cl | 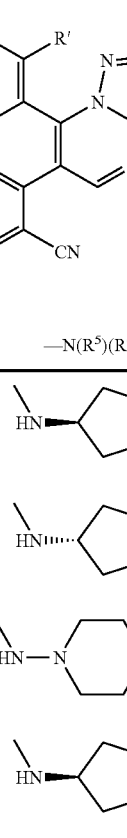 | powder MS(APCI):485/487 [M + H]+ |

TABLE 13-continued

| | | | | |
|---|---|---|---|---|
| 270 | Cl | | 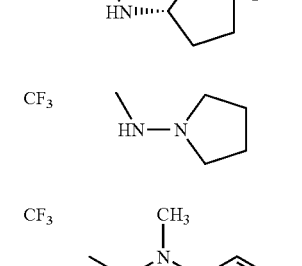 | powder MS(APCI):457/459 [M + H]+ |

(No.4)

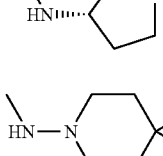

| Example Nos. | R' | R⁴ | —N(R⁵)(R⁶) | Physicochemical properties etc. |
|---|---|---|---|---|
| 271 | F | CH₃ | 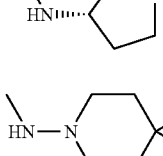 | solid MS(APCI):524/526 [M + H]+ |
| 272 | F | CH₃ | 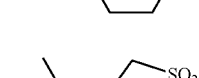 | solid MS(APCI):524/526 [M + H]+ |
| 273 | H | CH₃ | 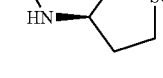 | solid MS(APCI):507/509 [M + H]+ |
| 274 | H | CF₃ | 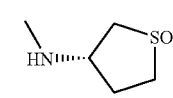 | powder MS(APCI):560/562 [M + H]+ |
| 275 | H | CF₃ |  | powder MS(APCI):560/562 [M + H]+ |
| 276 | H | CF₃ | 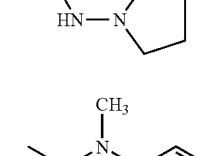 | powder MS(APCI):511/513 [M + H]+ |
| 277 | H | CF₃ | 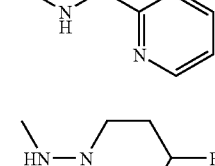 | powder MS(APCI):548/550 [M + H]+ |
| 278 | H | CH₃ |  | solid MS(APCI):489/491 [M + H]+ |

Examples 279 to 423

The corresponding starting materials were treated in the same manner as described in Example 3 to obtain the compounds as shown in the following Table 14.

TABLE 14

(No. 1)

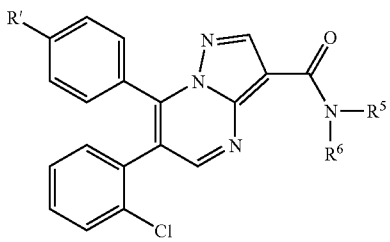

| Example Nos. | R' | —N(R⁵)(R⁶) | Physicochemical properties etc. |
|---|---|---|---|
| 279 | CHF₂ | (N-methyl-N'-methyl-2-pyridylhydrazine) | powder MS(APCI):505/507 [M + H]⁺ |
| 280 | Cl | (N-methyl-1-(6-methoxypyridin-2-yl)ethylamine) | powder MS(APCI):519/521 [M + H]⁺ |
| 281 | Cl | (N-methyl-N'-methyl-(6-methylpyridin-2-yl)hydrazine) | powder MS(APCI):503/505 [M + H]⁺ |
| 282 | Cl | (N-methyl-N'-methyl-(6-trifluoromethylpyridin-2-yl)hydrazine) | powder MS(APCI):557/559 [M + H]⁺ |
| 283 | CF₃ | (N-methyl-N'-methyl-(4-methoxypyridin-2-yl)hydrazine) | powder MS(APCI):553/555 [M + H]⁺ |
| 284 | CF₃ | (N-methyl-N'-methyl-(6-methylpyridin-2-yl)hydrazine) | powder MS(APCI):537/539 [M + H]⁺ |
| 285 | CF₃ | (N-methyl-N'-methyl-(6-trifluoromethylpyridin-2-yl)hydrazine) | powder MS(APCI):591/593 [M + H]⁺ |

TABLE 14-continued

(No. 2)

[Structure: pyrazolo-pyrimidine core with R' on one phenyl, Cl on other phenyl, and C(=O)-N(R5)(R6) amide group]

| Example Nos. | R' | —N(R⁵)(R⁶) | Physicochemical properties etc |
|---|---|---|---|
| 286 | CF₃ | HN(CH₃)(CH₂CH₃) | powder MS(APCI):445/447 [M + H]⁺ |
| 287 | CF₃ | N-methyl-isobutylamino | powder MS(APCI):473/475 [M + H]⁺ |
| 288 | CF₃ | HN—N(piperidinyl) (N-methyl) | powder MS(APCI):500/502 [M + H]⁺ |
| 289 | CF₃ | N-methyl-(6-chloroindolin-1-yl)amino | powder MS(APCI):557/559 [M + H]⁺ |
| 290 | CH₂F | N-methyl-(tetrahydrothiophene-3-yl,1,1-dioxide)amino | powder MS(APCI):499/501 [M + H]⁺ |
| 291 | CH₂F | N-methyl-(tetrahydrothiophene-3-yl,1,1-dioxide)amino | powder MS(APCI):499/501 [M + H]⁺ |
| 292 | Cl | H₃C-N(6-fluoropyridin-2-yl)-NH-(methyl) | powder MS(APCI):507/509 [M + H]⁺ |

(No. 3)

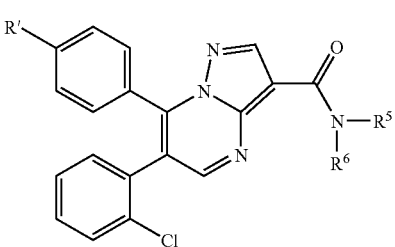

| Example Nos. | R' | —N(R⁵)(R⁶) | Physicochemical properties etc |
|---|---|---|---|
| 293 | Cl | H₃C-N(thiazol-2-yl)-NH-(methyl) | powder MS(APCI):495/497 [M + H]⁺ |

TABLE 14-continued

| Example Nos. | R⁴ | Structure | Physicochemical properties etc |
|---|---|---|---|
| 294 | CF₃ | (thiazole with N(CH₃)NH—) | powder MS(APCI):529/531 [M + H]⁺ |
| 295 | Cl | (6-methoxypyridin-3-yl with N(CH₃)NH—) | powder MS(APCI):519/521 [M + H]⁺ |
| 296 | Cl | (pyridin-3-yl with N(CH₃)NH—) | powder MS(APCI):489/491 [M + H]⁺ |
| 297 | CF₃ | (6-methoxypyridin-3-yl with N(CH₃)NH—) | powder MS(APCI):553/555 [M + H]⁺ |
| 298 | CF₃ | (pyridin-3-yl with N(CH₃)NH—) | powder MS(APCI):523/525 [M + H]⁺ |

(No. 4)

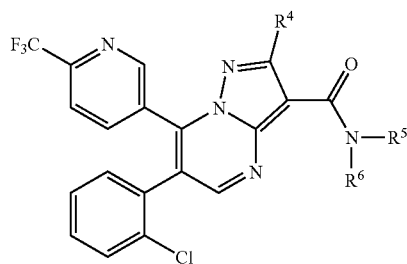

| Example Nos. | R⁴ | —N(R⁵)(R⁶) | Physicochemical properties etc |
|---|---|---|---|
| 299 | H | (3-tetrahydrothiophene-1,1-dioxide-yl, HN—) | powder MS(APCI):536/538 [M + H]⁺ |
| 300 | H | (pyridin-2-yl with N(CH₃)NH—) | powder MS(APCI):524/526 [M + H]⁺ |
| 301 | H | (cyclopentyl, HN—) | powder MS(APCI):486/488 [M + H]⁺ |
| 302 | CH₃ | (3-tetrahydrothiophene-1,1-dioxide-yl, HN—) | powder MS(APCI):550/552 [M + H]⁺ |
| 303 | CH₃ | (pyridin-2-yl with N(CH₃)NH—) | powder MS(APCI):538/540 [M + H]⁺ |
| 304 | CH₃ | (cyclopentyl, HN—) | powder MS(APCI):500/502 [M + H]⁺ |

TABLE 14-continued

| | | | |
|---|---|---|---|
| 305 | H | HN—N⟨pyrrolidine⟩ | solid MS(APCI):487/489 [M + H]+ |
| 306 | CH₃ | HN—N⟨pyrrolidine⟩ | powder MS(APCI):501/503 [M + H]+ |

(No. 5)

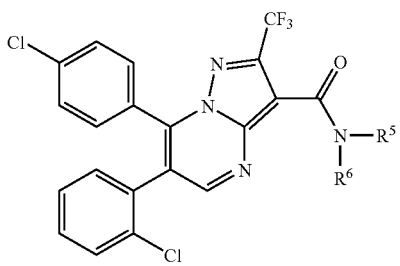

| Example Nos. | —N(R⁵)(R⁶) | Physicochemical properties etc |
|---|---|---|
| 307 | HN–⟨(S)-tetrahydrothiophene-1,1-dioxide⟩ | powder MS(APCI):569/571 [M + H]+ |
| 308 | HN–⟨(R)-tetrahydrothiophene-1,1-dioxide⟩ | powder MS(APCI):569/571 [M + H]+ |
| 309 | H₃C-N(pyridin-2-yl)-NH– | powder MS(APCI):557/559 [M + H]+ |
| 310 | HN–N⟨4,4-difluoropiperidine⟩ | powder MS(APCI):570/572 [M + H]+ |
| 311 | HN–N⟨pyrrolidine⟩ | powder MS(APCI):520/522 [M + H]+ |

(No. 6)

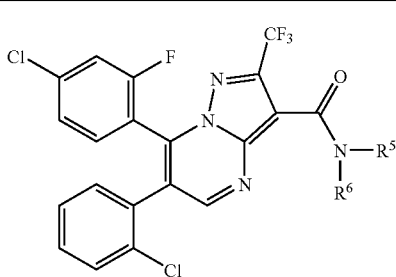

| Example Nos. | —N(R⁵)(R⁶) | Physicochemical properties etc |
|---|---|---|
| 312 | HN–⟨tetrahydrothiophene-1,1-dioxide⟩ | powder MS(APCI):587/589 [M + H]+ |

TABLE 14-continued

| Example Nos. | R¹ | —N(R⁵)(R⁶) | Physicochemical properties etc |
|---|---|---|---|
| 313 | | (S)-3-(methylamino)tetrahydrothiophene 1,1-dioxide group | powder MS(APCI):587/589 [M + H]⁺ |
| 314 | | N-methyl-N-(pyridin-2-yl)hydrazine group | powder MS(APCI):575/577 [M + H]⁺ |
| 315 | | 1-(methylamino)pyrrolidine group | powder MS(APCI):538/540 [M + H]⁺ |
| 316 | | 4,4-difluoro-1-(methylamino)piperidine group | powder MS(APCI):588/590 [M + H]⁺ |

(No. 7)

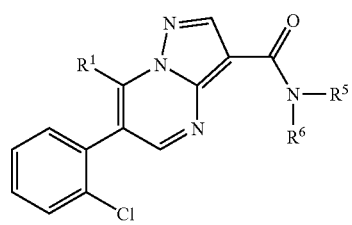

| Example Nos. | R¹ | —N(R⁵)(R⁶) | Physicochemical properties etc |
|---|---|---|---|
| 317 | 4-chloro-2-fluorophenyl | (R)-3-(methylamino)tetrahydrothiophene 1,1-dioxide | powder MS(APCI):519/521 [M + H]⁺ |
| 318 | 4-chloro-2-fluorophenyl | (S)-3-(methylamino)tetrahydrothiophene 1,1-dioxide | powder MS(APCI):519/521 [M + H]⁺ |
| 319 | 4-(difluoromethyl)phenyl | (S)-3-(methylamino)tetrahydrothiophene 1,1-dioxide | powder MS(APCI):517/519 [M + H]⁺ |
| 320 | 4-chlorophenyl | N-methyl-N-(3-fluoropyridin-2-yl)hydrazine | powder MS(APCI):507/509 [M + H]⁺ |
| 321 | 4-chlorophenyl | N-methyl-N-(5-fluoropyridin-2-yl)hydrazine | powder MS(APCI):507/509 [M + H]⁺ |
| 322 | 4-chloro-2-fluorophenyl | N-methyl-N-(pyridin-2-yl)hydrazine | powder MS(APCI):507/509 [M + H]⁺ |
| 323 | 4-methoxyphenyl | N-methyl-N-(pyridin-2-yl)hydrazine | powder MS(APCI):485/487 [M + H]⁺ |

TABLE 14-continued (No. 8)

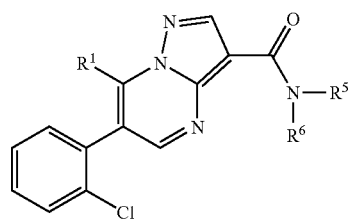

| Example Nos. | R¹ | —N(R⁵)(R⁶) | Physicochemical properties etc |
|---|---|---|---|
| 324 | Cl-C₆H₄- | HN-azetidine-S | powder MS(APCI):455/457 [M + H]⁺ |
| 325 | 4-(CF₂CH₃)C₆H₄- | HN-(3S)-tetrahydrothiophene-SO₂ | powder MS(APCI):531/533 [M + H]⁺ |
| 326 | 4-(CF₂CH₃)C₆H₄- | HN-(3R)-tetrahydrothiophene-SO₂ | powder MS(APCI):531/533 [M + H]⁺ |
| 327 | 4-(CF₂CH₃)C₆H₄- | H₃C-N(NH-)-2-pyridyl | powder MS(APCI):519/521 [M + H]⁺ |
| 328 | 4-(CF₂CH₃)C₆H₄- | HN-N-pyrrolidine | powder MS(APCI):482/484 [M + H]⁺ |
| 329 | 4-Cl-2-F-C₆H₃- | HN-N-pyrrolidine | solid MS(APCI):470/472 [M + H]⁺ |
| 330 | 4-Cl-C₆H₄- | HN-N-(3,3,4,4-tetrafluoropyrrolidine) | powder MS(APCI):524/526 [M + H]⁺ |
| 331 | 4-CF₃-C₆H₄- | HN-N-(3,3,4,4-tetrafluoropyrrolidine) | powder MS(APCI):558/560 [M + H]⁺ |

(No. 9)

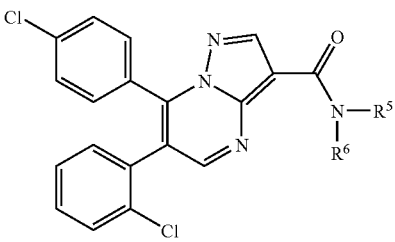

| Example Nos. | —N(R⁵)(R⁶) | Physicochemical properties etc |
|---|---|---|
| 332 | H₃C-N(NH-)-(6-bromopyridin-3-yl) | powder MS(APCI):569/571 [M + H]⁺ |

TABLE 14-continued

| | | |
|---|---|---|
| 333 | (structure: N-methyl-N'-methyl hydrazino pyrrolidine with CH2OCH3) | powder MS(APCI):496/498 [M + H]+ |
| 334 | (structure: 4-fluoropiperidin-1-yl methylamine) | solid MS(APCI):484/486 [M + H]+ |
| 335 | (structure: 6-methylpyridin-2-yl N,N'-dimethylhydrazine) | powder MS(APCI):474/476 [M + H]+ |
| 336 | (structure: 6-methylpyridin-3-yl N,N'-dimethylhydrazine) | powder MS(APCI):503/505 [M + H]+ |
| 337 | (structure: 6-trifluoromethylpyridin-3-yl N,N'-dimethylhydrazine) | powder MS(APCI):557/559 [M + H]+ |
| 338 | (structure: 6-ethoxypyridin-3-yl N,N'-dimethylhydrazine) | powder MS(APCI):533/535 [M + H]+ |

(No. 10)

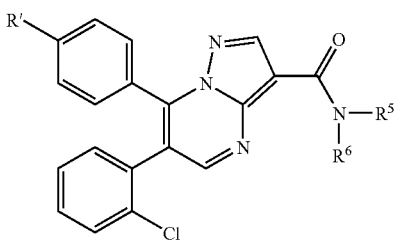

| Example Nos. | R' | —N(R⁵)(R⁶) | Physicochemical properties etc |
|---|---|---|---|
| 339 | Cl | (pyrrolidine with CH2OCH3, N-methylhydrazino) | powder MS(APCI):496/498 [M + H]+ |
| 340 | CF₃ | (pyrrolidine with CH2OCH3, N-methylhydrazino) | powder MS(APCI):530/532 [M + H]+ |
| 341 | CF₃ | (pyrrolidine with CH2OCH3, N-methylhydrazino) | powder MS(APCI):530/532 [M + H]+ |

TABLE 14-continued
| Example Nos. | R' | R⁴ | —N(R⁵)(R⁶) | Physicochemical properties etc |
|---|---|---|---|---|
| 342 | Cl | | 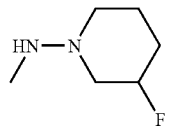 | solid MS(APCI):484/486 [M + H]⁺ |
| 343 | Cl | | 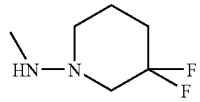 | solid MS(APCI):502/504 [M + H]⁺ |
| 344 | Cl | | 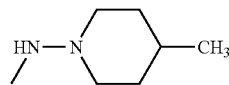 | solid MS(APCI):480/482 [M + H]⁺ |
(No. 11)
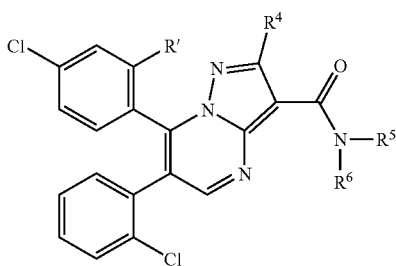
| Example Nos. | R' | R⁴ | —N(R⁵)(R⁶) | Physicochemical properties etc |
|---|---|---|---|---|
| 345 | H | H | 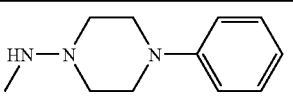 | solid MS(APCI):543/545 [M + H]⁺ |
| 346 | H | H | 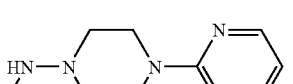 | solid MS(APCI):544/546 [M + H]⁺ |
| 347 | H | H | 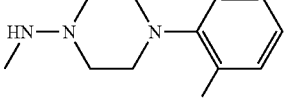 | solid MS(APCI):561/563 [M + H]⁺ |
| 348 | H | H | 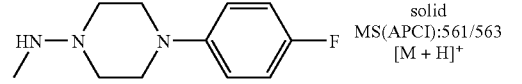 | solid MS(APCI):561/563 [M + H]⁺ |
| 349 | H | H |  | solid MS(APCI):491/493 [M + H]⁺ |
| 350 | F | CH₃ | 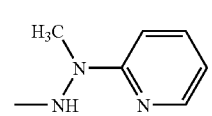 | solid MS(APCI):521/523 [M + H]⁺ |
| 351 | F | CH₃ | 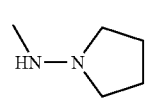 | solid MS(APCI):484/486 [M + H]⁺ |

TABLE 14-continued (No. 12)

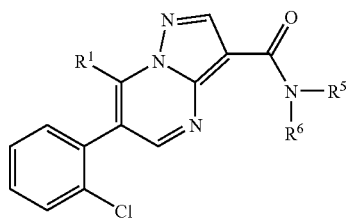

| Example Nos. | R¹ | —N(R⁵)(R⁶) | Physicochemical properties etc. |
|---|---|---|---|
| 352 | 2-fluoro-4-(difluoromethyl)phenyl (F, F₂HC) | N-methyl-N-(2-pyridyl)hydrazino (H₃C-N-NH, pyridyl) | powder MS(APCI):523/525 [M + H]⁺ |
| 353 | 2-fluoro-4-(difluoromethyl)phenyl | (3S)-1,1-dioxotetrahydrothiophen-3-yl-methylamino | powder MS(APCI):535/537 [M + H]⁺ |
| 354 | 3-fluoro-4-(difluoromethyl)phenyl | (3S)-1,1-dioxotetrahydrothiophen-3-yl-methylamino | powder MS(APCI):535/537 [M + H]⁺ |
| 355 | 3-fluoro-4-(difluoromethyl)phenyl | (3R)-1,1-dioxotetrahydrothiophen-3-yl-methylamino | powder MS(APCI):535/537 [M + H]⁺ |
| 356 | 3-fluoro-4-(difluoromethyl)phenyl | N-methyl-N-(2-pyridyl)hydrazino | powder MS(APCI):523/525 [M + H]⁺ |
| 357 | 4-(dimethylamino)phenyl | (3S)-1,1-dioxotetrahydrothiophen-3-yl-methylamino | powder MS(APCI):510/512 [M + H]⁺ |
| 358 | 4-(trifluoromethyl)phenyl | tetrahydrothiophen-3-yl-methylamino | powder MS(APCI):503/505 [M + H]⁺ |
| 359 | 4-(methylsulfonyl)phenyl | N-methyl-N-(2-pyridyl)hydrazino | powder MS(APCI):533/535 [M + H]⁺ |

TABLE 14-continued
(No. 13)
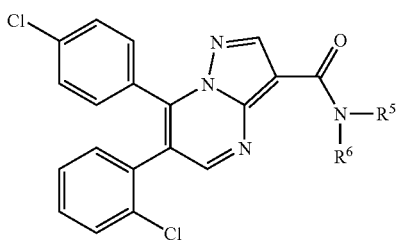
| Example Nos. | —N(R⁵)(R⁶) | Physicochemical properties etc. |
|---|---|---|
| 360 | | solid MS(APCI):551/553 [M + H]⁺ |
| 361 | | powder MS(APCI):490/492 [M + H]⁺ |
| 362 | | powder MS(APCI):515/517 [M + H]⁺ |
| 363 | | powder MS(APCI):501/503 [M + H]⁺ |
| 364 | | powder MS(APCI):498/500 [M + H]⁺ |
(No. 14)
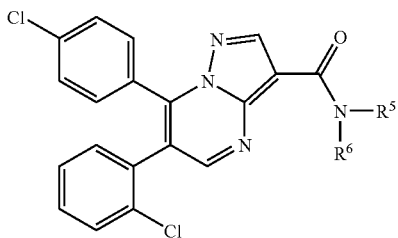
| Example Nos. | —N(R⁵)(R⁶) | Physicochemical properties etc. |
|---|---|---|
| 365 | | powder MS(APCI):451/453 [M + H]⁺ |
| 366 | | powder MS(APCI):557/559 [M + H]⁺ |

TABLE 14-continued

| | | |
|---|---|---|
| 367 | [structure: CH3-NH-CH2-CN] | solid<br>MS(ESI):422<br>[M + H]+ |
| 368 | [structure: CH3-NH-CH2-C(O)-morpholine] | solid<br>MS(ESI):510<br>[M + H]+ |
| 369 | [structure: CH3-NH-CH2CH2-pyrrolidine] | powder<br>MS(APCI):480/482<br>[M + H]+ |

(No. 15)

[Core structure: 7-(4-chlorophenyl)-pyrazolo[1,5-a]pyrimidine-3-carboxamide with R² at 5-position and N(R⁵)(R⁶) on the carboxamide]

| Example Nos. | R² | —N(R⁵)(R⁶) | Physicochemical properties etc. |
|---|---|---|---|
| 370 | 2-chloro-4-fluoro-phenyl | N(CH3)(NH)-2-pyridyl | solid<br>MS(APCI):507/509<br>[M + H]+ |
| 371 | 2,4-dichlorophenyl | (S)-3-(tetrahydrothiophene-1,1-dioxide)-NH-CH3 | powder<br>MS(APCI):535/537<br>[M + H]+ |
| 372 | 2,4-dichlorophenyl | (R)-3-(tetrahydrothiophene-1,1-dioxide)-NH-CH3 | powder<br>MS(APCI):535/537<br>[M + H]+ |
| 373 | 2,4-dichlorophenyl | CH3-N(NH)-pyrrolidine | powder<br>MS(APCI):486/488<br>[M + H]+ |
| 374 | 2,4-dichlorophenyl | N(CH3)(NH)-2-pyridyl | powder<br>MS(APCI):523/525<br>[M + H]+ |
| 375 | 2-(trifluoromethyl)phenyl | N(CH3)(NH)-2-pyridyl | powder<br>MS(APCI):523/525<br>[M + H]+ |
| 376 | 2-methoxyphenyl | 3-(tetrahydrothiophene-1,1-dioxide)-NH-CH3 | powder<br>MS(APCI):497/499<br>[M + H]+ |
| 377 | 2-methoxyphenyl | cyclohexyl-NH-CH3 | powder<br>MS(APCI):461/463<br>[M + H]+ |

TABLE 14-continued (No. 16)

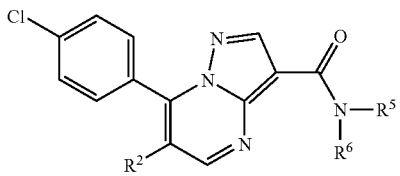

| Example Nos. | R² | —N(R⁵)(R⁶) | Physicochemical properties etc. |
|---|---|---|---|
| 378 | 2-methoxyphenyl | N-methyl-N-piperidinylamino | powder MS(APCI):462/464 [M + H]⁺ |
| 379 | 4-chlorophenyl | N-methyl-N'-methyl-N'-phenylhydrazino | powder MS(APCI):488/490 [M + H]⁺ |
| 380 | 3-chlorophenyl | N-methyl-N'-methyl-N'-phenylhydrazino | powder MS(APCI):488/490 [M + H]⁺ |

(No. 17)

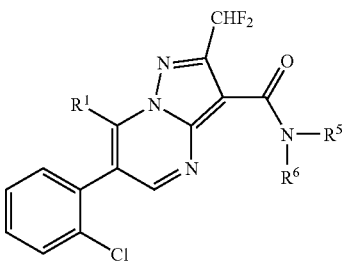

| Example Nos. | R¹ | —N(R⁵)(R⁶) | Physicochemical properties etc. |
|---|---|---|---|
| 381 | 4-chlorophenyl | (3S)-N-methyl-1,1-dioxotetrahydrothiophen-3-ylamino | powder MS(APCI):551/553 [M + H]⁺ |
| 382 | 4-chlorophenyl | (3R)-N-methyl-1,1-dioxotetrahydrothiophen-3-ylamino | powder MS(APCI):551/553 [M + H]⁺ |
| 383 | 4-chlorophenyl | N-methyl-N-pyrrolidinylamino | powder MS(APCI):502/504 [M + H]⁺ |
| 384 | 4-chlorophenyl | N-methyl-N'-methyl-N'-(2-pyridyl)hydrazino | powder MS(APCI):539/541 [M + H]⁺ |
| 385 | 4-trifluoromethylphenyl | (3S)-N-methyl-1,1-dioxotetrahydrothiophen-3-ylamino | powder MS(APCI):585/587 [M + H]⁺ |

TABLE 14-continued

| Example Nos. | R¹ | —N(R⁵)(R⁶) | Physicochemical properties etc. |
|---|---|---|---|
| 386 | F₃C—C₆H₄— | HN-(S)-tetrahydrothiophene-SO₂ | powder MS(APCI):585/587 [M + H]⁺ |
| 387 | F₃C—C₆H₄— | CH₃-N(NH—)-2-pyridyl | powder MS(APCI):573/575 [M + H]⁺ |
| 388 | 4-Cl-2-F-C₆H₃— | HN-(S)-tetrahydrothiophene-SO₂ | solid MS(APCI):569/571 [M + H]⁺ |
| 389 | 4-Cl-2-F-C₆H₃— | HN-(R)-tetrahydrothiophene-SO₂ | solid MS(APCI):569/571 [M + H]⁺ |

(No. 18)

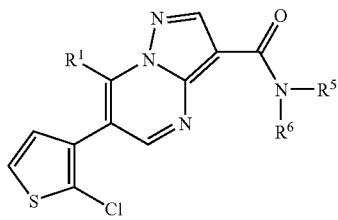

| Example Nos. | R¹ | —N(R⁵)(R⁶) | Physicochemical properties etc. |
|---|---|---|---|
| 390 | F₃C—C₆H₄— | HN-(S)-tetrahydrothiophene-SO₂ | powder MS(APCI):541/543 [M + H]⁺ |
| 391 | F₃C—C₆H₄— | HN-(R)-tetrahydrothiophene-SO₂ | powder MS(APCI):541/543 [M + H]⁺ |
| 392 | F₃C—C₆H₄— | HN—N(pyrrolidine) | powder MS(APCI):492/494 [M + H]⁺ |
| 393 | F₃C—C₆H₄— | CH₃-N(NH—)-2-pyridyl | powder MS(APCI):529/531 [M + H]⁺ |
| 394 | 4-Cl-C₆H₄— | HN-(S)-tetrahydrothiophene-SO₂ | powder MS(APCI):507/509 [M + H]⁺ |
| 395 | 4-Cl-C₆H₄— | HN—N(pyrrolidine) | powder MS(APCI):458/460 [M + H]⁺ |
| 396 | 4-Cl-C₆H₄— | CH₃-N(NH—)-2-pyridyl | powder MS(APCI):495/497 [M + H]⁺ |

TABLE 14-continued (No. 19)

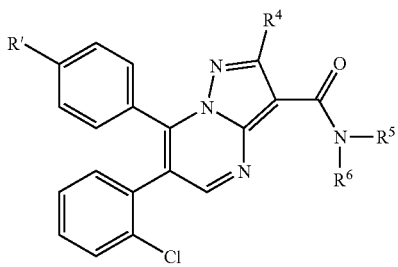

| Example Nos. | R' | R⁴ | —N(R⁵)(R⁶) | Physicochemical properties etc |
|---|---|---|---|---|
| 397 | CHF₂ | H | HN—N(pyrrolidine) | powder MS(APCI):468/470 [M + H]⁺ |
| 398 | CHF₂ | H | HN—N(piperidine) | powder MS(APCI):482/484 [M + H]⁺ |
| 399 | CHF₂ | H | HN—N(CH₃)₂ | powder MS(APCI):442/444 [M + H]⁺ |
| 400 | CHF₂ | H | HN—N(morpholine) | powder MS(APCI):484/486 [M + H]⁺ |
| 401 | Cl | CH₃OCH₂ | HN-(tetrahydrothiophene-SO₂) | powder MS(APCI):545/547 [M + H]⁺ |
| 402 | Cl | CH₃OCH₂ | HN-(tetrahydrothiophene-SO₂) | powder MS(APCI):545/547 [M + H]⁺ |
| 403 | Cl | CH₃OCH₂ | H₃C-N(pyridyl)-NH | powder MS(APCI):533/535 [M + H]⁺ |
| 404 | Cl | CH₃OCH₂ | HN—N(pyrrolidine) | powder MS(APCI):496/498 [M + H]⁺ |

(No. 20)

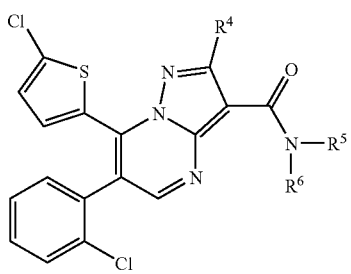

| Example Nos. | R⁴ | —N(R⁵)(R⁶) | Physicochemical properties etc. |
|---|---|---|---|
| 405 | H | HN-(tetrahydrothiophene-SO₂) | powder MS(APCI):507/509 [M + H]⁺ |

TABLE 14-continued

| | | | Physicochemical properties etc. |
|---|---|---|---|
| 406 | H | H₃C–N(–NH–)–(2-pyridyl) | powder MS(APCI):495/497 [M + H]⁺ |
| 407 | H | HN–N(pyrrolidine) | powder MS(APCI):458/460 [M + H]⁺ |
| 408 | CH₃ | HN–(tetrahydrothiophene-SO₂) (wedge) | powder MS(APCI):521/523 [M + H]⁺ |
| 409 | CH₃ | HN–(tetrahydrothiophene-SO₂) (dash) | powder MS(APCI):521/523 [M + H]⁺ |
| 410 | CH₃ | H₃C–N(–NH–)–(2-pyridyl) | powder MS(APCI):509/511 [M + H]⁺ |
| 411 | CH₃ | HN–N(pyrrolidine) | powder MS(APCI):472/474 [M + H]⁺ |

(No. 21)

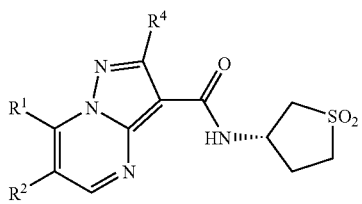

| Example Nos. | R¹ | R² | R⁴ | Physicochemical properties etc. |
|---|---|---|---|---|
| 412 | 4-Cl-2-F-phenyl | 2-Cl-phenyl | CH₃ | solid MS(APCI):533/535 [M + H]⁺ |
| 413 | 4-Cl-phenyl | 4-F-2-Cl-phenyl (with CH₃) | CH₃ | powder MS(APCI):533/535 [M + H]⁺ |
| 414 | 4-F-phenyl | 2-Cl-phenyl | CH₃ | powder MS(APCI):499/501 [M + H]⁺ |

(No. 22)

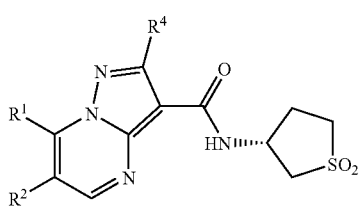

| Example Nos. | R¹ | R² | R⁴ | Physicochemical properties etc. |
|---|---|---|---|---|
| 415 | 4-Cl-phenyl | 4-F-2-Cl-phenyl (with CH₃) | | powder MS(APCI):533/535 [M + H]⁺ |

TABLE 14-continued
| | | | | |
|---|---|---|---|---|
| 416 | 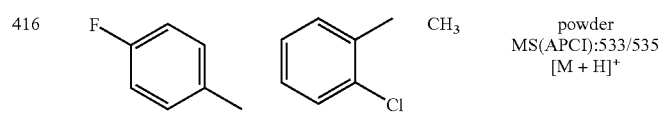 | | CH₃ | powder MS(APCI):533/535 [M + H]⁺ |
| 417 | 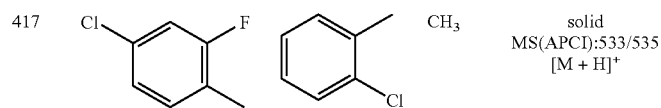 | | CH₃ | solid MS(APCI):533/535 [M + H]⁺ |
| 418 | 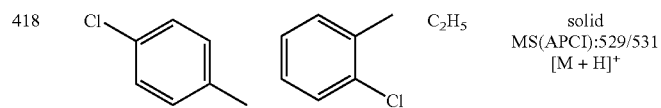 | | C₂H₅ | solid MS(APCI):529/531 [M + H]⁺ |
| 419 | 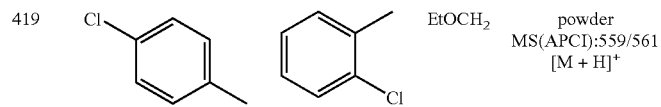 | | EtOCH₂ | powder MS(APCI):559/561 [M + H]⁺ |
(No. 23)
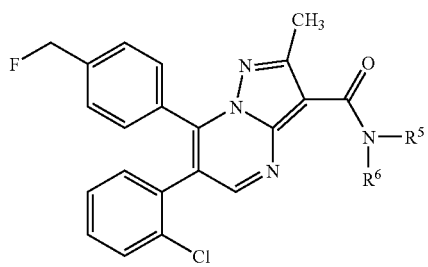
| Example Nos. | —N(R⁵)(R⁶) | Physicochemical properties etc. |
|---|---|---|
| 420 | 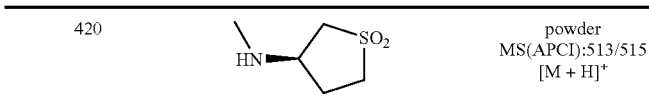 | powder MS(APCI):513/515 [M + H]⁺ |
| 421 | 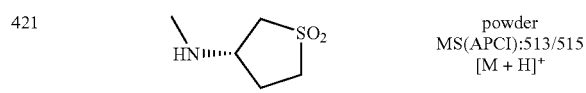 | powder MS(APCI):513/515 [M + H]⁺ |
| 422 | 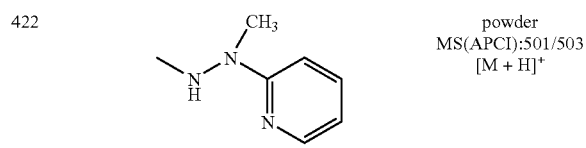 | powder MS(APCI):501/503 [M + H]⁺ |
| 423 | 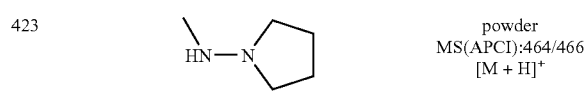 | powder MS(APCI):464/466 [M + H]⁺ |

Examples 424 to 427

The corresponding starting materials were treated in the same manner as described in Example 3 or 242 to obtain the compounds as shown in the following Table 15.

TABLE 15

| Example Nos. | R' | R" | $R^4$ | —N($R^5$)($R^6$) | Physicochemical properties etc. |
|---|---|---|---|---|---|
| 424 | H | F | H | (3-sulfolanylamino) | powder MS(APCI): 510/512 [M + H]$^+$ |
| 425 | H | F | H | (1-pyrrolidinylamino) | powder MS(APCI): 461/463 [M + H]$^+$ |
| 426 | H | F | H | (N-methyl-N'-methyl-N'-(2-pyridyl)hydrazino) | powder MS(APCI): 498/500 [M + H]$^+$ |
| 427 | F | H | $CH_3$ | (1-pyrrolidinylamino) | solid MS(APCI): 475/477 [M + H]$^+$ |

Examples 428 to 430

The corresponding starting materials were treated in the same manner as described in Example 28 to obtain the compounds as shown in the following Table 16.

TABLE 16

| Example Nos. | R' | $R^4$ | Physicochemical properties etc. |
|---|---|---|---|
| 428 | Cl | H | powder MS(APCI): 487/489 [M + H]$^+$ |
| 429 | $CF_3$ | H | powder MS(APCI): 521/523 [M + H]$^+$ |
| 430 | Cl | $CH_3$ | powder MS(APCI): 501/503 [M + H]$^+$ |

Examples 431 to 439

The corresponding starting materials were treated in the same manner as described in Example 1 to obtain the compounds as shown in the following Table 17.

TABLE 17

| Example Nos. | $R^1$ | $R^4$ | —N($R^5$)($R^6$) | Physicochemical properties etc. |
|---|---|---|---|---|
| 431 | 4-methyl-1-methylpiperidin-4-yl | H | (N-methyl-N'-methyl-N'-(2-pyridyl)hydrazino) | powder MS(APCI): 476/478 [M + H]$^+$ |

TABLE 17-continued

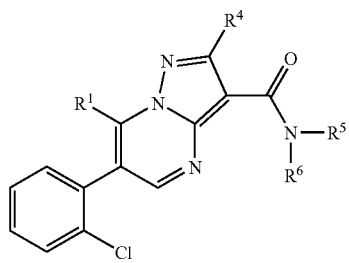

| Example Nos. | R¹ | R⁴ | —N(R⁵)(R⁶) | Physicochemical properties etc. |
|---|---|---|---|---|
| 432 | H₃CO-[1-methylpiperidin-4-yl] | H | CH₃-N(CH₃)-NH-(2-pyridyl) | powder MS(APCI): 492/494 [M + H]⁺ |
| 433 | H₃CO-[1-methylpyrrolidin-3-yl] | H | CH₃-N(CH₃)-NH-(2-pyridyl) | powder MS(APCI): 478/480 [M + H]⁺ |
| 434 | thiomorpholin-4-yl | CH₃ | CH₃-N(CH₃)-NH-(2-pyridyl) | powder MS(APCI): 494/496 [M + H]⁺ |
| 435 | H₃CO-[1-methylpiperidin-4-yl] | H | HN-(tetrahydrothiophene-1,1-dioxide-3-yl)-CH₃ | powder MS(APCI): 504/506 [M + H]⁺ |
| 436 | H₃C-[1-methylpiperidin-4-yl] | H | HN-(tetrahydrothiophene-1,1-dioxide-3-yl)-CH₃ | powder MS(APCI): 488/490 [M + H]⁺ |
| 437 | F₃C-[1-methylpiperidin-4-yl] | H | CH₃-N(CH₃)-NH-(2-pyridyl) | powder MS(APCI): 530/532 [M + H]⁺ |
| 438 | piperidin-1-yl | H | HN-N(CH₃)-piperidinyl | powder MS(APCI): 439/441 [M + H]⁺ |
| 439 | piperidin-1-yl | H | HN-cyclopentyl with CH₃ | powder MS(APCI): 424/425 [M + H]⁺ |

Example 440

(1) To a solution the compound obtained in Example 484 (2) (1.0 g) and triethylamine (1.81 mL) in tetrahydrofuran (20 mL) was added gradually methanesulfonyl chloride (1.0 g) under ice-cooling and the mixture was stirred at room temperature for 40 minutes. The reaction mixture was diluted with ethyl acetate and thereto was added water under ice-cooling. After stirring, the aqueous layer was extracted with ethyl acetate. The organic layer was dried over magnesium sulfate and filtered. The filtrate was concentrated in vacuo and the resultant crude product was purified by column chromatography on NH-silica gel (Chromatorex NH-silica gel, solvent: hexane/ethyl acetate=80/20 to 60/40) to give 6-(2-chlorophenyl)-7-(4-trifluoromethylphenyl)-3-ethoxycarbonyl-2-

[N,N-bis(methylsulfonyl)amino]-pyrazolo[1,5-a]pyrimidine (1.01 g, yield: 75%) as a pale yellow solid.

MS (APCI)m/z; 617/619 [M+H]+

(2) To a solution of the compound obtained in the above step (1) (1.01 g) in tetrahydrofuran (20 mL) was added tetrabutylammonium fluoride trihydrate (1.03 g) and the mixture was stirred at room temperature for 15 minutes. To the reaction mixture was added water and the mixture was stirred and extracted with chloroform. The extract was dried over magnesium sulfate and filtered and the filtrate was concentrated in vacuo. The resultant crude product was purified by column chromatography on silica gel (solvent: hexane/ethyl acetate=70/30 to 50/50) to give 6-(2-chlorophenyl)-7-(4-trifluoromethylphenyl)-3-ethoxycarbonyl-2-(methylsulfonylamino)pyrazolo[1,5-a]pyrimidine (0.71 g, yield: 81%) as a pale yellow powder.

MS (APCI)m/z; 539/541 [M+H]+

(3) A solution of the compound obtained in the above step (2) (0.69 g) and sodium ethoxide (0.87 g) in ethanol (20 mL) was stirred at 80° C. for 10 minutes. To the reaction mixture was added dropwise methyl iodide (1.59 mL) and the mixture was stirred overnight. The reaction mixture was concentrated in vacuo and to the residue was added water. The mixture was extracted with ethyl acetate and the organic layer was dried over magnesium sulfate and filtered. The filtrate was concentrated in vacuo and the resultant crude product was purified by column chromatography on NH-silica gel (Chromatorex NH-silica gel, solvent: hexane/ethyl acetate=75/25 to 60/40) to give 6-(2-chlorophenyl)-7-(4-trifluoromethylphenyl)-3-ethoxycarbonyl-2-[N-methyl-N-(methylsulfonyl)amino]pyrazolo[1,5-a]pyrimidine (0.70 g, yield: 99%) as a powder.

MS (APCI)m/z; 553/555 [M+H]+

Examples 441 to 452

The corresponding starting materials were treated in the same manner as described in Reference Example 1(3) and Example 3 to obtain the compounds as shown in the following Table 18.

TABLE 18

(No. 1)

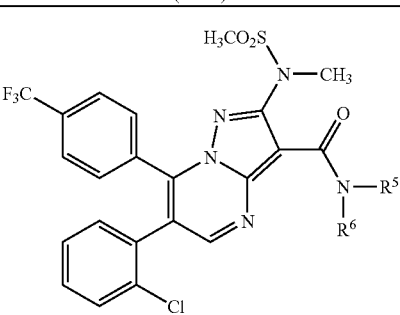

| Example Nos. | —N(R5)(R6) | Physicochemical properties etc. |
|---|---|---|
| 441 | 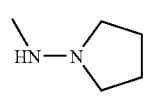 | powder MS(APCI): 567/569 [M + H]+ |
| 442 | 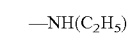 | powder MS(APCI): 593/595 [M + H]+ |
| 443 | —NH(C2H5) | powder MS(APCI): 552/554 [M + H]+ |

TABLE 18-continued

| 444 | 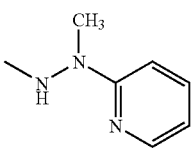 | powder MS(APCI): 630/632 [M + H]+ |
|---|---|---|
| 445 | 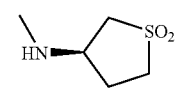 | powder MS(APCI): 642/644 [M + H]+ |
| 446 |  | powder MS(APCI): 642/644 [M + H]+ |

(No. 2)

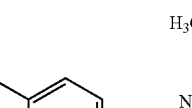

| Example Nos. | —N(R5)(R6) | Physicochemical properties etc. |
|---|---|---|
| 448 | 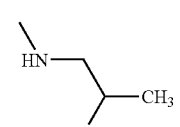 | powder MS(APCI): 608/610 [M + H]+ |
| 449 | 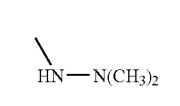 | powder MS(APCI): 546/548 [M + H]+ |
| 450 | 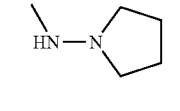 | powder MS(APCI): 533/535 [M + H]+ |
| 451 | 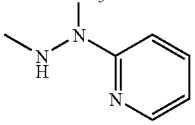 | powder MS(APCI): 559/561 [M + H]+ |
| 452 |  | powder MS(APCI): 596/598 [M + H]+ |

Examples 453 to 454

The corresponding starting materials were treated in the same manner as described in Example 3 to obtain the compounds as shown in the following Table 19.

TABLE 19

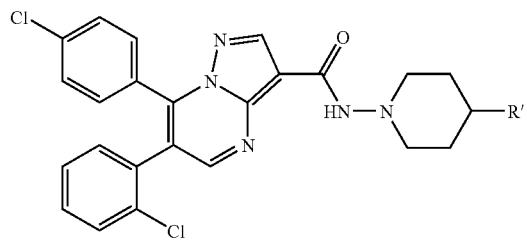

| Example Nos. | R' | Physicochemical properties etc. |
|---|---|---|
| 453 | —OCH₃ | yellow solid<br>MS(APCI): 496/498 [M + H]⁺ |
| 454 | —OH | solid<br>MS(APCI): 482/484 [M + H]⁺ |

Examples 455 to 460

The corresponding starting materials were treated in the same manner as described in Example 238 to obtain the compounds as shown in the following Table 20.

TABLE 20

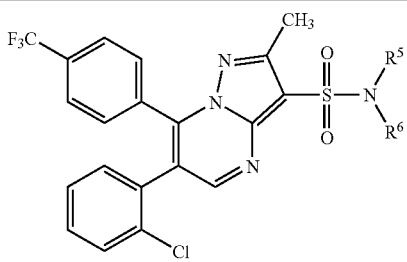

| Example Nos. | —N(R⁵)(R⁶) | Physicochemical properties etc. |
|---|---|---|
| 455 | HN—(tetrahydrothiophene-SO₂) | powder<br>MS(APCI): 585/587 [M + H]⁺ |
| 456 | HN—cyclopentyl | powder<br>MS(APCI): 535/537 [M + H]⁺ |
| 457 | —N(piperidine) | powder<br>MS(APCI): 535/537 [M + H]⁺ |
| 458 | —N(thiomorpholine-SO₂) | powder<br>MS(APCI): 585/587 [M + H]⁺ |
| 459 | H₃C—N(CH₃)—CH₂CH₃ | powder<br>MS(APCI): 509/511 [M + H]⁺ |
| 460 | H₃C—N—(2-pyridyl) | powder<br>MS(APCI): 558/560 [M + H]⁺ |

Example 461

To a solution of the compound obtained in Reference Example 53 (60 mg) in tetrahydrofuran (1 mL)-dimethylacetamide (0.2 mL) was added diiodopentane (34.5 μL) and sodium carbonate (24.5 mg) and the mixture was stirred at 70° C. for 17 hours. To the reaction mixture was added water and the mixture was extracted with ethyl acetate. The extract was concentrated in vacuo and the resultant crude product was purified by column chromatography on silica gel (solvent: hexane/ethyl acetate=85/15 to 60/40) to give 6-(2-chlorophenyl)-7-(4-trifluoromethylphenyl)-3-(piperidin-1-yl)pyrazolo[1,5-a]pyrimidine (17 mg, yield: 24%) as a red powder.

MS (APCI)m/z; 457/459 [M+H]⁺

Examples 462 to 465

The corresponding starting materials were treated in the same manner as described in Example 240 to obtain the compounds as shown in the following Table 21.

TABLE 21

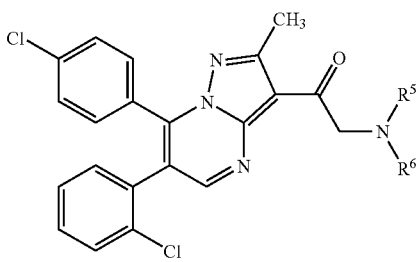

| Example Nos. | —N(R⁵)(R⁶) | Physicochemical properties etc. |
|---|---|---|
| 462 | —N(thiomorpholine-SO₂) | solid<br>MS(APCI): 529/531 [M + H]⁺ |
| 463 | —N(piperidine-F) | solid<br>MS(APCI): 497/499 [M + H]⁺ |
| 464 | —N(piperidine-F,F) | solid<br>MS(APCI): 515/517 [M + H]+ |
| 465 | H₃C—N—phenyl | solid<br>MS(APCI): 501/503 [M + H]+ |

Example 466

(1) The compound obtained in Reference Example 33 was treated in the same manner as described in Example 1 to give 6-(2-chlorophenyl)-7-(4-trifluoromethyl-phenyl)-3-[N-(1-hydroxy-4-methylthio-2-butyl)carbamoyl]pyrazolo[1,5-a]pyrimidine (357 mg, yield: 56%) as a yellow powder.

MS (APCI)m/z; 535/537 [M+H]⁺

(2) To a solution of the compound obtained in the above step (1) (349 mg) in methylene chloride (2 mL) was added thionyl chloride (170 μL) and the mixture was stirred at room temperature for 23 hours. To the reaction mixture was added chloroform (2 mL) and the mixture was stirred at 60° C. for 5 hours. After cooling to room temperature, the reaction mixture was concentrated in vacuo and the resultant crude product was purified by column chromatography on silica gel (solvent: hexane/ethyl acetate=85/15 to 60/40) to give 6-(2- chlorophenyl)-7-(4-trifluoromethylphenyl)-3-[(tetrahydrothiophene-3-yl)carbamoyl]pyrazolo[1,5-a]pyrimidine (106 mg, yield: 32%) as a pale yellow powder.

MS (APCI)m/z; 503/505 [M+H]$^+$ (3) To a solution of the compound obtained in the above step (2) (96 mg) in methylene chloride (3 mL) was added m-chloro-perbenzoic acid (75%, 44 mg) under ice-cooling and the mixture was stirred at the same temperature for 15 minutes. To the reaction mixture was added sodium sulfite and an aqueous sodium hydrogencarbonate solution and the mixture was extracted with chloroform. The extract was concentrated in vacuo and the resultant crude product was purified by column chromatography on silica gel (solvent: chloroform/methanol=100/0 to 92/8) to give 6-(2-chlorophenyl)-7-(4-trifluoromethylphenyl)-3-[(1-oxo-tetrahydrothiophene-3-yl)carbamoyl]pyrazolo[1,5-a]pyrimidine (81 mg, yield: 82%) as a colorless powder.

MS (APCI)m/z; 519/520 [M+H]$^+$

Example 467

The compound obtained in Reference Example 47 was treated in the same manner as described in Example 3 to give (R)-6-(2-chlorophenyl)-7-(4-chlorophenyl)-3-[(1,1-dioxo-tetrahydrothiophene-3-yl)carbamoyl]-2-(2-methoxyethoxy)pyrazolo[1,5-a]pyrimidine (77 mg, yield: 67%) as a powder.

MS (APCI)m/z; 575/577 [M+H]$^+$

Example 468

The corresponding starting materials were treated in the same manner as described in Example 3 to give (R)-6-(2-chlorophenyl)-7-(4-chlorophenyl)-3-[(1,1-dioxo-tetrahydrothiophene-3-yl)carbamoyl]-2-(2-hydroxyethoxy)pyrazolo[1,5-a]pyrimidine (91 mg, yield: 84%) as a powder.

MS (APCI)m/z; 561/563 [M+H]$^+$

Example 469

(1) The compound obtained in Reference Example 59 was treated in the same manner as described in Example 3 to give (R)-6-(2-chlorophenyl)-7-(4-chlorophenyl)-3-[(1,1-dioxo-tetrahydrothiophene-3-yl)carbamoyl]-2-methylthiomethylpyrazolo[1,5-a]pyrimidine (183.6 mg, yield: 91%) as a pale yellow powder.

MS (APCI)m/z; 561/563 [M+H]$^+$ (2) The compound obtained in the above step (1) (183 mg) was treated in the same manner as described in Example 29 to give (R)-6-(2-chlorophenyl)-7-(4-chlorophenyl)-3-[(1,1-dioxo-tetrahydrothiophene-3-yl)carbamoyl]-2-(methylsulfonyl methyl)pyrazolo[1,5-a]pyrimidine (91.6 mg, yield: 47%) as a powder.

MS (APCI)m/z; 593/595 [M+H]$^+$

Example 470

The compound obtained in Reference Example 9 (50 mg) and 3-pyridylacetate hydrochloride (31.8 mg) were treated in the same manner as described in Example 3 to give 6-(2-chlorophenyl)-7-(4-chlorophenyl)-3-[[2-(2-pyridyl)acetyl]amino]pyrazolo-[1,5-a]pyrimidine (52.6 mg, yield: 79%) as a yellow powder.

MS (APCI)m/z; 474/476 [M+H]$^+$

Example 471

(1) The compound obtained in Reference Example 5 (7.3 g) was treated in the same manner as described in Example 484 to give 6-(2-chlorophenyl)-7-(4-chlorophenyl)-3-ethoxycarbonyl-2-aminopyrazolo[1,5-a]pyrimidine (1.43 g).

MS (APCI)m/z; 427/429 [M+H]$^+$ (2) The compound obtained in the above step (1) (2.64 g) was treated in the same manner as described in Example 440(1) to (2) to give 6-(2-chlorophenyl)-7-(4-chlorophenyl)-3-ethoxycarbonyl-2-(methylsulfonylamino)pyrazolo[1,5-a]pyrimidine (2.20 g).

MS (APCI)m/z; 505/507 [M+H]$^+$ (3) The compound obtained in the above step (2) (70 mg) was treated in the same manner as described in Reference Example 1(3) to give 6-(2-chlorophenyl)-7-(4-chlorophenyl)-3-carboxy-2-(methylsulfonylamino)pyrazolo[1,5-a]pyrimidine as a crude product.

MS (APCI)m/z; 477/479 [M+H]$^+$ (4) The compound obtained in the above step (3) was treated in the same manner as described in Example 3 to give 6-(2-chlorophenyl)-7-(4-chlorophenyl)-3-[[N'-methyl-N'-(2-pyridyl)hydrazino]carbonyl]-2-(methylsulfonylamino)pyrazolo[1,5-a]pyrimidine (27 mg, yield: 32%) as a powder.

MS (APCI)m/z; 596/598 [M+H]$^+$

Example 472

The corresponding starting materials were treated in the same manner as described in Example 471 to give 6-(2-chlorophenyl)-7-(4-chlorophenyl)-3-(N-isobutylcarbamoyl)-2-(methylsulfonylamino)pyrazolo[1,5-a]pyrimidine (52 mg, yield: 79%) as a powder.

MS (APCI)m/z; 546/548 [M+H]$^+$

Example 473

To a solution of the compound obtained in Reference Example 9(2) (50 mg) in tetrahydrofuran (1.5 mL) was added phenyl isocyanate (30.5 µL) and triethylamine (49 µL) and the mixture was stirred at 60° C. overnight. To the reaction mixture was added water and the mixture was extracted with ethyl acetate. The extract was concentrated in vacuo and the resultant crude product was purified by column chromatography on silica gel (solvent: hexane/ethyl acetate=75/25 to 65/35) to obtain 6-(2-chlorophenyl)-7-(4-chlorophenyl)-3-(N'-phenylureido)pyrazolo[1,5-a]pyrimidine (37.8 mg, yield: 57%) as a powder.

MS (APCI)m/z; 474/476 [M+H]$^+$

Examples 474

The corresponding starting materials were treated in the same manner as described in Example 473 to obtain 6-(2-chlorophenyl)-7-(4-chlorophenyl)-3-(N'-cyclopentylureido)pyrazolo[1,5-a]pyrimidine (48.3 mg, yield: 74%) as a powder.

MS (APCI)m/z; 466/468 [M+H]$^+$

Examples 475 to 478

The corresponding starting materials were treated in the same manner as described in Example 3 to obtain the compounds as shown in the following Table 22.

TABLE 22

Boc: tert-butoxycarbonyl group

| Example Nos. | R¹ | R² | —N(R⁵)(R⁶) | Physicochemical properties etc. |
|---|---|---|---|---|
| 475 | 4-Cl-phenyl | 2-Cl-phenyl | HN-N(pyrrolidine with OH and NHBoc) | solid MS(APCI): 583/585 [M + H]+ |
| 476 | 4-Cl-phenyl | 3-Cl-4-methylpyridyl | HN-(tetrahydrothiophene-SO₂) | powder MS(APCI): 502/504 [M + H]+ |
| 477 | 4-Cl-phenyl | 2-Cl-phenyl | HN-CH₂CH₂-SO₂-CH₃ | powder MS(APCI): 489/491 [M + H]+ |
| 478 | 2-Cl-phenyl | 2-Cl-phenyl | HN-cyclopentyl | powder MS(APCI): 451/453 [M + H]+ |

Examples 479

The corresponding starting materials were treated in the same manner as described in Example 31 to obtain 6-(2-cyanophenyl)-7-(4-trifluoromethylphenyl)-3-[N-(1,1-dioxothiomorpholino)carbamoyl]pyrazolo[1,5-a]pyrimidine as a powder.

MS (APCI)m/z; 541 [M+H]⁺

Example 480

(1) The compound obtained in Example 471(1) (440 mg) was treated in the same manner as described in Reference Example 1(3) to give 6-(2-chlorophenyl)-7-(4-chlorophenyl)-3-carboxy-2-aminopyrazolo[1,5-a]pyrimidine as a crude product.

MS (APCI)m/z; 399/401 [M+H]⁺

(2) The compound obtained in the above step (1) was treated in the same manner as described in Example 3 to give (R)-6-(2-chlorophenyl)-7-(4-chlorophenyl)-3-[N-(1,1-dioxotetrahydrothiophen-3-yl)carbamoyl]-2-aminopyrazolo[1,5-a]pyrimidine (254 mg, yield: 48%) as a powder.

MS (APCI)m/z; 516/518 [M+H]⁺

(3) The compound obtained in the above step (2) (250 mg) was treated in the same manner as described in Example 43 to give (R)-6-(2-chlorophenyl)-7-(4-chloro-phenyl)-3-[N-(1,1-dioxotetrahydrothiophen-3-yl)carbamoyl]-2-(pyrrolidin-1-yl)-pyrazolo[1,5-a]pyrimidine (106 mg, yield: 38%) as a powder.

MS (APCI)m/z; 570/572 [M+H]⁺

(4) The compound obtained in the above step (3) (95 mg) was treated in the same manner as described in Example 33 to give the compound as shown in the following Table 23.

TABLE 23

| Example Nos. | —N(R⁵)(R⁶) | Physicochemical properties etc. |
|---|---|---|
| 480 | HN-(R)-(tetrahydrothiophene-SO₂) | powder MS(APCI): 586/588 [M + H]+ |

Example 481

The compound obtained in Reference Example 46 (3.0 g) and 3-(N,N-dimethylamino)-1-(4-chlorophenyl)-2-(2-chlorophenyl)-2-propen-1-one (6.18 g) were treated in the same manner as described in Reference Example 1(2) to give 6-(2-chlorophenyl)-7-(4-chlorophenyl)-2-ethoxycarbonylpyrazolo[1,5-a]pyrimidine (3.57 g, yield: 45%) as a colorless powder.
MS (APCI)m/z; 412/414 [M+H]$^+$

Example 482

(1) The compound obtained in Example 481 (2.5 g) was treated in the same manner as described in Reference Example 1(3) to give 2-carboxy-6-(2-chlorophenyl)-7-(4-chlorophenyl)pyrazolo[1,5-a]pyrimidine (1.65 g) as a crude product.
MS (APCI)m/z; 384/386 [M+H]$^+$ (2) The compound obtained in the above step (1) (80 mg) and 1-methyl-1-(2-pyridyl)hydrazine (26 mg) were treated in the same manner as described in Example 3 to give 6-(2-chlorophenyl)-7-(4-chlorophenyl)-2-[[N'-methyl-N'-(2-pyridyl)hydrazino]carbonyl]pyrazolo[1,5-a]pyrimidine (85 mg) as a colorless powder.
MS (APCI)m/z; 489/491 [M+H]$^+$

Example 483

The compound obtained in Reference Example 18 (5-amino-4-ethoxycarbonyl-3-methylthio-1H-pyrazole, 10.1 g) and 3-(N,N-dimethylamino)-1-(4-trifluoromethyl-phenyl)-2-(2-chlorophenyl)-2-propen-1-one (17.7 g) were treated in the same manner as described in Reference Example 5(1) to give 6-(2-chlorophenyl)-7-(4-chlorophenyl)-3-ethoxycarbonyl-2-methylthiopyrazolo[1,5-a]pyrimidine (11.4 g, yield: 45%) as a colorless powder.
MS (APCI)m/z; 492/494 [M+H]$^+$

Example 484

(1) The compound obtained in Example 483 (11 g) was treated in the same manner as described in Reference Example 5(2) to give 2-azido-6-(2-chlorophenyl)-7-(4-trifluoromethylphenyl)-3-ethoxycarbonylpyrazolo[1,5-a]pyrimidine (10.6 g, yield: 91%) as a crude product (colorless powder). The product (10.6 g) was treated in the same manner as described in Reference Example 11 to give 6-(2-chlorophenyl)-7-(4-chlorophenyl)-3-ethoxycarbonyl-2-(triphenylphosphoranylidenamino)pyrazolo[1,5-a]-pyrimidine (11.4 g) as a colorless powder.

(2) The compound obtained in the above step (1) (11.1 g) and acetic acid (70 mL) were treated in the same manner as described in Example 40 to give 6-(2-chlorophenyl)-7-(4-trifluoromethylphenyl)-3-ethoxycarbonyl-2-aminopyrazolo-[1,5-a]pyrimidine (5.2 g, yield: 73%) as a colorless solid.
MS (APCI)m/z; 461/463 [M+H]$^+$

Example 485

The compound obtained in Example 484 (2.1 g) and 1,4-dichlorobutane (2.9 g) were treated in the same manner as described in Example 43 to give 6-(2-chlorophenyl)-7-(4-trifluoromethylphenyl)-3-ethoxycarbonyl-2-(pyrrolidin-1-yl)pyrazolo[1,5-a]-pyrimidine (0.61 g, yield: 26%) as a yellow oil.
MS (APCI)m/z; 515/517 [M+H]$^+$

Example 486

The compound obtained in Example 485 (0.61 g) was treated in the same manner as described in Reference Example 8 to give 6-(2-chlorophenyl)-7-(4-trifluoromethylphenyl)-3-carboxy-2-(pyrrolidin-1-yl)pyrazolo[1,5-a]pyrimidine (0.45 g) as a crude product. The product (70 mg) and 1-aminopyrrolidine hydrochloride (17.6 mg) were treated in the same manner as described in Example 3 to give 6-(2-chlorophenyl)-7-(4-trifluoromethylphenyl)-3[N-pyrrolidin-1-yl)carbamoyl]-2-(pyrrolidin-1-yl)pyrazolo[1,5-a]pyrimidine (14.8 mg; compound a) and 6-(2-chlorophenyl)-7-(4-trifluoromethylphenyl)-2-(pyrrolidin-1-yl)pyrazolo[1,5-a]-pyrimidine (32.6 mg; compound b) as a yellow powder, respectively.

Compound a: MS (APCI)m/z; 555/557 [M+H]$^+$
Compound b: MS (APCI)m/z; 443/445 [M+H]$^+$

Example 487

(1) To a solution of the compound obtained in Reference Example 4B (300 mg) in dimethylformamide (5 mL) was added portionwise sodium hydride (60%, 137 mg) under nitrogen-gas atmosphere and the mixture was stirred. To the mixture was gradually added 4-chloro-N-methylaniline (125 μL) and the mixture was stirred at 80° C. for 30 minutes. After cooling to room temperature, to the reaction mixture was added water and ethyl acetate and the aqueous layer was neutralized with 2N HCl. The organic layer was washed with water, dried over magnesium sulfate and filtered. The filtrate was concentrated in vacuo and the resultant crude product was purified by column chromatography on silica gel (solvent: chloroform/methanol=98/2 to 85/15) to obtain 6-(2-chlorophenyl)-7-[N-methyl-N-(4-chlorophenyl)amino]-3-carboxy-2-methyl-pyrazolo[1,5-a]pyrimidine (54.2 mg, yield: 15%) as a colorless powder.
MS (APCI)m/z; 427/429 [M+H]$^+$ (2) The compound obtained in the above step (1) (27 mg) was treated in the same manner as described in Example 3 to give 6-(2-chlorophenyl)-7-[N-methyl-N-(4-chlorophenyl)amino]-3-[N'-methyl-N'-(pyridin-2-yl)hydrazino]-2-methylpyrazolo-[1,5-a]pyrimidine (18.5 mg, yield: 55%) as a colorless powder.
MS (APCI)m/z; 532/533 [M+H]$^+$

Examples 488 to 489

The corresponding starting materials were treated in the same manner as described in Example 487 to obtain the compounds as shown in the following Table 24.

TABLE 24

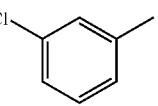

| Example Nos. | R¹ | —N(R⁵)(R⁶) | Physicochemical properties etc. |
|---|---|---|---|
| 488 | 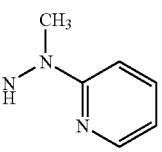 | 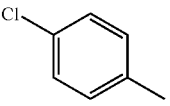 | powder<br>MS(APCI): 532/534 [M + H]⁺ |
| 489 | 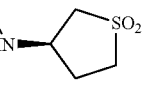 | 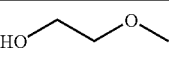 | powder<br>MS(APCI): 544/546 [M + H]⁺ |

Examples 490 to 500

The corresponding starting materials were treated in the same manner as described in Example 487 to obtain the compounds as shown in the following Table 25.

TABLE 25

(No. 1)

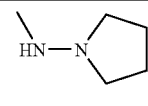

| Example Nos. | R⁴ | —N(R⁵)(R⁶) | Physicochemical properties etc. |
|---|---|---|---|
| 490 | 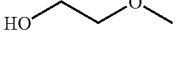 | 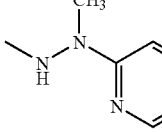 | powder<br>MS(APCI): 512/514 [M + H]⁺ |
| 491 | 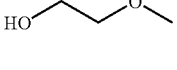 | 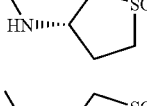 | powder<br>MS(APCI): 549/551 [M + H]⁺ |
| 492 | 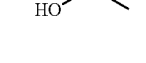 | 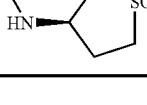 | powder<br>MS(APCI): 561/563 [M + H]⁺ |
| 493 | HO⁓ | 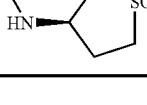 | powder<br>MS(APCI): 531/533 [M + H]⁺ |

TABLE 25

(No. 2)

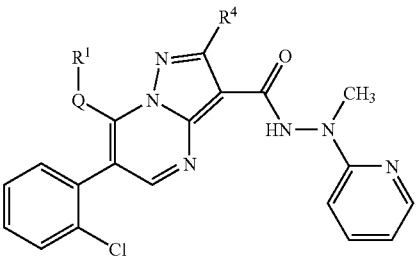

| Example Nos. | R¹—Q— | R⁴ | Physicochemical properties etc. |
|---|---|---|---|
| 494 | H₃C∼O—[1-methylpiperidin-4-yloxy] | H | powder MS(APCI): 506/508 [M + H]⁺ |
| 495 | (H₃C)₂N—[4-methylphenyl]— | H | powder MS(APCI): 498/500 [M + H]⁺ |
| 496 | H₃C—O—CH₂—[1-methylpiperidin-4-yl]— | H | powder MS(APCI): 520/522 [M + H]⁺ |
| 497 | H₃CO—CH₂CH₂—O—[1-methylpiperidin-4-yloxy] | H | powder MS(APCI): 544/546 [M + H]⁺ |
| 498 | Cl—[4-chlorobenzyl]—CH₂— | CH₃ | powder MS(APCI): 517/519 [M + H]⁺ |
| 499 | [azepan-1-yl]— | H | powder MS(APCI): 476/478 [M + H]⁺ |
| 500 | [thiomorpholin-4-yl]— | H | powder MS(APCI): 464/466 [M + H]⁺ |

Reference Example 1

(1) To diethylether (250 mL) was added magnesium (6.04 g) and a catalytic amount of iodine and the mixture was stirred and thereto was gradually added dropwise 2-chlorobenzyl chloride (20.0 g). After stirring for 1 hour from the time when the temperature of such mixture began to rise, thereto was added a solution of 4-chlorobenzonitrile (18.8 g) in tetrahydrofuran/diethylether (20 mL/50 mL) and the mixture was stirred for 3 hours. To the reaction mixture was added 2N HCl (150 mL) under ice-cooling and the mixture was stirred at room temperature for 2 hours. The reaction mixture was extracted with ethyl acetate and the organic layer was washed with 1N HCl, water and saturated brine, dried over magnesium sulfate and filtered. The filtrate was concentrated in vacuo and the resultant crude product was purified by column chromatography on silica gel (solvent: hexane/ethyl acetate=40/1 to 20/1) to obtain 2-(chlorobenzyl)(4-chlorophenyl)methanone (24.40 g; yield: 74%) as a powder.

MS (APCI)m/z; 265/267 [M+H]⁺

(2) A solution of the compound obtained in the above step (1) (6.4 g) and N, N-dimethylformamide dimethylacetal (6.4 mL) in N,N-dimethylformamide (24 mL) was stirred at 150° C. for 4 hours. After cooling the reaction mixture to room temperature, thereto was added water and the mixture was extracted with a mixture of ethyl acetate and hexane (×3). The organic layer was washed with saturated brine, dried over magnesium sulfate and filtered. The filtrate was concentrated in vacuo to obtain 3-(N,N-dimethylamino)-1-(4-chlorophenyl)-2-(2-chlorophenyl)-2-propen-1-one as an oil. To a solution of the compound in acetic acid (8 mL) was added 3-amino-4-ethoxycarbonyl-1H-pyrazole (3.75 g) and piperidine (0.48 mL) and the mixture was heated at 80° C. for 16 hours. After cooling the reaction mixture to room temperature, thereto was added water and ethyl acetate and the organic layer was washed with saturated brine, dried over magnesium sulfate and filtered. The filtrate was concentrated in vacuo and the resultant crude product was purified by column chromatography on silica gel (solvent: hexane/ethyl acetate=17/3 to 67/33) to obtain 6-(2-chlorophenyl)-7-(4-chlorophenyl)-3-ethoxycarbonylpyrazolo[1,5-a]pyrimidine (5.02 g, yield: 50%) as a powder.

MS (APCI)m/z; 412/414 [M+H]+

(3) To a solution of the compound obtained in the above step (2) (2.5 g) in ethanol (30 mL) was added 2N sodium hydroxide (6 mL) and the mixture was stirred at room temperature for 5 hour. To the reaction mixture was 2N HCl (6 mL) and the mixture was stirred and concentrated in vacuo. The residue was extracted with ethyl acetate and the organic layer was washed with saturated brine, dried over magnesium sulfate and filtered. The filtrate was concentrated in vacuo to obtain 6-(2-chlorophenyl)-7-(4-chlorophenyl)-3-carboxypyrazolo[1,5-a]pyrimidine (2.1 g, yield: 90%) as a powder.

MS (APCI)m/z; 384/386 M+H]+

Reference Example 2

(1) To dimethoxyethane (100 mL) was added 4-chlorobenzylbromide (4.1 g), 4-chlorobenzoylchloride (2.56 mL), bis(triphenylphosphine)palladium dichloride (702 mg) and zinc powder (2.6 g) and the mixture was stirred for 2 hours under nitrogen gas atmosphere. The reaction mixture was filtered and the filtrate was concentrated in vacuo and extracted with ethyl acetate. The organic layer was washed with saturated brine, dried over magnesium sulfate and filtered. The filtrate was concentrated in vacuo and the resultant crude product was purified by column chromatography on silica gel (solvent: hexane/ethyl acetate=49/1 to 9/1) to obtain (4-chlorobenzyl)(4-chlorophenyl)methanone (4.85 g, yield: 91%) as a powder.

MS (GC-EI)m/z; 264 [M]+

(2) The compound obtained in the above step (1) was treated in the same manner as described in Reference Example 1(2) and (3) to give 3-carboxyl-6-(4-chlorophenyl)-7-(4-chlorophenyl)pyrazolo[1,5-a]pyrimidine (165 mg, yield: 20%) as a powder.

MS (APCI)m/z; 384/386 M+H]+

Reference Example 3

The corresponding starting materials were treated in the same manner as described in Reference Example 1 to give 3-carboxyl-6-phenyl-7-(4-chlorophenyl)-pyrazolo[1,5-a]pyrimidine (2.06 g, yield: 22%) as a powder.

MS (APCI)m/z; 350/352 M+H]+

Reference Example 4

(1) To a solution of methyl 2-chlorophenylacetate (10 g) in dimethylformamide (150 mL) was added N,N-dimethylformamide dimethylacetal (14.4 mL) and the mixture was stirred at 85° C. overnight. After cooling to room temperature, to the reaction mixture was added ethyl acetate and water and the mixture was stirred. The organic layer was extracted, dried over sodium sulfate and filtered. The filtrate was concentrated in vacuo and the residue was diluted with acetic acid (18 mL). Thereto was added 3-amino-4-ethoxycarbonyl-1H-pyrazole (8.4 g) and piperidine (1.1 mL) and the mixture was stirred at 80° C. for 3.5 hours. After cooling to room temperature, to the reaction mixture was added ethyl acetate and water and the mixture was stirred and filtered. The resultant solid materials were dried to obtain 5-[2-(2-chlorophenyl)-2-methoxycarbonylvinylamino]-4-methoxycarbonyl-1H-pyrazole (11.8 g, yield: 62%) as a powder.

MS (APCI)m/z; 350/352 M+H]+

(2) To a solution of the compound obtained in the above step (1) (10.7 g) in ethanol (250 mL) was added sodium carbonate 3.24 g and the mixture was refluxed under heating for 4 days. After cooling to room temperature, the reaction mixture was filtered and the filtrate was concentrated in vacuo. To the residue was added water and the mixture was stirred and filtered (such filtration step was repeated in 5 times). The resultant solid materials were dried to obtain 6-(2-chlorophenyl)-3-ethoxycarbonyl-7-oxo-4,7-dihydropyrazolo[1,5-a]pyrimidine (8.5 g, yield: 87%) as a powder.

MS (APCI)m/z; 318/320 M+H]+

(3) To a solution of the compound obtained in the above step (2) (300 mg) in acetonitrile (2 mL) was added N,N-dimethylanilin (319 μL) and phosphorus oxychloride (270 μL) and the mixture was refluxed under heating for 1 day. After cooling to room temperature, the reaction mixture was poured to water with ice and extracted with methylene chloride. The extract was dried over magnesium sulfate and filtered and the filtrate was concentrated in vacuo. The resultant crude product was purified by a column chromatography on silica gel (solvent; hexane/ethyl acetate=80/20 to 60/40) to give 7-chloro-6-(2-chlorophenyl)-3-ethoxycarbonylpyrazolo[1,5-a]-pyrimidine (108 mg, yield: 34%) as a powder.

MS (APCI)m/z; 336/338 M+H]+

(4) A solution of the compound obtained in the above step (3) (100 mg), [1,1'-bis(diphenylphosphio)ferrocene]palladium (II) dichloride-methylene chloride complex (7.3 mg), potassium phosphate (189 mg) and 4-fluorophenylboronic acid 846 mg) in 1,4-dioxane (3 mL) was stirred at 80° C. for 5 hours under nitrogen gas atmosphere. After cooling to room temperature, to the reaction mixture was added methylene chloride and a brine and the mixture was stirred. The organic layer was extracted and the extract was dried over magnesium sulfate and filtered. The filtrate was concentrated in vacuo and the resultant crude product was purified by a column chromatography on silica gel (solvent; hexane/ethyl acetate=80/20 to 65/35) to give 6-(2-chlorophenyl)-3-ethoxycarbonyl-7-(4-fluorophenyl)pyrazolo[1,5-a]pyrimidine (106 mg, yield: 90%) as a powder.

MS (APCI)m/z; 396/398 M+H]+

Reference Example 4B

A solution of methyl 2-chlorophenylacetate (25 g) in dimethylformamide (400 mL) was added N,N-dimethylformamide dimethylacetal (36 mL) and the mixture was stirred at 90° C. overnight. After cooling to room temperature, to the reaction mixture was added ethyl acetate and water and the mixture was stirred and extracted. The organic layer was dried over magnesium sulfate and filtered. The filtrate was concentrated in vacuo and the residue was diluted with acetic acid (60 mL). Thereto was added 3-amino-4-ethoxycarbonyl-2-methyl-1H-pyrazole (19.7 g) and the mixture was stirred at 120° C. overnight. After cooling to room temperature, the precipitates were collected by filtration and washed to give 6-(2-chlorophenyl)-3-ethoxycarbonyl-2-methyl-7-oxo-4,7-dihydropyrazolo[1,5-a]pyrimidine (26.0 g, yield in the two steps: 62%) as a powder.

MS (APCI)m/z; 332/334 [M+H]+

Reference Example 5

(1) A solution of 5-amino-4-ethoxycarbonyl-3-methylthio-1H-pyrazole (compound obtained in Reference Example 18, 6.8 g), 3-(N,N-dimethylamino)-1-(4-chlorophenyl)-2-(2-chlorophenyl)-2-propene-1-one (10.9 g) and piperidine (578 mg) in acetic acid (13 mL) was stirred at 80° C. overnight. After cooling to room temperature, to the reaction mixture was added water and ethyl acetate. The organic layer was washed with a brine, dried over magnesium sulfate and filtered. The filtrate was concentrated in vacuo and the resultant crude product was purified by a column chromatography on silica gel (solvent; hexane/ethyl acetate=85/15 to 70/30) to give 6-(2-chlorophenyl)-7-(4-fluorophenyl)-3-ethoxycarbonyl-2-methylthiopyrazolo[1,5-a]pyrimidine (5.88 g, yield: 38%) as a yellow solid.

(2) To a solution of the compound obtained in the above step (1) (5.86 g) in methylene chloride (200 mL) was added 3-chloroperbenzoic acid (70%, 9.46 g) under ice-cooling and the mixture was stirred at the same temperature for 10 minutes and at room temperature for 3 hours. To the reaction mixture was added an aqueous sodium thiosulfate solution. The mixture was stirred at room temperature and thereto was added ethyl acetate and water. The organic layer was dried over magnesium sulfate and filtered. The filtrate was concentrated in vacuo and the resultant crystals were washed with ice-cooled ethanol and dried to give 6-(2-chlorophenyl)-7-(4-chlorophenyl)-3-ethoxycarbonyl-2-methylsulfonylpyrazolo[1,5-a]pyrimidine (5.52 g, yield: 88%) as a pale yellow solid.

(3) To a solution of the compound obtained in the above step (2) (1.0 g) in ethanol/tetrahydrofuran (26 mL/30 mL) was added sodium ethoxide (1.66 g) and the mixture was refluxed under heating. After cooling to room temperature, to the reaction mixture was added water and sodium acetate. The organic layer was washed with a brine, dried over magnesium sulfate and filtered. The filtrate was concentrated in vacuo and the resultant crude product was purified by a column chromatography on silica gel (solvent; hexane/ethyl acetate=80/20 to 40/60) to give 6-(2-chlorophenyl)-7-(4-fluorophenyl)-2-ethoxy-3-ethoxycarbonylpyrazolo[1,5-a]pyrimidine (86 mg, yield: 9.2%) as a pale yellow solid.

MS (APCI)m/z; 456/458 M+H]$^+$ (4) The compound obtained in the above step (3) (455 mg) was treated in the same manner as described in Reference Example 1(3) to give 3-carboxy-6-(2-chlorophenyl)-7-(4-fluorophenyl)-2-ethoxypyrazolo[1,5-a]pyrimidine (490 mg) as a pale yellow solid.

MS (APCI)m/z; 428/430 M+H]$^+$

Reference Example 6

(1) A mixture of 1-(4-chlorophenyl)ethanone (13.1 g) and C-tert-butoxy-N,N,N',N'-tetramethylmethylenediamine (16.3 g) was stirred at 60° C. overnight. After cooling to room temperature, the reaction mixture was concentrated in vacuo to give 1-(4-chlorophenyl)-3-(N,N-dimethylamino)-2-propen-1-one (18.4 g, yield: 100%) as a yellow solid.

MS (APCI)m/z; 210/212 M+H]$^+$ (2) To a solution of the compound obtained in the above step (1) (18.4 g) in methylene chloride (105 mL) was added dropwise bromine (13.6 g) under ice-cooling over a period of 10 minutes and the mixture was stirred at the same temperature for 30 minutes. To the reaction mixture was added dropwise a solution of triethylamine (11.8 mL) in diethylether (130 mL) over a period of 5 minutes and the mixture was stirred for 2 hours. After warming to room temperature, the reaction mixture was filtered and to the residue was added methylene chloride (20 mL) and diisopropylether (50 mL). After stirring for 1 hour, the resultant crystals were collected by filtration and dried in vacuo to give 2-bromo-1-(4-chlorophenyl)-3-(N,N-dimethylamino)-2-propene-1-one (20.2 g, yield: 82%) as a pale yellow solid.

MS (APCI)m/z; 288/290 M+H]$^+$ (3) To a solution of the compound obtained in the above step (2) (20.2 g) and 3-amino-4-ethoxycarbonylpyrazole (10.9 g) in ethanol (65 mL) was added 25% hydrogen bromide/acetic acid solution (13 mL) and the mixture was refluxed under heating for 1 hour. After cooling to room temperature, the reaction mixture was concentrated in vacuo and the residue was dissolved in chloroform (200 mL). The solution was washed with an aqueous saturated sodium hydrogencarbonate solution and a brine, dried over magnesium sulfate and filtered. The filtrate was concentrated in vacuo and the resultant crude product was purified by a column chromatography on silica gel (solvent; ethyl acetate/chloroform=0/100 to 10/90) and crystallized from diisopropylether to give 6-bromo-7-(4-fluorophenyl)-3-ethoxycarbonylpyrazolo[1,5-a]-pyrimidine (13.8 g, yield: 52%) as a colorless solid.

MS (APCI)m/z; 380/382 M+H]$^+$ (4) A solution of the compound obtained in the above step (3) (1.0 g), 2-(trifluoromethyl)phenylboronic acid (549 mg), [1,1'-bis(diphenylphosphio)ferrocene] palladium(II) dichloride-methylene chloride complex (77 mg) and potassium phosphate (1.55 g) in 1,4-dioxane (51 mL) was stirred at 80° C. overnight and at 90° C. for 8 hours under nitrogen gas atmosphere. After cooling to room temperature, the reaction mixture was diluted with ethyl acetate and filtered. The filtrate was concentrated in vacuo and the residue was diluted with tetrahydrofuran (34 mL). Thereto was added an aqueous 1N lithium hydroxide solution (16 mL) and the mixture was stirred at 55° C. overnight. After cooling to room temperature, to the reaction mixture was added chloroform, water and an aqueous 1N HCl and the organic layer was separated. The organic layer was washed with a brine, dried over sodium sulfate and filtered. The filtrate was concentrated in vacuo and the resultant product was recrystallized to give 3-carboxy-7-(4-chlorophenyl)-6-(2-trifluoromethylphenyl)pyrazolo[1,5-a]pyrimidine (370 mg, yield: 34%) as a pale yellow solid.

MS (APCI)m/z; 418/420 M+H]$^+$

Reference Example 7

To a solution of the compound obtained in Reference Example 4(3) (168 mg) in dimethylformamide (5 mL) was added pyrrolidine (50 μL) and potassium carbonate (138 mg) and the mixture was stirred at 160° C. for 5 minutes in a microwave reactor. After cooling to room temperature, to the reaction mixture was added water and the mixture was stirred and extracted with methylene chloride. The extract was concentrated in vacuo and the resultant crude product was purified by a column chromatography on silica gel (solvent; hexane/ethyl acetate=80/20 to 65/35) to give 6-(2-chlorophenyl)-3-ethoxycarbonyl-7-(1-pyrrolidinyl)pyrazolo[1,5-a]pyrimidine (116 mg, yield: 63%) as a powder.

MS (APCI)m/z; 371/373 M+H]$^+$

Reference Example 7B (1) The corresponding starting materials were treated in the same manner as described in Reference Example 4B and 4(3) to give 6-(2-chlorophenyl)-7-chloro-3-ethoxycarbonyl-2-methylpyrazolo[1,5-a]pyrimidine.

(2) To a solution of the compound obtained in the above step (1) (300 mg) in dimethylformamide (3 mL) was added thiomorpholine (103 μL) and potassium carbonate (237 mg) and the mixture was stirred at 80° C. for 40 minutes. After cooling to room temperature, to the reaction mixture was added water and the mixture was stirred and extracted with ethyl acetate. The extract was dried over magnesium sulfate and filtered. The filtrate was concentrated in vacuo and the resultant crude product was purified by a column chromatography on silica gel (solvent; hexane/ethyl acetate=5/2) to give 6-(2-chlorophenyl)-7-thiomorpholino-3-ethoxycarbonyl-2-methyl-pyrazolo[1,5-a]pyrimidine (324 mg, yield: 91%) as a powder.

MS (APCI)m/z; 417/419 M+H]$^+$

Reference Example 8

To a solution of the compound obtained in Reference Example 5(1) (11.5 g) in ethanol/tetrahydrofuran (58 mL/58 mL) was added an aqueous 2N sodium hydroxide solution (50.2 mL) and the mixture was stirred at 60° C. for 8 hours. After cooling to room temperature, the reaction mixture was concentrated in vacuo. To the residue was added chloroform, a brine and an aqueous 2N HCl and the mixture was stirred (pH 2 to 3). The organic layer was dried over magnesium sulfate and filtered. The filtrate was concentrated in vacuo and the precipitated crystals were washed with diethylether to give 3-carboxy-6-(2-chlorophenyl)-7-(4-chlorophenyl)-2-methylthiopyrazolo[1,5-a]pyrimidine (11.1 g, yield: 100%) as a pale yellow solid.

MS (APCI)m/z; 430/432 M+H]$^+$

Reference Example 9

(1) To a solution of the compound obtained in Reference Example 1(4) (2.0 g) in tert-butyl alcohol (15 mL) was added diphenyl phosphoryl azide (1.15 mL) and triethylamine (725 μL) and the mixture was stirred at 80° C. overnight. After cooling to room temperature, to the reaction mixture was added water and ethyl acetate and the mixture was stirred. The organic layer was washed with brine, dried over magnesium sulfate and filtered. The filtrate was concentrated in vacuo and the resultant crude product was purified by a column chromatography on silica gel (solvent; hexane/ethyl acetate=80/20 to 55/45) to give 3-tert-butoxycarbonylamino-6-(2-chlorophenyl)-7-(4-chlorophenyl)pyrazolo[1,5-a]pyrimidine (1.0 g, yield: 42%) as a powder.

MS (APCI)m/z; 455/457 M+H]$^+$ (2) To a solution of the compound obtained in the above step (1) (1.0 g) in 1,4-dioxane (8 mL) was added 4N HCl-1,4-dioxane (16 mL) and the mixture was stirred at room temperature for 1.5 hours. To the reaction mixture was added methanol (2 mL) and the mixture was stirred at room temperature for 3.5 hours. The reaction mixture was concentrated in vacuo and the residue was crystallized from diisopropylether to give 3-amino-6-(2-chlorophenyl)-7-(4-chlorophenyl)pyrazolo-[1,5-a]pyrimidine hydrochloride (809 mg, yield: 94%) as a pale orange powder.

MS (APCI)m/z; 355/357 M+H]$^+$

Reference Example 10

(1) To a solution of the compound obtained in Reference Example 1(4) (300 mg) in methylene chloride (4.0 mg) was added N-tert-butoxycarbonylhydrazine (135 mL), water-soluble carbodiimide HCl (224 mg), 1-hydroxybenzotriazole (179 mg) and triethylamine (326 mg) and the mixture was stirred at room temperature overnight. To the reaction mixture was an aqueous sodium hydrogencarbonate solution and methylene chloride and the mixture was stirred. The organic layer was washed with brine, dried over magnesium sulfate and filtered. The filtrate was concentrated in vacuo and the resultant crude product was purified by a column chromatography on NH-silica gel (Chromatorex NH-silica gel/Fuji Silicia Chem., solvent; hexane/ethyl acetate=70/30 to 40/60) to give 3-(N'-tert-butoxycarbonylhydrazino)carbonyl-6-(2-chlorophenyl)-7-(4-chlorophenyl)pyrazolo[1,5-a]pyrimidine (379 mg, yield: 97%) as a powder.

MS (APCI)m/z; 498/500 M+H]$^+$ (2) To a solution of the compound obtained in the above step (1) (345 mg) in 1,4-dioxane (5 mL) was added 4N HCl-1,4-dioxane (500 μL) and the mixture was stirred at 40° C. overnight. To the reaction mixture was added 2N HCl and the mixture was at 40° C. for 8 hours. To the reaction mixture was added an aqueous sodium hydrogencarbonate solution and methylene chloride and the mixture was stirred. The organic layer was extracted and the extract was dried and filtered. The filtrate was concentrated in vacuo and the resultant crude product was purified by a column chromatography on silica gel (solvent; hexane/ethyl acetate=80/20 to 0/100) to give 3-hydrazinocarbonyl-6-(2-chlorophenyl)-7-(4-chlorophenyl)pyrazolo[1,5-a]pyrimidine (142 mg, yield: 52%) as a yellow gum.

MS (APCI)m/z; 398/400 M+H]$^+$

Reference Example 11

(1) To a solution of the compound obtained in Example 33 (1.5 g) in dimethylformamide (20 mL) was added sodium azide (1.11 g) and the mixture was stirred at 110° C. overnight. After cooling to room temperature, to the reaction mixture was a saturated brine and the mixture was stirred and extracted with ethyl acetate. The organic layer was washed with water and concentrated in vacuo and the resultant crude product was purified by a column chromatography on silica gel (solvent; hexane/ethyl acetate=80/20 to 30/70) to give 2-azido-6-(2-chlorophenyl)-7-(4-chlorophenyl)-3-(N-cyclopentylcarbamoyl)pyrazolo[1,5-a]pyrimidine (1.15 g, a yellow viscosity). To a solution of the product (870 mg) in tetrahydrofuran (16 mL) was added triphenylphosphine (896 mg) and the mixture was stirred at 40° C. for 1 hour. After cooling to room temperature, the reaction mixture was concentrated in vacuo and the resultant crude product was purified by a column chromatography on silica gel (solvent; chloroform/methanol=100/0 to 97/3) to give 6-(2-chlorophenyl)-7-(4-chlorophenyl)-2-triphenylphosphoranylidenamino-pyrazolo[1,5-a]pyrimidine (942 mg, yield: 58%) as a yellow solid MS (APCI)m/z; 726/728 M+H]$^+$ Reference Example 12

(1) 7-Chloro-6-(2-chlorophenyl)-3-ethoxycarbonylpyrazolo[1,5-a]pyrimidine (1 g) was treated in the same manner as described in Reference Example 4(5) to give 6-(2-chlorophenyl)-3-ethoxycarbonyl-7-(4-formylphenyl)pyrazolo[1,5-a]pyrimidine (910 mg) as a pale yellow powder.

MS (APCI)m/z; 428/430 M+H]$^+$ (2) To a solution of the compound obtained in the above step (1) (406 mg) in methylene chloride (1 mL) was added bis-(2-methoxyethyl)aminosulfur trifluoride (trade name: Deoxo-Fluor, Scott Inc.) (184 μL) and the mixture was stirred at room temperature for 4 hours. The organic layer was washed with a brine and extracted with methylene chloride. The extract was dried over sodium sulfate and filtered. The filtrate was concentrated in vacuo and the resultant crude product was purified by a column chromatography on silica gel (solvent; hexane/ethyl acetate=70/30 to 60/40) to give 6-(2-chlorophenyl)-7-(4-difluoromethylphenyl)-3-ethoxy-carbonylpyrazolo[1,5-a]-pyrimidine (25 mg, yield: 37%) as a pale yellow solid.

MS (APCI)m/z; 428/430 M+H]$^+$ (3) The compound obtained in the above step (2) (278 mg) was treated in the same manner as described in Reference Example 1(3) to give 3-carboxy-6-(2-chlorophenyl)-7-(4-difluoromethylphenyl)pyrazolo[1,5-a]pyrimidine (223 mg, yield: 86%) as a pale yellow solid.

MS (APCI)m/z; 400/402 M+H]$^+$

Reference Example 13

(1) To a solution of tetrahydro-4H-thiopyran-4-one (2.32 g) in ethanol (100 mL) was added sodium acetate (3.28 g) and hydroxylamine HCl (1.81 g) at room temperature and the mixture was stirred at the same temperature for 2 hours. The reaction mixture was concentrated in vacuo and to the residue was added ethyl acetate and an aqueous sodium hydrogencarbonate solution. After stirring, the mixture was extracted with ethyl acetate and the organic layer was washed with a brine, dried over sodium sulfate and filtered. The filtrate was concentrated in vacuo to give 4-hydroxyimino-tetrahydro-4H-thiopyrane (2.53 g, yield: 96%) as a colorless solid.

MS (APCI)m/z; 132 M+H]$^+$ (2) To a solution of the compound obtained in the above step (1) (500 mg) in diethylether (10 mL) was added lithium aluminum hydride (289 mg) under nitrogen gas atmosphere and ice-cooling and the mixture was stirred at the same temperature for 30 minutes and at room temperature for 1 hour. To the reaction mixture was added lithium aluminum hydride (72 mg) and the mixture was stirred at 40° C. for 2 hours. To the reaction mixture was added water (1 mL) and an aqueous 2N sodium hydroxide solution (1 mL) at room temperature and the mixture was stirred and filtered. The filtrate was concentrated in vacuo to give 4-amino-tetrahydro-4H-thiopyrane (150 mg, yield: 34%) as a yellow fluid.

MS (APCI)m/z; 118 M+H]$^+$

Reference Example 14A (1) A mixture of (R)-methioninol (4.95 g), benzonitrile (8.3 mL) and zinc bromide (250 mg) was stirred at 120° C. for 90 hours under nitrogen gas atmosphere. After cooling to room temperature, the reaction mixture was filtered and the filtrate was washed with water and a brine, dried over magnesium sulfate and filtered again. The filtrate was concentrated in vacuo and the resultant crude product was purified by a column chromatography on silica gel (solvent; hexane/ethyl acetate=5/1 to 3/1) to give (R)-4-(2-methylthioethyl)-2-phenyl-4,5-dihydrooxazole (3.94 g, yield: 48.6%) as a colorless oil.

MS (APCI)m/z; 222 M+H]$^+$ (2) To a solution of the compound obtained in the above step (1) (3.94 g) in acetic acid (65 mL) was added conc. hydrochloric acid (7.7 mL) and the mixture was refluxed under heating overnight. After cooling to room temperature, the reaction mixture was concentrated in vacuo. To the residue was added an aqueous sodium hydroxide solution (50 mL) and chloroform (100 mL) and the mixture was stirred. To the organic layer was added magnesium sulfate and silica gel and the mixture was stirred and filtered. The filtrate was concentrated in vacuo and the resultant crude product was washed with isopropylether and dried to give (R)—N-(tetrahydrothiophen-3-yl)benzamide (2.80 g, yield: 76%) as a colorless solid.

MS (APCI)m/z; 208 M+H]$^+$ (3) To a solution of the compound obtained in the above step (2) (3.59 g) in methylene chloride (70 mL) was gradually added 3-chloroperbenzoic acid (75%, 10 g) under ice-cooling and the mixture was stirred at room temperature overnight. To the reaction mixture was added water (35 mL), sodium sulfite (3.5 g) and an aqueous saturated sodium hydrogencarbonate solution (100 mL) and the mixture was stirred for 30 minutes and extracted with chloroform. The extract was washed with an aqueous saturated sodium hydrogencarbonate solution and the organic layer was dried over sodium sulfate and filtered. The filtrate was concentrated in vacuo and the resultant solid materials were washed with ethyl acetate to give (R)—N-(1,1-dioxo-tetrahydrothiophen-3-yl)benzamide (3.5 g, yield: 85%) as a colorless solid.

MS (APCI)m/z; 240 M+H]$^+$ (4) To a solution of the compound obtained in the above step (3) (3.51 g) in ethanol (13 mL) was added 6N HCl (52 mL) and the mixture was refluxed under heating for 1 day. After cooling to room temperature, the aqueous layer was washed with ethyl acetate and concentrated in vacuo. The precipitated solid materials were washed with ethanol/diethylether, collected by filtration and further washed with diethylether to give (R)—N-(1,1-dioxo-tetrahydrothiophen-3-yl)amine hydrochloride (2.52 g, yield: 100%) as a colorless solid.

MS (APCI)m/z; 136 M+H]$^+$

Reference Example 14B (S)-Methioninol (4.83 g) was treated in the same manner as described in Reference Example 14A to give (S)—N-(1,1-dioxo-tetrahydrothiophen-3-yl)amine hydrochloride (3.86 g,) as a colorless solid.

MS (APCI)m/z; 136 M+H]$^+$

Reference Example 15

(1) To a solution of 4,4-difluoropiperidin hydrochloride (2.0 g) in water was added 2N sodium hydroxide (7.6 mL) and the mixture was stirred at room temperature for 1 hour. To the reaction mixture was added sodium nitrite (1.75 g) at room temperature and added acetic acid (1.27 mL) under ice-cooling, and the mixture was stirred at room temperature for 2 hours. To the reaction mixture was added an aqueous sodium hydrogencarbonate solution and the mixture was extracted with chloroform. The extract was dried over magnesium sulfate and filtered, and the filtrate was concentrated in vacuo. The resultant crude product was purified by a column chromatography on silica gel (solvent; hexane/ethyl acetate=4/1) to give 4,4-difluoro-1-nitrosopiperidine (1.89 g, yield: 99%) as a pale yellow solid.

MS (APCI)m/z; 151 M+H]$^+$ (2) To a solution of the compound obtained in the above step (1) (1.89 g) in tetrahydrofuran was added portionwise lithium aluminum hydride (837 mg) under ice-cooling and the mixture was refluxed under heating for 1 hour. To the reaction mixture was added water under ice-cooling and the mixture was refluxed under heating for 30 minutes. After cooling to room temperature, the reaction mixture was filtered and the filtrate was concentrated in vacuo. To the residue was added an aqueous sodium hydrogencarbonate solution and chloroform and the mixture was stirred. The organic layer was dried over sodium sulfate and filtered and the filtrate was concentrated in vacuo to give 1-amino-4,4-difluoropiperidin (500 mg, yield: 29%) as a pale yellow oil.

MS (APCI)m/z; 137 M+H]$^+$

Reference Example 16

(1) To a solution of 3-fluoromethoxyphenylmethylamine (278 mg) in water (400 μL) was added acetic acid (125 mL) and a solution of sodium nitrite (201 mg) in water (600 μL) under ice-cooling and the mixture was stirred. Thereto was added methanol (500 μL) and tetrahydrofuran (500 μL) and the mixture was stirred at room temperature overnight. To the reaction mixture was added an aqueous saturated sodium hydrogencarbonate solution and the mixture was stirred and extracted with ethyl acetate. The extract was concentrated in vacuo and the resultant crude product was purified by a column chromatography on silica gel (solvent; hexane/ethyl acetate 100/0 to 87/13) to give N-(3-trifluoromethoxyphenyl)methyl nitrosoamine (282 mg, yield: 88%) as a pale yellow oil.

MS (APCI)m/z; 192 M+H]$^+$ (2) To a solution of lithium aluminum hydride (82.7 mg) in tetrahydrofuran (5 mL) was added a solution of the compound obtained in the above step (1) (282 mg) in tetrahydrofuran (2.5 mL) under ice-cooling and the mixture was stirred at room temperature for 1 hour under nitrogen gas atmosphere. To the reaction mixture was added water (90 μL), an aqueous 15% sodium hydroxide solution (90 μL) and water (180 μL) and the mixture was stirred and filtered. The filtrate was concentrated in vacuo and the resultant crude product was purified by a column chromatography on silica gel (solvent; hexane/ethyl acetate=85/15 to 65/35) to give N-methyl-N-(3-trifluoromethoxyphenyl)hydrazine (187 mg, yield: 71%) as an orange viscosity.

MS (APCI)m/z; 207 M+H]$^+$

Reference Example 17

To a solution of tetrahydro-4H-thiopyran-4-one (500 mg) in water/ethanol (10 mL/10 mL) was added potassium cyanide (1.4 g) and ammonium chloride (1.15 g) and the mixture was stirred at room temperature for 4 days. To the reaction mixture was added diethylether and an aqueous 1N sodium hydroxide solution and the mixture was stirred. The organic layer was separated and the aqueous layer was extracted with diethylether and ethyl acetate. The combined organic layer was dried over calcium chloride and filtered. The filtrate was concentrated in vacuo and the resultant crude product was purified by a column chromatography on silica gel (solvent; hexane/ethyl acetate=70/30 to 30/70) to give 4-amino-4-cyano-tetrahydro-4H-thiopyrane (315 mg) as a colorless solid.

Reference Example 18

A solution of ethyl 2-cyano-3,3-bismethylthioacrylate (40 g), hydrazine hydrochloride (12.6 g) and sodium acetate (22.6 g) in ethanol was stirred at 90° C. for 2 hours. After cooling to room temperature, the reaction mixture was concentrated in vacuo. To the residue was added water and ethyl acetate and the organic layer was separated, dried over magnesium sulfate and filtered. The filtrate was concentrated in vacuo and to the residue was added ethyl acetate and hexane. The precipitated solid materials were collected by filtration and dried to give 5-amino-4-ethoxycarbonyl-3-methylthio-1H-pyrazole (17.4 g, yield: 47%) as a colorless solid.

Reference Examples 19 to 20

3-Carboxy-6-(2-chlorophenyl)-7-(4-trifluoromethoxyphenyl)pyrazolo[1,5-a]-pyrimidine or 3-carboxy-6-(2-chlorophenyl)-7-(4-trifluoromethylphenyl)pyrazolo-[1,5-a]pyrimidine was treated in the same manner as described in Reference Example 10 to give the following compound.

(Ref Ex. 19) 3-hydrazinocarbonyl-6-(2-chlorophenyl)-7-(4-trifluoromethoxy-phenyl)pyrazolo[1,5-a]pyrimidine; MS (APCI)m/z; 448/450 M+H]$^+$ (Ref. Ex. 20) 3-hydrazinocarbonyl-6-(2-chlorophenyl)-7-(4-trifluoromethyl-phenyl)pyrazolo[1,5-a]pyrimidine; MS (APCI)m/z; 432/434 M+H]$^+$

Reference Examples 21 to 40

The corresponding starting materials were treated in the same manner as described in either one of Reference Examples 1, 4 and 6 to give the compound as shown in the following Table B1.

TABLE B1

(No. 1)

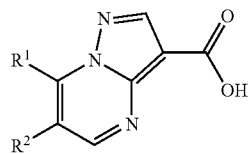

| Ref. Ex. | R$^1$ | R$^2$ | Physicochemical properties etc |
|---|---|---|---|
| 21 | 4-Cl-phenyl | 2-OCH$_3$-6-methylphenyl | MS(APCI): 380/382 [M + H]$^+$ |
| 22 | 4-Cl-phenyl | 2-OCH$_3$-phenyl | MS(APCI): 364/366 [M + H]$^+$ |

TABLE B1-continued
| Ref. Ex. | R¹ | R² | Physicochemical properties etc |
|---|---|---|---|
| 23 | 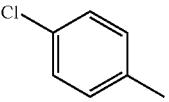 | 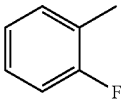 | MS(APCI): 368/370 [M + H]⁺ |
| 24 | 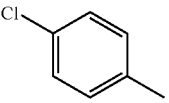 | 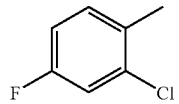 | MS(APCI): 402/404 [M + H]⁺ |
| 25 | 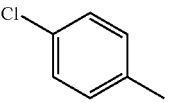 | 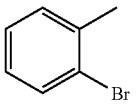 | MS(APCI): 428/430 [M + H]⁺ |
| 26 | 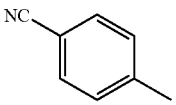 | 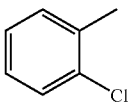 | MS(APCI): 375/377 [M + H]⁺ |
| 27 | 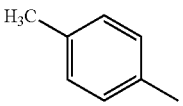 | 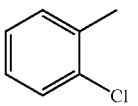 | MS(APCI): 364/366 [M + H]⁺ |
| 28 | 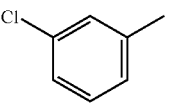 | 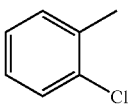 | MS(APCI): 384/386 [M + H]⁺ |
(No. 2)
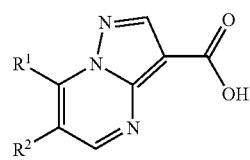
| Ref. Ex. | R¹ | R² | Physicochemical properties etc |
|---|---|---|---|
| 29 | 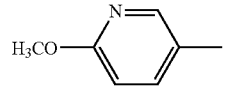 | 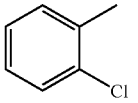 | MS(APCI): 381/383 [M + H]⁺ |
| 30 | 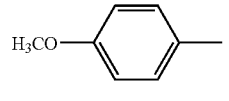 | 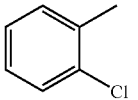 | MS(APCI): 380/382 [M + H]⁺ |
| 31 | 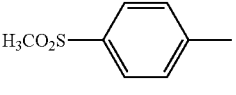 | 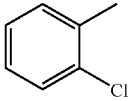 | MS(APCI): 428/430 [M + H]⁺ |
| 32 | 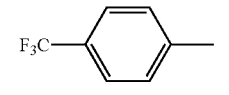 | 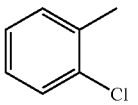 | MS(APCI): 418/420 [M + H]⁺ |
| 33 | 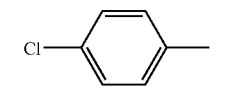 | 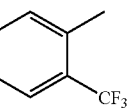 | MS(APCI): 418/420 [M + H]⁺ |

TABLE B1-continued
| 34 | 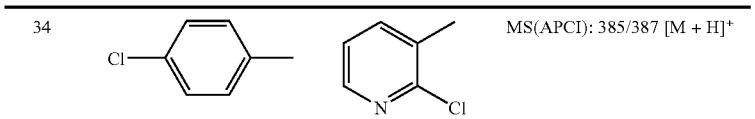 | MS(APCI): 385/387 [M + H]+ |
| 35 | 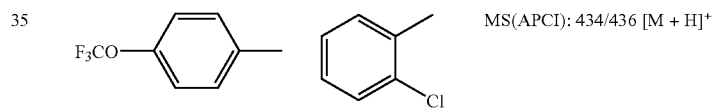 | MS(APCI): 434/436 [M + H]+ |
| 36 | 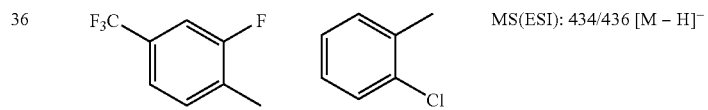 | MS(ESI): 434/436 [M − H]− |
(No. 3)
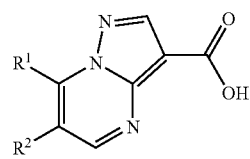
| Ref. Ex. | R1 | R2 | Physicochemical properties etc |
|---|---|---|---|
| 37 | 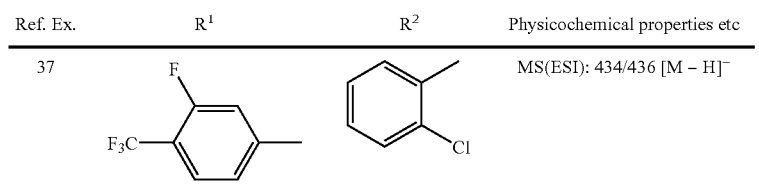 | | MS(ESI): 434/436 [M − H]− |
| 38 | 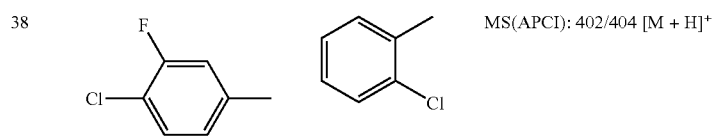 | | MS(APCI): 402/404 [M + H]+ |
(No. 4)
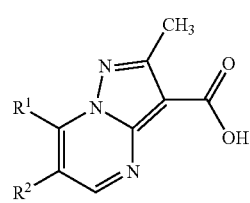
| Ref. Ex. | R1 | R2 | Physicochemical properties etc |
|---|---|---|---|
| 39 | 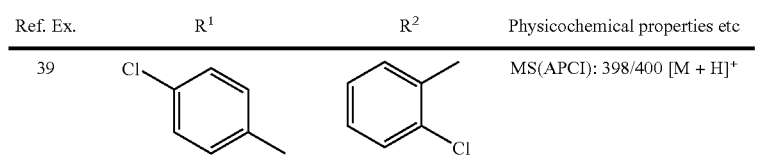 | | MS(APCI): 398/400 [M + H]+ |
| 40 | 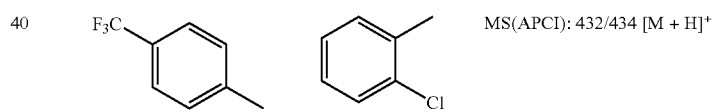 | | MS(APCI): 432/434 [M + H]+ |

Reference Examples 41 to 45

The corresponding starting materials were treated in the same manner as described in Reference Example 7 to give the compound as shown in the following Table B2.

TABLE B2

| Ref. Ex. | R¹ | R⁴ | Physicochemical properties etc |
|---|---|---|---|
| 41 | piperidin-1-yl | H | MS(APCI): 357/359 [M + H]⁺ |
| 42 | 4,4-difluoropiperidin-1-yl | H | MS(APCI): 393/395 [M + H]⁺ |
| 43 | 4-methylpiperidin-1-yl | H | MS(APCI): 351/373 [M + H]⁺ |
| 44 | 4-methoxypiperidin-1-yl | H | MS(APCI): 387/389 [M + H]⁺ |
| 45 | thiomorpholin-4-yl | CH₃ | MS(APCI): 389/391 [M + H]⁺ |

Reference Example 46

(1) To a solution of 5-nitropyrazol-3-carboxylic acid (19.9 g) in ethanol (200 mL) was added dropwise thionyl chloride (9.7 mL) over a period of 5 minutes and the mixture was refluxed for 4 hours. After cooling to room temperature, the reaction mixture was diluted with water (25 mL) and ethanol (50 mL) and to the mixture was neutralized with sodium hydrogencarbonate (54 g). The mixture was filtered and the residue was washed with ethanol. The filtrate and the washings were combined and concentrated in vacuo. The residue was azeotropically distilled with ethanol and the residue was dissolved in ethyl acetate, dried over magnesium sulfate and filtered. The filtrate was concentrated in vacuo and to the residue was added isopropylether. The precipitates were collected by filtration and washed with ethyl acetate/diisopropylether (1/2) to give ethyl 5-nitropyrazol-3-carboxylate (20 g, yield: 85%) as a colorless solid.

MS (APCI): 186 [M+H]⁺

(2) To a solution of the compound obtained in the above step (1) (22.5 g) in acetic acid (130 mL) and tetrahydrofuran (130 mL) was added 10% palladium-carbon (4.1 g) and the mixture was stirred under hydrogen-gas atmosphere for 4 hours. The reaction mixture was filtered and the filtrate was concentrated in vacuo. To the residue was added hexane and the mixture was stirred and decanted to remove hexane. To the residue was added ether/diisopropylether (1/1) and the precipitates were collected by filtration to give ethyl 5-aminopyrazole-3-carboxylate (17.2 g, yield: 91%) as a colorless solid.

MS (APCI): 156 [M+H]⁺

Reference Example 47

(1) To a solution of 2-[(cyano)(ethoxycarbonyl)vinyl]-1,3-dioxolane (2.0 g) in ethanol (20 mL) was added hydrazine hydrochloride (748 mg) and sodium acetate (1.34 g) and the mixture was stirred at 80° C. (external temperature) for 1 hour. After cooling to room temperature, the reaction mixture was filtered through Cerite and the filtrate was concentrated in vacuo. The resultant crude product was purified by a column chromatography on silica gel (solvent; chloroform/methanol=100/0 to 85/15) to give 3-amino-4-ethoxycarbonyl-5-(2-hydroxy)ethoxypyrazole (2.01 g, yield: 86%) as a pale pink solid.

MS (APCI)m/z; 216 M+H]⁺

(2) To the compound obtained in the above step (1) (2.65 g) and 3-(N,N-dimethylamino)-1-(4-chlorophenyl)-2-(2-chlorophenyl)-2-propen-1-one (cf. Reference Example 1(2)) was added ethanol (20 mL) and 21% sodium ethoxide in ethanol (5 mL) and the mixture was stirred at room temperature for 15 minutes. To the reaction mixture was added ethyl acetate and water and the mixture was acidified with 2N HCl and extracted with ethyl acetate. The organic layer was washed with a saturated brine, dried over magnesium sulfate and filtered. The filtrate was concentrated in vacuo and the resultant crude product was purified by a column chromatography on silica gel (solvent; hexane/ethyl acetate=72/28 to 30/70) and triturated in diethylether to give 6-(2-chlorophenyl)-7-(4-chlorophenyl)-3-ethoxycarbonyl-2-(2-hydroxyethoxy)pyrazolo[1,5-a]pyrimidine (2.25 g, yield: 39%) as a colorless solid.

MS (APCI)m/z; 472/474 M+H]⁺

(3) To a solution of the compound obtained in the above step (2) (100 mg) in acetonitrile (10 mL) was added silver(I) oxide (320 mg) and methyl iodide (350 μL) and the mixture was stirred at room temperature for 3 days. The reaction mixture was filtered through Cerite and the filtrate was concentrated in vacuo. The resultant crude product was purified by a column chromatography on silica gel (solvent; hexane/ethyl acetate=80/20 to 50/50) to give 6-(2-chlorophenyl)-7-(4-chlorophenyl)-3-ethoxycarbonyl-2-(2-methoxyethoxy) pyrazolo[1,5-a]pyrimidine (98.6 mg, yield: 96%) as a colorless powder.

MS (APCI)m/z; 486/488 M+H]⁺

(4) The compound obtained in the above step (3) (98 mg) was treated in the same manner as described in Reference Example 1(3) to give 6-(2-chlorophenyl)-7-(4-chlorophenyl)-3-carboxy-2-(2-hydroxyethoxy)pyrazolo[1,5-a]pyrimidine (92 mg, yield: 99%) as a colorless powder.

MS (APCI)m/z; 458/460 M+H]⁺

Reference Example 48

(1) To a solution 1,3-dibromo-2,2-dimethoxypropane (26.45 g) in dimethylsulfoxide (200 mL) was added sodium sulfate (9.46 g) and the mixture was stirred at 110 to 140° C. (external temperature) for 30 minutes. The reaction mixture was diluted with diethylether under ice-cooling and thereto was added an aqueous saturated sodium hydrogencarbonate solution and water. The mixture was extracted with diethylether (×2). The organic layer was washed with a saturated brine, dried over magnesium sulfate and filtered. The filtrate was concentrated in vacuo and the resultant crude product was purified by a column chromatography on silica gel (solvent; hexane/diethylether=100/0 to 15/1) to give 3,3-dimethoxythiacyclobutane (10.55 g, yield: 78%) as a pale yellow liquid.

MS (APCI)m/z; 103 [M+H-MeOH]$^+$ (2) To a solution of the compound obtained in the above step (1) (9.0 g) in acetone (70 mL) was added ion-exchange resin (Amberlyt 15E, 3.5 g) and the mixture was stirred at room temperature for 21 hours. The reaction mixture was filtered through Cerite and the residue was washed with acetone. The filtrate and the washings were combined and concentrated in vacuo. The precipitates were collected by filtration and washed with cooled hexane to give 3-oxothiacyclobutane (1.58 g, yield: 27%) as colorless crystals.

(3) To a solution of the compound obtained in the above step (2) (100 mg) in ethanol (3 mL) was added hydroxylamine hydrochloride (236 mg) and sodium carbonate (360 mg) and the mixture was refluxed under heating for 17 hours. After cooling to room temperature, to the reaction mixture was added an aqueous sodium hydrogencarbonate solution and water. The mixture was extracted with chloroform. The organic layer was concentrated in vacuo the resultant crude product was purified by column chromatography on silica gel (solvent; hexane/diethylether=90/10 to 50/50) to give 3-hydroxyiminothiacyclobutane (93 mg, yield: 80%) as a colorless solid.

(4) To a solution of lithium aluminum hydride (58 mg) in tetrahydrofuran (2 mL) was added dropwise a solution of the compound obtained in the above step (3) (93 mg) in tetrahydrofuran (1.5 mL) under ice-cooling and nitrogen-gas atmosphere. The mixture was stirred at room temperature for 1 hour. To the reaction mixture was successively added water (60 μL), 15% sodium hydroxide solution (60 μL) and water (120 μL) under ice-cooling and the mixture was stirred at room temperature and filtered through Cerite. The filtrate was concentrated in vacuo to give 3-aminothiacyclobutane as crude product.

Reference Example 49

(1) To a solution of sodium ethoxide (14.32 g) in ethanol (20 mL) was added dropwise ethyl cyanoacetate (4.7 mL) and the mixture was stirred at room temperature for 1 hour. To the reaction mixture was added difluoroacetic acid (4.85 mL) and the mixture was stirred at room temperature for 4 hours and then stirred at 60° C. (external temperature) for 17 hours. The reaction mixture was concentrated in vacuo and to the residue was added toluene (10 mL) and phosphorus chloride (3.2 g) and the mixture was stirred at 45° C. for 1 hour. To the reaction mixture was added phosphorus chloride (1.9 g) and the mixture was stirred at 55° C. for 2 hours. The reaction mixture was cooled with ice and filtered through Cerite and the filtrate was concentrated in vacuo. To the residue was added ethanol (20 mL), hydrazine monohydrate (0.8 mL) and triethylamine (3.0 mL) and the mixture was stirred at 60° C. for 2 hours. After cooling to room temperature, to the reaction mixture was added an aqueous saturated sodium hydrogencarbonate solution and water. The mixture was extracted with chloroform (×4) and the organic layer was dried over magnesium sulfate and filtered. The filtrate was concentrated in vacuo and the resultant crude product was purified by column chromatography on silica gel (solvent; chloroform/methanol=100/0 to 94/6) and washed with chloroform to give 3-amino-4-ethoxycarbonyl-5-difluoromethylpyrazole (1.26 g, yield: 41%) as a colorless solid.

MS (APCI)m/z; 206 [M+H]$^+$ (2) The compound obtained in the above step (1) (400 mg) was treated in the same manner as described in Reference Example 1(2) to (3) to give 3-carboxy-6-(2-chlorophenyl)-7-(4-chlorophenyl)-2-difluoromethylpyrazolo[1,5-a]pyrimidine (405 mg, yield: 48%) as a powder.

MS (APCI)m/z; 434/436 [M+H]$^+$

Reference Example 50

(1) To a solution of methyl cyanoacetate (14.6 g) in methylene chloride (260 mL) was added trifluoroacetic anhydride (37.2 g) and the mixture was stirred at room temperature. To the mixture was added dropwise triethylamine (51.7 mL) at 0° C. and the mixture was stirred at room temperature overnight. To the reaction mixture was added water and the mixture was extracted with methylene chloride. The organic layer was dried over magnesium sulfate and filtered. The filtrate was concentrated in vacuo to give methyl 2-cyano-2-(2-trifluoroacetyl)acetate (compound 2a) and methyl 2-cyano-4,4,4-trifluoro-3-trifluoromethoxycarbonyl-2-butenoate (compound 2b) as a mixture (55.3 g).

Compound 2a: MS (APCI)m/z; 196 [M+H]$^+$
Compound 2b: MS (APCI)m/z; 292 [M+H]$^+$ (2) To a solution of the mixture of the compound 2a and 2b (27.6 g) in methylene chloride (200 mL) was added dropwise oxalyl chloride (31.6 mL) and a few drops of pyridine and the mixture was refluxed under heating for 4 hours. The reaction mixture was poured to water gradually and the mixture was extracted with methylene chloride. The organic layer was dried over magnesium sulfate and filtered. The filtrate was concentrated in vacuo to give methyl 2-cyano-3-chloro-4,4,4-trifluoro-2-butenoate as a crude product.

(3) To the compound obtained in the above step (2) was added water (20 mL) and thereto was added dropwise hydrazine monohydrate (80%, 6.74 g) at 0° C. To the mixture was added triethylamine (2 mL) at room temperature and the mixture was stirred for 1 hour. To the reaction mixture was added water and the mixture was extracted with ethyl acetate. The organic layer was dried over magnesium sulfate and filtered. The filtrate was concentrated in vacuo and to the residue was added chloroform and the precipitates were collected by filtration to give 3-amino-4-ethoxycarbonyl-5-trifluoromethylpyrazole (3.96 g) as an orange solid.

MS (APCI)m/z; 210 [M+H]$^+$ (4) The compound obtained in the above step (3) (2.37 g) was treated in the same manner as described in Reference Example 1(2) to (3) to give 3-carboxy-6-(2-chlorophenyl)-7-(4-chlorophenyl)-2-trifluoromethylpyrazolo[1,5-a]pyrimidine (1.81 g) as a crude product (powder).

MS (APCI)m/z; 452/454 [M+H]$^+$

Reference Example 51

(1) To a solution of 6-(2-chlorophenyl)-7-(4-chlorophenyl)-3-ethoxycarbonyl-2-methylpyrazolo[1,5-a]pyrimidine (1.50 g: corresponding ethyl ester of the compound obtained in Reference Example 39) in carbon tetrachloride (20 mL) was added N-bromosuccinimide (1.88 g) and 2,2'-azobisisobutylonitrile (30 mg). The mixture was stirred at 85° C. (external temperature) for 26 hours. After cooling to room temperature, the reaction mixture was filtered through Cerite and the filtrate was concentrated in vacuo. The resultant crude product was purified by column chromatography on silica gel (solvent; hexane/diethylether=85/15 to 67/33) to give 2-bromomethyl-6-(2-chlorophenyl)-7-(4-chlorophenyl)-3-ethoxycarbonylpyrazolo[1,5-a]pyrimidine (827 mg, yield: 47%) as a pale yellow solid.

MS (APCI)m/z; 504/506 [M+H]$^+$ (2) To a solution of the compound obtained in the above step (1) (825 mg) in methanol/tetrahydrofuran (7 mL/4 mL) was added 28% sodium methoxide-methanol solution (3 mL) and the mixture was stirred at room temperature for 1 hour. The reaction mixture was diluted with ethyl acetate and thereto was added water. The mixture was extracted with ethyl acetate and the organic layer was washed with a saturated brine, dried over magnesium sulfate and filtered. The filtrate was concentrated in vacuo and the resultant crude product was purified by column chromatography on silica gel (solvent; hexane/ethyl acetate=75/25 to 60/40) to give 6-(2-chlorophenyl)-7-(4-chlorophenyl)-3-methoxycarbonyl-2-methoxymethylpyrazolo[1,5-a]pyrimidine (404 mg, yield: 56%) as a pale yellow solid.

MS (APCI)m/z; 442/444 [M+H]$^+$ (3) The compound obtained in the above step (2) (404 mg) was treated in the same manner as described in Reference Example 1(3) to give 3-carboxy-6-(2-chlorophenyl)-7-(4-chlorophenyl)-2-methoxymethylpyrazolo[1,5-a]pyrimidine (367 mg, yield: 94%) as a colorless solid.

MS (APCI)m/z; 428/430 [M+H]$^+$

Reference Example 52

(1) To dimethylformamide (75 mL) was added sodium hydride (60%, 6.77 g) under nitrogen-gas atmosphere and thereto was added dropwise a solution of ethyl cyanoacetate (9.57 g) in dimethylformamide (15 mL) over a period of 15 minutes and the mixture was stirred at room temperature for 10 minutes. To the mixture was added dropwise a solution of carbon disulfide (5.09 mL) in dimethylformamide (12 mL) under cooling at 0° C. (internal temperature≦10° C.) over a period of 20 minutes. The mixture was stirred at room temperature overnight and to the reaction mixture was added dropwise a solution of benzyl bromide (20.1 mL) in dimethylformamide (23 mL) under cooling at 0° C. (internal temperature≦25° C.) and the mixture was stirred at 70° C. for 7 hours and then stirred at room temperature overnight. The reaction mixture was poured to water with ice and the mixture was stirred. The precipitates were collected by filtration, recrystallized from hot ethanol and washed with cooled ethanol to give ethyl 2-cyano-3,3-bisbenzylthioacrylate (25.63 g, yield: 82%) as a colorless solid.

MS (APCI)m/z; 370 [M+H]$^+$ (2) To a solution of the compound obtained in the above step (1) (15.0 g) in tetrahydrofuran/ethanol (16 mL/41 mL) was added a solution of hydrazine monohydrate (2.04 g) in ethanol (18 mL) over a period of 5 minutes and the mixture was stirred at room temperature overnight. The reaction mixture was concentrated in vacuo and the residue was crystallized from diisopropylether/hexane. The precipitated crystals were collected by filtration and washed to give 3-amino-4-ethoxycarbonyl-5-benzylthio-pyrazole (9.45 g, yield 84%) as a colorless solid.

MS (APCI)m/z; 278 [M+H]$^+$ (3) The compound obtained in the above step (2) (8.15 g) was treated in the same manner as described in Reference Example 5(1) to give 2-benzylthio-6-(2-chlorophenyl)-7-(4-chlorophenyl)-3-ethoxycarbonylpyrazolo[1,5-a]pyrimidine (8.24 g, yield: 51%) as a pale yellow solid.

MS (APCI)m/z; 534/536 [M+H]$^+$

Reference Example 53

(1) The compound obtained in Reference Example 33 (3.0 g) was treated in the same manner as described in Reference Example 9(1) to give 6-(2-chlorophenyl)-7-(4-trifluoromethylphenyl)-3-(tert-butoxycarbonylamino)pyrazolo[1,5-a]pyrimidine (1.06 g, yield: 30%) as an orange powder.

MS (APCI)m/z; 489/491 [M+H]$^+$ (2) To a solution of the compound obtained in the above step (1) (1.06 g) in dioxane (5 mL) was added 4N HCl-dioxane (10 mL) and the mixture was stirred at room temperature for 7 hours. The reaction mixture was concentrated in vacuo and to the residue was added an aqueous saturated sodium hydrogencarbonate solution. The mixture was extracted with chloroform and the organic layer was concentrated in vacuo. The resultant crude product was purified by column chromatography on silica gel (solvent; hexane/ethyl acetate=70/30 to 40/60) to give 3-amino-6-(2-chlorophenyl)-7-(4-trifluoromethylphenyl)pyrazolo[1,5-a]pyrimidine (850 mg, yield: 80%) as a pale yellow solid.

MS (APCI)m/z; 389/391 [M+H]$^+$

Reference Example 54

(1) The corresponding starting materials were treated in the same manner as described in Reference Example 1(1) to give (2-chlorobenzyl)(4-trifluoromethylphenyl)methanone.

(2) The compound obtained in the above step (1) (3.0 g) and 3-amino-5-methylpyrazole (977 mg) were treated in the same manner as described in Reference Example 1(2) to give 6-(2-chlorophenyl)-7-(4-trifluoromethylphenyl)-2-methylpyrazolo[1,5-a]pyrimidine (2.63 g, yield: 67%) as a brown oil.

MS (APCI)m/z; 388/390 [M+H]$^+$ (3) To a solution of the compound obtained in the above step (2) (2.27 g) in chloroform (50 mL) was added gradually dropwise chlorosulfonic acid (1.35 mL) and the mixture was stirred at 70° C. for 3.5 hours. The reaction mixture was concentrated in vacuo and to the residue was added thionyl chloride (20 mL) and the mixture was refluxed under heating for 2 hours. The reaction mixture was concentrated in vacuo and to the residue was added ice-water and the mixture was extracted with chloroform. The organic layer was dried over sodium sulfate and filtered. The filtrate was concentrated in vacuo and the resultant crude product was purified by column chromatography on silica gel (solvent; hexane/ethyl acetate=85/15 to 60/40) to give 6-(2-chlorophenyl)-7-(4-trifluoromethylphenyl)-3-chlorosulfonyl-2-methylpyrazolo[1,5-a]pyrimidine (2.71 g, yield: 95%) as a pale yellow solid.

MS (APCI)m/z; 486/488 [M+H]$^+$

Reference Example 55

(1) To a solution of ethyl potassium malonate (465 mg) in acetonitrile (3.5 mL) was added magnesium chloride (309 mg) and triethylamine (580 µL) and the mixture was stirred at room temperature for 2 hours (solution A). To a solution of the compound obtained in Reference Example 1 (500 mg) in acetonitrile (3 mL) was added carbonyldiimidazole (232 mg) and tetrahydrofuran (2 mL) at room temperature and the mixture was stirred at the same temperature for 2 hours. To the reaction mixture was added the above obtained solution A at room temperature and the mixture was stirred for 4 hours. To the reaction mixture was added 2N HCl and the mixture was extracted with ethyl acetate. The organic layer was washed with water and a saturated brine, dried over magnesium sulfate and filtered. The filtrate was concentrated in vacuo and the resultant crude product was purified by column chromatography on silica gel (solvent; hexane/ethyl acetate=90/10 to 75/25) to give 6-(2-chlorophenyl)-7-(4-chlorophenyl)-3-(2-ethoxycarbonylacetyl)pyrazolo[1,5-a]pyrimidine (488 mg, yield: 83%).

MS (APCI)m/z; 454/456 [M+H]$^+$ (2) To a solution of the compound obtained in the above step (1) (475 mg) in ethanol/tetrahydrofuran (2.5 mL/2.5 mL) was added an aqueous 2N sodium hydroxide solution (1.05 mL) and the mixture was stirred at 60° C. for 1 hour. To the reaction mixture was added an aqueous 2N sodium hydroxide solution (1.05 mL) and ethanol (2.5 mL) and the mixture was stirred at the same temperature for 18 hours. After cooling to room temperature, to the reaction mixture was added an aqueous 2N HCl (2.1 mL) and the mixture was diluted with ethyl acetate. To the solution was added water and the mixture was extracted with ethyl acetate. The organic layer was concentrated in vacuo the resultant crude product was purified by column chromatography on silica gel (solvent; hexane/ethyl acetate=80/20 to 70/30) to give 3-acetyl-6-(2-chlorophenyl)-7-(4-chlorophenyl)pyrazolo[1,5-a]pyrimidine (233 mg, yield: 58%) as a pale yellow solid.

MS (APCI)m/z; 382/384 [M+H]$^+$

Reference Example 56

(1) The corresponding starting materials were treated in the same manner as described in Reference Example 2(1) to give (2-chlorobenzyl)(5-chlorothiophen-2-yl)methanone (5.06 g, yield: 61%).

(2) The compound obtained in the above step (1) (2.92 g) was treated in the same manner as described in Reference Example 1(2) to give 3-(N,N-dimethylamino)-2-(2-chlorophenyl)-1-(5-chlorothiophen-2-yl)-2-propen-1-one as a crude product.

(3) To a solution of the compound obtained in the above step (2) in acetic acid (2 mL) was added 3-amino-4-ethoxycarbonyl-5-methylpyrazole (1.3 g) and piperidine (153 µL) and the mixture was stirred at 80° C. overnight. To the reaction mixture was added acetic acid (3 mL) and toluene (30 mL) and the mixture was stirred at the same temperature for 7 hours. After cooling to room temperature, to the reaction mixture was added an aqueous saturated sodium hydrogencarbonate solution under ice-cooling. The mixture was extracted with ethyl acetate and the organic layer was washed successively with water and a saturated brine, dried over magnesium sulfate and filtered. The filtrate was concentrated in vacuo and the precipitates were collected by filtration and washed with diethylether. The filtrate was purified by column chromatography on silica gel (solvent; hexane/ethyl acetate=80/20 to 60/40) and the eluted fraction was concentrated. The precipitates were washed with ethyl acetate/hexane (1/10) and combined with the above-mentioned precipitates to give 6-(2-chlorophenyl)-7-(5-chlorothiophen-2-yl)-3-ethoxycarbonyl-2-methylpyrazolo[1,5-a]pyrimidine (1.52 g, yield in the two steps: 45%) as a yellow solid.

MS (APCI)m/z; 432/434 [M+H]$^+$ (4) The compound obtained in the above step (3) (1.51 g) was treated in the same manner as described in Reference Example 1(3) to give 3-carboxy-6-(2-chlorophenyl)-7-(5-chlorothiophen-2-yl)-2-methylpyrazolo[1,5-a]pyrimidine (1.18 g, yield: 84%) as a yellow solid.

MS (APCI)m/z; 404/406 [M+H]$^+$

Reference Example 57

(1) The corresponding starting materials were treated in the same manner as described in Reference Example 4(1) to (4) to give 6-(2-chlorophenyl)-7-chloro-3-ethoxycarbonylpyrazolo[1,5-a]pyrimidine.

(2) To a solution of the compound obtained in the above step (1) (672 mg) in tetrahydrofuran (6 mL) was added palladium acetate (2.2 mg), 2-dicyclohexyl-phosphino-2',6'-dimethoxybiphenyl (4.1 mg), potassium phosphate trihydrate (1.27 g) and water (120 µL) under nitrogen-gas atmosphere and the mixture was stirred at room temperature for 2 hours and then stirred at 100° C. for 24 hours. After cooling to room temperature, to the reaction mixture was added water and the mixture was extracted with ethyl acetate. The organic layer was washed successively with an aqueous 1N sodium hydroxide solution, water and a saturated brine, dried over magnesium sulfate and filtered. The filtrate was concentrated in vacuo and the resultant crude product was purified by column chromatography on silica gel (solvent; hexane/ethyl acetate=80/20 to 50/50). The eluted fraction was concentrated and the precipitates were washed with diethyl ether/hexane to give 6-(2-chlorophenyl)-7-(4-dimethylamino-phenyl)-3-ethoxycarbonylpyrazolo[1,5-a]pyrimidine (288 mg, yield: 34%) as a yellow powder.

MS (APCI)m/z; 421/423 [M+H]$^+$

Reference Example 58

The compound obtained in Example 440 (0.67 g) was treated in the same manner as described in Reference Example 1(3) to give 3-carboxy-6-(2-chlorophenyl)-7-(4-trifluoromethylphenyl)-2-[N-methyl-N-(methylsulfonyl) amino]pyrazolo[1,5-a]-pyrimidine (0.64 g) as a crude product (powder).

MS (APCI)m/z; 525/527 [M+H]$^+$

Reference Example 59

(1) The compound obtained in Reference Example 51(1) (200 mg) in dimethylsulfoxide (2 mL) was added sodium thiomethoxide (15 mg) and the mixture was stirred at room temperature for 1 hour. To the reaction mixture was added water and the mixture was extracted with ethyl acetate. The extract was concentrated in vacuo and the resultant crude product was purified by column chromatography on silica gel (solvent; hexane/ethyl acetate=87/13 to 60/40) to give 6-(2-chlorophenyl)-7-(4-trifluoromethylphenyl)-3-ethoxycarbonyl-2-methylthiopyrazolo[1,5-a]pyrimidine (170 mg, yield: 91%) as a pale yellow solid.

MS (APCI)m/z; 472/474 [M+H]$^+$ (2) The compound obtained in the above step (1) (170 mg) was treated in the same manner as described in Reference Example 1(3) to give 3-carboxy-6-(2-chlorophenyl)-7-(4-trifluoromethylphenyl)-2-methylthiomethylpyrazolo[1,5-a]-pyrimidine as a pale yellow powder.

MS (APCI)m/z; 444/446 [M+H]$^+$

Reference Example 60

(1) To a solution of 1-benzyloxycarbonyl-3-pyrroline (5.0 g) in methylene chloride (125 mL) was added m-chloroperbezoic acid (12.17 g) and the mixture was stirred at room temperature for 3 days. To the reaction mixture was added an aqueous saturated sodium thiosulfate solution (100 mL) and the mixture was stirred for 30 minutes. The reaction mixture was extracted with chloroform (×2) and the organic layer was washed successively with an aqueous 2N sodium hydroxide solution (1100 mL×2) and a saturated brine, dried over magnesium sulfate and concentrated in vacuo to give benzyl 6-oxa-3-azabicyclo[3,1,0]hexan-3-carboxylate (5.58 g, yield: 100%) as an oil.

MS (APCI)m/z; 220 [M+H]$^+$ (2) A mixture of the compound obtained in the above step (1) (26.5 g), (1R, 2R)-(−)-[1,2-cyclohexanediamino-N,N'-bis (3,5-di-tert-butylsalicylidene)]chromium chloride (1.57 g)

and trimethylsilylazide (17.7 mL) was stirred at room temperature for 2 days. To the reaction mixture was added chloroform and the mixture was washed successively with water and a saturated brine an dried over magnesium sulfate. The organic layer was concentrated in vacuo and the residue was purified by column chromatography on silica gel (solvent; hexane/ethyl acetate=10/1 to 2/1-chloroform/methanol=20/1 to 9/1) to give (3S,4S)-4-azido-1-benzyloxycarbonyl-3-trimethylsilyloxypyrrolidine (compound a: 20.6 g, yield: 55%) and (3S,4S)-4-azido-1-benzyloxycarbonyl-3-hydroxypyrrolidine (compound b: 8.16 g, yield: 28%) as an oil, respectively.

Compound a: MS (APCI)m/z; 335 [M+H]$^+$
Compound b: MS (APCI)m/z; 263 [M+H]$^+$ (3) To a solution of the compound a (20.6 g) and compound b (8.16 g) in tetrahydrofuran (740 mL) was added triphenylphosphine (26.67 g) and the mixture was stirred at room temperature overnight. The reaction mixture was concentrated in vacuo and to the residue was added methanol (380 mL) and an aqueous 0.5N sodium hydroxide solution (380 mL) and the mixture was stirred at room temperature overnight. The reaction mixture was concentrated in vacuo and to the residue was added an aqueous 6N HCl (pH 3). The mixture was washed with chloroform and the aqueous layer was basified (pH 9) with an aqueous 5N sodium hydroxide solution. The mixture was extracted with chloroform (×3) and the organic layer was dried over magnesium sulfate and concentrated in vacuo to give (3S,4S)-4-amino-1-benzyloxycarbonyl-3-hydroxypyrrolidine (19.6 g, yield: 90%) as an oil MS (APCI)m/z; 237 [M+H]$^+$ (4) To a solution of the compound obtained in the above step (3) (14.61 g) in chloroform (135 mL) was added dropwise a solution of di-tert-butyl dicarboxylate (16.18 g) in chloroform (20 mL) under ice-cooling and the mixture was stirred at room temperature for 2 hours. To the reaction mixture was added an aqueous saturated sodium hydrogencarbonate solution (100 mL) and the mixture was stirred. The mixture was extracted with chloroform and the organic layer was dried over magnesium sulfate. Thereto was added NH-silica gel (2 g) and the mixture was stirred and filtered. The filtrate was concentrated in vacuo and the resultant crude product was triturated in hexane/ethyl acetate to give (3S,4S)-1-benzyloxycarbonyl-3-hydroxy-4-(tert-butoxy-carbonyl)pyrrolidine (18.59 g, yield: 94%) as crystals.

MS (APCI)m/z; 337 [M+H]$^+$ (5) To a solution of the compound obtained in the above step (4) (18.56 g) in methanol (200 mL) was added 10% palladium-carbon (1.16 g) and the mixture was stirred at room temperature under hydrogen-gas atmosphere for 3 hours. The reaction mixture was filtered through Cerite and the filtrate was concentrated in vacuo. The residue was triturated in methanol/diisopropylether to give (3S,4S)-3-hydroxy-4-(tert-butoxycarbonyl)pyrrolidine (10.8 g, yield: 97%) as crystals.

MS (APCI)m/z; 203 [M+H]$^+$

Reference Example 61 to 83

The corresponding starting materials were treated in the same manner as described in Reference Example 1, 4 or 6 to obtain the compounds as shown in the following Table B3.

TABLE B3

(No. 1)

| Ref. Ex. Nos. | R$^1$ | R$^2$ | Physicochemical properties etc. |
|---|---|---|---|
| 61 | 4-Cl, 2-F-phenyl(methyl) | 2-Cl-phenyl(methyl) | MS(APCI): 402/404 [M + H]$^+$ |
| 62 | 4-(FH$_2$C)-phenyl(methyl) | 2-Cl-phenyl(methyl) | MS(APCI): 382/384 [M + H]$^+$ |
| 63 | 4-(F$_3$C)-phenyl(methyl) | 2-Br-phenyl(methyl) | MS(APCI): 462/464 [M + H]$^+$ |
| 64 | 6-(F$_3$C)-pyridin-3-yl(methyl) | 2-Cl-phenyl(methyl) | MS(APCI): 419/421 [M + H]$^+$ |
| 65 | 4-(CF$_2$CH$_3$)-phenyl(methyl) | 2-Cl-phenyl(methyl) | MS(APCI): 414/416 [M + H]$^+$ |

TABLE B3-continued
| Ref. Ex. Nos. | R¹ | R² | Physicochemical properties etc. |
|---|---|---|---|
| 66 | 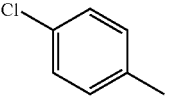 | 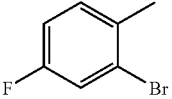 | MS(APCI): 446/448 [M + H]⁺ |
| 67 | 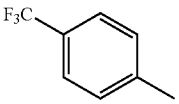 | 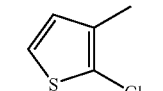 | MS(APCI): 424/426 [M + H]⁺ |
| 68 | 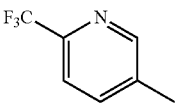 | 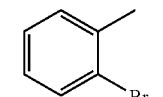 | MS(APCI): 463/465 [M + H]⁺ |
(No. 2)
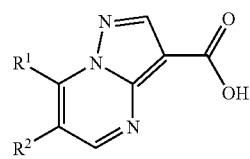
| Ref. Ex. Nos. | R¹ | R² | Physicochemical properties etc. |
|---|---|---|---|
| 69 | 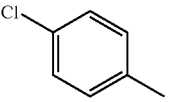 | 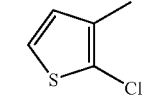 | MS(APCI): 390/392 [M + H]⁺ |
| 70 | 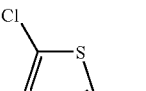 | 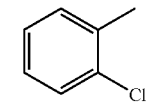 | MS(APCI): 390/392 [M + H]⁺ |
| 71 | 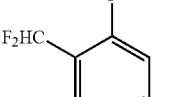 | 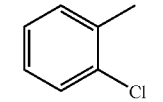 | MS(APCI): 418/420 [M + H]⁺ |
| 72 | 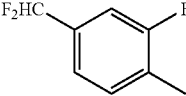 | 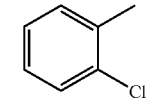 | MS(APCI): 418/420 [M + H]⁺ |
| 73 | 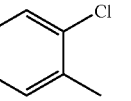 | 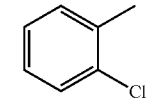 | MS(APCI): 384/386 [M + H]⁺ |
| 74 | 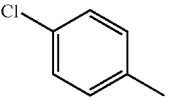 | 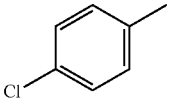 | MS(APCI): 384/386 [M + H]⁺ |
| 75 | 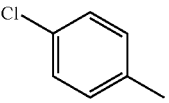 | 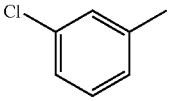 | MS(APCI): 384/386 [M + H]⁺ |

TABLE B3-continued (No. 3)

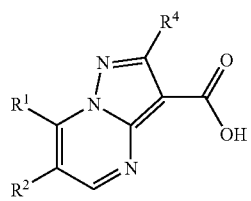

| Ref. Ex. Nos. | R¹ | R² | R² | Physicochemical properties etc. |
|---|---|---|---|---|
| 76 | 4-(F₃C)-C₆H₄- | 2-Br-C₆H₄- | CH₃ | MS(APCI): 476/478 [M + H]⁺ |
| 77 | 6-(F₃C)-pyridin-3-yl | 2-Cl-C₆H₄- | CH₃ | MS(APCI): 433/435 [M + H]⁺ |
| 78 | 4-Cl-C₆H₄- | 2-Br-C₆H₄- | CH₃ | MS(APCI): 442/444 [M + H]⁺ |
| 79 | 4-Cl-2-F-C₆H₃- | 2-Cl-C₆H₄- | CH₃ | MS(APCI): 416/418 [M + H]⁺ |
| 80 | 4-Cl-C₆H₄- | 2-Cl-4-F-C₆H₃- | CH₃ | MS(APCI): 416/418 [M + H]⁺ |
| 81 | 4-F-C₆H₄- | 3-Cl-pyridin-2-yl | CH₃ | MS(APCI): 382/384 [M + H]⁺ |
| 82 | 4-(FH₂C)-C₆H₄- | 2-Cl-C₆H₄- | CH₃ | MS(APCI): 396/398 [M + H]⁺ |
| 83 | 4-Cl-C₆H₄- | 2-Cl-C₆H₄- | C₂H₅ | MS(APCI): 412/414 [M + H]⁺ |

Note: R¹ and R² structures are drawn as substituted aryl/heteroaryl groups; the table reproduces the substituent positions shown in the figures.

Reference Example 84 to 87

The corresponding starting materials were treated in the same manner as described in Reference Example 40 or 50 to obtain the compounds as shown in the following Table B4.

TABLE B4

| Ref. Ex. Nos. | $R^1$ | $R^2$ | $R^4$ | Physicochemical properties etc. |
|---|---|---|---|---|
| 84 | 4-CF$_3$, 3-methylphenyl | 2-Cl-phenyl | CHF$_2$ | MS(APCI): 468/470 [M + H]$^+$ |
| 85 | 4-Cl, 2-F-phenyl (methyl) | 2-Cl-phenyl | CF$_3$ | MS(APCI): 470/472 [M + H]$^+$ |
| 86 | 4-Cl, 2-F-phenyl (methyl) | 2-Cl-phenyl | CHF$_2$ | MS(APCI): 452/454 [M + H]$^+$ |
| 87 | 4-Cl, 2-F-phenyl (methyl) | 2-Br-phenyl | CF$_3$ | MS(APCI): 497/499 [M + H]$^+$ |

Reference Example 88

The corresponding starting materials were treated in the same manner as described in Reference Example 51 to obtain 3-carboxy-6-(2-chlorophenyl)-7-(4-chlorophenyl)-2-ethoxymethylpyrazolo[1,5-a]pyrimidine (602 mg, yield: 95%) as a colorless solid.

MS (APCI)m/z; 442/444 [M+H]$^+$

Reference Example 89

(1) To a solution of 4-methoxypiperidine (202 mg) in water (4 mL) was added acetic acid (200 μL) under ice-cooling and the mixture was stirred at room temperature overnight. To the reaction mixture was added an aqueous saturated sodium hydrogencarbonate solution and the mixture was stirred and extracted with chloroform. The extract was concentrated in vacuo and the resultant crude product was purified by column chromatography on silica gel (solvent; ethyl acetate) to give 4-methoxy-1-nitrosopiperidine (260 mg, yield: 100%) as a pale yellow oil.

MS (APCI)m/z; 145 [M+H]$^+$ (2) To a solution of the compound obtained in the above step (1) (280 mg) in methanol (3 mL) was added zinc powder (654 mg). Thereto was added dropwise acetic acid (3 mL) under ice-cooling and the mixture was stirred at room temperature for 2 hours. The reaction mixture was filtered and the filtrate was concentrated in vacuo. To the residue was added an aqueous saturated sodium hydrogencarbonate solution and chloroform, and the mixture was stirred and extracted with chloroform. The extract was concentrated in vacuo to give 1-amino-4-methoxypiperidine (119 mg, yield: 57%) as a pale yellow oil.

MS (APCI)m/z; 131 [M+H]$^+$

Reference Example 90

A mixture of 2,5-dibromopyridine (500 mg) and methylhydrazine (1 mL) was heated at 100° C. After cooling to room temperature, the reaction mixture was diluted with ethyl acetate and washed with a saturated brine. The organic layer was dried over sodium sulfate and concentrated in vacuo. The resultant crude product was purified by column chromatography on silica gel (solvent; chloroform) and the eluted fraction was concentrated. The residue was dissolved in tert-butanol and lyophilized to give 5-bromo-2-(N-methylhydrazino)pyridine (460 mg) as an oil.

MS (APCI)m/z; 202/204 [M+H]$^+$

Reference Example 91 to 93

The corresponding starting materials were treated in the same manner as described in Reference Example 90 to obtain the compounds as shown in the following Table B5.

TABLE B5

| Ref. Ex. Nos. | Chemical structure | Physicochemical properties etc. |
|---|---|---|
| 91 | 6-fluoro-2-(N-methylhydrazino)pyridine | MS(APCI): 142 [M + H]$^+$ |

TABLE B5-continued

| Ref. Ex. Nos. | Chemical structure | Physicochemical properties etc. |
|---|---|---|
| 92 | F—pyridine—N(NH₂)(CH₃) | MS(APCI): 142 [M + H]⁺ |
| | H₃C\N(H₂N)—pyridine—Br | MS(APCI): 202/204 [M + H]⁺ |
| 93 | H₃C\N(H₂N)—pyridine | MS(APCI): 125 [M + H]⁺ |

Reference Example 94

(1) To a solution of the compound obtained in Reference Example 4(2) (1.0 g) in tetrahydrofuran (10 mL) was added 4-hydroxypiperidine (361 mg) and triethylamine (830 mL) and the mixture was stirred at 60° C. for 2 hours. After cooling to room temperature, to the reaction mixture was added water and the mixture was extracted with ethyl acetate. The extract was washed with a saturated brine, dried over sodium sulfate and filtered. The filtrate was concentrated in vacuo and the resultant crude product was triturated in diisopropylether to give 6-(2-chlorophenyl)-7-(4-hydroxy-1-piperidinyl)-3-ethoxycarbonylpyrazolo[1,5-a]pyrimidine (646 mg, yield: 54%) as a colorless solid.

MS (APCI)m/z; 401/403 [M+H]⁺

(2) To a solution of the compound obtained in the above step (1) (200 mg) in dimethylformamide (3 mL) was added sodium hydride (48 mg) under ice-cooling and the mixture was stirred at room temperature for 15 minutes. To the reaction mixture was added ethyl iodide (120 μL) and the mixture was stirred at room temperature for 1 hour. The reaction mixture was diluted with ethyl acetate and thereto was added an aqueous diluted HCl. The mixture was extracted with ethyl acetate and the extract was concentrated in vacuo. The resultant crude product was purified by column chromatography on silica gel (solvent; hexane/ethyl acetate=82/18 to 60/40) to give 6-(2-chlorophenyl)-7-(4-ethoxy-1-piperidinyl)-3-ethoxycarbonylpyrazolo[1,5-a]-pyrimidine (65 mg, yield: 30%) as a colorless viscosity.

MS (APCI)m/z; 429/431 [M+H]⁺

(3) The compound obtained in the above step (2) (65 mg) was treated in the same manner as described in Reference Example 1(3) to give 3-carboxy-6-(2-chlorophenyl)-7-(4-ethoxy-1-piperidinyl)pyrazolo[1,5-a]pyrimidine as a colorless powder.

MS (APCI)m/z; 401/403 [M+H]⁺

Reference Example 95

(1) The corresponding starting materials were treated in the same manner as described in Reference Example 4(3) to obtain 6-chloro-7-(4-chlorobenzyl)-3-ethoxycarbonyl-2-methylpyrazolo[1,5-a]pyrimidine.

(2) To a solution of the compound obtained in the above step (1) (525 mg) in dimethoxyethane (5 mL) was added p-chlorobenzyl bromide (370 mg), bis(triphenyl-phosphine) palladium dichloride (53 mg) and zinc powder (235 mg) and the mixture was refluxed under heating and nitrogen-gas atmosphere for 2 hours. The reaction mixture was filtered and the filtrate was concentrated in vacuo. To the residue was added water and the mixture was extracted with ethyl acetate. The organic layer was washed with a saturated brine, dried over magnesium sulfate and filtered. The filtrate was concentrated in vacuo and the resultant crude product was purified by column chromatography on silica gel (solvent; hexane/ethyl acetate=4/1) to give 7-(4-chlorobenzyl)-6-(2-chlorophenyl)-3-ethoxycarbonyl-2-methylpyrazolo[1,5-a]-pyrimidine (113 mg, yield: 17%) as a pale yellow powder.

MS (APCI)m/z; 440/442 [M+H]⁺

Reference Example 96

(1) To a solution of the compound obtained in Reference Example 51(1) (200 mg) in dimethylformamide (2 mL) was added potassium acetate (116 mg) and the mixture was stirred at 60° C. for 1 hours. After cooling to room temperature, to the reaction mixture was diluted with ethyl acetate and thereto was added water. The organic layer was separated and concentrated in vacuo. The resultant crude product was purified by column chromatography on silica gel (solvent; hexane/ethyl acetate=80/20 to 55/45) to give 6-(2-chlorophenyl)-7-(4-chlorophenyl)-3-ethoxycarbonyl-2-acetoxymethylpyrazolo[1,5-a]pyrimidine (109.4 mg, yield: 57%) as a colorless powder.

MS (APCI)m/z; 484/486 [M+H]⁺

(2) To a solution of the compound obtained in the above step (1) (109 mg) in ethanol/tetrahydrofuran (3 mL/3 mL) was added 21% sodium ethoxide/ethanol (0.2 mL) and the mixture was stirred at 60° C. for 30 minutes. After cooling to room temperature, to the reaction mixture was diluted with ethyl acetate and thereto was added water. The mixture was extracted with ethyl acetate and the organic layer was concentrated in vacuo. The resultant crude product was purified by column chromatography on silica gel (solvent; hexane/ethyl acetate=80/20 to 50/50) to give 6-(2-chlorophenyl)-7-(4-chlorophenyl)-3-ethoxycarbonyl-2-hydroxymethylpyrazolo[1,5-a]pyrimidine (75 mg, yield: 75%) as a colorless solid.

MS (APCI)m/z; 442/444 [M+H]⁺

(3) To a solution of the compound obtained in the above step (2) (75 mg) in dimethylformamide (2 mL) was added imidazole (23 mg) and tert-butyldimethylsilyl chloride (31 mg) and the mixture was stirred at room temperature for 22 hours. To the reaction mixture was added imidazole (10 mg) and tert-butyldimethylsilyl chloride (15 mg) and the mixture was stirred for 6 hours. To the reaction mixture was added water and the mixture was extracted with ethyl acetate. The extract was concentrated in vacuo and the resultant crude product was purified by column chromatography on silica gel (solvent; hexane/ethyl acetate=85/15 to 60/40) to give 6-(2-chlorophenyl)-7-(4-chlorophenyl)-3-ethoxycarbonyl-2-

(tert-butyldimethylsilyloxymethyl)pyrazolo[1,5-a]pyrimidine (66.8 mg, yield: 71%) as a colorless solid.

MS (APCI)m/z; 556/558 [M+H]+

(4) The compound obtained in the above step (3) (66.8 mg) was treated in the same manner as described in Reference Example 1(3) to give 3-carboxy-6-(2-chlorophenyl)-7-(4-chlorophenyl)-2-hydroxymethylpyrazolo[1,5-a]pyrimidine as a colorless powder.

MS (APCI)m/z; 414/416 [M+H]+

Reference Example 97

(1) To a solution of benzyl 4-hydroxy-1-piperidinecarboxylate (1.0 g) in toluene/aqueous 2N sodium hydroxide solution (10 mL/10 mL) was added tetrabutylammonium bromide (550 mg) and methoxyethyl bromide (1.2 mL) and the mixture was stirred at 60° C. for 2.5 hours and then stirred at 80° C. for 17 hours. To the reaction mixture was added sodium hydroxide (0.95 g) and methoxyethyl bromide (1.2 mL) and the mixture was stirred at 80° C. for 24 hours. After cooling to room temperature, to the reaction mixture was added water and the mixture was extracted with ethyl acetate. The organic layer was washed with a saturated brine, dried over magnesium sulfate and filtered. The filtrate was concentrated in vacuo and the resultant crude product was purified by column chromatography on silica gel (solvent; hexane/ethyl acetate=75/25 to 40/60) to give benzyl 4-(2-methoxyethoxy)-1-piperidinecarboxylate (266 mg, yield: 21%) as a pale yellow liquid.

MS (APCI)m/z; 294 [M+H]+

(2) To a solution of the compound obtained in the above step (1) (266 mg) in ethanol (5 mL) was added 10% palladium-carbon (30 mg) and the mixture was stirred at room temperature under hydrogen-gas atmosphere. The reaction mixture was filtered and the filtrate was concentrated in vacuo to give 4-(2-methoxyethoxy)piperidine (138 mg, yield: 96%) as a colorless liquid.

MS (APCI)m/z; 160 [M+H]+

Reference Example 98 to 99

The corresponding starting materials were treated in the same manner as described in Example 484 and then the resultant product was treated in Reference Example 1(3) to obtain the compounds as shown in the following Table B6.

TABLE B6

| Ref. Ex. Nos. | R¹ | Physicochemical properties etc. |
|---|---|---|
| 98 | Cl—⟨phenyl⟩— | MS(APCI): 399/4.1 [M + H]+ |
| 99 | F₃C—⟨phenyl⟩— | MS(APCI): 433/435 [M + H]+ |

Reference Example 100 to 102

The corresponding starting materials were treated in the same manner as described in Reference Example 7B to obtain the compounds as shown in the following Table B7.

TABLE B7

| Ref. Ex. Nos. | R¹ | Physicochemical properties etc. |
|---|---|---|
| 100 | H₃C–O–CH₂–(1-methylpiperidin-4-yl)methyl | MS(APCI): 415/417 [M + H]+ |
| 101 | H₃CO–CH₂CH₂–O–(1-methylpiperidin-4-yl) | MS(APCI): 431/433 [M + H]+ |
| 102 | 1-methylazepan-yl | MS(APCI): 371/373 [M + H]+ |

Experiment 1

Human Cb1 Receptor Binding Assay (1) Preparation of Human Cb1 Receptor (Membrane Fraction):

Materials)

Human CB1-expressing cell line: hCB1/CHO#C3 (Euroscreen)

Medium: F-12 (GIBCO#11765-062), 10% fetal calf serum, antibiotics (400 µg, Geneticin (GIBCO#11811-031)

Buffer A: 50 mM tris-HCl (pH 7.5) containing ethylenediaminetetraacetic acid (2.5 mM), $MgCl_2$ (5 mM) and sucrose (200 mM)

Procedure)

The receptor-expressing cells cultivated in the above medium were washed with phosphate buffer (×2) and thereto was added Buffer A (2 mL) under ice-cooling or 4° C. (the following procedures were also carried out at the same temperature). The cells were collected by using a cell-scraper, treated by a microtip-type ultrasonicator for 20 seconds (pulse-on: 2 sec, pulse-off: 1 sec) and centrifuged (500×g, 15 min). The supernatant was separated and centrifuged (43000×g, 60 min). The resultant pellet was suspended in Buffer A and homogenized with a potter-type homogenizer. To the homogenate was added an equal volume of 80% glycerol and stored at −80° C.

(2) Procedure of Cb1 Receptor Binding Assay:

Materials)

Buffer B: 50 mM tris-HCl (pH 7.5) containing ethylenediaminetetraacetic acid (2.5 mM), $MgCl_2$ (5 mM) and bovine serum albumine (2 mg/mL, fatty acid-free, SIGMA-A7030)

Buffer C: 50 mM tris-HCl (pH 7.5) containing ethylenediaminetetraacetic acid (2.5 mM), $MgCl_2$ (5 mM) and bovine serum albumine (2 mg/mL, SIGMA-A7906)

Coating solution: 0.3% ethyleneimine polymer

Radioligand: [$^3$H]-CP55940 (30 nM/7992 dpm/mL) prepared by diluting 8.3 µM solution of the radioligand with Buffer B Method)

Each well of the assay plate (96-well, Costar Code#3371) was filled with Buffer B (140 µL), a solution of each test compound in dimethylsulfoxide (20 µL, final concentration: 0.1%), radioligand (20 µL) and membrane preparation (20 µL, 0.5 µg/20 µL) and the mixture was incubated at 30° C. for 90 minutes to proceed the binding reaction. The reaction mixture was harvested to each well of a plate presoaked with the above coating solution (Packard Unifilter GF/B, #6005177). The plate was washed with Buffer C (200 µL×10) and dried at 50° C. for 1 hour and Microscinti 40 (40 µL) was added to each well. The bound radiolabel was quantitated by scintillation counting (Top Count NXT, Packard). $IC_{50}$ value of each test compound against the radioligand-binding to CB1 receptors was calculated on the basis of the quantitated radiolabel activity by using Graphpad Prism 3.02.

(3) Results:

$IC_{50}$ value of each test compound is shown in the following Table C1. Meanwhile, the symbols (++ and +++) are defined as follows:

++: 10 nM<$IC_{50}$<100 nM

+++: 10 nM>$IC_{50}$

TABLE C1

| Test Compounds | $IC_{50}$ (nM) |
|---|---|
| Compound of Example 10 | ++ |
| Compound of Example 131 | ++ |
| Compound of Example 185 | ++ |
| Compound of Example 224 | ++ |
| Compound of Example 238 | ++ |
| Compound of Example 287 | ++ |
| Compound of Example 289 | ++ |
| Compound of Example 309 | +++ |
| Compound of Example 324 | ++ |
| Compound of Example 410 | ++ |
| Compound of Example 252 | ++ |
| Compound of Example 253 | +++ |
| Compound of Example 427 | ++ |
| Compound of Example 452 | +++ |
| Compound of Example 462 | ++ |

INDUSTRIAL APPLICABILITY

The compounds [I] of the present invention are useful for treatment and/or prophylaxis of various CB1 receptor-mediated diseases such as psychosis including schizophrenia. The compounds [I] of the present invention are also useful for withdrawal from a chronic treatment, alcohol dependence or drug abuse. Furthermore, the compounds [I] of the present invention are useful as an agent for enhancing analgesic activity or an agent for smoking cessation.

The invention claimed is:

1. A compound of the formula [I]:

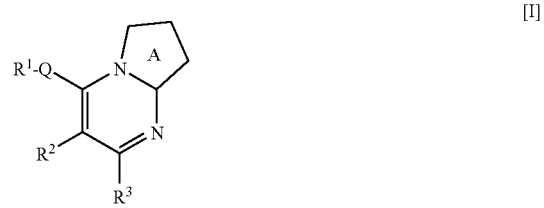

wherein $R^1$ and $R^2$ are the same or different and a 6- to 10-membered monocyclic or bicyclic aryl group optionally substituted by one to three group(s) selected from a halogen atom, a cyano group, a $C_{1-6}$ alkyl group optionally substituted by one to three halogen atom(s), a $C_{1-6}$ alkyloxy group optionally substituted by one to three halogen atom(s), an amino group optionally substituted by one to two $C_{1-6}$ alkyl group(s), a $C_{1-6}$ alkylthio group, a $C_{1-6}$ alkylsulfinyl group and a $C_{1-6}$ alkylsulfonyl group, Q is single bond, a methylene group or a group of the formula: —N($R^Q$)—, $R^Q$ is a $C_{1-6}$ alkyl group, 5-membered Ring A is a substituted pyrazole ring fused to the adjacent pyrimidine ring having the following formula (A), (B) or (C),

-continued

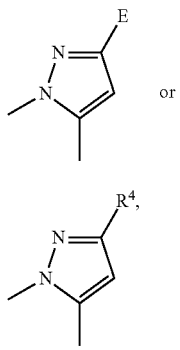

(B) or (C)

$R^3$ and $R^4$ are the same or different and each is (a) a hydrogen atom, (b) a cyano group, (c) a $C_{1-6}$ alkyl group optionally substituted by one to three halogen atom(s), (d) a $C_{1-6}$ alkyloxy group (the alkyl moiety of said group being optionally substituted by one to three group(s) selected from a halogen atom, a hydroxyl group, an amino group optionally substituted by one or two $C_{1-6}$ alkyl group(s), a $C_{1-6}$ alkyloxy group and a $C_{1-6}$ alkylsulfonyl group), (e) a $C_{1-6}$ alkylthio group, (f) a $C_{1-6}$ alkylsulfinyl group, (g) a $C_{1-6}$ alkylsulfonyl group or (h) a group of the formula: —N(R')(R''), R' and R'' are the same or different and (a) a hydrogen atom, (b) a $C_{1-6}$ alkyl group optionally substituted by one to three group(s) selected from a halogen atom, an amino group optionally substituted by one or two $C_{1-6}$ alkyl group(s) and a $C_{1-6}$ alkyloxy group, (c) an acyl group, (d) a $C_{1-6}$ alkylsulfonyl group or (e) an amino sulfonyl group optionally substituted by one to two $C_{1-6}$ alkyl group(s), or both R' and R'' combine each other at their termini to form together with an adjacent nitrogen atom a saturated or unsaturated 5- to 6-membered nitrogen-containing heterocyclic group optionally substituted by a hydroxyl group or a $C_{1-6}$ alkyloxy group, E is one of the following groups (ii) to (v):

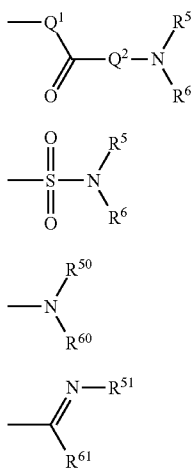

$Q^1$ is a single bond, a $C_{1-6}$ alkylene group or a group of the formula: —N($R^7$)—, $R^7$ is a hydrogen atom or a $C_{1-6}$ alkyl group,
$Q^2$ is a single bond or a $C_{1-6}$ alkylene group, one of $R^5$ and $R^6$ is a hydrogen atom or a $C_{1-6}$ alkyl group and the other is (A) a $C_{1-6}$ alkyl group optionally substituted by one to three group(s) selected from the group consisting of (a) a halogen atom; (b) a cyano group; (c) a $C_{1-6}$ alkyloxy group; (d) a $C_{3-8}$ cycloalkyl group optionally substituted by one to two group(s) selected from a cyano group and a $C_{1-6}$ alkyl group; (e) an amino group optionally substituted by one or two $C_{1-6}$ alkyl group(s); (f) a $C_{1-6}$ alkylthio group; (g) a $C_{1-6}$ alkylsulfinyl group; (h) a $C_{1-6}$ alkylsulfonyl group; (i) an acyl group; (j) a 6- to 10-membered monocyclic or bicyclic aryl group optionally substituted by one to two halogen atom(s); (k) a saturated or unsaturated 4- to 7-membered heteromonocyclic group (said heteromonocyclic group containing one to four heteroatom(s) selected from oxygen atom, sulfur atom and nitrogen atom); (l) a saturated or unsaturated 8- to 15-membered nitrogen-containing bi-cyclic or tri-cyclic heterocyclic group formed by fusing the aforementioned heteromonocyclic group with one or two other cyclic group(s) selected from a $C_{3-8}$ cycloalkyl group, a 5- to 6-membered monocyclic aryl group and a saturated or unsaturated 4- to 7-membered heteromonocyclic group (said heteromonocyclic group containing one to four heteroatom(s) selected from oxygen atom, sulfur atom and nitrogen atom); and (m) a saturated or unsaturated 8- to 11-membered nitrogen-containing spiro-heterocyclic group, (B) a $C_{3-8}$ cycloalkyl group optionally substituted by one to two group(s) selected from a cyano group and a $C_{1-6}$ alkyl group, (C) a group of the formula: —N($R^8$)($R^9$), (D) a 6- to 10-membered monocyclic or bicyclic aryl group optionally substituted by one to two halogen atom(s), or (E) a saturated or unsaturated heterocyclic group selected from the group consisting of i) a saturated or unsaturated 4- to 7-membered heteromonocyclic group (said heteromonocyclic group containing one to four heteroatom(s) selected from oxygen atom, sulfur atom and nitrogen atom), ii) a saturated or unsaturated 8- to 15-membered nitrogen-containing bi-cyclic or tri-cyclic heterocyclic group formed by fusing the aforementioned heteromonocyclic group with one or two other cyclic group(s) selected from a $C_{3-8}$ cycloalkyl group, a 5- to 6-membered monocyclic aryl group and a saturated or unsaturated 4- to 7-membered heteromonocyclic group (said heteromonocyclic group containing one to four heteroatom(s) selected from oxygen atom, sulfur atom and nitrogen atom) and iii) a saturated or unsaturated 8- to 11-membered nitrogen-containing spiro-heterocyclic group, or both of $R^5$ and $R^6$ combine each other to form together with an adjacent nitrogen atom a saturated or unsaturated nitrogen-containing heterocyclic group selected from the group consisting of (a) a saturated or unsaturated, 4- to 7-membered nitrogen-containing heteromonocyclic group, said heteromonocyclic group optionally containing two or more nitrogen atoms and optionally containing one to two hetero atom(s) other than such nitrogen atom(s) selected from oxygen atom and sulfur atom;

(b) a saturated or unsaturated, 8- to 15-membered nitrogen-containing bicyclic or tricyclic heterocyclic group formed by fusing the aforementioned heteromonocyclic group with one or two other cyclic group(s) selected from a $C_{3-8}$ cycloalkyl group, a 5- to 6-membered monocyclic aryl group and a saturated or unsaturated, 4- to 7-membered heteromonocyclic group, said heteromonocyclic group containing one to four heteroatom(s) selected from oxygen atom, sulfur atom and nitrogen atom; and (c) a saturated or unsaturated, 8- to 11-membered nitrogen-containing spiro-heterocyclic group, $R^8$ is a hydrogen atom or a $C_{1-6}$ alkyl group, $R^9$ is (a) a $C_{1-6}$ alkyl group optionally substituted by one to three group(s) selected from a halogen atom, a cyano group and a phenyl group, (b) a $C_{3-8}$ cycloalkyl group, (c) a 6- to 10-membered monocyclic or bicyclic aryl group optionally substituted by one to two halogen atom(s) or (d) an acyl group or (e) a saturated or unsaturated heterocyclic group selected from the group consisting of i) a saturated or unsaturated 4- to 7-membered heteromonocyclic group said heteromonocyclic group containing one to four heteroatom(s) selected from oxygen atom, sulfur atom and nitrogen atom), ii) a saturated or unsaturated 8- to 15-membered nitrogen-containing bi-cyclic or tri-cyclic heterocyclic group formed by fusing the aforementioned heteromonocyclic group with one or two other cyclic group(s) selected from a $C_{3-8}$ cycloalkyl group, a 5- to 6-membered monocyclic aryl group and a saturated or unsaturated 4- to 7-membered heteromonocyclic group (said heteromonocyclic group containing one to four heteroatom(s) selected from oxygen atom, sulfur atom and nitrogen atom) and iii) a saturated or unsaturated 8- to 11-membered nitrogen-containing spiro-heterocyclic group, $R^{50}$ is a hydrogen atom or a $C_{1-6}$ alkyl group, $R^{60}$ is a hydrogen atom, a $C_{1-6}$ alkyl group or an acyl group, or both of them combine together with the adjacent nitrogen atom to form a cyclic group of the following formula:

in which Ring $A^1$ is a 5- to 7-membered aliphatic nitrogen-containing heterocyclic group optionally substituted by an oxo group, $R^{51}$ is an alkyl group or a 6- to 10-membered monocyclic or bicyclic arylsulfonyl group optionally substituted by one to two halogen atom(s), $R^{61}$ is a $C_{1-6}$ alkylamino group or an azido group, and wherein (a) the above-mentioned saturated or unsaturated heterocyclic group in $R^5$, $R^6$, $R^8$ or $R^9$ may be substituted by one to four groups selected from the group consisting of a halogen atom;

a hydroxyl group;
a cyano group;
an oxo group;
a $C_{1-6}$ alkyl group;
a $C_{1-6}$ alkyl group substituted by one to three halogen atom(s);
a $C_{1-6}$ alkyloxy-$C_{1-6}$ alkyl group;
an amino-$C_{1-6}$ alkyl group;
a $C_{3-8}$ cycloalkyl group;
a phenyl-$C_{1-6}$ alkyl group;
a $C_{1-6}$ alkyloxy group;
a $C_{1-6}$ alkyloxy group substituted by one to three halogen atom(s);
an acyl group;
an amino group optionally substituted by one to two $C_{1-6}$ alkyl group(s);
an acylamino group;
a $C_{1-6}$ alkylsulfonyl group;
an aminosulfonyl group optionally substituted by one to two $C_{1-6}$ alkyl group(s);
a phenyl group optionally substituted by one to two halogen atom(s); and
a saturated or unsaturated 5- to 6-membered nitrogen-containing heterocyclic group, and wherein
(b) the above-mentioned saturated or unsaturated heterocyclic group formed by combining $R^5$ with $R^6$ may be substituted by one to three group(s) selected from the group consisting of
a halogen atom;
a hydroxyl group;
a cyano group;
an oxo group;
a $C_{1-6}$ alkyl group;
a $C_{1-6}$ alkyl group substituted by one to three halogen atom(s);
a $C_{1-6}$ alkyloxy-$C_{1-6}$ alkyl group;
an amino-$C_{1-6}$ alkyl group;
a $C_{3-8}$ cycloalkyl group;
a phenyl-$C_{1-6}$ alkyl group;
a $C_{1-6}$ alkyloxy group;
a $C_{1-6}$ alkyloxy group substituted by one to three halogen atom(s);
an acyl group;
an amino group optionally substituted by one to two $C_{1-6}$ alkyl group(s);
an acylamino group;
a $C_{1-6}$ alkylsulfonyl group;
an aminosulfonyl group optionally substituted by one to two $C_{1-6}$ alkyl group(s); and
a phenyl group,
or a pharmaceutically acceptable salt thereof.

2. The compound according to claim 1 wherein the group of the formula (II) is one of the following groups (a) to (d):

$$—C(=O)—N(R^5)(R^6), \quad (a)$$

$$—C(=O)\text{-Alk-}N(R^5)(R^6), \quad (b)$$

$$\text{-Alk-}C(=O)—N(R^5)(R^6), \quad (c)$$

$$—N(R^7)—C(=O)—N(R^5)(R^6) \quad (d)$$

in which Alk is a straight or branched chain $C_{1-6}$ alkylene group, or a pharmaceutically acceptable salt thereof.

3. A compound of the formula [I]:

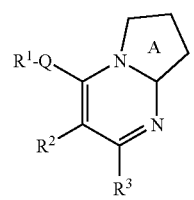

wherein
$R^1$ and $R^2$ are the same or different and each is a phenyl group optionally substituted by one to two group(s) selected from a halogen atom and a trihalogeno-$C_{1-6}$ alkyl group,
Q is a single bond, R³ is (a) a hydrogen atom, (b) a cyano group, (c) a C$_{1-6}$ alkyl group optionally substituted by one to three halogen atom(s), (d) a C$_{1-6}$ alkyloxy group (the alkyl moiety of said group being optionally substituted by one to three group(s) selected from a halogen atom, a hydroxyl group, an amino group optionally substituted by one or two C$_{1-6}$ alkyl group(s), a C$_{1-6}$ alkyloxy group and a C$_{1-6}$ alkylsulfonyl group), (e) a C$_{1-6}$ alkylthio group, (f) a C$_{1-6}$ alkylsulfinyl group, (g) a C$_{1-6}$ alkylsulfonyl group or (h) a group of the formula: —N(R')(R"), wherein R' and R" are the same or different and each is (a) a hydrogen atom, (b) a C$_{1-6}$ alkyl group optionally substituted by one to three group(s) selected from a halogen atom, an amino group optionally substituted by one or two C$_{1-6}$ alkyl group(s) and a C$_{1-6}$ alkyloxy group, (c) an acyl group, (d) a C$_{1-6}$ alkylsulfonyl group or (e) an amino sulfonyl group optionally substituted by one to two C$_{1-6}$ alkyl group(s), or both R' and R" combine each other at their termini to form together with an adjacent nitrogen atom a saturated or unsaturated 5- to 6-membered nitrogen-containing heterocyclic group optionally substituted by a hydroxyl group or a C$_{1-6}$ alkyloxy group, Ring A is a substituted pyrazole ring of the formula (A)

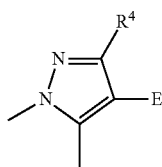

(A)

E is a group of the following formula: —C(=O)O—R$^{00}$ (i)

R⁴ is an amino group optionally substituted by one to two group(s) selected from a C$_{1-6}$ alkyl group and a C$_{1-6}$ alkylsulfonyl group, or a pharmaceutically acceptable salt thereof.

4. The compound according to claim 3 wherein R¹ is a chlorophenyl group or a trifluoro-C$_{1-4}$ alkyl-phenyl group, R² is a chlorophenyl group, R³ is a 4 alkyl group and R⁴ is (a) an amino group substituted by one to two group(s) selected from a C$_{1-4}$ alkyl group and a C$_{1-4}$ alkylsulfonyl group or (b) an aminosulfonyl group substituted by one to two C$_{1-4}$ alkyl group(s), or a pharmaceutically acceptable salt thereof.

5. The compound according to claim 1 wherein

R¹ and R² are the same or different and a phenyl group optionally substituted by one to three group(s) selected from a halogen atom, a cyano group, a C$_{1-6}$ alkyl group optionally substituted by one to three halogen atom(s), a C$_{1-6}$ alkyloxy group optionally substituted by one to three halogen atom(s), an amino group optionally substituted by one to two C$_{1-6}$ alkyl group(s) and a C$_{1-6}$ alkylsulfonyl group, Ring A is a substituted pyrazole ring of the formula (A) or (B), E is one of the groups of the following formula (a) to (e):

  a)

  b)

  c)

  d)

  e)

in which Alk is a straight or branched chain C$_{1-6}$ alkylene group,

R³ is a hydrogen atom, a cyano group or a C$_{1-6}$ alkyloxy group,

R⁴ is (a) a hydrogen atom, (b) a cyano group, (c) a C$_{1-6}$ alkyl group optionally substituted by one to three group(s) selected from a halogen atom and a hydroxyl group, (d) a C$_{1-6}$ alkyloxy group optionally substituted by one to three group(s) selected from a halogen atom, a hydroxyl group, an amino group optionally substituted by one to two C$_{1-6}$ alkyl group(s), a C$_{1-6}$ alkyloxy group and a C$_{1-6}$ alkylsulfonyl group, (e) a C$_{1-6}$ alkylthio group, (f) a C$_{1-6}$ alkylsulfinyl group, (g) a C$_{1-6}$ alkylsulfonyl group or (h) a group of the formula: —N(R')(R"), R' and R" are the same or different and (a) a hydrogen atom, (b) a C$_{1-6}$ alkyl group optionally substituted by one to three group(s) selected from a halogen atom, an amino group optionally substituted by one to two C$_{1-6}$ alkyl group(s) and a C$_{1-6}$ alkyloxy group, (c) an acyl group, (d) a C$_{1-6}$ alkylsulfonyl group or (e) an aminosulfonyl group optionally substituted by one to two C$_{1-6}$ alkyl group(s), or (f) both of them combine together with the adjacent nitrogen atom to form a saturated or unsaturated 5- to 6-membered nitrogen-containing heteromonocyclic group optionally substituted by a hydroxyl group or a C$_{1-6}$ alkyloxy group, R⁵ is a hydrogen atom or a C$_{1-6}$ alkyl group, R⁶ is (1) an alkyl group optionally substituted by one to three group(s) selected from a halogen atom, a C$_{1-6}$ alkyloxy group, a C$_{3-8}$ cycloalkyl group, a C$_{1-6}$ alkylthio group, a C$_{1-6}$ alkylsulfonyl group, an amino group optionally substituted by one or two C$_{1-6}$ alkyl group(s), a morpholinocarbonyl group, a phenyl group optionally substituted by a cyano group and a saturated or unsaturated 5- to 6-membered nitrogen-containing heteromonocyclic group, said heteromonocyclic group being optionally substituted by a group selected from a halogen atom, a C$_{1-6}$ alkyl group and a trihalogeno-C$_{1-6}$ alkyl group;

(2) a C$_{3-8}$ cycloalkyl group optionally substituted by a cyano group or a C$_{1-6}$ alkyl group;

(3) a group of the formula: —N(R⁸)(R⁹); or (4) a phenyl group; or (5) a saturated or unsaturated 4- to 10-membered monocyclic- or bicyclic heterocyclic group optionally substituted by one to four group(s) selected from a halogen atom, a cyano group, a hydroxyl group, an oxo group, a C$_{1-6}$ alkyl group optionally substituted by one to three halogen atom(s), a C$_{3-8}$ cycloalkyl group, a C$_{1-6}$ alkylcarbonyl group, a C$_{1-6}$ alkyloxycarbonyl group, a C$_{1-6}$ alkylsulfonyl group, an aminosulfonyl group optionally substituted by one or two C$_{1-6}$ alkyl group(s), a carbamoyl group optionally substituted by one to two C$_{1-6}$ alkyl group(s), a C$_{1-6}$ alkyloxycarbonyl group, a C$_{1-6}$ alkyloxycarbonylamino group a phenyl group optionally substituted by one to two halogen atom(s) and saturated or unsaturated 5- to 6-membered heteromonocyclic group; or (6) both of R⁵ and R⁶ combine each other together with the adjacent nitrogen atom to form a saturated or unsaturated 5- to 7-membered nitrogen-containing heterocyclic group optionally substituted by one to two group(s) selected from a halogen atom and an oxo group, R⁸ is hydrogen atom or a C$_{1-6}$ alkyl group, R⁹ is (a) a C$_{1-6}$ alkyl group optionally substituted by one to three group(s) selected from a halogen atom, a cyano group and a phenyl group; (b) a phenyl group optionally substituted by a group selected from a halogen atom, a cyano group, a $C_{1-6}$ alkyl group, a trihalogeno-$C_{1-6}$ alkyl group, a $C_{3-8}$ cycloalkyl group, a trihalogeno-$C_{1-6}$ alkyloxy group, a $C_{1-6}$ alkyloxy group, a $C_{1-6}$ alkylthio group and a $C_{1-6}$ alkylsulfonyl group; (c) a $C_{1-6}$ alkyloxycarbonyl group; or (d) a saturated or unsaturated 5- to 6-membered heteromonocyclic group optionally substituted by a group selected from a halogen atom, a cyano group, a $C_{1-6}$ alkyl group, a $C_{1-6}$ alkyloxy group and a trihalogeno-$C_{1-6}$ alkyl group, $R^7$ is a hydrogen atom, $R^{51}$ is a $C_{1-6}$ alkyl group or a phenylsulfonyl group optionally substituted by one to two halogen atom(s) and $R^{61}$ is a $C_{1-6}$ alkylamino group or an azido group, or a pharmaceutically acceptable salt thereof.

6. The compound according to claim 5 wherein $R^1$ is a phenyl group optionally substituted by one or two group(s) selected from a halogen atom, a cyano group, a dihalogeno-$C_{1-6}$ alkyl group, a trihalogeno-$C_{1-6}$ alkyl group, a $C_{1-6}$ alkyloxy group, a $C_{1-6}$ alkyloxy-$C_{1-6}$alkyl group and di($C_{1-6}$alkyl) amino group, $R^2$ is a phenyl group optionally substituted by one or two group(s) selected from a halogen atom and a cyano group, $R^3$ is a hydrogen atom, $R^4$ is a hydrogen atom, a $C_{1-6}$ alkyl group, a dihalogeno-$C_{1-6}$ alkyl group, a hydroxy-$C_{1-6}$ alkyl group, a trihalogeno-$C_{1-6}$ alkyl group, a $C_{1-6}$ alkyloxy-$C_{1-6}$ alkyl group, a hydroxy-$C_{1-6}$ alkyloxy group, a $C_{1-6}$ alkyloxy-$C_{1-6}$ alkyloxy group, a $C_{1-6}$ alkylsulfonyl-$C_{1-6}$ alkyl group or a group of the formula: —N(R')(R''), one of R' and R'' is a hydrogen atom or an alkyl group and the other is (a) an acyl group or (b) a $C_{1-6}$ alkylsulfonyl group, E is one of the groups of the following formula (a), (b) and (e):

  (a)

  (b)

  (e)

one of $R^5$ and $R^6$ is a hydrogen atom or a $C_{1-6}$ alkyl group, the other is (a) a $C_{1-6}$ alkyl group, (b) a $C_{3-8}$ cycloalkyl group, (c) a phenyl group, (d) a saturated or unsaturated 4- to 10-membered mono- or bi-cyclic heterocyclic group optionally substituted by one to four group(s) selected from a halogen atom, an oxo group, a cyano group, a hydroxyl group, a $C_{1-6}$ alkyl group, a trihalogeno-$C_{1-6}$ alkyl group, a $C_{1-6}$ alkyloxy group, a $C_{1-6}$ alkyloxy-$C_{1-6}$ alkyl group, a $C_{1-6}$ alkylcarbonyl group, a di($C_{1-6}$ alkyl)carbamoyl group, a $C_{1-6}$ alkylsulfonyl group, a di($C_{1-6}$ alkyl)aminosulfonyl group, a phenyl group, a halogenophenyl group and a pyridyl group or (e) a group of the formula: —N($R^8$)($R^9$), or (f) both of them combine together with the adjacent nitrogen atom to form a saturated or unsaturated 5- to 6-membered heteromonocyclic group optionally substituted by one to two group(s) selected from a halogen atom and an oxo group, $R^8$ is a $C_{1-6}$ alkyl group, $R^9$ is (a) a $C_{1-6}$ alkyl group, (b) a phenyl group optionally substituted by a halogen atom, (c) a $C_{1-6}$ alkyl group optionally substituted by a pyridyl group or (d) a saturated or unsaturated 4- to 6-membered heteromonocyclic group optionally substituted by a group selected from a halogen atom, a $C_{1-6}$ alkyl group, a trihalogeno-$C_{1-6}$ alkyl group and a $C_{1-6}$alkyloxy group, $R^{51}$ is an alkyl group or a halogenophenyl-sulfonyl group, and $R^{61}$ is an alkylamino group or an azido group, or a pharmaceutically acceptable salt thereof.

7. The compound according to claim 5 wherein $R^1$ is a phenyl group optionally substituted by a group selected from a chlorine atom, a fluorine atom, a cyano group, a difluoro-$C_{1-4}$ alkyl group and a trifluoro-$C_{1-4}$ alkyl group, $R^2$ is a phenyl group optionally substituted by one to two groups selected from a chlorine atom, a fluorine atom, a bromine atom and a cyano group, $R^3$ is a hydrogen atom, $R^4$ is a hydrogen atom, a $C_{1-4}$ alkyl group, a difluoro-$C_{1-4}$ alkyl group, a trifluoro-$C_{1-4}$ alkyl group, a $C_{1-4}$ alkyloxy-$C_{1-4}$ alkyl group or a $C_{1-4}$ alkyl-carbonyl-amino group, E is one of the groups of the following formula (a) and (b):

  (a)

  (b)

$R^5$ is a hydrogen atom, $R^6$ is a $C_{1-4}$ alkyl group, a pyridyl-$C_{1-4}$ alkyl group, a $C_{5-7}$ cycloalkyl group, a chlorophenyl group, a saturated or unsaturated 4- to 6-membered heteromonocyclic group optionally substituted by one to two group(s) selected from a halogen atom, an oxo group and $C_{1-4}$ alkyloxy-$C_{1-4}$ alkyl group or a group of the formula: —N($R^8$)($R^9$), or both of them combine together with the adjacent nitrogen atom to form a saturated or unsaturated 5- to 6-membered heteromonocyclic group optionally substituted by one to two oxo group(s), $R^8$ is a $C_{1-4}$ alkyl group and $R^9$ is a $C_{1-4}$ alkyl group, a chlorophenyl group, a pyridyl group or a $C_{1-4}$ alkyl-pyridyl group, or a pharmaceutically acceptable salt thereof.

8. The compound according to claim 1 wherein $R^1$ and $R^2$ are the same or different and a phenyl group optionally substituted by one to two group(s) selected from a halogen atom and a trihalogeno-$C_{1-6}$ alkyl group, Q is a single bond, Ring A is a substituted pyrazole ring of the formula (A), $R^3$ is a hydrogen atom, $R^4$ is a hydrogen atom or a $C_{1-6}$ alkyl group, E is a group of the formula (iii):

  (iii)

$R^5$ is a hydrogen atom or a $C_{1-6}$ alkyl group, $R^6$ is (a) a $C_{1-6}$ alkyl group, (b) a $C_{3-8}$ cycloalkyl group or (c) a saturated or unsaturated 5- to 6-membered sulfur- or nitrogen-containing heteromonocyclic group, or (d) both of them combine together with the adjacent nitrogen atom to form a saturated or unsaturated 5- to 6-membered nitrogen-containing heterocyclic group optionally substituted by one to two oxo group(s), or a pharmaceutically acceptable salt thereof.

9. The compound according to claim 8 wherein $R^1$ is a trihalogeno-$C_{1-6}$ alkyl-phenyl group, $R^2$ is a halogenophenyl group, $R^4$ is a $C_{1-6}$alkyl group, $R^5$ is a hydrogen atom or a $C_{1-6}$ alkyl group, $R^6$ is (a) a $C_{1-6}$ alkyl group, (b) a $C_{3-8}$ cycloalkyl group, (c) a saturated or unsaturated 5- to 6-membered sulfur- or nitrogen-containing heteromonocyclic group optionally substituted by one to two oxo group(s), or (d) both of them combine together with the adjacent nitrogen atom to form a saturated or unsaturated 5- to 6-membered heteromonocyclic group optionally substituted by one to two oxo group(s),
or a pharmaceutically acceptable salt thereof.

10. The compound according to claim 1 wherein $R^1$ and $R^2$ are the same or different and a phenyl group optionally substituted by one to two group(s) selected from a halogen atom and a trihalogeno-$C_{1-6}$ alkyl group, Ring A is a substituted pyrazole ring of the formula (A), $R^3$ is a hydrogen atom, $R^4$ is a hydrogen atom or a $C_{1-6}$ alkyl group, E is a group of the formula (iv):

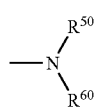

$R^{50}$ is a hydrogen atom or a $C_{1-6}$ alkyl group,
$R^{60}$ is (a) a $C_{1-6}$alkyl group or (b) an acyl group, or both of them combine together with the adjacent nitrogen atom to form a saturated or unsaturated 5- to 6-membered nitrogen-containing heterocyclic group optionally substituted by one to two oxo group(s), or a pharmaceutically acceptable salt thereof.

11. The compound according to claim 1 wherein $R^1$ and $R^2$ are the same or different and a phenyl group optionally substituted by one to two group(s) selected from a halogen atom and a trihalogeno-$C_{1-6}$ alkyl group, Q is a single bond, Ring A is a substituted pyrazole ring of the formula (C), $R^3$ is a hydrogen atom, $R^4$ is a group of the formula —N(R')(R"), R' and R" are the same or different and a hydrogen atom or a $C_{1-6}$ alkyl group, or both of them combine together with the adjacent nitrogen atom to form a saturated or unsaturated 5- to 6-membered nitrogen-containing heterocyclic group, or a pharmaceutically acceptable salt thereof.

12. A compound according to claim 1, selected from the group consisting of:
6-(2-chlorophenyl)-7-(4-chlorophenyl)-3-(N-piperidinocarbamoyl)pyrazolo[1,5-a]-pyrimidine;
6-(2-chlorophenyl)-7-(4-chlorophenyl)-3-[(N'-methyl-N'-phenylhydrazino)-carbonyl]pyrazolo[1,5-a]pyrimidine;
6-(2-chlorophenyl)-7-(4-chlorophenyl)-3-(N-cyclohexylcarbamoyl)pyrazolo pyrimidine;
6-(2-chlorophenyl)-7-(4-chlorophenyl)-3-[(N',N'-dimethylhydrazino)carbonyl]-pyrazolo[1,5-a]pyrimidine;
6-(2-chlorophenyl)-7-(4-chlorophenyl)-3-(N-pyrrolidinocarbamoyl)pyrazolo[1,5-a]-pyrimidine;
6-(2-chlorophenyl)-7-(4-chlorophenyl)-3-(N-cyclopentylcarbamoyl)pyrazolo[1,5-a]-pyrimidine;
6-(2-chlorophenyl)-7-(4-chlorophenyl)-3-[N-(4-tetrahydropyranyl)carbamoyl]-pyrazolo[1,5-a]pyrimidine;
6-(2-chlorophenyl)-7-(4-chlorophenyl)-3-[N-(1,1-dioxotetrahydrothiophen-3-yl)-carbamoyl]pyrazolo[1,5-a]pyrimidine;
(R)-6-(2-chlorophenyl)-7-(4-difluoromethylphenyl)-3[N-(1,1-dioxo-tetrahydro-thiophen-3-yl)carbamoyl]pyrazolo[1,5-a]pyrimidine;
(R)-6-(2-chlorophenyl)-7(4-trifluoromethylphenyl)-2-methyl-3-[N-(1,1-dioxo-tetrahydrothiophen-3-yl)carbamoyl]pyrazolo[1,5-a]pyrimidine;
(S)-6-(2-chlorophenyl)-7-(4-trifluoromethylphenyl)-2-methyl-3-[N-(1,1-dioxo-tetrahydrothiophen-3-yl)carbamoyl]pyrazolo[1,5-a]pyrimidine;
6-(2-chlorophenyl)-7-(4-chlorophenyl)-3-[N-[2-(2-pyridyl)ethyl]carbamoyl]-pyrazolo[1,5-a]pyrimidine;
6-(2-clorophenyl)-7-(4-clorophenyl)-3-(N-cyclopentylcarbamoyl)-2-methoxy-pyrazolo[1,5-a]pyrimidine;
(R)-6-(2-chlorophenyl)-7-(4-chlorophenyl)-2-methyl-3-[N-(1,1-dioxo-tetrahydro-thiophen-3-yl)carbamoyl]pyrazolo[1,5-a]pyrimidine;
(S)-6-(2-chlorophenyl)-7-(4-chlorophenyl)-2-methyl-3-[N-(1,1-dioxo-tetrahydro-thiophen-3-yl)carbamoyl]pyrazolo[1,5-a]pyrimidine;
6-(2-bromophenyl)-7-(4-chlorophenyl)-3-(N-cyclopentylcarbamoyl)pyrazolo[1,5-a]-pyrimidine;
(R,S)-6-(2-bromophenyl)-7-(4-chlorophenyl)-3-[N-(1,1-dioxo-tetrahydrothiophen-3-yl)carbamoyl]pyrazolo[1,5-a]pyrimidine;
(S)-6-(2-chlorophenyl)-7-(4-trifluoromethylphenyl)-3-[N-(1,1-dioxo-tetrahydro-thiophen-3-yl)carbamoyl]pyrazolo[1,5-a]pyrimidine;
(R)-6-(2-chlorophenyl)-7-(4-trifluoromethylphenyl)-3-[N-(1,1-dioxo-tetrahydro-thiophen-3-yl)carbamoyl]pyrazolo[1,5-a]pyrimidine;
6(2-chlorophenyl)-7-(4-chlorophenyl)-3-[N—[N-(3-chlorophenyl)-N-methylamino]-carbamoyl]pyrazolo[1,5-a]pyrimidine;
6-(2-cyanophenyl)-7-(4-chlorophenyl)-3-[N—[N-methyl-N-(2-pyridyl)amino]-carbamoyl]pyrazolo[1,5-a]pyrimidine;
6-(2-chlorophenyl)-7-(4-chlorophenyl)-3-(N-isobutylcarbamoyl)pyrazolo[1,5-a]pyrimidine;
6-(2-chlorophenyl)-7-(4-trifluoromethylphenyl)-3-[N-(1,1-dioxo-tetrahydro-thiophen-3-yl)carbamoyl]pyrazolo[1,5-a]pyrimidine;
6-(2-chlorophenyl)-7-(4-trifluoromethylphenyl)-3-(N-cyclopentylcarbamoyl)-pyrazolo[1,5-a]pyrimidine;
6-(2-chlorophenyl)-7-(4-trifluoromethylphenyl)-3-[N—[N-methyl-N-(2-pyridyl)-amino]carbamoyl]pyrazolo[1,5-a]pyrimidine;
(R)-6-(2-chlorophenyl)-7-(4-chlorophenyl)-3[N-(1,1-dioxo-tetrahydrothiophen-3-yl)carbamoyl]pyrazolo[1,5-a]pyrimidine;
6-(2-chlorophenyl)-7-(4-cyanophenyl)-3-(N-cyclopentylcarbamoyl)pyrazolo[1,5-a]-pyrimidine;
(R,S)-6-(2-chlorophenyl)-7-(4-chlorophenyl)-2-methyl-3-[N-(1,1-dioxo-tetrahydro-thiophen-3-yl]carbamoyl]pyrazolo[1,5-a]pyrimidine;
6(2-chlorophenyl)-7-(4-fluorophenyl)-3-(N-cyclopentylcarbamoyl)pyrazolo[1,5-a]-pyrimidine;
6(2-chlorophenyl)-7-(4-chlorophenyl)-3-[N—[N-methyl-N-(2-pyridyl)amino]-carbamoyl]pyrazolo[1,5-a]pyrimidine;
(S)-6-(2-chlorophenyl)-7-(4-chlorophenyl)-3-[N-(1,1-dioxo-tetrahydrothiophen-3-yl)carbamoyl]pyrazolo[1,5-a]pyrimidine;
6-(2-chlorophenyl)-7-(4-chlorophenyl)-3-(N-ethylcarbamoyl)pyrazolo[1,5-a]-pyrimidine;
6-(2-chlorophenyl)-7-(4-chlorophenyl)-3-(N-cyclopropylcarbamoyl)-pyrazolo[1,5-a]pyrimidine;
(S)-6-(2-chlorophenyl)-7-(4-chloro-2-fluorophenyl)-3[N-(1,1-dioxotetrahydro-thiophen-3-yl)carbamoyl]pyrazolo[1,5-a]pyrimidine;
(S)-6-(2-chlorophenyl)-7-(4-difluoromethylphenyl)-3[N-(1,1-dioxotetrahydro-thiophen-3-yl)carbamoyl]pyrazolo[1,5-a]pyrimidine;

(R)-6-(2-cyanophenyl)-7-(4-trifluoromethylphenyl)-3-[N-(1,1-dioxotetrahydro-thiophen-3-yl)carbamoyl]-2-methylpyrazolo[1,5-a]pyrimidine;
(S)-6-(2-cyanophenyl)-7-(4-trifluoromethylphenyl)-3-[N-(1,1-dioxotetrahydro-thiophen-3-yl)carbamoyl]-2-methylpyrazolo[1,5-a]pyrimidine;
6-(2-chlorophenyl)-7-(4-chlorophenyl)-3-[[N'-methyl-N'-(2-methoxypyridin-5-yl)-hydrazino]carbonyl]pyrazolo[1,5-a]pyrimidine;
6-(2-cyanophenyl)-7-(4-chlorophenyl)-3-[N-(1-pyrrolidinyl)carbamoyl]-pyrazolo[1,5-a]pyrimidine;
(R)-6-(2-cyanophenyl)-7-(4-chlorophenyl)-3-[N-(1,1-dioxotetrahydro-thiophen-3-yl)carbamoyl]-2-methylpyrazolo[1,5-a]pyrimidine;
6-(2-cyanophenyl)-7-(4-chlorophenyl)-3-[[N'-methyl-N'-(2-pyridyl)hydrazino]-carbonyl]-2-methylpyrazolo[1,5-a]pyrimidine;
(R)-6-(2-chlorophenyl)-7-(4-chlorophenyl)-3-[N-(1,1-dioxotetrahydro-thiophen-3-yl)carbamoyl]-2-trifluoromethylpyrazolo[1,5-a]pyrimidine;
6-(2-chlorophenyl)-7-(4-trifluoromethylphenyl)-3-[(N',N'-dimethylhydrazino)-carbonyl]-2-acetylaminopyrazolo[1,5-a]pyrimidine;
6-(2-chlorophenyl)-7-(4-chlorophenyl)-3[N-methyl-N'-(2-pyridyl)hydrazino-carbonyl]-2-acetylaminopyrazolo[1,5-a]pyrimidine;
6-(2-chlorophenyl)-7-(4-chlorophenyl)-3-[[N'-methyl-N'-(2-pyridyl)hydrazino]-carbonyl]-2-(trifluoromethyl)pyrazolo[1,5-a]pyrimidine;
6-(2-chlorophenyl)-7-(4-chlorophenyl)-3-[N-(1-pyrrolidinyl)carbamoyl]-2-difluoromethylpyrazolo[1,5-a]pyrimidine;
(R)-6-(2-chlorophenyl)-7-(4-trifluoromethylphenyl)-3-[N-(1,1-dioxotetrahydro-thiophen-3-yl)carbamoyl]-2-difluoromethylpyrazolo[1,5-a]pyrimidine;
(S)-6-(2-chlorophenyl)-7-(4-trifluoromethylphenyl)-3-[N-(1,1-dioxotetrahydro-thiophen-3-yl)carbamoyl]-2-difluoromethylpyrazolo[1,5-a]pyrimidine;
6-(2-cyanophenyl)-7-(4-chlorophenyl)-3-(N-piperidinocarbamoyl)-2-difluoromethylpyrazolo[1,5-a]pyrimidine;
6-(2-chlorophenyl)-7-(4-chlorophenyl)-3[N-(1,1-dioxothiacyclobutan-3-yl)-carbamoyl]pyrazolo[1,5-a]pyrimidine;
7-(4-chlorophenyl)-6-(2-cyano-4-fluorophenyl)-3-[N-(1-pyrrolidinyl)carbamoyl]-pyrazolo[1,5-a]pyrimidine;
7-(4-chlorophenyl)-6-(2-cyanophenyl)-3-(N-piperidinocarbamoyl)-2-methyl-pyrazolo[1,5-a]pyrimidine;
7-(4-chlorophenyl)-6-(2-cyanophenyl)-3-[N-(1-pyrrolidinyl)carbamoyl]-2-methyl-pyrazolo[1,5-a]pyrimidine;
(S)-6-(2-chlorophenyl)-7-(4-chlorophenyl)-3-[N-(2-methoxymethyl-1-pyrrolidinyl)-carbamoyl]pyrazolo[1,5-a]pyrimidine;
6-(2-chlorophenyl)-7-(4-chlorophenyl)-3[(N-(4-fluoropiperidino)carbamoyl]-pyrazolo[1,5-a]pyrimidine;
(R)-7-(4-chloro-2-fluorophenyl)-6-(2-cyanophenyl)-3-[N-(1,1-dioxotetrahydro-thiophen-3-yl)carbamoyl]-2-methylpyrazolo[1,5-a]pyrimidine;
6-(2-chlorophenyl)-7-(4-chlorophenyl)-3-[[N'-methyl-N'-(2-ethoxypyridin-5-yl)-hydrazino]carbonyl]pyrazolo[1,5-a]pyrimidine;
(R)-6-(2-chlorophenyl)-7-(4-chlorophenyl)-3-[N-(1,1-dioxotetrahydro-thiophen-3-yl)carbamoyl]-2-methoxymethylpyrazolo[1,5-a]pyrimidine;
(S)-6-(2-chlorophenyl)-7-(4-chlorophenyl)-3[N-(1,1-dioxotetrahydro-thiophen-3-yl)carbamoyl]-2-methoxymethylpyrazolo[1,5-a]pyrimidine;
6-(2-chlorophenyl)-7-(4-chlorophenyl)-3-[[N'-methyl-N'-(2-pyridyl)hydrazino]-carbonyl]-2-methoxymethylpyrazolo[1,5-a]pyrimidine;
6-(2-chlorophenyl)-7-(4-chlorophenyl)-3-[N-(1-pyrrolidinyl)carbamoyl]-2-methoxymethylpyrazolo[1,5-a]pyrimidine;
7-(4-chloro-2-fluorophenyl)-6-(2-cyanophenyl)-3[N-(1-pyrrolidinyl)carbamoyl]-2-methylpyrazolo[1,5-a]pyrimidine;
6-(2-chlorophenyl)-7-(4-chlorophenyl)-3-[2-(1,1-dioxothiomorpholino)acetyl]-2-methylpyrazolo[1,5-a]pyrimidine;
6-(2-cyanophenyl)-7-(4-chlorophenyl)-3-[N-(4-fluoropiperidino)carbamoyl]-2-methylpyrazolo[1,5-a]pyrimidine; and
6-(2-chlorophenyl)-7-(4-trifluoromethylphenyl)-3-[N-(tetrahydrothiophen-3-yl)-carbamoyl]pyrazolo[1,5-a]pyrimidine, or a pharmaceutically acceptable salt thereof.

13. The compound according to claim 1, wherein the compound is:

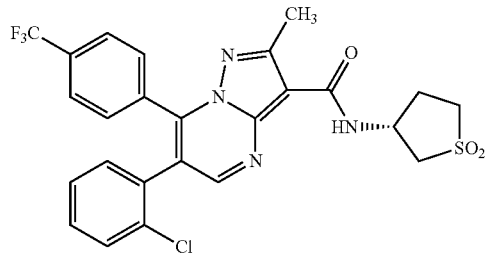

or a pharmaceutically acceptable salt thereof.

14. The compound according to claim 1, wherein the compound is:

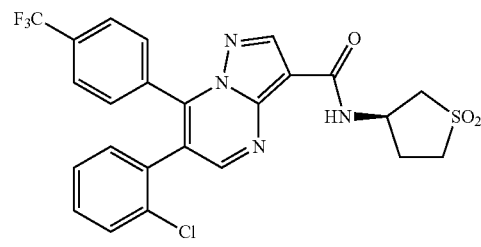

or a pharmaceutically acceptable salt thereof.

15. The compound according to claim 1, wherein the compound is:

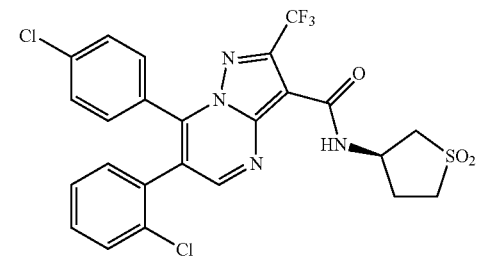

or a pharmaceutically acceptable salt thereof.

16. The compound according to claim 1, wherein the compound is:

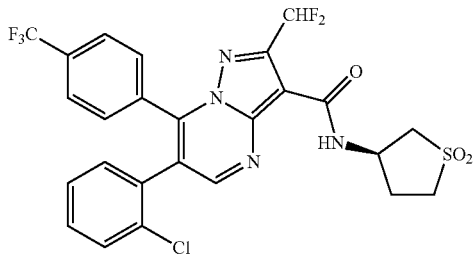

or a pharmaceutically acceptable salt thereof.

17. A pharmaceutical composition comprising as an active ingredient a pyrazolo[1,5-a]pyrimidine compound of the formula [I]:

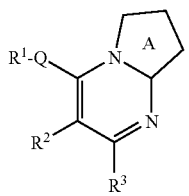

wherein

R$^1$ and R$^2$ are the same or different and a 6- to 10-membered monocyclic or bicyclic aryl group optionally substituted by one to three group(s) selected from a halogen atom, a cyano group, a C$_{1-6}$ alkyl group optionally substituted by one to three halogen atom(s), a C$_{1-6}$ alkyloxy group optionally substituted by one to three halogen atom(s), an amino group optionally substituted by one to two C$_{1-6}$ alkyl group(s), a C$_{1-6}$ alkylthio group, a alkylsulfinyl group and a C$_{1-6}$ alkylsulfonyl group, Q is single bond, a methylene group or a group of the formula: —N(R$^Q$)—, R$^Q$ is a C$_{1-6}$ alkyl group, 5-membered Ring A is a substituted pyrazole ring fused to the adjacent pyrimidine ring having the following formula (A), (B) or (C),

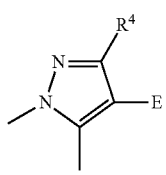 (A)

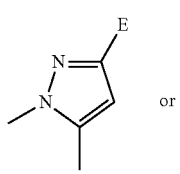 or (B)

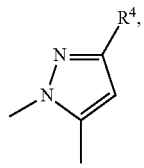 (C)

R$^3$ and R$^4$ are the same or different and (a) a hydrogen atom, (b) a cyano group, (c) a C$_{1-6}$ alkyl group optionally substituted by one to three halogen atom(s), (d) a C$_{1-6}$ alkyloxy group (the alkyl moiety of said group being optionally substituted by one to three group(s) selected from a halogen atom, a hydroxyl group, an amino group optionally substituted by one or two C$_{1-6}$ alkyl group(s), a C$_{1-6}$ alkyloxy group and a C$_{1-6}$ alkylsulfonyl group), (e) a C$_{1-6}$ alkylthio group, (f) a C$_{1-6}$ alkylsulfinyl group, (g) a C$_{1-6}$ alkylsulfonyl group or (h) a group of the formula: —N(R')(R"), R' and R" are the same or different and (a) a hydrogen atom, (b) a C$_{1-6}$ alkyl group optionally substituted by one to three group(s) selected from a halogen atom, an amino group optionally substituted by one or two C$_{1-6}$ alkyl group(s) and a C$_{1-6}$ alkyloxy group, (c) an acyl group, (d) a C$_{1-6}$ alkylsulfonyl group or (e) an amino sulfonyl group optionally substituted by one to two C$_{1-6}$ alkyl group(s), or both R' and R" combine each other at their termini to form together with an adjacent nitrogen atom a saturated or unsaturated 5- to 6-membered nitrogen-containing heterocyclic group optionally substituted by a hydroxyl group or a C$_{1-6}$ alkyloxy group, E is one of the following groups (ii) to (v):

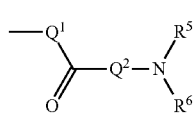 (ii)

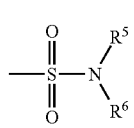 (iii)

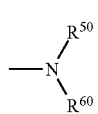 (iv)

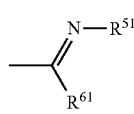 (v)

Q$^1$ is a single bond, a C$_{1-6}$ alkylene group or a group of the formula: —N(R$^7$)—, R$^7$ is a hydrogen atom or a C$_{1-6}$ alkyl group, Q$^2$ is a single bond or a C$_{1-6}$ alkylene group, one of R$^5$ and R$^6$ is a hydrogen atom or a C$_{1-6}$ alkyl group and the other is (A) a C$_{1-6}$ alkyl group optionally substituted by one to three group(s) selected from the group consisting of (a) a halogen atom; (b) a cyano group; (c) a C$_{1-6}$ alkyloxy group; (d) a C$_{3-8}$ cycloalkyl group optionally substituted by one to two group(s) selected from a cyano group and a C$_{1-6}$ alkyl group; (e) an amino group optionally substituted by one or two a $C_{1-6}$ alkyl group(s); (f) a $C_{1-6}$ alkylthio group; (g) a $C_{1-6}$ alkylsulfinyl group; (h) a $C_{1-6}$ alkylsulfonyl group; (i) an acyl group; (j) a 6- to 10-membered monocyclic or bicyclic aryl group optionally substituted by one to two halogen atom(s); (k) a saturated or unsaturated 4- to 7-membered heteromonocyclic group (said heteromonocyclic group containing one to four heteroatom(s) selected from oxygen atom, sulfur atom and nitrogen atom); (l) a saturated or unsaturated 8- to 15-membered nitrogen-containing bi-cyclic or tri-cyclic heterocyclic group formed by fusing the aforementioned heteromonocyclic group with one or two other cyclic group(s) selected from a $C_{3-8}$ cycloalkyl group, a 5- to 6-membered monocyclic aryl group and a saturated or unsaturated 4- to 7-membered heteromonocyclic group (said heteromonocyclic group containing one to four heteroatom(s) selected from oxygen atom, sulfur atom and nitrogen atom); and (m) a saturated or unsaturated 8- to 11-membered nitrogen-containing spiro-heterocyclic group, (B) a $C_{3-8}$ cycloalkyl group optionally substituted by one to two group(s) selected from a cyano group and a $C_{1-6}$ alkyl group, (C) a group of the formula: —N($R^8$)($R^9$), (D) a 6- to 10-membered monocyclic or bicyclic aryl group optionally substituted by one to two halogen atom(s), or (E) a saturated or unsaturated heterocyclic group selected from the group consisting of i) a saturated or unsaturated 4- to 7-membered heteromonocyclic group (said heteromonocyclic group containing one to four heteroatom(s) selected from oxygen atom, sulfur atom and nitrogen atom), ii) a saturated or unsaturated 8- to 15-membered nitrogen-containing bi-cyclic or tri-cyclic heterocyclic group formed by fusing the aforementioned heteromonocyclic group with one or two other cyclic group(s) selected from a $C_{3-8}$ cycloalkyl group, a 5- to 6-membered monocyclic aryl group and a saturated or unsaturated 4- to 7-membered heteromonocyclic group (said heteromonocyclic group containing one to four heteroatom(s) selected from oxygen atom, sulfur atom and nitrogen atom) and iii) a saturated or unsaturated 8- to 11-membered nitrogen-containing spiro-heterocyclic group, or both $R^5$ and $R^6$ combine each other to form together with an adjacent nitrogen atom a saturated or unsaturated nitrogen-containing heterocyclic group selected from the group consisting of (a) a saturated or unsaturated, 4- to 7-membered nitrogen-containing heteromonocyclic group, said heteromonocyclic group optionally containing two or more nitrogen atoms and optionally containing one to two heteroatom(s) other than such nitrogen atom(s) selected from oxygen atom and sulfur atom, (b) a saturated or unsaturated, 8- to 15-membered nitrogen-containing bicyclic or tricyclic heterocyclic group formed by fusing the aforementioned heteromonocyclic group with one or two other cyclic group(s) selected from a $C_{3-8}$ cycloalkyl group, a 5- to 6-membered monocyclic aryl group and a saturated or unsaturated, 4- to 7-membered heteromonocyclic group, said heteromonocyclic group containing one to four heteroatom(s) selected from oxygen atom, sulfur atom and nitrogen atom; and (c) a saturated or unsaturated, 8- to 11-membered nitrogen-containing spiro-heterocyclic group, $R^8$ is a hydrogen atom or a $C_{1-6}$ alkyl group, $R^9$ is (a) a $C_{1-6}$ alkyl group optionally substituted by one to three group(s) selected from a halogen atom, a cyano group and a phenyl group, (b) a $C_{3-8}$ cycloalkyl group, (c) a 6- to 10-membered monocyclic or bicyclic aryl group optionally substituted by one to two halogen atom(s) or (d) an acyl group or (e) a saturated or unsaturated heterocyclic group selected from the group consisting of i) a saturated or unsaturated 4- to 7-membered heteromonocyclic group (said heteromonocyclic group containing one to four heteroatom(s) selected from oxygen atom, sulfur atom and nitrogen atom), ii) a saturated or unsaturated 8- to 15-membered nitrogen-containing bi-cyclic or tri-cyclic heterocyclic group formed by fusing the aforementioned heteromonocyclic group with one or two other cyclic group(s) selected from a $C_{3-8}$ cycloalkyl group, a 5- to 6-membered monocyclic aryl group and a saturated or unsaturated 4- to 7-membered heteromonocyclic group (said heteromonocyclic group containing one to four heteroatom(s) selected from oxygen atom, sulfur atom and nitrogen atom) and iii) a saturated or unsaturated 8- to 11-membered nitrogen-containing spiro-heterocyclic group, $R^{50}$ is a hydrogen atom or a $C_{1-6}$ alkyl group, $R^{60}$ is a hydrogen atom, a $C_{1-6}$ alkyl group or an acyl group, or both of them combine together with the adjacent nitrogen atom to form a cyclic group of the following formula:

in which Ring $A^1$ is a 5- to 7-membered aliphatic nitrogen-containing heterocyclic group optionally substituted by an oxo group, $R^{51}$ is an alkyl group or a 6- to 10-membered monocyclic or bicyclic aryl-sulfonyl group optionally substituted by one to two halogen atom(s), $R^{61}$ is a $C_{1-6}$ alkylamino group or an azido group, and wherein (a) the above-mentioned saturated or unsaturated heterocyclic group in $R^5$, $R^6$, $R^8$ or $R^9$ may be substituted by one to four groups selected from the group consisting of
a halogen atom;
a hydroxyl group;
a cyano group;
an oxo group;
a $C_{1-6}$ alkyl group;
a $C_{1-6}$ alkyl group substituted by one to three halogen atom(s);
a $C_{1-6}$ alkyloxy-$C_{1-6}$ alkyl group;
an amino-$C_{1-6}$ alkyl group;
a $C_{3-8}$ cycloalkyl group;
a phenyl-$C_{1-6}$ alkyl group;
a $C_{1-6}$ alkyloxy group;
a $C_{1-6}$ alkyloxy group substituted by one to three halogen atom(s);
an acyl group;
an amino group optionally substituted by one to two $C_{1-6}$ alkyl group(s);
an acylamino group;
a $C_{1-6}$ alkylsulfonyl group;

an aminosulfonyl group optionally substituted by one to two $C_{1-6}$ alkyl group(s);
a phenyl group optionally substituted by one to two halogen atom(s); and
a saturated or unsaturated 5- to 6-membered nitrogen-containing heterocyclic group, and wherein
(b) the above-mentioned saturated or unsaturated heterocyclic group formed by combining $R^5$ with $R^6$ may be substituted by one to three group(s) selected from the group consisting of a halogen atom;
a hydroxyl group;
a cyano group;
an oxo group;
a $C_{1-6}$ alkyl group;
a $C_{1-6}$ alkyl group substituted by one to three halogen atom(s);
a $C_{1-6}$ alkyloxy-$C_{1-6}$ alkyl group;
an amino-$C_{1-6}$ alkyl group;
a $C_{3-8}$ cycloalkyl group;
a phenyl-$C_{1-6}$ alkyl group;
a $C_{1-6}$ alkyloxy group;
a $C_{1-6}$ alkyloxy group substituted by one to three halogen atom(s);
an acyl group;
an amino group optionally substituted by one to two $C_{1-6}$ alkyl group(s);
an acylamino group;
a $C_{1-6}$ alkylsulfonyl group;
an aminosulfonyl group optionally substituted by one to two $C_{1-6}$ alkyl group(s); and
a phenyl group,
or a pharmaceutically acceptable salt thereof.

* * * * *